United States Patent
Chan et al.

(10) Patent No.: US 11,345,712 B2
(45) Date of Patent: May 31, 2022

(54) PROTEIN-TARGETING COMPOUNDS AND PHARMACEUTICAL COMPOSITIONS THEREOF, AND THEIR THERAPEUTIC APPLICATIONS

(71) Applicant: BioTheryX, Inc., San Diego, CA (US)

(72) Inventors: Kyle W. H. Chan, San Diego, CA (US); Paul E. Erdman, San Diego, CA (US); Leah Fung, San Diego, CA (US); David Aaron Hecht, Chula Vista, CA (US); Imelda Lam, San Diego, CA (US); Robert Sullivan, Vista, CA (US); Eduardo Torres, San Diego, CA (US)

(73) Assignee: BioTheryX, Inc., San Diego, CA (US)

( * ) Notice: Subject to any disclaimer, the term of this patent is extended or adjusted under 35 U.S.C. 154(b) by 0 days.

(21) Appl. No.: 16/882,750

(22) Filed: May 26, 2020

(65) Prior Publication Data

US 2020/0369679 A1     Nov. 26, 2020

Related U.S. Application Data

(60) Provisional application No. 62/852,844, filed on May 24, 2019.

(51) Int. Cl.
*C07D 495/04* (2006.01)
*C07D 401/04* (2006.01)
*C07D 401/14* (2006.01)

(52) U.S. Cl.
CPC ......... *C07D 495/04* (2013.01); *C07D 401/04* (2013.01); *C07D 401/14* (2013.01)

(58) Field of Classification Search
CPC .................................................. C07D 495/04
See application file for complete search history.

(56) References Cited

U.S. PATENT DOCUMENTS

2018/0170948 A1   6/2018   Chan et al.

FOREIGN PATENT DOCUMENTS

| WO | 2002059106 A1 | 8/2002 |
| WO | 2017120422 A1 | 7/2017 |
| WO | 2020023782 A1 | 1/2020 |

OTHER PUBLICATIONS

Han, H. "Targeted Prodrug Design to Optimize Drug Delivery." AAPS Pharmsci. (2000), vol. 2 (1) article 6, pp. 1-11. (Year: 2000).*
Ettmayer, P., et al. "Lessons Learned from Marketed and Investigational Prodrugs." J. Med. Chem. (2004) 47(10), pp. 2393-2404. (Year: 2004).*
Testa, B. "Prodrug research: futile or fertile?" Biochem. Pharm. (2004) 68, pp. 2097-2106. (Year: 2004).*
Wang, Yingwei, et al. "C—H bond cleavage-enabled aerobic ring-opening reaction of in situ formed 2-aminobenzofuran-3(2H)-ones." Org. Biomol. Chem. (2021), vol. 19, pp. 9448-9459. (Year: 2021).*
Brito et al., "Polyglycine expansions in eRF3/GSPT1 are associated with gastric cancer susceptibility," Carcinogenesis 2005, 26, 2046-9.
Chauvin et al., "Human eukaryotic release factor 3a depletion causes cell cycle arrest at G1 phase through inhibition of the mTOR pathway," Mol. Cell. Biol. 2007, 27, 5619-29.
Desagher et al., "Phosphorylation of Bid by casein kinases I and II regulates its cleavage by caspase 8," Mol. Cell., 2001, 8, 601-11.
Hashimoto et al., "Translation termination factor eRF3 is targeted for caspase-mediated proteolytic cleavage and degradation during DNA damage-induced apoptosis," Apoptosis 2012, 17, 1287-99.
Ishii et al., "A Novel Rac1-GSPT1 signaling pathway controls astrogliosis following central nervous system injury," J. Biol. Chem. 2017, 292, 1240-50.
Knippschild et al., "The casein kinase 1 family: participation in multiple cellular processes in eukaryotes," Cell. Signal. 2005, 17, 675-89.
Li et al., "eRF3b, a biomarker for hepatocellular carcinoma, influences cell cycle and phosphoralation status of 4E-BP1," PLoS One 2014, 9, e86371.
Malta-Vacas et al., "Differential expression of GSPT1 GGCn alleles in cancer," Cancer Genet. Cytogenet. 2009, 195, 132-42.
Miri et al., "GGCn polymorphism of eRF3a/GSPT1 gene and breast cancer susceptibility," Med. Oncol. 2012, 29, 1581-5.
Netea et al., "Differential requirement for the activation of the inflammasome for processing and release of IL-1β in monocytes and macrophages," Blood 2009, 113, 2324-35.
Wallach, "The TNF cytokine family: One track in a road paved by many," Cytokine 2013, 63, 225-9.
Wright and Lange, "Newer potential biomarkers in prostate cancer," Rev. Urol. 2007, 9, 207-13.

\* cited by examiner

*Primary Examiner* — John S Kenyon
(74) *Attorney, Agent, or Firm* — Juniv LLP; Lin Yu, Esq.

(57) ABSTRACT

The present disclosure provides compounds, for example, a compound of Formula (I), that modulate a protein function and/or restore protein homeostasis. The disclosure provides a method of modulating a protein-mediated disease, disorder, condition, or response. Compositions, including in combination with other therapeutic agents, are provided.

(I)

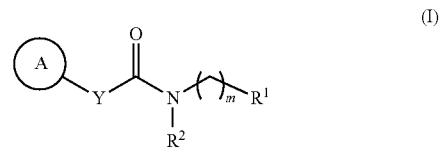

51 Claims, No Drawings

PROTEIN-TARGETING COMPOUNDS AND PHARMACEUTICAL COMPOSITIONS THEREOF, AND THEIR THERAPEUTIC APPLICATIONS

CROSS REFERENCE TO RELATED APPLICATION

This application claims the benefit of the priority of U.S. Provisional Application No. 62/852,844, filed May 24, 2019; the disclosure of which is incorporated herein by reference in its entirety.

FIELD

The present disclosure provides compounds that modulate a protein function and/or restore protein homeostasis. The disclosure provides a method of modulating a protein-mediated disease, disorder, condition, or response. Compositions, including in combination with other therapeutic agents, are provided.

BACKGROUND

Aberrant protein function, and/or protein imbalance is a hallmark of many disease states. For example, the functioning of the immune system is finely balanced by the activities of pro-inflammatory and anti-inflammatory mediators or cytokines. Some cytokines promote inflammation (pro-inflammatory cytokines), whereas other cytokines suppress the activity of the pro-inflammatory cytokines (anti-inflammatory cytokines). For example, IL-4, IL-10, and IL-13 are potent activators of B lymphocytes, and also act as anti-inflammatory agents. They are anti-inflammatory cytokines by virtue of their ability to suppress genes for pro-inflammatory cytokines such as IL-1, TNF, and chemokines.

Unregulated activities of these mediators can lead to the development of serious inflammatory conditions. For example, autoimmune diseases arise when immune system cells (lymphocytes, macrophages) become sensitized against the "self." Lymphocytes, as well as macrophages, are usually under control in this system. However, a misdirection of the system toward the body's own tissues may happen in response to still unexplained triggers. One hypothesis is that lymphocytes recognize an antigen which mimics the "self" and a cascade of activation of different components of the immune system takes place, ultimately leading to tissue destruction. Genetic predisposition has also been postulated to be responsible for autoimmune disorders.

Misregulation of protein synthesis may contribute to uncontrolled cell growth, proliferation, and migration, leading to cancer. For example, the translation termination factor GSPT1 (eRF3a) mediates stop codon recognition and facilitates release of a nascent peptide from the ribosome. In addition to its role in translation termination, GSPT1 is also involved in several other critical cellular processes, such as cell cycle regulation, cytoskeleton organization, and apoptosis. GSPT1 has been implicated as an oncogenic driver of several different cancer types, including breast cancer, hepatocellular carcinoma, gastric cancer, and prostate cancer. Brito et al., *Carcinogenesis,* 26:2046-9 (2005); Malta-Vacas et al., *Cancer Genet. Cytogenet.,* 195:132-42 (2009); Miri et al., *Med. Oncol.,* 29:1581-5 (2011); Wright and Lange, *Rev. Urol.,* 9:207-13 (2007); Hashimoto et al., *Apoptosis,* 17:1287-99 (2012); Liu et. al., *PLOS One,* 9:e86371 (2014); and Chauvin et al., *Mol. Cell. Biol.,* 27: 5619-29 (2007). GSPT1 also contributes to glial scar formation and astrogliosis after a central nervous system (CNS) injury. Ishii et al., *J. Biol. Chem.,* 292:1240-50 (2017).

Tumor necrosis factor-alpha (TNF-alpha) and interleukin-1 (IL-1) are pro-inflammatory cytokines that mediate inflammatory responses associated with infectious agents and other cellular stresses. Overproduction of these cytokines is believed to underlie the progression of many inflammatory diseases, including rheumatoid arthritis (RA), Crohn's disease, inflammatory bowel disease, multiple sclerosis, endotoxin shock, osteoporosis, Alzheimer's disease, congestive heart failure, and psoriasis.

TNF-alpha is produced by a variety of activated immune cells, particularly monocytes and macrophages. Elevated levels of TNF-alpha have been implicated in several pathological conditions, including inflammation, infection, autoimmune disease, and cancer development. Indeed, virtually all of the players in the human immune system have been reported to have some level of functional relationship with TNF-alpha. Wallach, *Cytokine,* 63:225-9 (2013). TNF-alpha is able to induce fever, apoptotic cell death, cachexia, inflammation, and to inhibit tumorigenesis and viral replication.

IL-1α and IL-1β are proinflammatory cytokines that activate cells by binding the IL-1 receptor type I (IL-1RI). These proteins are the most powerful endogenous pyrogens known. IL-1α is constitutively expressed as a precursor in cells forming biological barriers, such as epithelial cells, keratinocytes, and mucosal and endothelial cells. IL-1α does not require processing for activation and is released from damaged or dying cells. In contrast, IL-1β must be proteolytically cleaved into its active form. Active IL-1β is primarily generated in a subset of blood monocytes, dendritic cells, and tissue macrophages, where its activation and release are tightly regulated, although studies systematically assessing other cells capable of producing IL-1β are limited. Netea et al., *Blood,* 113:2324-35 (2009).

Recent data from clinical trials support the use of protein antagonists of cytokines, for example, a soluble TNF-alpha receptor fusion protein (etanercept) or a monoclonal TNF-alpha antibody (infliximab), for the treatment of rheumatoid arthritis, Crohn's disease, juvenile chronic arthritis, and psoriatic arthritis. Thus, the reduction of pro-inflammatory cytokines such as TNF-alpha and interleukin-1 (IL-I) has become an accepted therapeutic approach for potential drug intervention in these conditions.

Moreover, IL-2 is now FDA approved for the treatment of renal cancer and melanoma, with durable, complete remissions achieved with IL-2 up to 148 months. However, the short half-life of IL-2 in serum requires a large amount of IL-2 to be injected to achieve therapeutic levels. Many attempts have been made to minimize side effects of systemic IL-2 treatment, for example, introducing IL-2 directly into the tumor, though this complicates treatment, and has largely been unsuccessful.

Local delivery of cytokines is appealing compared to systemic delivery for a variety of reasons. It takes advantage of the natural biology of cytokines that have evolved to act locally in a paracrine or autocrine fashion. Local expression also dramatically minimizes many of the side effects of systemic delivery of cytokines. Thus, compounds and methods to increase local expression of IL-2 would be better tolerated than high dose IL-2 treatment, which would expand therapeutic utility of strategies that increase IL-2.

Additional targets include several candidate genes involved in apoptosis and cell survival, including the zinc-finger transcription factor Aiolos. Aiolos is a transcription factor whose expression is restricted to lymphoid lineages. Aiolos binds to the Bcl-2 promoter, and also interacts with the Bcl-2 and Bcl-XL proteins to promote cell survival. Upregulation of Aiolos expression, for example, can reduce apoptosis of HIV-1 infected cells.

Likewise, expression of Aiolos in lung and breast cancers predicts significantly reduced patient survival. Aiolos decreases expression of a large set of adhesion-related genes, disrupting cell-cell and cell-matrix interactions, facilitating metastasis. Aiolos may also function as an epigenetic driver of lymphocyte mimicry in certain metastatic epithelial cancers. Thus, downregulation of Aiolos may reduce or eliminate metastasis.

Similarly, the casein kinase 1 family of proteins plays a role in the mitotic spindle formation, DNA repair, and RNA metabolism. Knippschild et al., *Cell Signal.*, 17:675-89 (2005). There are six isoforms in humans: α, γ1, γ2, γ3, δ, and ε. CK1α has been shown to have an anti-apoptotic function; its inhibition increased Fas-induced apoptosis, whereas the overexpression of CK1α delayed BID-mediated cell death. Desagher et al., *Mol Cell.*, 8:601-11 (2001). In addition, CK1α inhibits TRAIL induced apoptosis by modification of the TNF receptor or FADD at the death-inducing signaling complex (DISC). Thus, downregulation of CK1α leads to enhancement of TRAIL-induced cell death. CK1α also promotes cell survival by interacting with the retinoid X receptor (RXR). Downregulation of CK1α enhances the apoptotic effect of RXR agonists. Likewise, the ikaros family of proteins are tumor suppressors that play a role in leukemia.

One mechanism to disrupt protein drivers of a disease is to decrease the cellular concentration of these proteins. For example, proteolytic degradation of cellular proteins is essential to normal cell function. Hijacking this process, by targeting specific disease-related proteins, presents a mechanism for the treatment of disease. The irreversible nature of proteolysis makes it well-suited to serve as a regulatory switch for controlling unidirectional processes.

Ubiquitin-mediated proteolysis begins with ligation of one or more ubiquitin molecules to a particular protein substrate. Ubiquitination occurs through the activity of ubiquitin-activating enzymes (E1), ubiquitin-conjugating enzymes (E2), and ubiquitin-protein ligases (E3), acting sequentially to attach ubiquitin to lysine residues of substrate proteins. The E3 ligases confer specificity to ubiquitination reactions by binding directly to particular substrates.

SUMMARY OF THE DISCLOSURE

Provided herein is a compound of Formula (I):

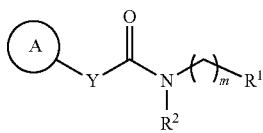

(I)

or a pharmaceutically acceptable salt thereof, wherein:
$R^1$ is selected from the group consisting of

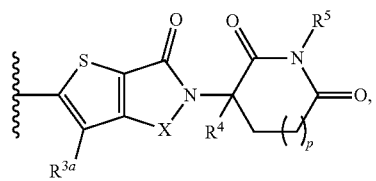

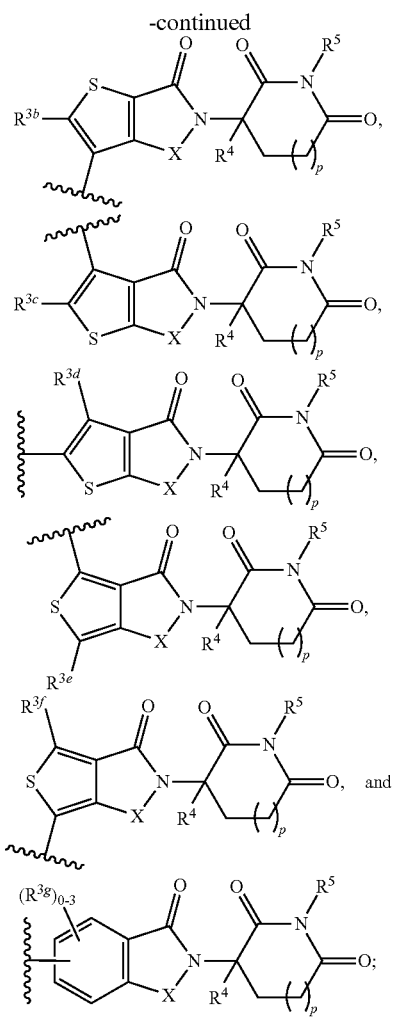

each X is independently $CH_2$ or $C(=O)$;
Y is $C(=O)$, $C(=O)-(CR^{6a}R^{6b})_{n1}$, $C(=S)$, or $C(=S)-(CR^{6c}R^{6d})_{n2}$;
$R^2$ is H, deuterium, optionally substituted $C_1$-$C_6$ alkyl, optionally substituted $C_3$-$C_8$ carbocyclyl, optionally substituted $C_6$-$C_{10}$ aryl, optionally substituted 3 to 10 membered heterocyclyl, or optionally substituted 5 to 10 membered heteroaryl;
ring A is $C_6$-$C_{10}$ aryl, 5 to 10 membered heteroaryl, $C_3$-$C_8$ carbocyclyl, or 3 to 10 membered heterocyclyl, each optionally substituted with one or more $R^A$;
$R^{3a}$, $R^{3b}$, $R^{3c}$, $R^{3d}$, $R^{3e}$, and $R^{3f}$ are each independently H, deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $-(CH_2)_t-NR^{7a}R^{8a}$, $-O(CH_2)_t-NR^{7a}R^{8a}$, $-C(O)NR^{7b}R^{8b}$, $-S(O)_2NR^{7c}R^{8c}$, $-OR^9$, $-SR^{10a}$, $-C(O)OR^{10b}$, $-C(O)R^{11a}$, $-NR^{7d}C(O)R^{11b}$, $-S(O)_2R^{11c}$, $-NR^{7e}S(O)_2R^{11d}$, $(C_1$-$C_6$ alkoxy)$C_1$-$C_6$ alkyl, $-O(C_1$-$C_6$ alkoxy)$C_1$-$C_6$ alkyl, optionally substituted $C_3$-$C_8$ carbocyclyl, optionally substituted $C_6$-$C_{10}$ aryl, optionally substituted 3 to 10 membered heterocyclyl, or optionally substituted 5 to 10 membered heteroaryl;
each $R^{3g}$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $-(CH_2)_t-NR^{7a}R^{8a}$, $-O(CH_2)_t-NR^{7a}R^{8a}$, —C(O)NR$^{7b}$R$^{8b}$, —S(O)$_2$NR$^{7c}$R$^{8c}$, —OR$^9$, —SR$^{10a}$, —C(O)OR$^{10b}$, —C(O)R$^{11a}$, —NR$^{7d}$C(O)R$^{11b}$, —S(O)$_2$R$^{11c}$, —NR$^{7e}$S(O)$_2$R$^{11d}$, (C$_1$-C$_6$ alkoxy)C$_1$-C$_6$ alkyl, —O(C$_1$-C$_6$ alkoxy)C$_1$-C$_6$ alkyl, optionally substituted C$_3$-C$_8$ carbocyclyl, optionally substituted C$_6$-C$_{10}$ aryl, optionally substituted 3 to 10 membered heterocyclyl, or optionally substituted 5 to 10 membered heteroaryl;

each R$^4$ is independently H, deuterium, halogen, or optionally substituted C$_1$-C$_6$ alkyl;

each R$^5$ is independently H, deuterium, C$_1$-C$_6$ alkyl,

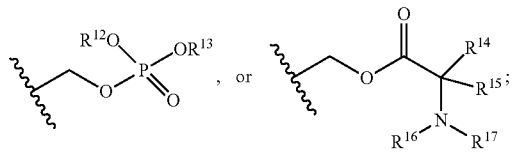
, or each R$^{6a}$, R$^{6b}$, R$^{6c}$, R$^{6d}$, R$^{14}$, and R$^{15}$ is independently H, substituted or unsubstituted amino, halogen, C$_1$-C$_6$ alkyl, C$_1$-C$_6$ alkoxy, C$_1$-C$_6$ haloalkyl, C$_1$-C$_6$ haloalkoxy, or C$_3$-C$_8$ carbocyclyl; or R$^{6a}$ and R$^{6b}$ together with the carbon atom to which they are attached form a C$_3$-C$_8$ carbocyclyl; or R$^{6a}$ and R$^{6d}$ together with the carbon atom to which they are attached form a C$_3$-C$_8$ carbocyclyl; wherein each C$_3$-C$_8$ carbocyclyl is optionally substituted with one or more R$^{6c}$;

each R$^{7a}$, R$^{7b}$, R$^{7c}$, R$^{7d}$, R$^{7e}$, R$^{8a}$, R$^{8b}$, R$^{8c}$, R$^{16}$, and R$^{17}$ is independently H, optionally substituted C$_1$-C$_6$ alkyl, optionally substituted C$_6$-C$_{10}$ aryl, optionally substituted C$_7$-C$_{14}$ aralkyl, or optionally substituted C$_3$-C$_8$ carbocyclyl; or R$^{7a}$ and R$^{8a}$ together with the nitrogen atom to which they are attached form optionally substituted 3 to 7 membered heterocyclyl; or R$^{7b}$ and R$^{8b}$ together with the nitrogen atom to which they are attached form optionally substituted 3 to 7 membered heterocyclyl; or R$^{7c}$ and R$^{8c}$ together with the nitrogen atom to which they are attached form optionally substituted 3 to 7 membered heterocyclyl; wherein each of C$_6$-C$_{10}$ aryl, C$_7$-C$_{14}$ aralkyl, C$_3$-C$_8$ carbocyclyl, and 3 to 7 membered heterocyclyl is optionally substituted with one or more R$^B$;

each R$^9$ is independently optionally substituted C$_1$-C$_6$ alkyl, optionally substituted C$_2$-C$_6$ alkenyl, optionally substituted C$_2$-C$_6$ alkynyl, optionally substituted C$_6$-C$_{10}$ aryl, optionally substituted 5 to 10 membered heteroaryl, optionally substituted C$_7$-C$_{14}$ aralkyl, optionally substituted 3 to 10 membered heterocyclyl, or optionally substituted C$_3$-C$_8$ carbocyclyl;

each of R$^{10a}$, R$^{10b}$, R$^{12}$, and R$^{13}$ is independently H, optionally substituted C$_1$-C$_6$ alkyl, optionally substituted C$_2$-C$_6$ alkenyl, optionally substituted C$_2$-C$_6$ alkynyl, optionally substituted C$_6$-C$_{10}$ aryl, optionally substituted 5 to 10 membered heteroaryl, optionally substituted C$_7$-C$_{14}$ aralkyl, optionally substituted 3 to 10 membered heterocyclyl, or optionally substituted C$_3$-C$_8$ carbocyclyl;

each R$^{11a}$, R$^{11b}$, R$^{11c}$, and R$^{11d}$ is independently optionally substituted C$_1$-C$_6$ alkyl, optionally substituted C$_2$-C$_6$ alkenyl, optionally substituted C$_2$-C$_6$ alkynyl, optionally substituted C$_6$-C$_{10}$ aryl, optionally substituted 5 to 10 membered heteroaryl, optionally substituted C$_7$-C$_{14}$ aralkyl, optionally substituted 3 to 10 membered heterocyclyl, or optionally substituted C$_3$-C$_8$ carbocyclyl;

each R$^A$ is independently halogen, cyano, nitro, hydroxyl, optionally substituted C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, —(CH$_2$)$_t$—NR$^{7a}$R$^{8a}$, —O(CH$_2$)$_t$—NR$^{7a}$R$^{8a}$, —C(O)NR$^{7b}$R$^{8b}$, —S(O)$_2$NR$^{7c}$R$^{8c}$, —OR$^9$, —SR$^{10a}$, —C(O) OR$^{10b}$, —C(O)R$^{11a}$, —NR$^{7d}$C(O)R$^{11b}$, —S(O)$_2$R$^{11c}$, —NR$^{7e}$S(O)$_2$R$^{11d}$, (C$_1$-C$_6$ alkoxy)C$_1$-C$_6$ alkyl, —O(C$_1$-C$_6$ alkoxy)C$_1$-C$_6$ alkyl, phenyl, 5 to 10 membered heteroaryl, C$_3$-C$_8$ carbocyclyl, or 3 to 10 membered heterocyclyl, wherein each of phenyl, 5 to 10 membered heteroaryl, C$_3$-C$_8$ carbocyclyl, and 3 to 10 membered heterocyclyl is optionally substituted with one or more R$^B$;

each R$^B$ is independently C$_1$-C$_6$ alkyl, C$_1$-C$_6$ alkoxy, C$_1$-C$_6$ haloalkyl, C$_1$-C$_6$ haloalkoxy, (C$_1$-C$_6$ alkoxy)C$_1$-C$_6$ alkyl, —O(C$_1$-C$_6$ alkoxy)C$_1$-C$_6$ alkyl, halogen, or cyano; or two geminal R$^B$ form oxo;

m is an integer of 0, 1, 2, 3, 4, or 5;

n1 and n2 are each independently an integer of 0, 1, 2, or 3;

each p is independently an integer of 0, 1, or 2; and each t is independently an integer of 0, 1, 2, 3, 4, or 5.

Also provided herein is a compound of Formula (III):

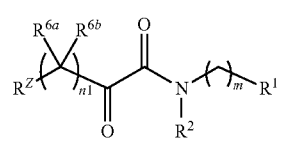

(III)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

R$^1$ is selected from the group consisting of

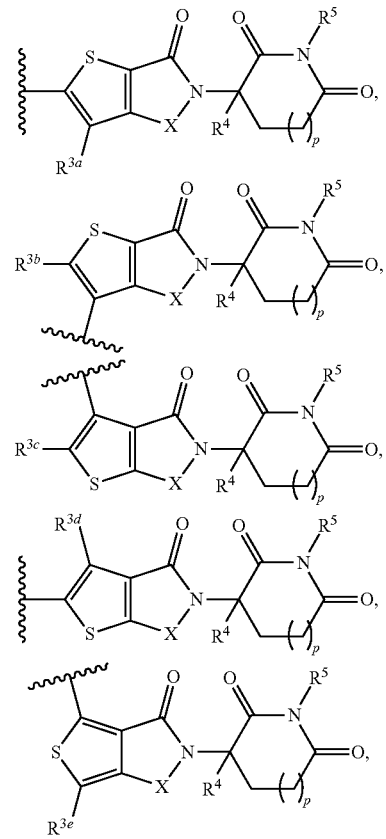

-continued

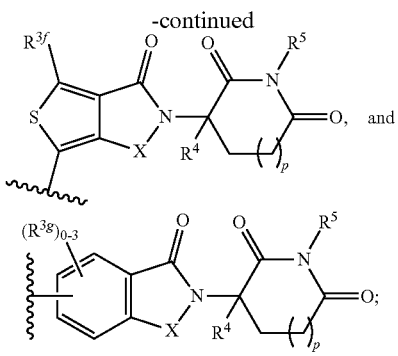

each X is independently CH$_2$ or C(=O);

R$^Z$ is —NR$^{7a}$R$^{8a}$ or ring A; and ring A is C$_6$-C$_{10}$ aryl, 5 to 10 membered heteroaryl, C$_3$-C$_8$ carbocyclyl, or 3 to 10 membered heterocyclyl, each optionally substituted with one or more R$^A$;

R$^2$ is H, deuterium, optionally substituted C$_1$-C$_6$ alkyl, optionally substituted C$_3$-C$_8$ carbocyclyl, optionally substituted C$_6$-C$_{10}$ aryl, optionally substituted 3 to 10 membered heterocyclyl, or optionally substituted 5 to 10 membered heteroaryl;

R$^{3a}$, R$^{3b}$, R$^{3c}$, R$^{3d}$, R$^{3e}$, and R$^{3f}$ are each independently H, deuterium, hydroxyl, halogen, cyano, nitro, optionally substituted C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, —(CH$_2$)$_t$—NR$^{7a}$R$^{8a}$, —O(CH$_2$)$_t$—NR$^{7a}$R$^{8a}$, —C(O)NR$^{7b}$R$^{8b}$, —S(O)$_2$NR$^{7c}$R$^{8c}$, —OR$^9$, —SR$^{10a}$, —C(O)OR$^{10b}$, —C(O)R$^{11a}$, —NR$^{7d}$C(O)R$^{11b}$, —S(O)$_2$R$^{11c}$, —NR$^{7e}$S(O)$_2$R$^{11d}$, (C$_1$-C$_6$ alkoxy)C$_1$-C$_6$ alkyl, —O(C$_1$-C$_6$ alkoxy)C$_1$-C$_6$ alkyl, optionally substituted C$_3$-C$_8$ carbocyclyl, optionally substituted C$_6$-C$_{10}$ aryl, optionally substituted 3 to 10 membered heterocyclyl, or optionally substituted 5 to 10 membered heteroaryl;

each R$^{3g}$ is independently deuterium, hydroxyl, halogen, cyano, nitro, optionally substituted C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, —(CH$_2$)$_t$—NR$^{7a}$R$^{8a}$, —O(CH$_2$)$_t$—NR$^{7a}$R$^{8a}$, —C(O)NR$^{7b}$R$^{8b}$, —S(O)$_2$NR$^{7c}$R$^{8c}$, —OR$^9$, —SR$^{10a}$, —C(O)OR$^{10b}$, —C(O)R$^{11a}$, —NR$^{7d}$C(O)R$^{11b}$, —S(O)$_2$R$^{11c}$, —NR$^{7e}$S(O)$_2$R$^{11d}$, (C$_1$-C$_6$ alkoxy)C$_1$-C$_6$ alkyl, —O(C$_1$-C$_6$ alkoxy)C$_1$-C$_6$ alkyl, optionally substituted C$_3$-C$_8$ carbocyclyl, optionally substituted C$_6$-C$_{10}$ aryl, optionally substituted 3 to 10 membered heterocyclyl, or optionally substituted 5 to 10 membered heteroaryl;

each R$^4$ is independently H, deuterium, halogen, or optionally substituted C$_1$-C$_6$ alkyl;

each R$^5$ is independently H, deuterium, C$_1$-C$_6$ alkyl,

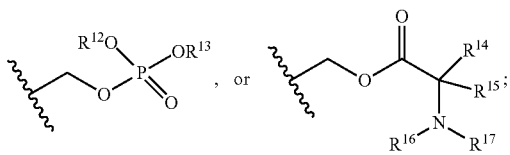

each R$^{6a}$, R$^{6b}$, R$^{6c}$, R$^{6d}$, R$^{14}$, and R$^{15}$ is independently H, substituted or unsubstituted amino, halogen, C$_1$-C$_6$ alkyl, C$_1$-C$_6$ alkoxy, C$_1$-C$_6$ haloalkyl, C$_1$-C$_6$ haloalkoxy, or C$_3$-C$_8$ carbocyclyl; or R$^{6a}$ and R$^{6b}$ together with the carbon atom to which they are attached form a C$_3$-C$_8$ carbocyclyl; or R$^{6c}$ and R$^{6d}$ together with the carbon atom to which they are attached form a C$_3$-C$_8$ carbocyclyl; wherein each C$_3$-C$_8$ carbocyclyl is optionally substituted with one or more R$^B$;

each R$^{7a}$, R$^{7b}$, R$^{7c}$, R$^{7d}$, R$^{7e}$, R$^{8a}$, R$^{8b}$, R$^{8c}$, R$^{16}$, and R$^{17}$ is independently H, optionally substituted C$_1$-C$_6$ alkyl, optionally substituted C$_6$-C$_{10}$ aryl, optionally substituted C$_7$-C$_{14}$ aralkyl, or optionally substituted C$_3$-C$_8$ carbocyclyl; or R$^{7a}$ and R$^{8a}$ together with the nitrogen atom to which they are attached form optionally substituted 3 to 7 membered heterocyclyl; or R$^{7b}$ and R$^{8b}$ together with the nitrogen atom to which they are attached form optionally substituted 3 to 7 membered heterocyclyl; or R$^{7c}$ and R$^{8c}$ together with the nitrogen atom to which they are attached form optionally substituted 3 to 7 membered heterocyclyl; or R$^{16}$ and R$^{17}$ together with the nitrogen atom to which they are attached form optionally substituted 3 to 7 membered heterocyclyl; wherein each of C$_6$-C$_{10}$ aryl, C$_7$-C$_{14}$ aralkyl, C$_3$-C$_8$ carbocyclyl, and 3 to 7 membered heterocyclyl is optionally substituted with one or more R$^B$;

each R$^9$ is independently optionally substituted C$_1$-C$_6$ alkyl, optionally substituted C$_2$-C$_6$ alkenyl, optionally substituted C$_2$-C$_6$ alkynyl, optionally substituted C$_6$-C$_{10}$ aryl, optionally substituted 5 to 10 membered heteroaryl, optionally substituted C$_7$-C$_{14}$ aralkyl, optionally substituted 3 to 10 membered heterocyclyl, or optionally substituted C$_3$-C$_8$ carbocyclyl;

each of R$^{10a}$, R$^{10b}$, R$^{12}$, and R$^{13}$ is independently H, optionally substituted C$_1$-C$_6$ alkyl, optionally substituted C$_2$-C$_6$ alkenyl, optionally substituted C$_2$-C$_6$ alkynyl, optionally substituted C$_6$-C$_{10}$ aryl, optionally substituted 5 to 10 membered heteroaryl, optionally substituted C$_7$-C$_{14}$ aralkyl, optionally substituted 3 to 10 membered heterocyclyl, or optionally substituted C$_3$-C$_8$ carbocyclyl;

each R$^{11a}$, R$^{11b}$b, R$^{11c}$, and R$^{11d}$ is independently optionally substituted C$_1$-C$_6$ alkyl, optionally substituted C$_2$-C$_6$ alkenyl, optionally substituted C$_2$-C$_6$ alkynyl, optionally substituted C$_6$-C$_{10}$ aryl, optionally substituted 5 to 10 membered heteroaryl, optionally substituted C$_7$-C$_{14}$ aralkyl, optionally substituted 3 to 10 membered heterocyclyl, or optionally substituted C$_3$-C$_8$ carbocyclyl;

each R$^A$ is independently halogen, cyano, nitro, hydroxyl, optionally substituted C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, —(CH$_2$)$_t$—NR$^{7a}$R$^{8a}$, —O(CH$_2$)$_t$—NR$^{7a}$R$^{8a}$, —C(O)NR$^{7b}$R$^{8b}$, —S(O)$_2$NR$^{7c}$R$^{8c}$, —OR$^9$, —SR$^{10a}$, —C(O)OR$^{10b}$, —C(O)R$^{11a}$, —NR$^{7d}$C(O)R$^{11b}$, —S(O)$_2$R$^{11c}$, —NR$^{7e}$S(O)$_2$R$^{11d}$, (C$_1$-C$_6$ alkoxy)C$_1$-C$_6$ alkyl, —O(C$_1$-C$_6$ alkoxy)C$_1$-C$_6$ alkyl, phenyl, 5 to 10 membered heteroaryl, C$_3$-C$_8$ carbocyclyl, or 3 to 10 membered heterocyclyl, wherein each of phenyl, 5 to 10 membered heteroaryl, C$_3$-C$_8$ carbocyclyl, and 3 to 10 membered heterocyclyl is optionally substituted with one or more R$^B$;

each R$^B$ is independently C$_1$-C$_6$ alkyl, C$_1$-C$_6$ alkoxy, C$_1$-C$_6$ haloalkyl, C$_1$-C$_6$ haloalkoxy, (C$_1$-C$_6$ alkoxy)C$_1$-C$_6$ alkyl, —O(C$_1$-C$_6$ alkoxy)C$_1$-C$_6$ alkyl, halogen, or cyano; or two geminal R$^B$ form oxo;

m is an integer of 0, 1, 2, 3, 4, or 5;

n1 is an integer of 0, 1, 2, or 3;

each p is independently an integer of 0, 1, or 2; and each t is independently an integer of 0, 1, 2, 3, 4, 5, 6, 7, or 8.

Additionally provided herein is a compound of Formula (IIa), (IIb), or (IIc):

(IIa)

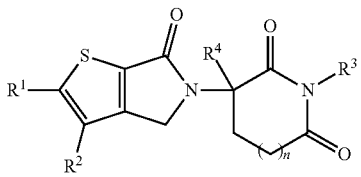

(IIb)

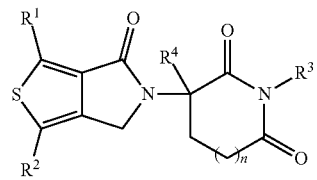

(IIc)

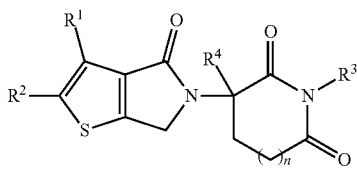

or a pharmaceutically acceptable salt thereof, wherein:

each n is independently an integer of 0, 1, or 2;

one of $R^1$ and $R^2$ is selected from the group consisting of H, deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, —$(CH_2)_t$—$NR^{7a}R^{8a}$, —$O(CH_2)_t$—$NR^{7a}R^{8a}$, —$C(O)NR^{7b}R^{8b}$, —$S(O)_2NR^{7c}R^{8c}$, —$OR^9$, —$SR^{10a}$, —$C(O)OR^{10b}$, —$C(O)R^{11a}$, —$NR^{7d}C(O)R^{11b}$, —$S(O)_2R^{11c}$, —$NR^{7e}S(O)_2R^{11d}$, ($C_1$-$C_6$ alkoxy)$C_1$-$C_6$ alkyl, —$O(C_1$-$C_6$ alkoxy)$C_1$-$C_6$ alkyl, optionally substituted $C_3$-$C_8$ carbocyclyl, optionally substituted $C_6$-$C_{10}$ aryl, optionally substituted 3 to 10 membered heterocyclyl, and optionally substituted 5 to 10 membered heteroaryl; and the other of $R^1$ and $R^2$ is

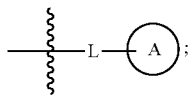

each $R^{3g}$ is independently H, deuterium, $C_1$-$C_6$ alkyl,

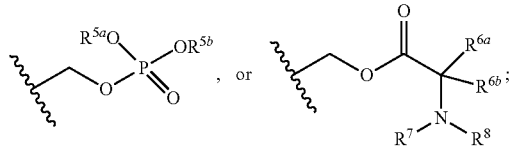

each $R^4$ is independently H, deuterium, halogen, or optionally substituted $C_1$-$C_6$ alkyl;

L is

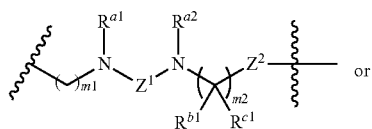

or

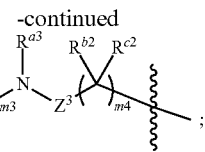

$Z^1$ is C(=O), C(=NH), S(O)$_2$, or (CH$_2$)$_k$;

$Z^2$ is a bond, S, O, or NH;

$Z^3$ is C(=O) or S(O)$_2$;

ring A is $C_6$-$C_{10}$ aryl, 5 to 10 membered heteroaryl, $C_3$-$C_8$ carbocyclyl, or 3 to 10 membered heterocyclyl, each optionally substituted with one or more $R^A$;

each of $R^{a1}$, $R^{a2}$, and $R^{a3}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl;

each $R^{b1}$, $R^{b2}$, $R^{c1}$, and $R^{c2}$ is independently H, hydroxyl, substituted or unsubstituted amino, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl; or $R^{b1}$ and $R^{c1}$ together with the carbon atom to which they are attached form a $C_3$-$C_8$ carbocyclyl; or $R^{b2}$ and $R^{c2}$ together with the carbon atom to which they are attached form a $C_3$-$C_8$ carbocyclyl; wherein each $C_3$-$C_8$ carbocyclyl is optionally substituted with one or more $R^B$;

each $R^{5a}$, $R^{5b}$, $R^{10a}$, and $R^{10b}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{6a}$ and $R^{6b}$ is independently H, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl;

each $R^{7a}$, $R^{7b}$, $R^{7c}$, $R^{7d}$, $R^{7e}$, $R^{8a}$, $R^{8b}$, $R^{8c}$, $R^7$, and $R^8$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl; or $R^{7a}$ and $R^{8a}$ together with the nitrogen atom to which they are attached form optionally substituted 3 to 7 membered heterocyclyl; or $R^{7b}$ and $R^{8b}$ together with the nitrogen atom to which they are attached form optionally substituted 3 to 7 membered heterocyclyl; or $R^{7c}$ and $R^{8c}$ together with the nitrogen atom to which they are attached form optionally substituted 3 to 7 membered heterocyclyl; or $R^7$ and $R^8$ together with the nitrogen atom to which they are attached form optionally substituted 3 to 7 membered heterocyclyl; wherein each of $C_6$-$C_{10}$ aryl, $C_7$-$C_{14}$ aralkyl, $C_3$-$C_8$ carbocyclyl, or 3 to 7 membered heterocyclyl is optionally substituted with one or more $R^B$;

each $R^9$ is independently optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each $R^{11a}$, $R^{11b}$, $R^{11c}$, and $R^{11d}$ is independently optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each $R^A$ is independently halogen, cyano, nitro, hydroxyl, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, —$(CH_2)_t$—$NR^{7a}R^{8a}$, —$O(CH_2)_t$—$NR^{7a}R^{8a}$, —$C(O)NR^{7b}R^{8b}$, —$S(O)_2NR^{7c}R^{8c}$, —$OR^9$, —$SR^{10a}$, —$C(O)OR^{10b}$, —$C(O)R^{11a}$, —$NR^{7d}C(O)R^{11b}$, —$S(O)_2R^{11c}$, —$NR^{7e}S(O)_2R^{11d}$, $(C_1$-$C_6$ alkoxy$)C_1$-$C_6$ alkyl, —$O(C_1$-$C_6$ alkoxy$)C_1$-$C_6$ alkyl, phenyl, 5 to 10 membered heteroaryl, $C_3$-$C_8$ carbocyclyl, or 3 to 10 membered heterocyclyl, wherein each of phenyl, 5 to 10 membered heteroaryl, $C_3$-$C_8$ carbocyclyl, and 3 to 10 membered heterocyclyl is optionally substituted with one or more $R^B$;

each $R^B$ is independently $C_1$-$C_6$ alkyl, $C_1$-$C_6$ alkoxy, $C_1$-$C_6$ haloalkyl, $C_1$-$C_6$ haloalkoxy, $(C_1$-$C_6$ alkoxy$)C_1$-$C_6$ alkyl, —$O(C_1$-$C_6$ alkoxy$)C_1$-$C_6$ alkyl, halogen, or cyano; or two geminal $R^B$ form oxo;

m1, m2, m3, and m4 are each independently an integer of 0, 1, 2, 3, 4 or 5;

k is an integer of 1, 2, 3, 4, 5 or 6; and each t is independently an integer of 0, 1, 2, 3, 4, or 5.

In certain embodiments, in Formula (a), one of $R^1$ and $R^2$ is H, n is an integer of 1 or 2, $R^3$ is H, $R^4$ is H, L is —$CH_2$—$NH$—$C(=O)$—$NH$—$CH_2$— or —$CH_2$—$NH$—$C(=O)$—$NH$—*, then ring A is not

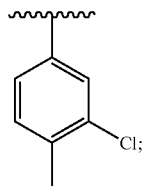

wherein the symbol "*" indicates the attachment point to ring A.

In certain embodiments, in Formula (IIb), $R^1$ is H, n is an integer of 1 or 2, $R^3$ is H, $R^4$ is H, L is —$NH$—$C(=O)$—$CH_2$—*, —$CH_2$—$NH$—$C(=O)$—$CH_2$—*, or —$CH_2$—$NH$—$C(=S)$—$NH$—*, then ring A is not

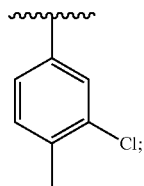

wherein the symbol "*" indicates the attachment point to ring A.

In certain embodiments, in Formula (IIb), $R^1$ is H, n is an integer of 1 or 2, $R^3$ is H, $R^4$ is H, L is —$NH$—$C(=O)$—$NH$—, —$CH_2$—$NH$—$C(=O)$—$NH$—$CH_2$—, or —$CH_2$—$NH$—$C(=O)$—$NH$—*, then ring A is

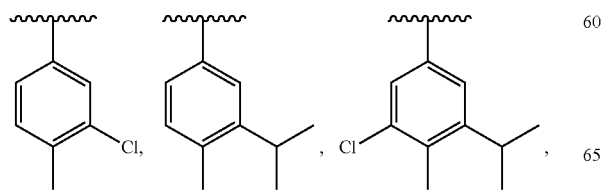

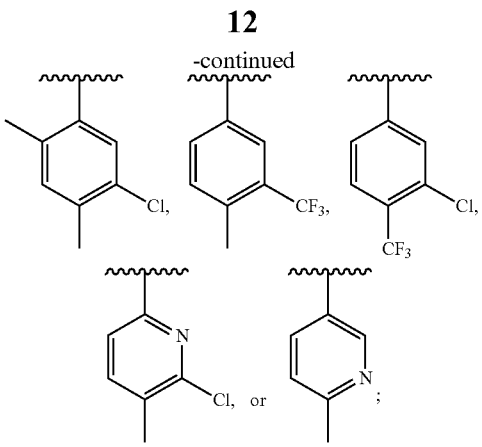

wherein the symbol "*" indicates the attachment point to ring A.

In certain embodiments, in Formula (IIc), $R^1$ is H, n is an integer of 1, $R^3$ is H, $R^4$ is H, L is —$CH_2$—$NH$—$C(=O)$—$NH$—*, then ring A is not

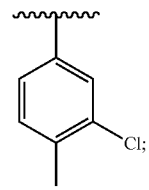 [SMILES: *c1ccc(C)c(Cl)c1]

wherein the symbol "*" indicates the attachment point to ring A.

Furthermore, provided herein is a compound of Formula (IV):

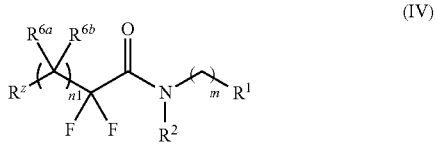

(IV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is selected from the group consisting of

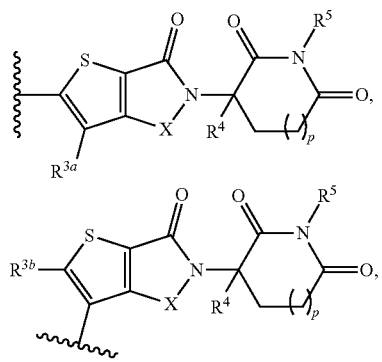

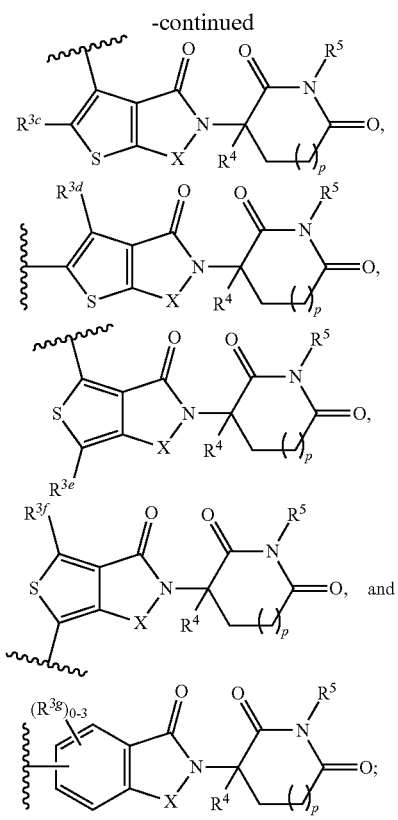

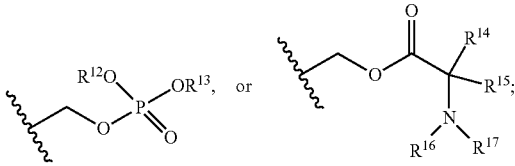

each X is independently CH$_2$ or C(=O);

R$^Z$ is —NR$^{7a}$R$^{8a}$ or ring A; and ring A is C$_6$-C$_{10}$ aryl, 5 to 10 membered heteroaryl, C$_3$-C$_8$ carbocyclyl, or 3 to 10 membered heterocyclyl, each optionally substituted with one or more R$^A$;

R$^2$ is H, deuterium, optionally substituted C$_1$-C$_6$ alkyl, optionally substituted C$_3$-C$_8$ carbocyclyl, optionally substituted C$_6$-C$_{10}$ aryl, optionally substituted 3 to 10 membered heterocyclyl, or optionally substituted 5 to 10 membered heteroaryl;

R$^{3a}$, R$^{3b}$, R$^{3c}$, R$^{3d}$, R$^{3e}$, and R$^{3f}$ are each independently H, deuterium, hydroxyl, halogen, cyano, nitro, optionally substituted C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, —(CH$_2$)$_t$—NR$^{7a}$R$^{8a}$, —O(CH$_2$)$_t$—NR$^{7a}$R$^{8a}$, —C(O)NR$^{7b}$R$^{8b}$, —S(O)$_2$NR$^{7c}$R$^{8c}$, —OR$^9$, —SR$^{10a}$, —C(O)OR$^{10b}$, —C(O)R$^{11a}$, —NR$^{7d}$C(O)R$^{11b}$, —S(O)$_2$R$^{11c}$, —NR$^{7e}$S(O)$_2$R$^{11d}$, (C$_1$-C$_6$ alkoxy)C$_1$-C$_6$ alkyl, —O(C$_1$-C$_6$ alkoxy)C$_1$-C$_6$ alkyl, optionally substituted C$_3$-C$_8$ carbocyclyl, optionally substituted C$_6$-C$_{10}$ aryl, optionally substituted 3 to 10 membered heterocyclyl, or optionally substituted 5 to 10 membered heteroaryl;

each R$^{3g}$ is independently deuterium, hydroxyl, halogen, cyano, nitro, optionally substituted C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, —(CH$_2$)$_t$—NR$^{7a}$R$^{8a}$, —O(CH$_2$)$_t$—NR$^{7a}$R$^{8a}$, —C(O)NR$^{7b}$R$^{8b}$, —S(O)$_2$NR$^{7c}$R$^{8c}$, —OR$^9$, —SR$^{10a}$, —C(O)OR$^{10b}$, —C(O)R$^{11a}$, —NR$^{7d}$C(O)R$^{11b}$, —S(O)$_2$R$^{11c}$, —NR$^{7e}$S(O)$_2$R$^{11d}$, (C$_1$-C$_6$ alkoxy)C$_1$-C$_6$ alkyl, —O(C$_1$-C$_6$ alkoxy)C$_1$-C$_6$ alkyl, optionally substituted C$_3$-C$_8$ carbocyclyl, optionally substituted C$_6$-C$_{10}$ aryl, optionally substituted 3 to 10 membered heterocyclyl, or optionally substituted 5 to 10 membered heteroaryl;

each R$^4$ is independently H, deuterium, halogen, or optionally substituted C$_1$-C$_6$ alkyl;

each R$^5$ is independently H, deuterium, C$_1$-C$_6$ alkyl, each R$^{6a}$, R$^{6b}$, R$^{6c}$, R$^{6d}$, R$^{14}$, and R$^{15}$ is independently H, substituted or unsubstituted amino, halogen, C$_1$-C$_6$ alkyl, C$_1$-C$_6$ alkoxy, C$_1$-C$_6$ haloalkyl, C$_1$-C$_6$ haloalkoxy, or C$_3$-C$_8$ carbocyclyl; or R$^{6a}$ and R$^{6b}$ together with the carbon atom to which they are attached form a C$_3$-C$_8$ carbocyclyl; or R$^{6c}$ and R$^{6d}$ together with the carbon atom to which they are attached form a C$_3$-C$_8$ carbocyclyl; wherein each C$_3$-C$_8$ carbocyclyl is optionally substituted with one or more R$^B$;

each R$^{7a}$, R$^{7b}$, R$^{7c}$, R$^{7d}$, R$^{7e}$, R$^{8a}$, R$^{8b}$, R$^{8c}$, R$^{16}$, and R$^{17}$ is independently H, optionally substituted C$_1$-C$_6$ alkyl, optionally substituted C$_6$-C$_{10}$ aryl, optionally substituted C$_7$-C$_{14}$ aralkyl, or optionally substituted C$_3$-C$_8$ carbocyclyl; or R$^{7a}$ and R$^{8a}$ together with the nitrogen atom to which they are attached form optionally substituted 3 to 7 membered heterocyclyl; or R$^{7b}$ and R$^{8b}$ together with the nitrogen atom to which they are attached form optionally substituted 3 to 7 membered heterocyclyl; or R$^{7c}$ and R$^{8c}$ together with the nitrogen atom to which they are attached form optionally substituted 3 to 7 membered heterocyclyl; or R$^{16}$ and R$^{17}$ together with the nitrogen atom to which they are attached form optionally substituted 3 to 7 membered heterocyclyl; wherein each of C$_6$-C$_{10}$ aryl, C$_7$-C$_{14}$ aralkyl, C$_3$-C$_8$ carbocyclyl, and 3 to 7 membered heterocyclyl is optionally substituted with one or more R$^B$;

each R$^9$ is independently optionally substituted C$_1$-C$_6$ alkyl, optionally substituted C$_2$-C$_6$ alkenyl, optionally substituted C$_2$-C$_6$ alkynyl, optionally substituted C$_6$-C$_{10}$ aryl, optionally substituted 5 to 10 membered heteroaryl, optionally substituted C$_7$-C$_{14}$ aralkyl, optionally substituted 3 to 10 membered heterocyclyl, or optionally substituted C$_3$-C$_8$ carbocyclyl;

each of R$^{10a}$, R$^{10b}$, R$^{12}$, and R$^{13}$ is independently H, optionally substituted C$_1$-C$_6$ alkyl, optionally substituted C$_2$-C$_6$ alkenyl, optionally substituted C$_2$-C$_6$ alkynyl, optionally substituted C$_6$-C$_{10}$ aryl, optionally substituted 5 to 10 membered heteroaryl, optionally substituted C$_7$-C$_{14}$ aralkyl, optionally substituted 3 to 10 membered heterocyclyl, or optionally substituted C$_3$-C$_8$ carbocyclyl;

each R$^{11a}$, R$^{11b}$, R$^{11c}$, and R$^{11d}$ is independently optionally substituted C$_1$-C$_6$ alkyl, optionally substituted C$_2$-C$_6$ alkenyl, optionally substituted C$_2$-C$_6$ alkynyl, optionally substituted C$_6$-C$_{10}$ aryl, optionally substituted 5 to 10 membered heteroaryl, optionally substituted C$_7$-C$_{14}$ aralkyl, optionally substituted 3 to 10 membered heterocyclyl, or optionally substituted C$_3$-C$_8$ carbocyclyl;

each R$^A$ is independently halogen, cyano, nitro, hydroxyl, optionally substituted C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ haloalkoxy, —(CH$_2$)$_t$—NR$^{7a}$R$^{8a}$, —O(CH$_2$)$_t$—NR$^{7a}$R$^{8a}$, —C(O)NR$^{7b}$R$^{8b}$, —S(O)$_2$NR$^{7c}$R$^{8c}$, —OR$^9$, —SR$^{10a}$, —C(O)OR$^{10b}$, —C(O)R$^{11a}$, —NR$^{7d}$C(O)R$^{11b}$, —S(O)$_2$R$^{11c}$, —NR$^{7e}$S(O)$_2$R$^{11d}$, (C$_1$-C$_6$ alkoxy)C$_1$-C$_6$ alkyl, —O(C$_1$-C$_6$ alkoxy)C$_1$-C$_6$ alkyl, phenyl, 5 to 10 membered heteroaryl, C$_3$-C$_8$ carbocyclyl, or 3 to 10 membered heterocyclyl, wherein each of phenyl, 5 to 10 membered heteroaryl, C$_3$-C$_8$ carbocyclyl, and 3 to 10 membered heterocyclyl is optionally substituted with one or more $R^B$;

each $R^B$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, —O($C_1$-$C_6$ alkoxy)$C_1$-$C_6$ alkyl, halogen, or cyano; or two geminal $R^B$ form oxo;

m is an integer of 0, 1, 2, 3, 4, or 5;

n1 is an integer of 0, 1, 2, or 3;

each p is independently an integer of 0, 1, or 2; and each t is independently an integer of 0, 1, 2, 3, 4, 5, 6, 7, or 8.

Provided herein is a compound of Formula (V):

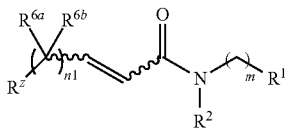

(V)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is selected from the group consisting of

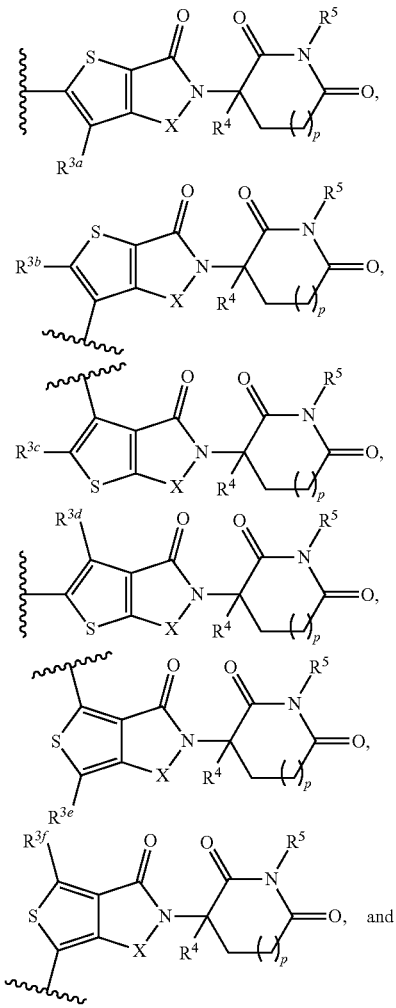

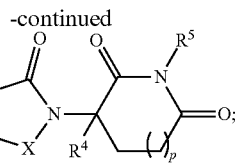

each X is independently $CH_2$ or C(=O);

$R^Z$ is —$NR^{7a}R^{8a}$ or ring A; and ring A is $C_6$-$C_{10}$ aryl, 5 to 10 membered heteroaryl, $C_3$-$C_8$ carbocyclyl, or 3 to 10 membered heterocyclyl, each optionally substituted with one or more $R^4$;

$R^2$ is H, deuterium, optionally substituted $C_1$-$C_6$ alkyl, optionally substituted $C_3$-$C_8$ carbocyclyl, optionally substituted $C_6$-$C_{10}$ aryl, optionally substituted 3 to 10 membered heterocyclyl, or optionally substituted 5 to 10 membered heteroaryl;

$R^{3a}$, $R^{3b}$, $R^{3c}$, $R^{3d}$, $R^{3e}$, and $R^{3f}$ are each independently H, deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, —($CH_2$)$_t$—$NR^{7a}R^{8a}$, —O($CH_2$)$_t$—$NR^{7a}R^{8a}$, —C(O)$NR^{7b}R^{8b}$, —S(O)$_2NR^{7c}R^{8c}$, —$OR^9$, —$SR^{10a}$, —C(O)$OR^{10b}$, —C(O)$R^{11a}$, —$NR^{7d}$C(O)$R^{11b}$, —S(O)$_2R^{11c}$, —$NR^{7e}$S(O)$_2R^{11d}$, ($C_1$-$C_6$ alkoxy)$C_1$-$C_6$ alkyl, —O($C_1$-$C_6$ alkoxy)$C_1$-$C_6$ alkyl, optionally substituted $C_3$-$C_8$ carbocyclyl, optionally substituted $C_6$-$C_{10}$ aryl, optionally substituted 3 to 10 membered heterocyclyl, or optionally substituted 5 to 10 membered heteroaryl;

each $R^{3g}$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, —($CH_2$)$_t$—$NR^{7a}R^{8a}$, —O($CH_2$)$_t$—$NR^{7a}R^{8a}$, —C(O)$NR^{7b}R^{8b}$, —S(O)$_2NR^{7c}R^{8c}$, —$OR^9$, —$SR^{10a}$, —C(O)$OR^{10b}$, —C(O)$R^{11a}$, —$NR^{7d}$C(O)$R^{11b}$, —S(O)$_2R^{11c}$, —$NR^{7e}$S(O)$_2R^{11d}$, ($C_1$-$C_6$ alkoxy)$C_1$-$C_6$ alkyl, —O($C_1$-$C_6$ alkoxy)$C_1$-$C_6$ alkyl, optionally substituted $C_3$-$C_8$ carbocyclyl, optionally substituted $C_6$-$C_{10}$ aryl, optionally substituted 3 to 10 membered heterocyclyl, or optionally substituted 5 to 10 membered heteroaryl;

each $R^4$ is independently H, deuterium, halogen, or optionally substituted $C_1$-$C_6$ alkyl;

each $R^5$ is independently H, deuterium, $C_1$-$C_6$ alkyl,

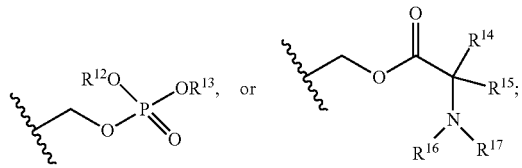

each $R^{6a}$, $R^{6b}$, $R^{6c}$, $R^{6d}$, $R^{14}$, and $R^{15}$ is independently H, substituted or unsubstituted amino, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl; or $R^{6a}$ and $R^{6b}$ together with the carbon atom to which they are attached form a $C_3$-$C_8$ carbocyclyl; or $R^{6c}$ and $R^{6d}$ together with the carbon atom to which they are attached form a $C_3$-$C_8$ carbocyclyl; wherein each $C_3$-$C_8$ carbocyclyl is optionally substituted with one or more $R^B$;

each $R^{7a}$, $R^{7b}$, $R^{7c}$, $R^{7d}$, $R^{7e}$, $R^{8a}$, $R^{8b}$, $R^{8c}$, $R^{16}$, and $R^{17}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl; or $R^{7a}$ and $R^{8a}$ together with the nitrogen atom to which they are attached form optionally substituted 3 to 7 membered heterocyclyl; or $R^{7b}$ and $R^{8b}$ together with the nitrogen atom to which they are attached form optionally substituted 3 to 7 membered heterocyclyl; or $R^{7c}$ and $R^{8c}$ together with the nitrogen atom to which they are attached form optionally substituted 3 to 7 membered heterocyclyl; or $R^{16}$ and $R^{17}$ together with the nitrogen atom to which they are attached form optionally substituted 3 to 7 membered heterocyclyl; wherein each of $C_6$-$C_{10}$ aryl, $C_7$-$C_{14}$ aralkyl, $C_3$-$C_8$ carbocyclyl, and 3 to 7 membered heterocyclyl is optionally substituted with one or more $R^B$;

each $R^9$ is independently optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{10a}$, $R^{10b}$, $R^{12}$, and $R^{13}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each $R^{11a}$, $R^{11b}$, $R^{11c}$, and $R^{11d}$ is independently optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each $R^A$ is independently halogen, cyano, nitro, hydroxyl, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, —$(CH_2)_t$—$NR^{7a}R^{8a}$, —$O(CH_2)_t$—$NR^{7a}R^{8a}$, —$C(O)NR^{7b}R^{8b}$, —$S(O)_2NR^{7c}R^{8c}$, —$OR^9$, —$SR^{10a}$, —$C(O)OR^{10b}$, —$C(O)R^{11a}$, —$NR^{7d}C(O)R^{11b}$, —$S(O)_2R^{11c}$, —$NR^{7e}S(O)_2R^{11d}$, $(C_1$-$C_6$ alkoxy)$C_1$-$C_6$ alkyl, —$O(C_1$-$C_6$ alkoxy)$C_1$-$C_6$ alkyl, phenyl, 5 to 10 membered heteroaryl, $C_3$-$C_8$ carbocyclyl, or 3 to 10 membered heterocyclyl, wherein each of phenyl, 5 to 10 membered heteroaryl, $C_3$-$C_8$ carbocyclyl, and 3 to 10 membered heterocyclyl is optionally substituted with one or more $R^B$;

each $R^B$ is independently $C_1$-$C_6$ alkyl, $C_1$-$C_6$ alkoxy, $C_1$-$C_6$ haloalkyl, $C_1$-$C_6$ haloalkoxy, $(C_1$-$C_6$ alkoxy)$C_1$-$C_6$ alkyl, —$O(C_1$-$C_6$ alkoxy)$C_1$-$C_6$ alkyl, halogen, or cyano; or two geminal $R^B$ form oxo;

m is an integer of 0, 1, 2, 3, 4, or 5;

n1 is an integer of 0, 1, 2, or 3;

each p is independently an integer of 0, 1, or 2; and each t is independently an integer of 0, 1, 2, 3, 4, 5, 6, 7, or 8.

Provided herein is a pharmaceutical composition comprising a compound provided herein, e.g., a compound of Formula (I), (IIa), (IIb), (IIc), (III), (IV), or (V), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

Provided herein is a method of treating, ameliorating, or preventing a disease, disorder, or condition associated with a protein in a subject, comprising administering to the subject a therapeutically effective amount of a compound provided herein, e.g., a compound of Formula (I), (IIa), (IIb), (IIc), (III), (IV), or (V), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In one embodiment, the protein is cytokine, aiolos, ikaros, helios, CK1α, or GSPT1. In another embodiment, the protein is IL-1β, IL-6, TNFα, or IL-2.

In one embodiment, the disease, disorder, or condition is inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, or cancer. In another embodiment, the disease, disorder, or condition is cancer.

Provided herein is a method of modulating protein activity in a cell, comprising contacting the cell with a compound provided herein, e.g., a compound of Formula (I), (IIa), (IIb), (IIc), (III), (IV), or (V)), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In one embodiment, the protein is a cytokine, aiolos, ikaros, helios, CK1α, or GSPT1. In another embodiment, the protein is IL-1β, IL-6, TNFα, or IL-2. In one embodiment, the method is to inhibit protein activity. In another embodiment, the method is to stimulate or activate protein activity.

DETAILED DESCRIPTION

The section headings used herein are for organizational purposes only and are not to be construed as limiting the subject matter described.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques, and pharmacology are employed. The use of "or" or "and" means "and/or" unless stated otherwise. Furthermore, use of the term "including" as well as other forms, such as "include", "includes," and "included," is not limiting.

Unless otherwise defined, all terms (including technical and scientific terms) are to be given their ordinary and customary meaning to a person of ordinary skill in the art and are not to be limited to a special or customized meaning unless expressly so defined herein. It should be noted that the use of a particular terminology when describing certain features or aspects of the disclosure should not be taken to imply that the terminology is being re-defined herein to be restricted to include any specific characteristics of the features or aspects of the disclosure with which that terminology is associated.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The terms "effective amount" and "therapeutically effective amount" are to be given their ordinary and customary meaning to a person of ordinary skill in the art and refer without limitation to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease symptom. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" optionally refers to the dosage approved by the FDA or its counterpart foreign agency for treatment of the identified disease or condition.

As used herein, any "R" group(s) represent substituents that can be attached to the indicated atom. If two "R" groups are described as being "taken together," the R groups and the atoms they are attached to can form a cycloalkyl, aryl, heteroaryl, or heterocycle. For example, without limitation, if $R^a$ and $R^b$, and the atom to which it is attached, are indicated to be "taken together" or "joined together," it means that they are covalently bonded to one another to form a ring:

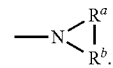

Whenever a group is described as being "optionally substituted," that group may be unsubstituted or substituted with one or more of the indicated substituents. Likewise, when a group is described as being "substituted," the substituent may be selected from one or more of the indicated substituents. If no substituents are indicated, it is meant that the indicated "optionally substituted" or "substituted" group may be one or more group(s) individually and independently selected from alkyl (e.g., $C_1$-$C_6$ alkyl); alkenyl (e.g., $C_2$-$C_6$ alkenyl); alkynyl (e.g., $C_2$-$C_6$ alkynyl); $C_3$-$C_8$ carbocyclyl (e.g., $C_3$-$C_8$ cycloalkyl, $C_3$-$C_8$ cycloalkenyl, or $C_3$-$C_8$ cycloalkynyl, each further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); ($C_3$-$C_7$ carbocyclyl)$C_1$-$C_6$ alkyl (further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); 5-10 membered heterocyclyl (further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (5-10 membered heterocyclyl)$C_1$-$C_6$ alkyl (further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy) $C_1$-$C_6$ alkyl, or —O($C_1$-$C_6$ alkoxy)$C_1$-$C_6$ alkyl); aryl (further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (aryl)$C_1$-$C_6$ alkyl (further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); 5-10 membered heteroaryl (further optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy) $C_1$-$C_6$ alkyl, or —O($C_1$-$C_6$ alkoxy)$C_1$-$C_6$ alkyl); (5-10 membered heteroaryl)$C_1$-$C_6$ alkyl (further optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); halo (e.g., fluoro, chloro, bromo, or iodo); cyano; hydroxy; protected hydroxy; alkoxy (e.g., $C_1$-$C_6$ alkoxy); haloalkyl (e.g., $C_1$-$C_6$ haloalkyl, such as —$CF_3$); haloalkyl (e.g., $C_1$-$C_6$ haloalkoxy, such as —$OCF_3$); ($C_1$-$C_6$ alkoxy)$C_1$-$C_6$ alkyl; —O($C_1$-$C_6$ alkoxy) $C_1$-$C_6$ alkyl; ($C_1$-$C_6$ haloalkoxy)$C_1$-$C_6$ alkyl; —O($C_1$-$C_6$ haloalkoxy)$C_1$-$C_6$ alkyl; aryloxy; sulfhydryl (mercapto);

alkylthio (e.g., $C_1$-$C_6$ alkylthio); arylthio; azido; nitro; O-carbamyl; N-carbamyl; O-thiocarbamyl; N-thiocarbamyl; C-amido; N-amido; S-sulfonamido; N-sulfonamido; C-carboxy; protected C-carboxy; O-carboxy; acyl; cyanate; isocyanato; thiocyanato; isothiocyanato; silyl; sulfenyl; sulfinyl; sulfonyl; trihalomethanesulfonyl; trihalomethanesulfonamido; amino (including protected derivatives thereof); mono-substituted amino (for example, NH($C_1$-$C_6$ alkyl); di-substituted amino (for example, N($C_1$-$C_6$ alkyl)$_2$); oxo (=O); and thioxo (=S).

As used herein, "$C_a$ to $C_b$" in which "a" and "b" are integers refer to the number of carbon atoms in an alkyl, alkenyl, or alkynyl group, or the number of carbon atoms in the ring of a cycloalkyl, cycloalkenyl, cycloalkynyl, aryl, heteroaryl, or heterocyclyl group. That is, the alkyl, alkenyl, alkynyl, ring of the cycloalkyl, ring of the cycloalkenyl, ring of the cycloalkynyl, ring of the aryl, ring of the heteroaryl, or ring of the heterocyclyl can contain from "a" to "b," inclusive, carbon atoms. Thus, for example, a "$C_1$ to $C_4$ alkyl" group refers to all alkyl groups having from 1 to 4 carbons, that is, —$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, and —C($CH_3$)$_3$. If no "a" and "b" are designated with regard to an alkyl, alkenyl, alkynyl, cycloalkyl cycloalkenyl, cycloalkynyl, aryl, heteroaryl or heterocyclyl group, the broadest range described in these definitions is to be assumed. As used herein, the term "$C_1$-$C_6$" includes $C_1$, $C_2$, $C_3$, $C_4$, $C_5$, and $C_6$, and a range defined by any of the two numbers. For example, $C_1$-$C_6$ alkyl includes $C_1$, $C_2$, $C_3$, $C_4$, $C_5$, and $C_6$ alkyl, $C_2$-$C_6$ alkyl, $C_1$-$C_3$ alkyl, etc. Similarly, $C_3$-$C_8$ carbocyclyl or cycloalkyl each include a hydrocarbon ring containing 3, 4, 5, 6, 7, or 8 carbon atoms, or a range defined by any of the two numbers, such as $C_3$-$C_7$ cycloalkyl or $C_1$-$C_6$ cycloalkyl.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl." By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, n-propyl, isopropyl, butyl, isobutyl, tertiary butyl, pentyl (straight chain or branched), and hexyl (straight chain or branched). The alkyl group may be substituted or unsubstituted.

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, and 2-butenyl. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, and 2-butynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged, or spiro fashion. As used herein, the term "fused" refers to two rings which have two atoms and one bond in common. As used herein, the term "bridged cycloalkyl" refers to a cycloalkyl that contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s), or 3 to 6 atoms in the ring(s). A cycloalkyl group may be unsubstituted or substituted. Examples of monocycloalkyl groups include, but are in no way limited to, cyclopropyl, cyclobutyl, cyclopentyl, cyclohexyl, cycloheptyl, and cyclooctyl. Examples of fused cycloalkyl groups are decahydronaphthalenyl, dodecahydro-1H-phenalenyl, and tetradecahydroanthracenyl. Examples of bridged cycloalkyl groups are bicyclo[1.1.1]pentyl, adamantanyl and norbornenyl. Examples of spiro cycloalkyl groups include spiro[3.3]heptyl and spiro[4.5]decanyl.

As used herein, "carbocyclyl" refers to a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s), or 3 to 6 atoms in the ring(s). A carbocyclyl group may be unsubstituted or substituted. Multicyclic carbocyclyl groups can include, for example, a non-aromatic hydrocarbon ring fused to an aromatic hydrocarbon ring. Examples of carbocyclyl groups include, but are in no way limited to, cycloalkyl groups and cycloalkenyl groups, as defined herein, as well as 1,2,3,4-tetrahydronaphthalyl, 2,3-dihydro-1H-indenyl, 5,6,7,8-tetrahydroquinolinyl, and 6,7-dihydro-5H-cyclopenta[b]pyridyl.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, phenyl, naphthyl, and azulenyl. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furanyl, furazanyl, thienyl, benzothienyl, phthalazinyl, pyrrolyl, oxazolyl, benzoxazolyl, 1,2,3-oxadiazolyl, 1,2,4-oxadiazolyl, thiazolyl, 1,2,3-thiadiazolyl, 1,2,4-thiadiazolyl, benzothiazolyl, imidazolyl, benzimidazolyl, indolyl, indazolyl, pyrazolyl, benzopyrazolyl, isoxazolyl, benzoisoxazolyl, isothiazolyl, triazolyl, benzotriazolyl, thiadiazolyl, tetrazolyl, pyridinyl, pyridazinyl, pyrimidinyl, pyrazinyl, purinyl, pteridinyl, quinolinyl, isoquinolinyl, quinazolinyl, quinoxalinyl, cinnolinyl, and triazinyl. A heteroaryl group may be substituted or unsubstituted.

As used herein, "heterocyclyl" refers to three-, four-, five-, six-, seven-, eight-, nine-, ten-, up to 18-membered monocyclic, bicyclic and tricyclic ring system, wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., the ring system is not aromatic). The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, and cyclic carbamates. When composed of two or more rings, the rings may be joined together in a fused, bridged, or spiro fashion. As used herein, the term "fused" refers to two rings which have two atoms and one bond in common. As used herein, the term "bridged heterocyclyl" refers to a heterocyclyl containing a linkage of one or more atoms connecting non-adjacent atoms. As used herein, the term "spiro" refers to two rings which have one atom in common and the two rings are not linked by a bridge. Heterocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include, but are not limited to, aziridinyl, oxiranyl, thiiranyl, azetidinyl, oxetanyl, 1,3-dioxinyl, 1,3-dioxanyl, 1,4-dioxanyl, 1,2-dioxolanyl, 1,3-dioxolanyl, 1,4-dioxolanyl, 1,3-oxathianyl, 1,4-oxathiinyl, 1,3-oxathiolanyl, 1,3-dithiolyl, 1,3-dithiolanyl, 1,4-oxathianyl, tetrahydro-1,4-thiazinyl, 2H-1,2-oxazinyl, maleimidyl, succinimidyl, barbituryl, thiobarbituryl, dioxopiperazinyl, hydantoinyl, dihydrouracyl, trioxanyl, hexahydro-1,3,5-triazinyl, imidazolinyl, imidazolidinyl, isoxazolinyl, isoxazolidinyl, oxazolinyl, oxazolidinyl, oxazolidinonyl, thiazolinyl, thiazolidinyl, morpholinyl, oxiranyl, N-oxopiperidinyl, piperidinyl, piperazinyl, pyrrolidinyl, azepanyl, pyrrolidinyl, pyrrolidionyl, 4-piperidonyl, pyrazolinyl, pyrazolidinyl, 2-oxopyrrolidinyl, tetrahydropyranyl, 4H-pyranyl, tetrahydrothiopyranyl, thiamorpholinyl, dioxothiomorpholinyl, oxothiomorpholinyl, benzimidazolidinonyl, tetrahydroquinolinyl, and 3,4-methylenedioxyphenyl. Examples of spiro heterocyclyl groups include, but are not limited to, 2-azaspiro[3.3]heptanyl, 2-oxaspiro[3.3]heptanyl, 2-oxa-6-azaspiro[3.3]heptanyl, 2,6-diazaspiro[3.3]heptanyl, 2-oxaspiro[3.4]octanyl, and 2-azaspiro[3.4]octanyl.

"Lower alkylene groups" are straight-chained —$CH_2$— tethering groups, forming bonds to connect molecular fragments via their terminal carbon atoms. Lower alkylene groups contain from 1 to 6 carbon atoms. Examples include, but are not limited to, methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "aralkyl" and "(aryl)alkyl" refer to an aryl group, as defined above, connected, as a substituent, via a lower alkylene group, as described above. The lower alkylene and aryl group of an aralkyl may be substituted or unsubstituted. Examples include, but are not limited to, benzyl, 2-phenylalkyl, 3-phenylalkyl, and naphthylalkyl.

As used herein, "heteroaralkyl" and "(heteroaryl)alkyl" refer to a heteroaryl group, as defined above, connected, as a substituent, via a lower alkylene group, as defined above. The lower alkylene and heteroaryl group of heteroaralkyl may be substituted or unsubstituted. Examples include, but are not limited to, 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heterocyclyl)alkyl" is a heterocyclic or a heterocyclyl group, as defined above, connected, as a substituent, via a lower alkylene group, as defined above. The lower alkylene and heterocyclyl groups of a (heterocyclyl)alkyl may be substituted or unsubstituted. Examples include, but are not limited to, (tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

As used herein, "alkoxy" refers to the formula —OR, wherein R is an alkyl, an alkenyl, an alkynyl, a cycloalkyl, a cycloalkenyl or a cycloalkynyl, as defined above. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "acyl" refers to a hydrogen, alkyl, alkenyl, alkynyl, or aryl, as defined above, connected, as substituents, via a carbonyl group. Examples include, but are not limited to, formyl, acetyl, propanoyl, benzoyl, and acryl.

As used herein, "hydroxyalkyl" refers to an alkyl group in which one or more of the hydrogen atoms are replaced by a hydroxy group. Exemplary hydroxyalkyl groups include, but are not limited to, 2-hydroxyethyl, 3-hydroxypropyl, 2-hydroxypropyl, and 2,2-dihydroxyethyl.

As used herein, "haloalkyl" refers to an alkyl group in which one or more of the hydrogen atoms are replaced by a halogen (e.g., mono-haloalkyl, di-haloalkyl, and tri-haloalkyl). Such groups include, but are not limited to, chloromethyl, fluoromethyl, difluoromethyl, trifluoromethyl, 1-chloro-2-fluoromethyl, and 2-fluoroisobutyl.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include, but are not limited to, chloromethoxy, fluoromethoxy, difluoromethoxy, trifluoromethoxy, 1-chloro-2-fluoromethoxy, and 2-fluoroisobutoxy. A haloalkoxy may be substituted or unsubstituted.

As used herein, "aryloxy" and "arylthio" refers to RO— and RS—, respectively, in which R is an aryl, as defined above, such as phenyl. Both an aryloxy and arylthio may be substituted or unsubstituted.

A "sulfenyl" group refers to an "—SR" group in which R can be hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein X is a halogen.

A "trihalomethanesulfonamido" group refers to an "X$_3$CS(O)$_2$N(R)—" group wherein X is a halogen and R is hydrogen, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, $C_3$-$C_7$ cycloalkynyl, aryl, 5 to 10 membered heteroaryl, 5 to 10 membered heterocyclyl, aralkyl, or (5 to 10 membered heterocyclyl)alkyl.

An "alkoxyalkyl" or "(alkoxy)alkyl" group refers to an alkoxy group connected via an lower alkylene group, such as $C_2$-$C_8$ alkoxyalkyl, or ($C_1$-$C_6$ alkoxy)$C_1$-$C_6$ alkyl, for example, —(CH$_2$)$_{1-3}$—OCH$_3$.

An "—O-alkoxyalkyl" or "—O-(alkoxy)alkyl" group refers to an alkoxy group connected via an —O-(lower alkylene) group, such as —O—($C_1$-$C_6$ alkoxy)$C_1$-$C_6$ alkyl, for example, —O(CH$_2$)$_{1-3}$—OCH$_3$.

The terms "amino" and "unsubstituted amino" as used herein refer to a —NH$_2$ group. The term "mono-substituted amino group" as used herein refers to an amino (—NH$_2$) group where one of the hydrogen atom is replaced by a substituent. The term "di-substituted amino group" as used herein refers to an amino (—NH$_2$) group where each of the two hydrogen atoms is replaced by a substituent. In one embodiment, the substituent may be independently $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, $C_3$-$C_7$ cycloalkynyl, aryl, 5 to 10 membered heteroaryl, 5 to 10 membered heterocyclyl, aralkyl, or (5 to 10 membered heterocyclyl)alkyl, as defined herein.

As used herein, the term "hydroxy" refers to a —OH group.

The term "cyano" refers to a —CN group.

The term "azido" as used herein refers to a —N$_3$ group.

The term "isocyanato" refers to an —NCO group.

The term "thiocyanato" refers to a —CNS group.

The term "isothiocyanato" refers to an —NCS group.

The term "mercapto" refers to an —SH group.

The term "S-sulfonamido" refers to an —SO$_2$N(R$_2$) group in which each R is independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. An S-sulfonamido may be substituted or unsubstituted.

The term "N-sulfonamido" group refers to an RSO$_2$N(R)— group in which each R is independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. An N-sulfonamido may be substituted or unsubstituted.

The term "O-carbamyl" refers to an —OC(=O)N(R$_2$) group in which each R is independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. An O-carbamyl may be substituted or unsubstituted.

The term "N-carbamyl" refers to an ROC(=O)N(R)— group in which each R is independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. An N-carbamyl may be substituted or unsubstituted.

The term "O-thiocarbamyl" refers to an —OC(=S)—N(R$_2$) group in which each R is independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. An O-thiocarbamyl may be substituted or unsubstituted.

The term "N-thiocarbamyl" refers to an ROC(=S)N(R)— group in which each R is independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. An N-thiocarbamyl may be substituted or unsubstituted.

The term "C-amido" refers to a —C(=O)N(R$_2$) group in which each R is independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. A C-amido may be substituted or unsubstituted.

The term "N-amido" refers to an RC(=O)N(R)— group in which each R is independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. An N-amido may be substituted or unsubstituted.

The term "urea" refers to an —N(R$_2$)—C(=O)—N(R$_2$)— group in which each R is independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. A urea group may be substituted or unsubstituted.

The term "thiourea" refers to an —N(R$_2$)—C(=S)—N(R$_2$)— group in which each R is independently hydrogen, alkyl, alkenyl, alkynyl, cycloalkyl, cycloalkenyl, cycloalkynyl, aryl, heteroaryl, heterocyclyl, aralkyl, or heterocyclyl(alkyl), as defined above. A thiourea group may be substituted or unsubstituted.

The term "halogen atom" or "halogen" as used herein means any one of the radio-stable atoms of column 7 of the Periodic Table of the Elements, such as, fluorine, chlorine, bromine, and iodine.

Where the numbers of substituents are not specified (e.g., haloalkyl), there may be one or more substituents present. For example, "haloalkyl" may include one or more of the same or different halogens. As another example, "$C_1$-$C_3$ alkoxyphenyl" may include one or more of the same or different alkoxy groups containing one, two, or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The term "pharmaceutically acceptable salt" as used herein is to be given its ordinary and customary meaning to a person of ordinary skill in the art and refers without limitation to a salt of a compound that does not cause significant irritation to an organism to which it is administered and does not abrogate the biological activity and properties of the compound. In certain embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example, formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluenesulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl)amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, or sodium hydroxide.

The term "solvate" as used herein is to be given its ordinary and customary meaning to a person of ordinary skill in the art and refers without limitation to mean that the solvent is complexed with a compound in a reproducible molar ratio, including, but not limited to, 0.5:1, 1:1, or 2:1. Thus, the term "pharmaceutically acceptable solvate" refers to a solvate wherein the solvent is one that does not cause significant irritation to an organism to which it is administered and does not abrogate the biological activity and properties of the compound.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition, it is understood that, in any compound described herein having one or more double bond(s) generating geometrical isomers that can be defined as E or Z, each double bond may independently be E or Z, or a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

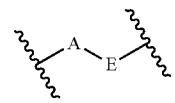

includes the substituent being oriented such that the A is attached at the leftmost attachment point of the molecule as well as the case in which A is attached at the rightmost attachment point of the molecule.

It is to be understood that, where compounds disclosed herein have unfilled valencies, the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including, but not limited to, hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In certain embodiments, the compounds described herein exist in solvated forms with pharmaceutically acceptable solvents such as water or ethanol. In certain embodiments, the compounds described herein exist in unsolvated form. Solvates contain either stoichiometric or non-stoichiometric amounts of a solvent and may be formed during the process of crystallization with pharmaceutically acceptable solvents such as water or ethanol. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms, and nano-particulate forms.

Likewise, it is understood that the compounds described herein, such as compounds of preferred embodiments, include the compound in any of the forms described herein (e.g., pharmaceutically acceptable salts, crystalline forms, amorphous form, solvated forms, enantiomeric forms, and tautomeric forms).

Compounds of Formulae (I) and (III)

In one embodiment, provided herein is a compound of Formula (I):

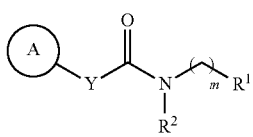
(I)

or a pharmaceutically acceptable salt or solvate thereof, wherein ring A, $R^1$, $R^2$, Y, and m are each as described herein.

In certain embodiments, X is $CH_2$. In certain embodiments, X is C(=O).

In one embodiment, the compound of Formula (I) has the structure of:

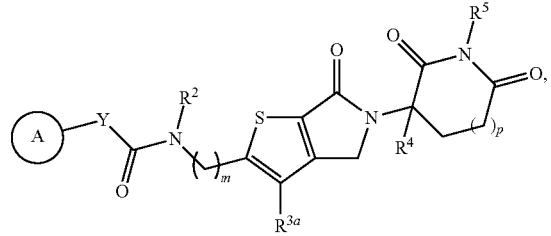
(Ia)

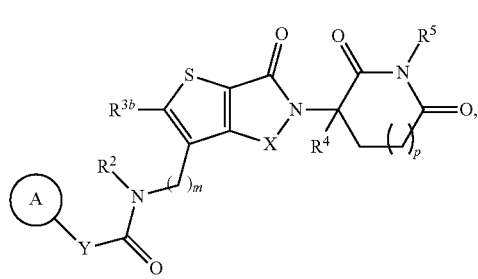
(Ib)

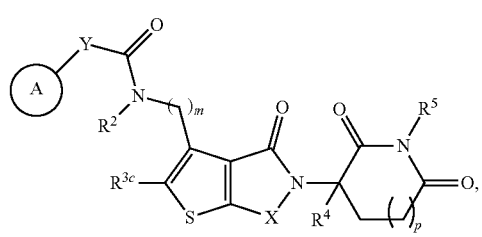
(Ic)

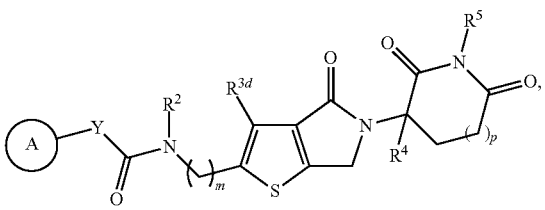
(Id)

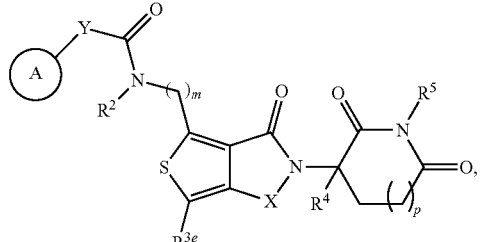
(Ie)

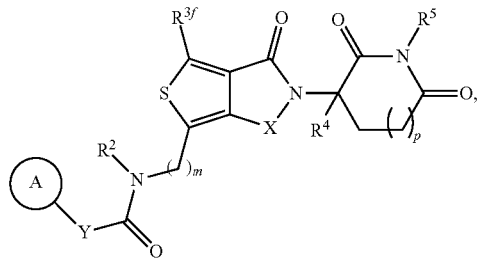
(If)

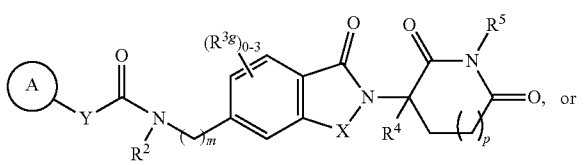
(Ig)

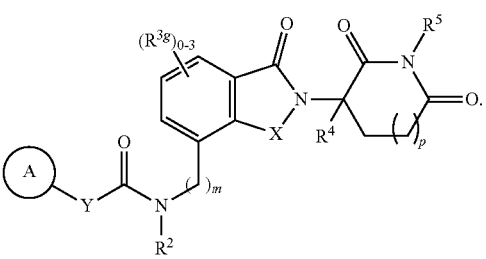
(Ih)

In certain embodiments, in any one of Formulae (I) and (Ia) to (Ih), p is an integer of 1. In certain embodiments, in any one of Formulae (I) and (Ia) to (Ih), p is an integer of 2. In certain embodiments, in any one of Formulae (I) and (Ia) to (Ih), p is an integer of 0. In certain embodiments, in any one of Formulae (I) and (Ia) to (Ih), p is an integer of 1 or 2.

In certain embodiments, in any one of Formulae (I) and (Ia) to (If), each of $R^{3a}$, $R^{3b}$, $R^{3c}$, $R^{3d}$, $R^{3e}$, and $R^{3f}$ is hydrogen. In certain embodiments, in Formula (I), (Ig), or (Ih), the corresponding

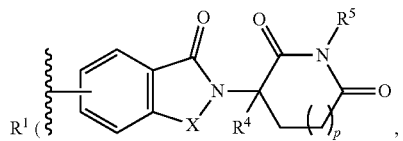

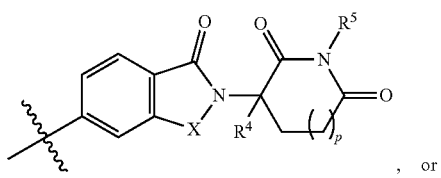, or

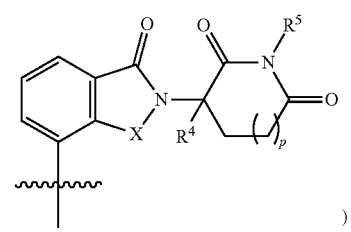)

is unsubstituted (i.e., —(R$^{3g}$)$_0$) or substituted with one R$^{3g}$ (i.e., —(R$^{3g}$)$_1$). In certain embodiments, in Formula (I), (Ig), or (Ih), R$^{3g}$ is halo, C$_1$-C$_6$ alkyl, or C$_1$-C$_6$ haloalkyl, for example, fluoro, methyl, or trifluoromethyl. In certain embodiments, in Formula (I), (Ig), or (Ih), the corresponding R$^1$ is substituted with two R$^{3g}$ (i.e., —(R$^{3g}$)$_2$). In certain embodiments, in Formula (I), (Ig), or (Ih), R$^{3g}$ is halo, C$_1$-C$_6$ alkyl, or C$_1$-C$_6$ haloalkyl. In certain embodiments, in Formula (I), (Ig), or (Ih), R$^{3g}$ is fluoro or methyl. In certain embodiments, in Formula (I), (Ig), or (Ih), R$^{3g}$ is fluoro. In certain embodiments, in Formula (I), (Ig), or (Ih), R$^{3g}$ is methyl.

In certain embodiments, R$^1$ is

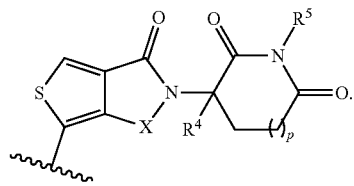

In certain embodiments, R$^1$ is

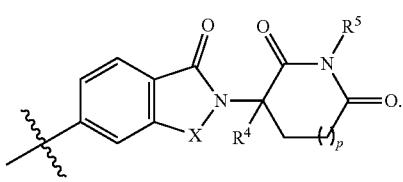

optionally substituted with one R$^{3g}$. In certain embodiments, R$^1$ is wherein R$^1$ is

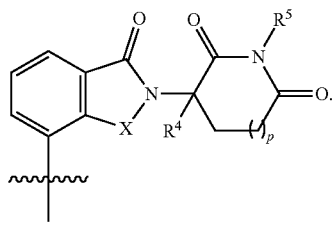

optionally substituted with one R$^{3g}$.

In certain embodiments, in anyone of Formulae (I) and (Ia) to (Ih), R$^4$ is H. In certain embodiments, in any one of Formulae (I) and (Ia) to (Ih), R$^4$ is methyl.

In certain embodiments, in anyone of Formulae (I) and (Ia) to (Ih), R$^5$ is H. In certain embodiments, in any one of Formulae (I) and (Ia) to (Ih), R$^5$ is C$_1$-C$_6$ alkyl, for example, methyl, ethyl, or isopropyl. In certain embodiments, in any one of Formulae (I) and (Ia) to (Ih), R$^5$ is

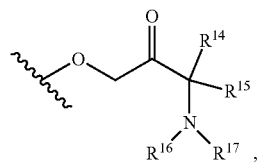

wherein R$^{14}$, R$^{15}$, R$^{16}$, and R$^{17}$ are each independently H or C$_1$-C$_6$ alkyl. In one embodiment, in any one of Formulae (I) and (Ia) to (Ih), R$^5$ is

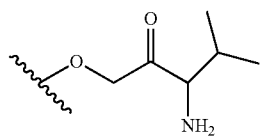 [SMILES: *OCC(=O)C(N)C(C)C]

(i.e., valyloxymethyl). In another embodiment, in any one of Formulae (I) and (Ia) to (Ih), R$^5$ is

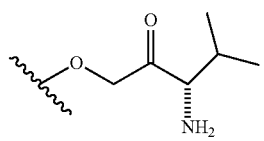 [SMILES: *OCC(=O)[C@@H](N)C(C)C]

(i.e., L-valyloxymethyl). In yet another embodiment, in any one of Formulae (I) and (Ia) to (Ih), R$^5$ is

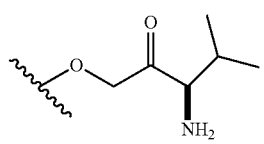 [SMILES: *OCC(=O)[C@H](N)C(C)C]

(i.e., D-valyloxymethyl). In certain embodiments, in any one of Formulae (I) and (Ia) to (Ih), R$^5$ is

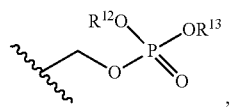

where $R^{12}$ and $R^{13}$ are each independently H or $C_1$-$C_6$ alkyl. In one embodiment, in any one of Formulae (I) and (Ia) to (Ih), $R^5$ is

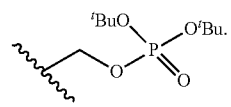

In certain embodiments, in any one of Formulae (I) and (Ia) to (Ih), $R^2$ is H. In certain embodiments, in any one of Formulae (I) and (Ia) to (Ih), $R^2$ is $C_1$-$C_6$ alkyl, for example, methyl, ethyl, or isopropyl. In certain embodiments, in any one of Formulae (I) and (Ia) to (Ih), $R^2$ is methyl. In certain embodiments, in any one of Formulae (I) and (Ia) to (Ih), $R^2$ is H or methyl.

In certain embodiments, in any one of Formulae (I) and (Ia) to (Ih), Y is C(=O). In certain embodiments, in any one of Formulae (I) and (Ia) to (Ih), Y is C(=O)—(CR$^{6a}$R$^{6b}$)$_{n1}$, wherein each $R^{6a}$, $R^{6b}$, and n1 is as defined herein. In certain embodiments, in any one of Formulae (I) and (a) to (Ih), Y is C(=O)—(CH$_2$) or C(=O)—(CH$_2$)$_2$. In certain embodiments, in any one of Formulae (I) and (a) to (Ih), Y is C(=O), C(=O)—(CH$_2$), or C(=O)—(CH$_2$)$_2$.

In certain embodiments, in any one of Formulae (I) and (Ia) to (Ih), ring A is phenyl, unsubstituted or substituted with one or more $R^A$. In certain embodiments, in any one of Formulae (I) and (Ia) to (Ih), ring A is 5, 6, 9, or 10 membered heteroaryl containing 1, 2, or 3 heteroatoms selected from the group consisting of N, O, and S, for example, ring A is pyridyl, thienyl, furyl, pyrimidinyl, pyrazolyl, imidazolyl, thiazolyl, isothiazolyl, oxazolyl, isoxazolyl, or thiadiazolyl, each independently unsubstituted or substituted with one or more $R^A$. In one embodiment, in any one of Formulae (I) and (Ia) to (Ih), ring A is thienyl, unsubstituted or substituted with one or more $R^A$. In certain embodiments, in any one of Formulae (I) and (Ia) to (Ih), ring A is $C_3$-$C_7$ carbocyclyl, for example, cyclopentyl or cyclohexyl, each independently unsubstituted or substituted with one or more $R^A$. In certain embodiments, in any one of Formulae (I) and (Ia) to (Ih), ring A is 5, 6, 9, or 10 membered heterocyclyl containing 1, 2, or 3 heteroatoms selected from the group consisting of N, O, and S, for example, ring A is

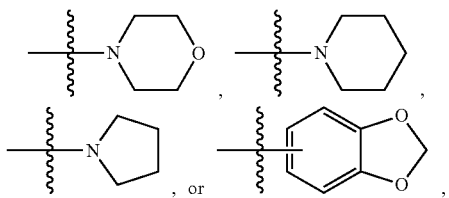

each optionally substituted with one or more $R^A$. In certain embodiments, in any one of Formulae (I) and (Ia) to (Ih), ring A is substituted with one, two, or three $R^A$. In certain embodiments, in any one of Formulae (I) and (Ia) to (Ih), ring A is unsubstituted.

In certain embodiments, in anyone of Formulae (I) and (Ia) to (Ih), ring A is $C_6$-$C_{10}$ aryl, 5 to 10 membered heteroaryl, $C_3$-$C_8$ carbocyclyl, or 3 to 10 membered heterocyclyl, each of which is optionally substituted with one, two, or three substituents $R^A$; wherein each substituent $R^A$ is independently (i) halogen, cyano, hydroxyl, $C_1$-$C_6$ alkyl, $C_1$-$C_6$ alkoxy, $C_1$-$C_6$ haloalkyl, —(CH$_2$)$_t$—NR$^{7a}$R$^{8a}$, or —NR$^{7d}$C(O)R$^{11b}$, or (ii) phenyl, $C_3$-$C_8$ carbocyclyl, or 3 to 10 membered heterocyclyl, each of which is optionally substituted with one or more $R^B$.

In certain embodiments, in anyone of Formulae (I) and (Ia) to (Ih), ring A is $C_6$-$C_{10}$ aryl, optionally substituted with one, two, or three substituents $R^A$; wherein each substituent $R^A$ is independently (i) halogen, cyano, hydroxyl, $C_1$-$C_6$ alkyl, $C_1$-$C_6$ alkoxy, $C_1$-$C_6$ haloalkyl, —(CH$_2$)$_t$—NR$^{7a}$R$^{8a}$, or —NR$^{7d}$C(O)R$^{11b}$, or (ii) phenyl, $C_3$-$C_8$ carbocyclyl, or 3 to 10 membered heterocyclyl, each of which is optionally substituted with one or more $R^B$.

In certain embodiments, in anyone of Formulae (I) and (Ia) to (Ih), ring A is phenyl, naphthyl, thienyl, pyridyl, piperidinyl, or cyclohexyl, each of which is optionally substituted with one, two, or three substituents $R^A$; wherein each substituent $R^A$ is independently (i) halogen, cyano, hydroxyl, $C_1$-$C_6$ alkyl, $C_1$-$C_6$ alkoxy, $C_1$-$C_6$ haloalkyl, —(CH$_2$)$_t$—NR$^{7a}$R$^{8a}$, or —NR$^{7d}$C(O)R$^{11b}$, or (ii) phenyl, $C_3$-$C_8$ carbocyclyl, or 3 to 10 membered heterocyclyl, each of which is optionally substituted with one or more $R^B$.

In certain embodiments, in any one of Formulae (I) and (Ia) to (Ih), ring A is phenyl, optionally substituted with one, two, or three substituents $R^A$; wherein each substituent $R^A$ is independently (i) halogen, cyano, hydroxyl, $C_1$-$C_6$ alkyl, $C_1$-$C_6$ alkoxy, $C_1$-$C_6$ haloalkyl, —(CH$_2$)$_t$—NR$^{7a}$R$^{8a}$, or —NR$^{7d}$C(O)R$^{11b}$, or (ii) phenyl, $C_3$-$C_8$ carbocyclyl, or 3 to 10 membered heterocyclyl, each of which is optionally substituted with one or more $R^B$.

In certain embodiments, in any one of Formulae (I) and (Ia) to (Ih), ring A is phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, propyl, butyl, hydroxyl-butyl, cyclopropyl, methylcyclopropyl, trifluoromethyl-cyclopropyl, phenyl, methyl-piperidinyl, hydroxyl, methoxy, dimethylamino, or acetamido.

In certain embodiments, in any one of Formulae (I) and (Ia) to (Ih), ring A is phenyl, optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, propyl, butyl, hydroxyl-butyl, cyclopropyl, methylcyclopropyl, trifluoromethyl-cyclopropyl, phenyl, methyl-piperidinyl, hydroxyl, methoxy, dimethylamino, or acetamido.

In certain embodiments, in any one of Formulae (I) and (Ia) to (Ih), ring A is phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, isopropyl, sec-butyl, tert-butyl, (hydroxyl-tert-butyl), cyclopropyl, methylcyclopropyl, trifluoromethyl-cyclopropyl, phenyl, methyl-piperidinyl, hydroxyl, methoxy, dimethylamino, or acetamido.

In certain embodiments, in any one of Formulae (I) and (Ia) to (Ih), ring A is phenyl, optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, isopropyl, sec-butyl, tert-butyl, (hydroxyl-tert-butyl), cyclopropyl, methylcyclopropyl, trifluoromethyl-cyclopropyl, phenyl, methyl-piperidinyl, hydroxyl, methoxy, dimethylamino, or acetamido.

In certain embodiments, in any one of Formulae (I) and (Ia) to (Ih), ring A is phenyl, cyanophenyl, fluorophenyl, chlorophenyl, bromophenyl, methylphenyl, (1-trifluoromethylethyl)-phenyl, trifluoromethylphenyl, dimethylaminomethylphenyl, morpholin-4-ylmethylphenyl, isopropylphenyl, sec-butylphenyl, tert-butylphenyl, (hydroxyl-tert-butyl)phenyl, cyclopropylphenyl, (1-methylcyclopropyl) phenyl, (1-trifluoromethylcyclopropyl)-phenyl, phenylphenyl, (1-methylpiperidin-4-yl)phenyl, hydroxylphenyl, methoxyphenyl, dimethylaminophenyl, acetamidophenyl, difluorophenyl, dichlorophenyl, chloro-methylphenyl, methyl-tert-butylphenyl, dimethylphenyl, trimethylphenyl, trimethoxyphenyl, dimethyl-tert-butylphenyl, dimethylamino-methylphenyl, naphthyl, thienyl, isopropylthienyl, pyridyl, tert-butylcyclohexyl, piperidinyl, or tert-butylpiperidinyl.

In certain embodiments, in any one of Formulae (I) and (Ia) to (Ih), ring A is phenyl, 4-cyanophenyl, 2-fluorophenyl, 3-fluorophenyl, 4-fluorophenyl, 3-chlorophenyl, 4-chlorophenyl, 4-bromophenyl, 4-methylphenyl, 4-(1-trifluoromethylethyl)phenyl, 4-trifluoromethylphenyl, 4-dimethylaminomethylphenyl, 4-morpholin-4-ylmethylphenyl, 4-isopropylphenyl, 4-sec-butylphenyl, 3-tert-butylphenyl, 4-tert-butylphenyl, 4-(hydroxyl-tert-butyl)phenyl, 4-cyclopropylphenyl, 4-(1-methylcyclopropyl)phenyl, 4-(1-trifluoromethylcyclopropyl)phenyl, 4-phenylphenyl, 4-(1-methylpiperidin-4-yl)phenyl, 4-hydroxylphenyl, 3-methoxyphenyl, 4-methoxyphenyl, 4-dimethylaminophenyl, 4-acetamidophenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 3-dimethylamino-4-methylphenyl, 2-naphthyl, thien-2-yl, 5-isopropylthien-2-yl, 4-pyridyl, 4-tert-butylcyclohexyl, piperidin-4-yl, or 4-tert-butylpiperidin-1-yl.

In certain embodiments, in any one of Formulae (I) and (Ia) to (Ih), each $R^A$ is independently halogen, hydroxyl, $C_1$-$C_6$ alkyl, $C_1$-$C_6$ haloalkyl, $C_1$-$C_6$ haloalkoxy, —$(CH_2)_t$—$NR^{7a}R^{8a}$, —$O(CH_2)_t$—$NR^{7a}R^{8a}$, —$C(O)NR^{7b}R^{8b}$, —$SR^{10a}$, —$C(O)OR^{10b}$, —$NR^{7d}C(O)R^{11b}$, phenyl, or $C_3$-$C_7$ cycloalkyl, wherein each phenyl and $C_3$-$C_7$ cycloalkyl is optionally substituted with one or more $R^B$. In certain embodiments, in any one of Formulae (I) and (Ia) to (Ih), each $R^A$ is independently —$(CH_2)$—$NR^{7a}R^{8a}$ or —$O(CH_2)_t$—$NR^{7a}R^{8a}$; where t is 0 or 1; and each $R^{7a}$ and $R^{8a}$ is independently $C_1$-$C_6$ alkyl, or $R^{7a}$ and $R^{8a}$ together with the nitrogen atoms to which they are attached form a 5 or 6 membered heterocyclyl, for example,

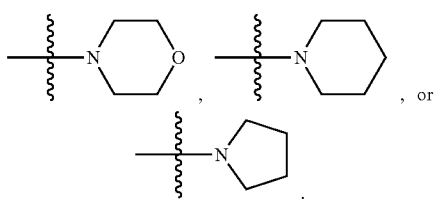

In certain embodiments, in any one of Formulae (I) and (Ia) to (Ih), each $R^A$ is independently —$C(O)NR^{7b}R^{8b}$; where $R^{7b}$ and $R^{8b}$ are each independently $C_1$-$C_6$ alkyl, or $R^{7b}$ and $R^{8b}$ together with the nitrogen atoms to which they are attached form a 5 or 6 membered heterocyclyl, for example,

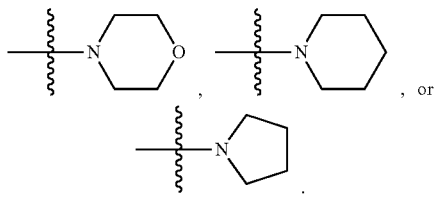

In certain embodiments, in any one of Formulae (I) and (Ia) to (Ih), each $R^A$ is independently —$C(O)OR^{10b}$, where $R^{10b}$ is $C_1$-$C_6$ alkyl, for example, methyl. In certain embodiments, in any one of Formulae (I) and (Ia) to (Ih), each $R^A$ is independently —$NR^{7d}C(O)R^{11b}$, where $R^{7d}$ is H and $R^{11b}$ is $C_1$-$C_6$ alkyl. In certain embodiments, in any one of Formulae (I) and (Ia) to (Ih), each $R^A$ is independently halogen, methyl, isopropyl, t-butyl, isobutyl, hydroxyl, methoxy, ethoxy, propoxy, trifluoromethyl, trifluoromethoxy, —$S(C_3H_7)$, —$N(CH_3)_2$, —$N(C_2H)_2$, —$NHC(=O)CH_3$, —$CH_2N(CH_3)_2$, —$O(CH_2)_2N(CH_3)_2$, —$C(=O)NH_2$, —$C(=O)N(CH_3)_2$, cyclopropyl, cyclopentyl, cyclohexyl,

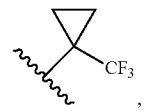

phenyl,

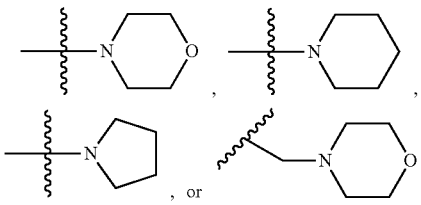

In certain embodiments, in any one of Formulae (I) and (Ia) to (Ih), each $R^A$ is independently halogen, cyano, hydroxyl, $C_1$-$C_6$ alkyl, $C_1$-$C_6$ alkoxy, $C_1$-$C_6$ haloalkyl, —$(CH_2)_t$—$NR^{7a}R^{8a}$, —$NR^{7d}C(O)R^{11b}$, phenyl, $C_3$-$C_8$ carbocyclyl, or 3 to 10 membered heterocyclyl, wherein each of phenyl, 5 to 10 membered heteroaryl, $C_3$-$C_8$ carbocyclyl, and 3 to 10 membered heterocyclyl is optionally substituted with one or more $R^B$.

In certain embodiments, each $R^A$ is independently cyano, fluoro, chloro, bromo, methyl, trifluoromethyl-ethyl, trifluoromethyl, dimethylaminomethyl, morpholinylmethyl, propyl, butyl, hydroxyl-butyl, cyclopropyl, methylcyclopropyl, trifluoromethyl-cyclopropyl, phenyl, methyl-piperidinyl, hydroxyl, methoxy, dimethylamino, or acetamido.

In certain embodiments, each $R^A$ is independently cyano, fluoro, chloro, bromo, methyl, trifluoromethylethyl, trifluoromethyl, dimethylaminomethyl, morpholinyl, isopropyl, sec-butyl, tert-butyl, hydroxyl-tert-butyl, cyclopropyl, methylcyclopropyl, trifluoromethylcyclopropyl, phenyl, methylpiperidinyl, hydroxyl, methoxy, dimethylamino, or acetamido.

In certain embodiments, each $R^A$ is independently cyano, fluoro, chloro, bromo, methyl, 1-trifluoromethylethyl, trifluoromethyl, dimethylaminomethyl, morpholin-4-yl, isopropyl, sec-butyl, tert-butyl, hydroxyl-tert-butyl, cyclopropyl, 1-methylcyclopropyl, 1-trifluoromethylcyclopropyl, phenyl, 1-methylpiperidin-4-yl, hydroxyl, methoxy, dimethylamino, or acetamido.

In certain embodiments, ring A is substituted with two substituents, such as $C_1$-$C_6$ alkyl and halogen; two $C_1$-$C_6$ alkyl (identical or different); two halogens (identical or different); halogen and $C_1$-$C_6$ alkoxy (e.g., methoxy, ethoxy, or isopropoxy); $C_1$-$C_6$ alkyl and $C_1$-$C_6$ haloalkyl; $C_1$-$C_6$ alkyl and mono-substituted amino (e.g., —NH($C_1$-$C_6$ alkyl), such as —NHCH$_3$ or —NHC$_2$H); $C_1$-$C_6$ alkyl and di-substituted amino (e.g., —N($C_1$-$C_6$ alkyl)$_2$, where the two $C_1$-$C_6$ alkyl may be identical or different, such as —N(CH$_3$)$_2$, —N(CH$_3$)C$_2$H$_5$, or —N(C$_2$H$_5$)$_2$); halogen and mono-substituted amino (e.g., —NH($C_1$-$C_6$ alkyl), such as —NHCH$_3$ or —NHC$_2$H$_5$); halogen and di-substituted amino (e.g., —N($C_1$-$C_6$ alkyl)$_2$, where the two $C_1$-$C_6$ alkyl may be identical or different, such as —N(CH$_3$)$_2$, —N(CH$_3$)C$_2$H, or —N(C$_2$H)$_2$); $C_1$-$C_6$ haloalkyl and mono-substituted amino (e.g., —NH($C_1$-$C_6$ alkyl), such as —NHCH$_3$ or —NHC$_2$H$_5$); $C_1$-$C_6$ haloalkyl and di-substituted amino (e.g., —N($C_1$-$C_6$ alkyl)$_2$, where the two $C_1$-$C_6$ alkyl may be identical or different, such as —N(CH$_3$)$_2$, —N(CH$_3$)C$_2$H$_5$, or —N(C$_2$H)$_2$); $C_1$-$C_6$ alkyl and hydroxy; $C_1$-$C_6$ alkyl and $C_1$-$C_6$ alkoxy (e.g., methoxy, ethoxy, or isopropoxy); $C_1$-$C_6$ alkyl and —(CH$_2$)$_t$—NR$^{7a}$R$^{8a}$ (where t is 0 or 1; each $R^{7a}$ and $R^{8a}$ is independently $C_1$-$C_6$ alkyl, or $R^{7a}$ and $R^{8a}$ together with the nitrogen atoms to which they are attached form a 5 or 6 membered heterocyclyl, such as

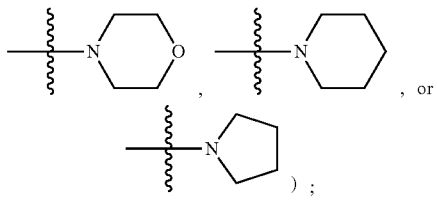

);

$C_1$-$C_6$ alkyl and —C(O)NR$^{7b}$R$^{8b}$; $C_1$-$C_6$ alkoxy and —C(O)NR$^{7b}$R$^{8b}$ (where, for —C(O)NR$^{7b}$R$^{8b}$, each $R^{7b}$ and $R^{8b}$ is independently $C_1$-$C_6$ alkyl, or $R^{7b}$ and $R^{8b}$ together with the nitrogen atoms to which they are attached form a 5 or 6 membered heterocyclyl, such as

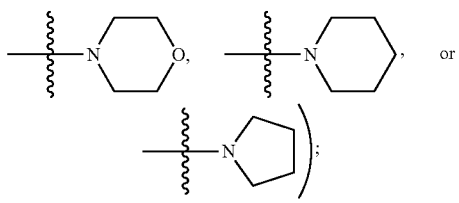

$C_1$-$C_6$ alkyl and —NR$^{7d}$C(O)R$^{11b}$ (where $R^{7d}$ is H, and $R^{11b}$ is $C_1$-$C_6$ alkyl).

In one embodiment, in any one of Formulae (I) and (Ia) to (Ih),
X, if present, is CH$_2$ or C(=O);
Y is (C=O)—(CH$_2$)$_{n1}$;
ring A is $C_6$-$C_{10}$ aryl, 5 to 10 membered heteroaryl, $C_3$-$C_8$ carbocyclyl, or 3 to 10 membered heterocyclyl, each of which is optionally substituted with one, two, or three substituents $R^A$, wherein each substituent $R^A$ is independently (i) halogen, cyano, hydroxyl, $C_1$-$C_6$ alkyl, $C_1$-$C_6$ alkoxy, $C_1$-$C_6$ haloalkyl, —(CH$_2$)$_t$—NR$^{7a}$R$^{8a}$, or —NR$^{7d}$C(O)R$^{11b}$, or (ii) phenyl, $C_3$-$C_8$ carbocyclyl, or 3 to 10 membered heterocyclyl, each of which is optionally substituted with one or more $R^B$;
$R^2$ is H or $C_1$-$C_6$ alkyl;
$R^4$ is H or $C_1$-$C_6$ alkyl;
$R^5$ is H or

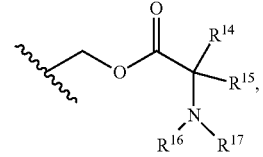

where $R^{14}$, $R^{15}$, $R^{16}$, and $R^{17}$ are each as defined herein;
$R^{3a}$, $R^{3b}$, $R^{3c}$, $R^{3d}$, $R^{3e}$, or $R^{3f}$, if present, is H;
each $R^3$, if present, is independently halogen or $C_1$-$C_6$ alkyl;
m is an integer of 0, 1, or 2;
p is an integer of 0, 1, or 2; and
n1 is an integer of 0, 1, 2, or 3.
In another embodiment, in any one of Formulae (I) and (Ia) to (Ih),
X, if present, is CH$_2$ or C(=O);
Y is (C=O)—(CH$_2$)$_{n1}$;
ring A is phenyl, naphthyl, thienyl, pyridyl, piperidinyl, or cyclohexyl, each of which is optionally substituted with one, two, or three substituents $R^A$, wherein each substituent $R^A$ is independently halogen, cyano, hydroxyl, $C_1$-$C_6$ alkyl, $C_1$-$C_6$ alkoxy, $C_1$-$C_6$ haloalkyl, —(CH$_2$)$_t$—NR$^{7a}$R$^{8a}$, —NR$^{7d}$C(O)R$^{11b}$, phenyl, $C_3$-$C_8$ carbocyclyl, or 3 to 10 membered heterocyclyl, wherein each of phenyl, 5 to 10 membered heteroaryl, $C_3$-$C_8$ carbocyclyl, and 3 to 10 membered heterocyclyl is optionally substituted with one or more $R^B$;
$R^2$ is H or methyl;
$R^4$ is H or methyl;
$R^5$ is H or valyloxymethyl;
$R^{3a}$, $R^{3b}$, $R^{3c}$, $R^{3d}$, $R^{3e}$, or $R^{3f}$, if present, is H;
each $R^{3g}$, if present, is independently fluoro or methyl;
m is an integer of 0, 1, or 2;
p is an integer of 0, 1 or 2; and
n1 is an integer of 0, 1, 2, or 3.
In yet another embodiment, in any one of Formulae (I) and (Ia) to (Ih),
X, if present, is CH$_2$ or C(=O);
Y is (C=O)—(CH$_2$)$_{n1}$;
ring A is phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, propyl, butyl, hydroxyl-butyl, cyclopropyl, methylcyclopropyl, trifluoromethyl-cyclopropyl, phenyl, methyl-piperidinyl, hydroxyl, methoxy, dimethylamino, or acetamido;
$R^2$ is H or methyl;
$R^4$ is H;

$R^5$ is H or D-valyloxymethyl;

$R^{3a}$, $R^{3b}$, $R^{3c}$, $R^{3d}$, $R^{3e}$, or $R^{3f}$, if present, is H;

each $R^{3g}$, if present, is independently fluoro or methyl;

m is an integer of 0, 1, or 2;

p is an integer of 1 or 2; and n1 is an integer of 0, 1, 2, or 3.

In yet another embodiment, in any one of Formulae (I) and (Ia) to (Ih),

X, if present, is $CH_2$ or C(=O);

Y is (C=O)—$(CH_2)_{n1}$;

ring A is phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, isopropyl, sec-butyl, tert-butyl, hydroxyl-tert-butyl, cyclopropyl, methylcyclopropyl, trifluoromethyl-cyclopropyl, phenyl, methyl-piperidinyl, hydroxyl, methoxy, dimethylamino, or acetamido;

$R^2$ is H or methyl;

$R^4$ is H;

$R^5$ is H or D-valyloxymethyl;

$R^{3a}$, $R^{3b}$, $R^{3c}$, $R^{3d}$, $R^{3e}$, or $R^{3f}$, if present, is H;

each $R^{3g}$, if present, is independently fluoro or methyl;

m is an integer of 0, 1, or 2;

p is an integer of 1 or 2; and n1 is an integer of 0, 1, 2, or 3.

In yet another embodiment, in any one of Formulae (I) and (Ia) to (Ih),

X, if present, is $CH_2$ or C(=O);

Y is (C=O)—$(CH_2)_{n1}$;

ring A is phenyl, cyanophenyl, fluorophenyl, chlorophenyl, bromophenyl, methylphenyl, (1-trifluoromethylethyl)phenyl, trifluoromethylphenyl, dimethylaminomethylphenyl, morpholin-4-ylmethylphenyl, isopropylphenyl, sec-butylphenyl, tert-butylphenyl, (hydroxyl-tert-butyl)phenyl, cyclopropylphenyl, (1-methylcyclopropyl)-phenyl, (1-trifluoromethylcyclopropyl)-phenyl, phenylphenyl, (1-methylpiperidin-4-yl)phenyl, hydroxylphenyl, methoxyphenyl, dimethylaminophenyl, acetamidophenyl, difluorophenyl, dichlorophenyl, chloro-methylphenyl, methyl-tert-butylphenyl, dimethylphenyl, trimethylphenyl, trimethoxyphenyl, dimethyl-tert-butylphenyl, dimethylamino-methylphenyl, naphthyl, thienyl, isopropylthienyl, pyridyl, tert-butylcyclohexyl, piperidinyl, or tert-butylpiperidinyl;

$R^2$ is H or methyl;

$R^4$ is H;

$R^5$ is H or D-valyloxymethyl;

$R^{3a}$, $R^{3b}$, $R^{3c}$, $R^{3d}$, $R^{3e}$, or $R^{3f}$, if present, is H;

each $R^{3g}$, if present, is independently fluoro or methyl;

m is an integer of 0, 1, or 2;

p is an integer of 1 or 2; and n1 is an integer of 0, 1, 2, or 3.

In still another embodiment, in any one of Formulae (I) and (Ia) to (Ih),

X, if present, is $CH_2$ or C(=O);

Y is C(=O), $CH_2C(O)$, $CH_2CH_2C(O)$;

ring A is phenyl, 4-cyanophenyl, 2-fluorophenyl, 3-fluorophenyl, 4-fluorophenyl, 3-chlorophenyl, 4-chlorophenyl, 4-bromophenyl, 4-methylphenyl, 4-(1-trifluoromethylethyl)-phenyl, 4-trifluoromethylphenyl, 4-dimethylaminomethylphenyl, 4-morpholin-4-ylmethylphenyl, 4-isopropylphenyl, 4-sec-butylphenyl, 3-tert-butylphenyl, 4-tert-butylphenyl, 4-(hydroxyl-tert-butyl)phenyl, 4-cyclopropylphenyl, 4-(1-methylcyclopropyl)phenyl, 4-(1-trifluoromethylcyclopropyl) phenyl, 4-phenylphenyl, 4-(1-methylpiperidin-4-yl) phenyl, 4-hydroxylphenyl, 3-methoxyphenyl, 4-methoxyphenyl, 4-dimethylaminophenyl, 4-acetamidophenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 3-dimethylamino-4-methylphenyl, 2-naphthyl, thien-2-yl, 5-isopropylthien-2-yl, 4-pyridyl, 4-tert-butylcyclohexyl, piperidin-4-yl, or 4-tert-butylpiperidin-1-yl;

$R^2$ is H or methyl;

$R^4$ is H;

$R^5$ is H or D-valyloxymethyl;

$R^{3a}$, $R^{3b}$, $R^{3c}$, $R^{3d}$, $R^{3e}$, or $R^{3f}$, if present, is H;

each $R^3$, if present, is independently fluoro or methyl;

m is an integer of 0, 1, or 2; and p is an integer of 1 or 2.

In one embodiment, provided herein is a compound of Formula (Ia):

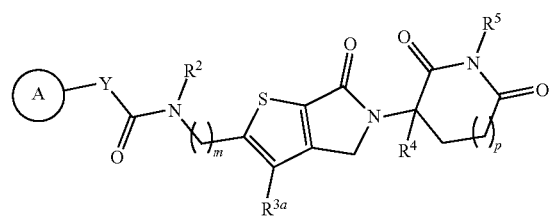

(Ia)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A, $R^2$, $R^4$, $R^5$, $R^{3a}$, Y, m, and p are each as defined herein.

In another embodiment, provided herein is a compound of Formula (Ib):

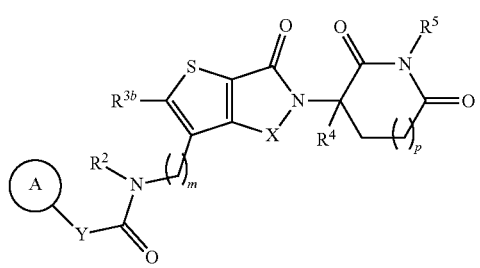

(Ib)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A, $R^2$, $R^4$, $R^5$, $R^{3b}$, X, Y, m, and p are each as defined herein.

In yet another embodiment, provided herein is a compound of Formula (Ic):

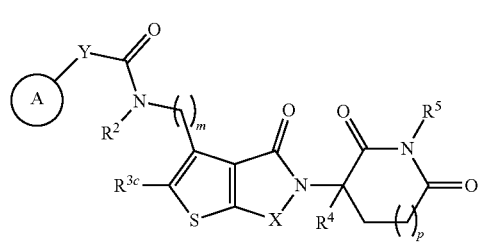
(Ic)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A, $R^2$, $R^4$, $R^5$, $R^{3c}$, X, Y, m, and p are each as defined herein.

In yet another embodiment, provided herein is a compound of Formula (Id):

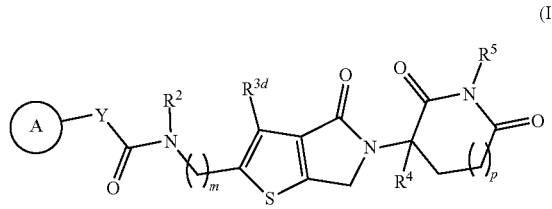
(Id)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A, $R^2$, $R^4$, $R^5$, $R^{3d}$, Y, m, and p are each as defined herein.

In yet another embodiment, provided herein is a compound of Formula (Ie):

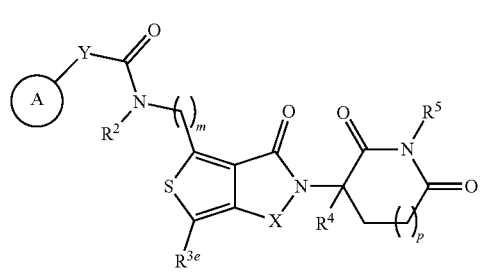
(Ie)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A, $R^2$, $R^4$, $R^5$, $R^{3e}$, X, Y, m, and p are each as defined herein.

In still another embodiment, provided herein is a compound of Formula (If):

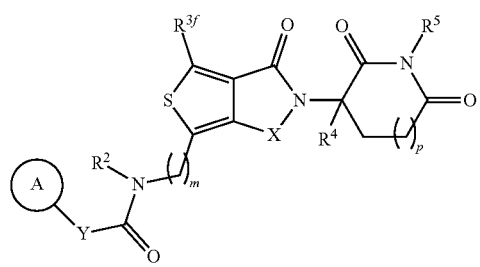
(If)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A, $R^2$, $R^4$, $R^5$, $R^{3f}$, X, Y, m, and p are each as defined herein.

In one embodiment, in any one of Formulae (Ia) to (If),
X, if present, is $CH_2$ or $C(=O)$;
Y is $(C=O)-(CH_2)_{n1}$;
ring A is $C_6$-$C_{10}$ aryl, 5 to 10 membered heteroaryl, $C_3$-$C_8$ carbocyclyl, or 3 to 10 membered heterocyclyl, each of which is optionally substituted with one, two, or three substituents $R^A$, wherein each substituent $R^A$ is independently (i) halogen, cyano, hydroxyl, $C_1$-$C_6$ alkyl, $C_1$-$C_6$ alkoxy, $C_1$-$C_6$ haloalkyl, $-(CH_2)_t-NR^{7a}R^{8a}$, or $-NR^{7d}C(O)R^{11b}$, or (ii) phenyl, $C_3$-$C_8$ carbocyclyl, or 3 to 10 membered heterocyclyl, each of which is optionally substituted with one or more $R^B$;
$R^2$ is H or $C_1$-$C_6$ alkyl;
$R^4$ is H or $C_1$-$C_6$ alkyl;
$R^5$ is H or

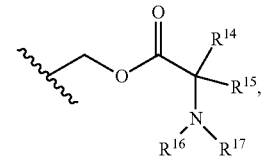

where $R^{14}$, $R^{15}$, $R^{16}$, and $R^{17}$ are each as defined herein;
$R^{3a}$, $R^{3b}$, $R^{3c}$, $R^{3d}$, $R^{3e}$, or $R^{3f}$, if present, is H;
m is an integer of 0, 1, or 2;
p is an integer of 0, 1, or 2;
n1 is an integer of 0, 1, 2, or 3.

In another embodiment, in any one of Formulae (Ia) to (If),
X, if present, is $CH_2$ or $C(=O)$;
Y is $(C=O)-(CH_2)_{n1}$;
ring A is phenyl, naphthyl, thienyl, pyridyl, piperidinyl, or cyclohexyl, each of which is optionally substituted with one, two, or three substituents $R^A$, wherein each substituent $R^A$ is independently halogen, cyano, hydroxyl, $C_1$-$C_6$ alkyl, $C_1$-$C_6$ alkoxy, $C_1$-$C_6$ haloalkyl, $-(CH_2)_t-NR^{7a}R^{8a}$, $-NR^{7d}C(O)R^{11b}$, phenyl, $C_3$-$C_8$ carbocyclyl, or 3 to 10 membered heterocyclyl, wherein each of phenyl, 5 to 10 membered heteroaryl, $C_3$-$C_8$ carbocyclyl, and 3 to 10 membered heterocyclyl is optionally substituted with one or more $R^B$;
$R^2$ is H or methyl;
$R^4$ is H or methyl;
$R^5$ is H or valyloxymethyl;
$R^{3a}$, $R^{3b}$, $R^{3c}$, $R^{3d}$, $R^{3e}$, or $R^{3f}$, if present, is H;

m is an integer of 0, 1, or 2;
p is an integer of 0, 1 or 2; and
n1 is an integer of 0, 1, 2, or 3.

In yet another embodiment, in any one of Formulae (Ia) to (If),

X, if present, is $CH_2$ or $C(=O)$;
Y is $(C=O)-(CH_2)_{n1}$;
ring A is phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, propyl, butyl, hydroxyl-butyl, cyclopropyl, methylcyclopropyl, trifluoromethyl-cyclopropyl, phenyl, methyl-piperidinyl, hydroxyl, methoxy, dimethylamino, or acetamido;
$R^2$ is H or methyl;
$R^4$ is H;
$R^5$ is H or D-valyloxymethyl;
$R^{3a}$, $R^{3b}$, $R^{3c}$, $R^{3d}$, $R^{3e}$, or $R^{3f}$, if present, is H;
m is an integer of 0, 1, or 2;
p is an integer of 1 or 2; and
n1 is an integer of 0, 1, 2, or 3.

In yet another embodiment, in any one of Formulae (Ia) to (If),

X, if present, is $CH_2$ or $C(=O)$;
Y is $(C=O)-(CH_2)_{n1}$;
ring A is phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, isopropyl, sec-butyl, tert-butyl, hydroxyl-tert-butyl, cyclopropyl, methylcyclopropyl, trifluoromethyl-cyclopropyl, phenyl, methyl-piperidinyl, hydroxyl, methoxy, dimethylamino, or acetamido;
$R^2$ is H or methyl;
$R^4$ is H;
$R^5$ is H or D-valyloxymethyl;
$R^{3a}$, $R^{3b}$, $R^{3c}$, $R^{3d}$, $R^{3e}$, or $R^{3f}$, if present, is H;
m is an integer of 0, 1, or 2;
p is an integer of 1 or 2; and
n1 is an integer of 0, 1, 2, or 3.

In yet another embodiment, in any one of Formulae (Ia) to (If),

X, if present, is $CH_2$ or $C(=O)$;
Y is $(C=O)-(CH_2)_{n1}$;
ring A is phenyl, cyanophenyl, fluorophenyl, chlorophenyl, bromophenyl, methylphenyl, (1-trifluoromethyl-ethyl)phenyl, trifluoromethylphenyl, dimethylaminomethylphenyl, morpholin-4-ylmethylphenyl, isopropylphenyl, sec-butylphenyl, tert-butylphenyl, (hydroxyl-tert-butyl)phenyl, cyclopropylphenyl, (1-methylcyclopropyl)phenyl, (1-trifluoromethylcyclopropyl)-phenyl, phenylphenyl, (1-methylpiperidin-4-yl)phenyl, hydroxylphenyl, methoxyphenyl, dimethylaminophenyl, acetamidophenyl, difluorophenyl, dichlorophenyl, chloro-methylphenyl, methyl-tert-butylphenyl, dimethylphenyl, trimethylphenyl, trimethoxyphenyl, dimethyl-tert-butylphenyl, dimethylamino-methylphenyl, naphthyl, thienyl, isopropylthienyl, pyridyl, tert-butylcyclohexyl, piperidinyl, or tert-butylpiperidinyl;
$R^2$ is H or methyl;
$R^4$ is H;
$R^5$ is H or D-valyloxymethyl;
$R^{3a}$, $R^{3b}$, $R^{3c}$, $R^{3d}$, $R^{3e}$, or $R^{3f}$, if present, is H;
m is an integer of 0, 1, or 2;
p is an integer of 1 or 2; and
n1 is an integer of 0, 1, 2, or 3.

In still another embodiment, in any one of Formulae (Ia) to (If),

X, if present, is $CH_2$ or $C(=O)$;
Y is $C(=O)$, $CH_2C(O)$, $CH_2CH_2C(O)$;
ring A is phenyl, 4-cyanophenyl, 2-fluorophenyl, 3-fluorophenyl, 4-fluorophenyl, 3-chlorophenyl, 4-chlorophenyl, 4-bromophenyl, 4-methylphenyl, 4-(1-trifluoromethylethyl)-phenyl, 4-trifluoromethylphenyl, 4-dimethylaminomethylphenyl, 4-morpholin-4-ylmethylphenyl, 4-isopropylphenyl, 4-sec-butylphenyl, 3-tert-butylphenyl, 4-tert-butylphenyl, 4-(hydroxyl-tert-butyl)phenyl, 4-cyclopropylphenyl, 4-(1-methylcyclopropyl)phenyl, 4-(1-trifluoromethylcyclopropyl)phenyl, 4-phenylphenyl, 4-(1-methylpiperidin-4-yl)phenyl, 4-hydroxylphenyl, 3-methoxyphenyl, 4-methoxyphenyl, 4-dimethylaminophenyl, 4-acetamidophenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 3-dimethylamino-4-methylphenyl, 2-naphthyl, thien-2-yl, 5-isopropylthien-2-yl, 4-pyridyl, 4-tert-butylcyclohexyl, piperidin-4-yl, or 4-tert-butylpiperidin-1-yl;
$R^2$ is H or methyl;
$R^4$ is H;
$R^5$ is H or D-valyloxymethyl;
$R^{3a}$, $R^{3b}$, $R^{3c}$, $R^{3d}$, $R^{3e}$, or $R^{3f}$, if present, is H;
m is an integer of 0, 1, or 2; and
p is an integer of 1 or 2.

In one embodiment, provided herein is a compound of Formula (Ig):

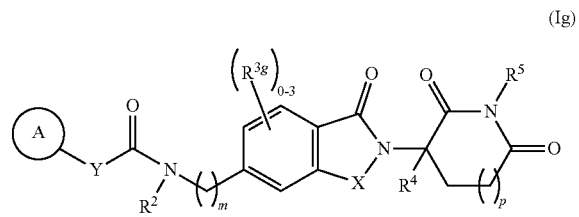

(Ig)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A, $R^2$, $R^4$, $R^5$, $R^{3g}$, X, Y, m, and p are each as defined herein.

In another embodiment, provided herein is a compound of Formula (Ih):

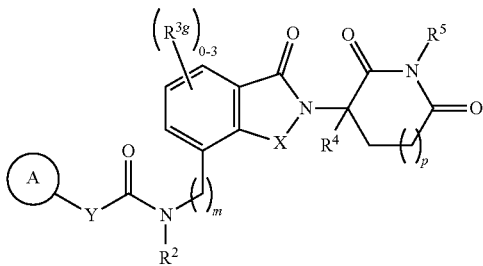

(Ih)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A, $R^2$, $R^4$, $R^5$, $R^{3g}$, X, Y, m, and p are each as defined herein.

In one embodiment, in Formula (Ig) or (Ih),
X is $CH_2$ or C(=O);
Y is (C=O)—$(CH_2)_{n1}$;
ring A is $C_6$-$C_{10}$ aryl, 5 to 10 membered heteroaryl, $C_3$-$C_8$ carbocyclyl, or 3 to 10 membered heterocyclyl, each of which is optionally substituted with one, two, or three substituents $R^A$, wherein each substituent $R^A$ is independently (i) halogen, cyano, hydroxyl, $C_1$-$C_6$ alkyl, $C_1$-$C_6$ alkoxy, $C_1$-$C_6$ haloalkyl, —$(CH_2)_t$—$NR^{7a}R^{8a}$, or —$NR^{7d}C(O)R^{11b}$, or (ii) phenyl, $C_3$-$C_8$ carbocyclyl, or 3 to 10 membered heterocyclyl, each of which is optionally substituted with one or more $R^B$;
$R^2$ is H or $C_1$-$C_6$ alkyl;
$R^4$ is H or $C_1$-$C_6$ alkyl;
$R^5$ is H or

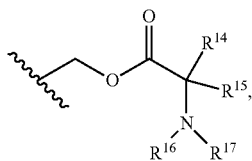

where $R^{14}$, $R^{15}$, $R^{16}$, and $R^{17}$ are each as defined herein;
$R^{3g}$ is halogen or $C_1$-$C_6$ alkyl;
m is an integer of 0, 1, or 2;
p is an integer of 0, 1, or 2; and
n1 is an integer of 0, 1, 2, or 3.
In another embodiment, in Formula (Ig) or (Ih),
X is $CH_2$ or C(=O);
Y is (C=O)—$(CH_2)_{n1}$;
ring A is phenyl, naphthyl, thienyl, pyridyl, piperidinyl, or cyclohexyl, each of which is optionally substituted with one, two, or three substituents $R^A$, wherein each substituent $R^A$ is independently halogen, cyano, hydroxyl, $C_1$-$C_6$ alkyl, $C_1$-$C_6$ alkoxy, $C_1$-$C_6$ haloalkyl, —$(CH_2)_t$—$NR^{7a}R^{8a}$, —$NR^{7d}C(O)R^{11b}$, phenyl, $C_3$-$C_8$ carbocyclyl, or 3 to 10 membered heterocyclyl, wherein each of phenyl, 5 to 10 membered heteroaryl, $C_3$-$C_8$ carbocyclyl, and 3 to 10 membered heterocyclyl is optionally substituted with one or more $R^B$;
$R^2$ is H or methyl;
$R^4$ is H or methyl;
$R^5$ is H or valyloxymethyl;
$R^{3g}$ is fluoro or methyl;

m is an integer of 0, 1, or 2;
p is an integer of 0, 1 or 2; and
n1 is an integer of 0, 1, 2, or 3.
In yet another embodiment, in Formula (Ig) or (Ih),
X is $CH_2$ or C(=O);
Y is (C=O)—$(CH_2)_{n1}$;
ring A is phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, propyl, butyl, hydroxyl-butyl, cyclopropyl, methylcyclopropyl, trifluoromethyl-cyclopropyl, phenyl, methyl-piperidinyl, hydroxyl, methoxy, dimethylamino, or acetamido;
$R^2$ is H or methyl;
$R^4$ is H;
$R^5$ is H or D-valyloxymethyl;
$R^{3g}$ is fluoro or methyl;
m is an integer of 0, 1, or 2;
p is an integer of 1 or 2; and
n1 is an integer of 0, 1, 2, or 3.
In yet another embodiment, in Formula (Ig) or (Ih),
X is $CH_2$ or C(=O);
Y is (C=O)—$(CH_2)_{n1}$;
ring A is phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, isopropyl, sec-butyl, tert-butyl, hydroxyl-tert-butyl, cyclopropyl, methylcyclopropyl, trifluoromethyl-cyclopropyl, phenyl, methyl-piperidinyl, hydroxyl, methoxy, dimethylamino, or acetamido;
$R^2$ is H or methyl;
$R^4$ is H;
$R^5$ is H or D-valyloxymethyl;
$R^{3g}$ is fluoro or methyl;
m is an integer of 0, 1, or 2;
p is an integer of 1 or 2;
n1 is an integer of 0, 1, 2, or 3.
In yet another embodiment, in Formula (Ig) or (Ih),
X is $CH_2$ or C(=O);
Y is (C=O)—$(CH_2)_{n1}$;
ring A is phenyl, cyanophenyl, fluorophenyl, chlorophenyl, bromophenyl, methylphenyl, (1-trifluoromethylethyl)phenyl, trifluoromethylphenyl, dimethylaminomethylphenyl, morpholin-4-ylmethylphenyl, isopropylphenyl, sec-butylphenyl, tert-butylphenyl, (hydroxyl-tert-butyl)phenyl, cyclopropylphenyl, (1-methylcyclopropyl)phenyl, (1-trifluoromethylcyclopropyl)-phenyl, phenylphenyl, (1-methylpiperidin-4-yl)phenyl, hydroxylphenyl, methoxyphenyl, dimethylaminophenyl, acetamidophenyl, difluorophenyl, dichlorophenyl, chloro-methylphenyl, methyl-tert-butylphenyl, dimethylphenyl, trimethylphenyl, trimethoxyphenyl, dimethyl-tert-butylphenyl, dimethylamino-methylphenyl, naphthyl, thienyl, isopropylthienyl, pyridyl, tert-butylcyclohexyl, piperidinyl, or tert-butylpiperidinyl;
$R^2$ is H or methyl;
$R^4$ is H;
$R^5$ is H or D-valyloxymethyl;
$R^{3g}$ is fluoro or methyl;
m is an integer of 0, 1, or 2;

p is an integer of 1 or 2; and
n1 is an integer of 0, 1, 2, or 3.

In yet another embodiment, in Formula (Ig) or (Ih),
X is $CH_2$ or $C(=O)$;
Y is $C(=O)$, $CH_2C(O)$, $CH_2CH_2C(O)$;
ring A is phenyl, 4-cyanophenyl, 2-fluorophenyl, 3-fluorophenyl, 4-fluorophenyl, 3-chlorophenyl, 4-chlorophenyl, 4-bromophenyl, 4-methylphenyl, 4-(1-trifluoromethylethyl)-phenyl, 4-trifluoromethylphenyl, 4-dimethylaminomethylphenyl, 4-morpholin-4-ylmethylphenyl, 4-isopropylphenyl, 4-sec-butylphenyl, 3-tert-butylphenyl, 4-tert-butylphenyl, 4-(hydroxyl-tert-butyl)phenyl, 4-cyclopropylphenyl, 4-(1-methylcyclopropyl)phenyl, 4-(1-trifluoromethylcyclopropyl)phenyl, 4-phenylphenyl, 4-(1-methylpiperidin-4-yl)phenyl, 4-hydroxylphenyl, 3-methoxyphenyl, 4-methoxyphenyl, 4-dimethylaminophenyl, 4-acetamidophenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 3-dimethylamino-4-methylphenyl, 2-naphthyl, thien-2-yl, 5-isopropylthien-2-yl, 4-pyridyl, 4-tert-butylcyclohexyl, piperidin-4-yl, or 4-tert-butylpiperidin-1-yl;
$R^2$ is H or methyl;
$R^4$ is H;
$R^5$ is H or D-valyloxymethyl;
$R^{3g}$ is fluoro or methyl;
p is an integer of 1 or 2; and
m is an integer of 0, 1, or 2.

In still another embodiment, in Formula (Ig) or (Ih),
X is $CH_2$ or $C(=O)$;
Y is $C(=O)$ or $CH_2C(O)$;
ring A is phenyl, 4-cyanophenyl, 2-fluorophenyl, 3-fluorophenyl, 3-chlorophenyl, 4-trifluoromethylphenyl, 3-tert-butylphenyl, 4-tert-butylphenyl, 4-(1-trifluoromethyl-cyclopropyl)phenyl, 3-methoxyphenyl, 4-methoxyphenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 2-naphthyl, 5-isopropylthien-2-yl, 4-pyridyl, 4-tert-butylcyclohexyl, or 4-tert-butylpiperidin-1-yl;
$R^2$ is H or methyl;
$R^4$ is H;
$R^5$ is H or D-valyloxymethyl;
$R^{3g}$ is methyl;
m is an integer of 1 or 2; and
p is an integer of 1 or 2.

In one embodiment, provided herein is a compound of Formula (III):

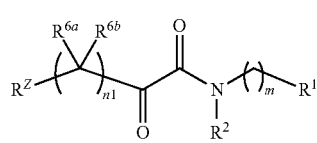

(III)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^Z$ is $-NR^{7a}R^{8a}$ or ring A; and ring A, $R^1$, $R^2$, $R^{6a}$, $R^{6b}$, $R^{7a}$, $R^{8a}$, m, and n1 are each as defined herein for Formula (I).

In certain embodiments, $R^Z$ is $-NR^{7a}R^{8a}$, wherein $R^{7a}$ and $R^{8a}$ are each as defined herein for Formula (I). In certain embodiments, R is $-NR^{7a}R^{8a}$, wherein $R^{7a}$ and $R^{8a}$ are each independently H or optionally substituted $C_1$-$C_6$ alkyl. In certain embodiments, $R^Z$ is $-NHCH_3$, $-NHC_2H$, $-N(CH_3)_2$, $-N(CH_3)C_2H$, or $-N(C_2H)_2$. In certain embodiments, $R^Z$ is dimethylamino. In certain embodiments, $R^Z$ is ring A as defined herein for Formula (I).

In one embodiment, provided herein is a compound of Formula (IIIa):

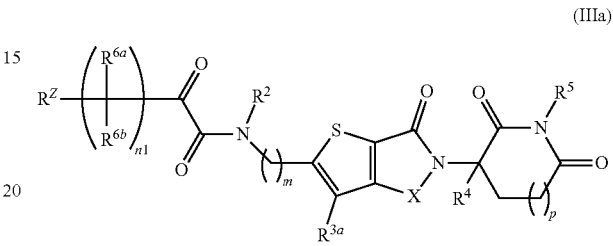

(IIIa)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3a}$, $R^{6a}$, $R^{6b}$, $R^Z$, X, m, p, and n1 are each as defined herein.

In another embodiment, provided herein is a compound of Formula (IIIb):

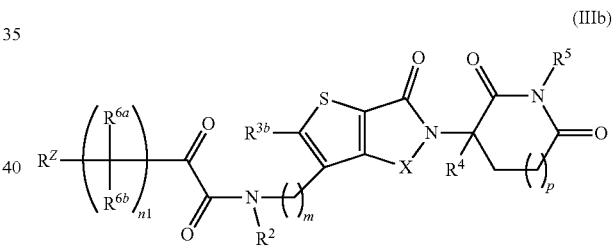

(IIIb)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3b}$, $R^{6a}$, $R^{6b}$, $R^Z$, X, m, p, and n1 are each as defined herein.

In yet another embodiment, provided herein is a compound of Formula (IIIc):

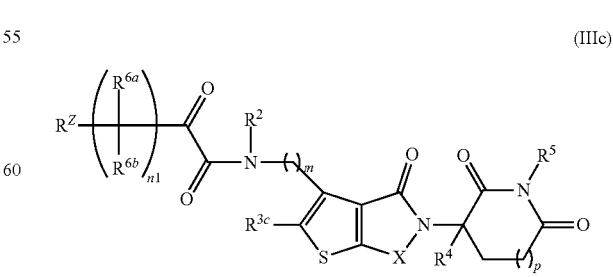

(IIIc)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3c}$, $R^{6a}$, $R^{6b}$, $R^Z$, X, m, p, and n1 are each as defined herein.

In yet another embodiment, provided herein is a compound of Formula (IIId):

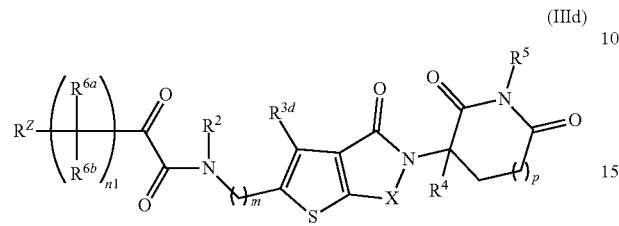

(IIId)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3d}$, $R^{6a}$, $R^{6b}$, $R^Z$, X, m, p, and n1 are each as defined herein.

In yet another embodiment, provided herein is a compound of Formula (IIIe):

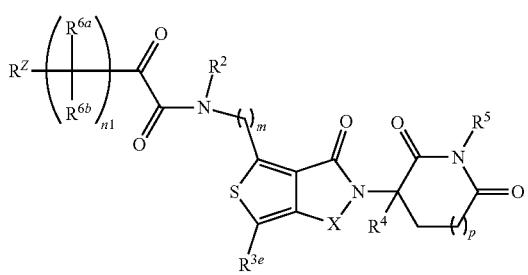

(IIIe)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^3$, $R^{6a}$, $R^{6b}$, $R^Z$, X, m, p, and n1 are each as defined herein.

In still another embodiment, provided herein is a compound of Formula (IIIf):

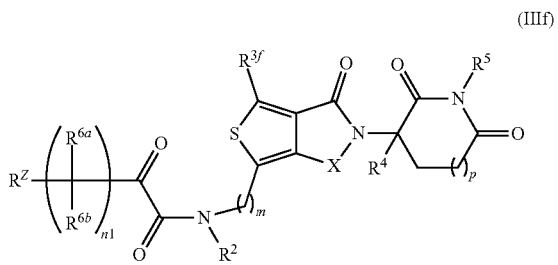

(IIIf)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^3$, $R^{6a}$, $R^{6b}$, $R^Z$, X, m, p, and n1 are each as defined herein.

In one embodiment, in any one of Formulae (IIIa) to (IIIf), X is $CH_2$ or C(=O);
$R^Z$ is (a) amino, mono-substituted amino, or di-substituted amino; or (b) $C_6$-$C_{10}$ aryl, 5 to 10 membered heteroaryl, $C_3$-$C_8$ carbocyclyl, or 3 to 10 membered heterocyclyl, each of which is optionally substituted with one, two, or three substituents $R^A$, wherein each substituent $R^A$ is independently (i) halogen, cyano, hydroxyl, $C_1$-$C_6$ alkyl, $C_1$-$C_6$ alkoxy, $C_1$-$C_6$ haloalkyl, —$(CH_2)_t$—$NR^{7a}R^{8a}$, or —$NR^{7d}C(O)R^{11b}$, or (ii) phenyl, $C_3$-$C_8$ carbocyclyl, or 3 to 10 membered heterocyclyl, each of which is optionally substituted with one or more $R^B$;
$R^2$ is H or $C_1$-$C_6$ alkyl;
$R^4$ is H or $C_1$-$C_6$ alkyl;
$R^5$ is H or

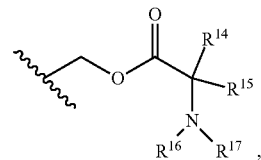

where $R^{14}$, $R^{15}$, $R^{16}$, and $R^{17}$ are each as defined herein;
$R^{3a}$, $R^{3b}$, $R^{3c}$, $R^{3d}$, $R^{3e}$, or $R^{3f}$, if present, is H;
each $R^{6a}$ and $R^{6b}$ is independently H or $C_1$-$C_6$ alkyl;
m is an integer of 0, 1, or 2;
p is an integer of 0, 1, or 2; and
n1 is an integer of 0, 1, 2, or 3.

In another embodiment, in any one of Formulae (IIIa) to (IIIf),
X is $CH_2$ or C(=O);
$R^Z$ is (a) mono-substituted amino or di-substituted amino; or (b) phenyl, naphthyl, thienyl, pyridyl, piperidinyl, or cyclohexyl, each of which is optionally substituted with one, two, or three substituents $R^A$, wherein each substituent $R^A$ is independently halogen, cyano, hydroxyl, $C_1$-$C_6$ alkyl, $C_1$-$C_6$ alkoxy, $C_1$-$C_6$ haloalkyl, —$(CH_2)_t$—$NR^{7a}R^{8a}$, —$NR^{7d}C(O)R^{11b}$, phenyl, $C_3$-$C_8$ carbocyclyl, or 3 to 10 membered heterocyclyl, wherein each of phenyl, 5 to 10 membered heteroaryl, $C_3$-$C_8$ carbocyclyl, and 3 to 10 membered heterocyclyl is optionally substituted with one or more $R^B$;
$R^2$ is H or methyl;
$R^4$ is H;
$R^5$ is H or valyloxymethyl;
$R^{3a}$, $R^{3b}$, $R^{3c}$, $R^{3d}$, $R^{3e}$, or $R^{3f}$, if present, is H;
each $R^{6a}$ and $R^{6b}$ is independently H or methyl;
m is an integer of 0, 1, or 2;
p is an integer of 0, 1 or 2; and
n1 is an integer of 0, 1, 2, or 3, In yet another embodiment, in any one of Formulae (IIIa) to (IIIf),
X is $CH_2$ or C(=O);
$R^Z$ is (a) dimethylamino; or (b) phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethylethyl, trifluoromethyl, dimethylaminomethyl, morpholinylmethyl, propyl, butyl, hydroxyl-butyl, cyclopropyl, methylcyclopropyl, trifluoromethylcyclopropyl, phenyl, methyl-piperidinyl, hydroxyl, methoxy, dimethylamino, or acetamido;
$R^2$ is H or methyl;
$R^4$ is H;
$R^5$ is H or D-valyloxymethyl;
$R^{3a}$, $R^{3b}$, $R^{3c}$, $R^{3d}$, $R^{3e}$, or $R^{3f}$, if present, is H;
each $R^{6a}$ and $R^{6b}$ is H;
m is an integer of 0, 1, or 2;
p is an integer of 1 or 2; and
n1 is an integer of 0, 1, 2, or 3.

In yet another embodiment, in any one of Formulae (IIIa) to (IIIf),
X is $CH_2$ or C(=O);
$R^Z$ is dimethylamino, phenyl, naphthyl, thienyl, pyridyl, piperidinyl, or cyclohexyl, each of which is optionally substituted with one, two, or three substituents $R^4$, wherein each substituent $R^4$ is independently cyano, fluoro, chloro, bromo, methyl, trifluoromethyl-ethyl, trifluoromethyl, dimethylaminomethyl, morpholinylmethyl, isopropyl, sec-butyl, tert-butyl, hydroxyl-tert-butyl, cyclopropyl, methylcyclopropyl, trifluoromethyl-cyclopropyl, phenyl, methyl-piperidinyl, hydroxyl, methoxy, dimethylamino, or acetamido;
$R^2$ is H or methyl;
$R^4$ is H;
$R^5$ is H or D-valyloxymethyl;
$R^{3a}$, $R^{3b}$, $R^{3c}$, $R^{3d}$, $R^{3e}$, or $R^{3f}$, if present, is H;
each $R^{6a}$ and $R^{6b}$ is H;
m is an integer of 0, 1, or 2;
p is an integer of 1 or 2; and
n1 is an integer of 0, 1, 2, or 3.

In yet another embodiment, in any one of Formulae (IIIa) to (IIIf),
X is $CH_2$ or C(=O);
$R^Z$ is dimethylamino, phenyl, cyanophenyl, fluorophenyl, chlorophenyl, bromophenyl, methylphenyl, (1-trifluoromethylethyl)phenyl, trifluoromethylphenyl, dimethylaminomethylphenyl, morpholin-4-ylmethylphenyl, isopropylphenyl, sec-butylphenyl, tert-butylphenyl, (hydroxyl-tert-butyl)phenyl, cyclopropylphenyl, (1-methylcyclopropyl)phenyl, (1-trifluoromethylcyclopropyl)-phenyl, phenylphenyl, (1-methylpiperidin-4-yl)phenyl, hydroxylphenyl, methoxyphenyl, dimethylaminophenyl, acetamidophenyl, difluorophenyl, dichlorophenyl, chloro-methylphenyl, methyl-tert-butylphenyl, dimethylphenyl, trimethylphenyl, trimethoxyphenyl, dimethyl-tert-butylphenyl, dimethylamino-methylphenyl, naphthyl, thienyl, isopropylthienyl, pyridyl, tert-butylcyclohexyl, piperidinyl, or tert-butylpiperidinyl;
$R^2$ is H or methyl;
$R^4$ is H;
$R^5$ is H or D-valyloxymethyl;
$R^{3a}$, $R^{3b}$, $R^{3c}$, $R^{3d}$, $R^{3e}$, or $R^{3f}$, if present, is H;
each $R^{6a}$ and $R^{6b}$ is H;
m is an integer of 0, 1, or 2;
p is an integer of 1 or 2; and
n1 is an integer of 0, 1, or 2.

In still another embodiment, in any one of Formulae (IIIa) to (IIIf),
X is $CH_2$ or C(=O);
$R^Z$ is dimethylamino, phenyl, 4-cyanophenyl, 2-fluorophenyl, 3-fluorophenyl, 4-fluorophenyl, 3-chlorophenyl, 4-chlorophenyl, 4-bromophenyl, 4-methylphenyl, 4-(1-trifluoromethylethyl)phenyl, 4-trifluoromethylphenyl, 4-dimethylaminomethylphenyl, 4-morpholin-4-ylmethylphenyl, 4-isopropylphenyl, 4-sec-butylphenyl, 3-tert-butylphenyl, 4-tert-butylphenyl, 4-(hydroxyl-tert-butyl)phenyl, 4-cyclopropylphenyl, 4-(1-methylcyclopropyl)phenyl, 4-(1-trifluoromethylcyclopropyl)phenyl, 4-phenylphenyl, 4-(1-methylpiperidin-4-yl)phenyl, 4-hydroxylphenyl, 3-methoxyphenyl, 4-methoxyphenyl, 4-dimethylaminophenyl, 4-acetamidophenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 3-dimethylamino-4-methylphenyl, 2-naphthyl, thien-2-yl, 5-isopropylthien-2-yl, 4-pyridyl, 4-tert-butylcyclohexyl, piperidin-4-yl, or 4-tert-butylpiperidin-1-yl;
$R^2$ is H or methyl;
$R^4$ is H;
$R^5$ is H or D-valyloxymethyl;
$R^{3a}$, $R^{3b}$, $R^{3c}$, $R^{3d}$, $R^{3e}$, or $R^{3f}$, if present, is H;
each $R^{6a}$ and $R^{6b}$ is H;
m is an integer of 0, 1, or 2;
p is an integer of 1 or 2; and
n1 is an integer of 0, 1, or 2.

In one embodiment, provided herein is a compound of Formula (IIIg):

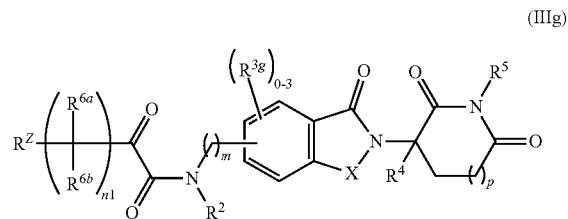

(IIIg)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3g}$, $R^{6a}$, $R^{6b}$, $R^Z$, X, m, p, and n1 are each as defined herein.

In another embodiment, provided herein is a compound of Formula (IIIh):

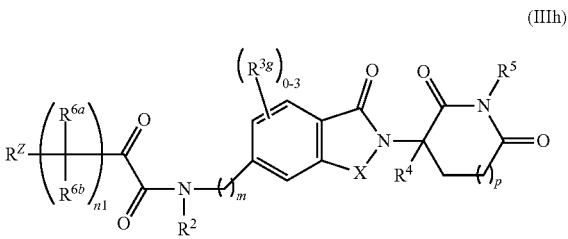

(IIIh)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3g}$, $R^{6a}$, $R^{6b}$, $R^Z$, X, m, p, and n1 are each as defined herein.

In yet another embodiment, provided herein is a compound of Formula (IIIi):

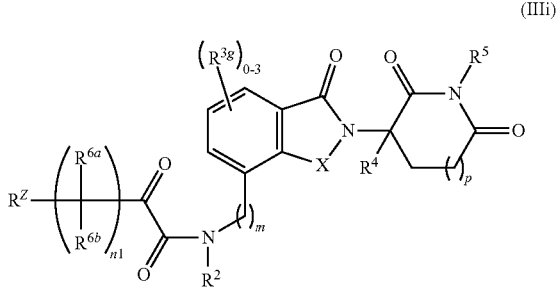
(IIIi)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3g}$, $R^{6a}$, $R^{6b}$, $R^Z$, X, m, p, and n1 are each as defined herein.

In one embodiment, in any one of Formulae (IIIg) to (IIIi),
X is $CH_2$ or C(=O);
$R^Z$ is (a) amino, mono-substituted amino, or di-substituted amino; or (b) $C_6$-$C_{10}$ aryl, 5 to 10 membered heteroaryl, $C_3$-$C_8$ carbocyclyl, or 3 to 10 membered heterocyclyl, each of which is optionally substituted with one, two, or three substituents $R^A$, wherein each substituent $R^A$ is independently (i) halogen, cyano, hydroxyl, $C_1$-$C_6$ alkyl, $C_1$-$C_6$ alkoxy, $C_1$-$C_6$ haloalkyl, —$(CH_2)_t$—$NR^{7a}R^{8a}$, or —$NR^{7d}C(O)R^{11b}$, or (ii) phenyl, $C_3$-$C_8$ carbocyclyl, or 3 to 10 membered heterocyclyl, each of which is optionally substituted with one or more $R^B$;
$R^2$ is H or $C_1$-$C_6$ alkyl;
$R^4$ is H or $C_1$-$C_6$ alkyl;
$R^5$ is H or

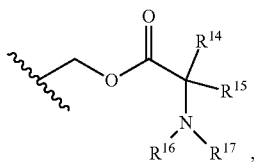

where $R^{14}$, $R^{15}$, $R^{16}$, and $R^{17}$ are each as defined herein;
$R^{3g}$ is halogen or $C_1$-$C_6$ alkyl;
each $R^{6a}$ and $R^{6b}$ is independently H or $C_1$-$C_6$ alkyl;
m is an integer of 0, 1, or 2;
p is an integer of 0, 1, or 2; and
n1 is an integer of 0, 1, 2, or 3.

In another embodiment, in any one of Formulae (IIIg) to (IIIi),
X is $CH_2$ or C(=O);
$R^Z$ is (a) mono-substituted amino or di-substituted amino; or (b) phenyl, naphthyl, thienyl, pyridyl, piperidinyl, or cyclohexyl, each of which is optionally substituted with one, two, or three substituents $R^A$, wherein each substituent $R^A$ is independently halogen, cyano, hydroxyl, $C_1$-$C_6$ alkyl, $C_1$-$C_6$ alkoxy, $C_1$-$C_6$ haloalkyl, —$(CH_2)$—$NR^{7a}R^{8a}$, —$NR^{7d}C(O)R^{11b}$, phenyl, $C_3$-$C_8$ carbocyclyl, or 3 to 10 membered heterocyclyl, wherein each of phenyl, 5 to 10 membered heteroaryl, $C_3$-$C_8$ carbocyclyl, and 3 to 10 membered heterocyclyl is optionally substituted with one or more $R^B$;
$R^2$ is H or methyl;
$R^4$ is H;
$R^5$ is H or D-valyloxymethyl;
$R^{3g}$ is fluoro or methyl;
each $R^{6a}$ and $R^{6b}$ is independently H or methyl;
m is an integer of 0, 1, or 2;
p is an integer of 0, 1 or 2; and
n1 is an integer of 0, 1, 2, or 3, In yet another embodiment, in any one of Formulae (IIIg) to (IIIi),
X is $CH_2$ or C(=O);
$R^Z$ is (a) dimethylamino; or (b) phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, propyl, butyl, hydroxyl-butyl, cyclopropyl, methylcyclopropyl, trifluoromethyl-cyclopropyl, phenyl, methyl-piperidinyl, hydroxyl, methoxy, dimethylamino, or acetamido;
$R^2$ is H or methyl;
$R^4$ is H;
$R^5$ is H or D-valyloxymethyl;
$R^{3g}$ is fluoro or methyl;
each $R^{6a}$ and $R^{6b}$ is H;
m is an integer of 0, 1, or 2;
p is an integer of 1 or 2; and
n1 is an integer of 0, 1, 2, or 3.

In yet another embodiment, in any one of Formulae (IIIg) to (IIIi),
X is $CH_2$ or C(=O);
$R^Z$ is dimethylamino, phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, isopropyl, sec-butyl, tert-butyl, hydroxyl-tert-butyl, cyclopropyl, methylcyclopropyl, trifluoromethyl-cyclopropyl, phenyl, methyl-piperidinyl, hydroxyl, methoxy, dimethylamino, or acetamido;
$R^2$ is H or methyl;
$R^4$ is H;
$R^5$ is H or D-valyloxymethyl;
$R^{3g}$ is fluoro or methyl;
each $R^{6a}$ and $R^{6b}$ is H;
m is an integer of 0, 1, or 2;
p is an integer of 1 or 2; and
n1 is an integer of 0, 1, 2, or 3.

In yet another embodiment, in any one of Formulae (IIIg) to (IIIi),
X is $CH_2$ or C(=O);
$R^Z$ is dimethylamino, phenyl, cyanophenyl, fluorophenyl, chlorophenyl, bromophenyl, methylphenyl, (1-trifluoromethylethyl)phenyl, trifluoromethylphenyl, dimethylaminomethylphenyl, morpholin-4-ylmethylphenyl, isopropylphenyl, sec-butylphenyl, tert-butylphenyl, (hydroxyl-tert-butyl)phenyl, cyclopropylphenyl, (1-methylcyclopropyl)phenyl, (1-trifluoromethylcyclopropyl)-phenyl, phenylphenyl, (1-methylpiperidin-4-yl)phenyl, hydroxylphenyl, methoxyphenyl, dimethylaminophenyl, acetamidophenyl, difluorophenyl, dichlorophenyl, chloro-methylphenyl, methyl-tert-butylphenyl, dimethylphenyl, trimethylphenyl, trimethoxyphenyl, dimethyl-tert-butylphenyl, dimethylamino-methylphenyl, naphthyl, thienyl, isopropylthienyl, pyridyl, tert-butylcyclohexyl, piperidinyl, or tert-butylpiperidinyl;

R² is H or methyl;
R⁴ is H;
R⁵ is H or D-valyloxymethyl;
$R^{3g}$ is fluoro or methyl;
each $R^{6a}$ and $R^{6b}$ is H;
m is an integer of 0, 1, or 2;
p is an integer of 1 or 2; and
n1 is an integer of 0, 1, or 2.

In yet another embodiment, in any one of Formulae (IIIg) to (IIIi),

X is CH₂ or C(=O);
$R^Z$ is dimethylamino, phenyl, 4-cyanophenyl, 2-fluorophenyl, 3-fluorophenyl, 4-fluorophenyl, 3-chlorophenyl, 4-chlorophenyl, 4-bromophenyl, 4-methylphenyl, 4-(1-trifluoromethylethyl)phenyl, 4-trifluoromethylphenyl, 4-dimethylaminomethylphenyl, 4-morpholin-4-ylmethylphenyl, 4-isopropylphenyl, 4-sec-butylphenyl, 3-tert-butylphenyl, 4-tert-butylphenyl, 4-(hydroxyl-tert-butyl)phenyl, 4-cyclopropylphenyl, 4-(1-methylcyclopropyl)phenyl, 4-(1-trifluoromethylcyclopropyl)phenyl, 4-phenylphenyl, 4-(1-methylpiperidin-4-yl)phenyl, 4-hydroxylphenyl, 3-methoxyphenyl, 4-methoxyphenyl, 4-dimethylaminophenyl, 4-acetamidophenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 3-dimethylamino-4-methylphenyl, 2-naphthyl, thien-2-yl, 5-isopropylthien-2-yl, 4-pyridyl, 4-tert-butylcyclohexyl, piperidin-4-yl, or 4-tert-butylpiperidin-1-yl;
R² is H or methyl;
R⁴ is H;
R⁵ is H or D-valyloxymethyl;
$R^{3g}$ is methyl;
each $R^{6a}$ and $R^{6b}$ is H;
m is an integer of 0, 1, or 2;
p is an integer of 1 or 2; and
n1 is an integer of 0, 1, or 2.

In still another embodiment, in any one of Formulae (IIIg) to (IIIi),

X is CH₂ or C(=O);
$R^Z$ is dimethylamino, phenyl, 4-cyanophenyl, 2-fluorophenyl, 3-fluorophenyl, 3-chlorophenyl, 4-trifluoromethylphenyl, 3-tert-butylphenyl, 4-tert-butylphenyl, 4-(1-trifluoromethylcyclopropyl)phenyl, 3-methoxyphenyl, 4-methoxyphenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 2-naphthyl, 5-isopropylthien-2-yl, 4-pyridyl, 4-tert-butylcyclohexyl, or 4-tert-butylpiperidin-1-yl;
R² is H or methyl;
R⁴ is H;
R⁵ is H or D-valyloxymethyl;
$R^{3g}$ is methyl;
m is an integer of 1 or 2;
p is an integer of 1 or 2; and
n1 is an integer of 0, 1, or 2.

In one embodiment, the compound of Formula (I) is:
2-(4-(tert-butyl)phenyl)-N-((5-(2,6-dioxopiperidin-3-yl)-4-oxo-5,6-dihydro-4H-thieno[3,4-c]pyrrol-1-yl)methyl)-2-oxoacetamide I-1;
2-(4-(tert-butyl)phenyl)-N-((2-(2,6-dioxopiperidin-3-yl)-1-oxoisoindolin-5-yl)methyl)-2-oxoacetamide I-2;
N-((5-(2,6-dioxopiperidin-3-yl)-4-oxo-5,6-dihydro-4H-thieno[3,4-c]pyrrol-1-yl)methyl)-2-oxo-2-(4-(1-(trifluoromethyl)cyclopropyl)phenyl)acetamide I-3;
N-((5-(2,6-dioxopiperidin-3-yl)-4-oxo-5,6-dihydro-4H-thieno[3,4-c]pyrrol-1-yl)methyl)-2-(5-isopropylthiophen-2-yl)-2-oxoacetamide I-4;
N-((2-(2,6-dioxopiperidin-3-yl)-1-oxoisoindolin-5-yl)methyl)-2-oxo-2-(4-(1-(trifluoromethyl)cyclopropyl)phenyl)acetamide I-5;
2-(3-chloro-4-methylphenyl)-N-((5-(2,6-dioxopiperidin-3-yl)-4-oxo-5,6-dihydro-4H-thieno[3,4-c]pyrrol-1-yl)methyl)-2-oxoacetamide I-6;
2-(4-dimethylaminophenyl)-N-((5-(2,6-dioxopiperidin-3-yl)-4-oxo-5,6-dihydro-4H-thieno[3,4-c]pyrrol-1-yl)methyl)-2-oxoacetamide I-7;
2-phenyl-N-((5-(2,6-dioxopiperidin-3-yl)-4-oxo-5,6-dihydro-4H-thieno[3,4-c]pyrrol-1-yl)methyl)-2-oxoacetamide I-8;
N-((5-(2,6-dioxopiperidin-3-yl)-4-oxo-5,6-dihydro-4H-thieno[3,4-c]pyrrol-1-yl)methyl)-2-(thiophen-2-yl)-2-oxoacetamide I-9;
(S)-2-(4-(tert-butyl)phenyl)-N-((2-(2,7-dioxoazepan-3-yl)-1-oxoisoindolin-5-yl)methyl)-2-oxoacetamide I-10;
2-(4-methoxyphenyl)-N-((5-(2,6-dioxopiperidin-3-yl)-4-oxo-5,6-dihydro-4H-thieno[3,4-c]pyrrol-1-yl)methyl)-2-oxoacetamide I-11;
2-(4-cyclopropylphenyl)-N-((5-(2,6-dioxopiperidin-3-yl)-4-oxo-5,6-dihydro-4H-thieno[3,4-c]pyrrol-1-yl)methyl)-2-oxoacetamide I-12;
2-(4-(tert-butyl)phenyl)-N-((5-(2,6-dioxopiperidin-3-yl)-4,6-dioxo-5,6-dihydro-4H-thieno[3,4-c]pyrrol-1-yl)methyl)-2-oxoacetamide I-13;
2-(4-isopropylphenyl)-N-((5-(2,6-dioxopiperidin-3-yl)-4-oxo-5,6-dihydro-4H-thieno[3,4-c]pyrrol-1-yl)methyl)-2-oxoacetamide I-14;
2-(4-(sec-butyl)phenyl)-N-((5-(2,6-dioxopiperidin-3-yl)-4-oxo-5,6-dihydro-4H-thieno[3,4-c]pyrrol-1-yl)methyl)-2-oxoacetamide I-15;
2-(4-hydroxyphenyl)-N-((5-(2,6-dioxopiperidin-3-yl)-4-oxo-5,6-dihydro-4H-thieno[3,4-c]pyrrol-1-yl)methyl)-2-oxoacetamide I-16;
2-(4-methylphenyl)-N-((5-(2,6-dioxopiperidin-3-yl)-4-oxo-5,6-dihydro-4H-thieno[3,4-c]pyrrol-1-yl)methyl)-2-oxoacetamide I-17;
2-(4-chlorophenyl)-N-((5-(2,6-dioxopiperidin-3-yl)-4-oxo-5,6-dihydro-4H-thieno[3,4-c]pyrrol-1-yl)methyl)-2-oxoacetamide I-18;
2-(3-tert-butylphenyl)-N-((5-(2,6-dioxopiperidin-3-yl)-4-oxo-5,6-dihydro-4H-thieno[3,4-c]pyrrol-1-yl)methyl)-2-oxoacetamide I-19;
2-(4-acetamidophenyl)-N-((5-(2,6-dioxopiperidin-3-yl)-4-oxo-5,6-dihydro-4H-thieno[3,4-c]pyrrol-1-yl)methyl)-2-oxoacetamide I-20;
2-([1,1'-biphenyl]-4-yl)-N-((5-(2,6-dioxopiperidin-3-yl)-4-oxo-5,6-dihydro-4H-thieno[3,4-c]pyrrol-1-yl)methyl)-2-oxoacetamide I-21;
2-(4-fluorophenyl)-N-((5-(2,6-dioxopiperidin-3-yl)-4-oxo-5,6-dihydro-4H-thieno[3,4-c]pyrrol-1-yl)methyl)-2-oxoacetamide I-22;
2-(4-trifluoromethylphenyl)-N-((5-(2,6-dioxopiperidin-3-yl)-4-oxo-5,6-dihydro-4H-thieno[3,4-c]pyrrol-1-yl)methyl)-2-oxoacetamide I-23;
2-(3,4-dichlorophenyl)-N-((5-(2,6-dioxopiperidin-3-yl)-4-oxo-5,6-dihydro-4H-thieno[3,4-c]pyrrol-1-yl)methyl)-2-oxoacetamide I-24;

2-(4-((dimethylamino)methyl)phenyl)-N-((5-(2,6-dioxopiperidin-3-yl)-4-oxo-5,6-dihydro-4H-thieno[3,4-c]pyrrol-1-yl)methyl)-2-oxoacetamide I-25;

2-(4-(morpholinomethyl)phenyl)-N-((5-(2,6-dioxopiperidin-3-yl)-4-oxo-5,6-dihydro-4H-thieno[3,4-c]pyrrol-1-yl)methyl)-2-oxoacetamide I-26;

2-(3-methyl-4-(tert-butyl)phenyl)-N-((5-(2,6-dioxopiperidin-3-yl)-4-oxo-5,6-dihydro-4H-thieno[3,4-c]pyrrol-1-yl)methyl)-2-oxoacetamide I-27;

2-(4-(tert-butyl)phenyl)-N-((2-(2,6-dioxopiperidin-3-yl)-1-oxoisoindolin-4-yl)methyl)-2-oxoacetamide I-28;

2-(4-(tert-butyl)phenyl)-N-((2-(2,6-dioxopiperidin-3-yl)-6-fluoro-1-oxoisoindolin-4-yl)methyl)-2-oxoacetamide I-29; or N-((2-(2,6-dioxopiperidin-3-yl)-1-oxoisoindolin-4-yl)methyl)-2-oxo-2-(4-(1-(trifluoromethyl)cyclopropyl)phenyl)acetamide I-30;

or a pharmaceutically acceptable salt thereof.

In another embodiment, provided herein is:

2-(4-(tert-butyl)phenyl)-N-((5-(2,6-dioxopiperidin-3-yl)-4-oxo-5,6-dihydro-4H-thieno[3,4-c]pyrrol-1-yl)methyl)-2-oxoacetamide I-1;

N-((5-(2,6-dioxopiperidin-3-yl)-4-oxo-5,6-dihydro-4H-thieno[3,4-c]pyrrol-1-yl)methyl)-2-oxo-2-(4-(1-(trifluoromethyl)cyclopropyl)phenyl)acetamide I-3;

N-((5-(2,6-dioxopiperidin-3-yl)-4-oxo-5,6-dihydro-4H-thieno[3,4-c]pyrrol-1-yl)methyl)-2-(5-isopropylthiophen-2-yl)-2-oxoacetamide I-4;

2-(3-chloro-4-methylphenyl)-N-((5-(2,6-dioxopiperidin-3-yl)-4-oxo-5,6-dihydro-4H-thieno[3,4-c]pyrrol-1-yl)methyl)-2-oxoacetamide I-6;

2-(4-dimethylaminophenyl)-N-((5-(2,6-dioxopiperidin-3-yl)-4-oxo-5,6-dihydro-4H-thieno[3,4-c]pyrrol-1-yl)methyl)-2-oxoacetamide I-7;

2-phenyl-N-((5-(2,6-dioxopiperidin-3-yl)-4-oxo-5,6-dihydro-4H-thieno[3,4-c]pyrrol-1-yl)methyl)-2-oxoacetamide I-8;

N-((5-(2,6-dioxopiperidin-3-yl)-4-oxo-5,6-dihydro-4H-thieno[3,4-c]pyrrol-1-yl)methyl)-2-(thiophen-2-yl)-2-oxoacetamide I-9;

2-(4-methoxyphenyl)-N-((5-(2,6-dioxopiperidin-3-yl)-4-oxo-5,6-dihydro-4H-thieno[3,4-c]pyrrol-1-yl)methyl)-2-oxoacetamide I-11;

2-(4-cyclopropylphenyl)-N-((5-(2,6-dioxopiperidin-3-yl)-4-oxo-5,6-dihydro-4H-thieno[3,4-c]pyrrol-1-yl)methyl)-2-oxoacetamide I-12;

2-(4-(tert-butyl)phenyl)-N-((5-(2,6-dioxopiperidin-3-yl)-4,6-dioxo-5,6-dihydro-4H-thieno[3,4-c]pyrrol-1-yl)methyl)-2-oxoacetamide I-13;

2-(4-isopropylphenyl)-N-((5-(2,6-dioxopiperidin-3-yl)-4-oxo-5,6-dihydro-4H-thieno[3,4-c]pyrrol-1-yl)methyl)-2-oxoacetamide I-14;

2-(4-(sec-butyl)phenyl)-N-((5-(2,6-dioxopiperidin-3-yl)-4-oxo-5,6-dihydro-4H-thieno[3,4-c]pyrrol-1-yl)methyl)-2-oxoacetamide I-15;

2-(4-hydroxyphenyl)-N-((5-(2,6-dioxopiperidin-3-yl)-4-oxo-5,6-dihydro-4H-thieno[3,4-c]pyrrol-1-yl)methyl)-2-oxoacetamide I-16;

2-(4-methylphenyl)-N-((5-(2,6-dioxopiperidin-3-yl)-4-oxo-5,6-dihydro-4H-thieno[3,4-c]pyrrol-1-yl)methyl)-2-oxoacetamide I-17;

2-(4-chlorophenyl)-N-((5-(2,6-dioxopiperidin-3-yl)-4-oxo-5,6-dihydro-4H-thieno[3,4-c]pyrrol-1-yl)methyl)-2-oxoacetamide I-18;

2-(3-tert-butylphenyl)-N-((5-(2,6-dioxopiperidin-3-yl)-4-oxo-5,6-dihydro-4H-thieno[3,4-c]pyrrol-1-yl)methyl)-2-oxoacetamide I-19;

2-(4-acetamidophenyl)-N-((5-(2,6-dioxopiperidin-3-yl)-4-oxo-5,6-dihydro-4H-thieno[3,4-c]pyrrol-1-yl)methyl)-2-oxoacetamide I-20;

2-([1,1'-biphenyl]-4-yl)-N-((5-(2,6-dioxopiperidin-3-yl)-4-oxo-5,6-dihydro-4H-thieno[3,4-c]pyrrol-1-yl)methyl)-2-oxoacetamide I-21;

2-(4-fluorophenyl)-N-((5-(2,6-dioxopiperidin-3-yl)-4-oxo-5,6-dihydro-4H-thieno[3,4-c]pyrrol-1-yl)methyl)-2-oxoacetamide I-22;

2-(4-trifluoromethylphenyl)-N-((5-(2,6-dioxopiperidin-3-yl)-4-oxo-5,6-dihydro-4H-thieno[3,4-c]pyrrol-1-yl)methyl)-2-oxoacetamide I-23;

2-(3,4-dichlorophenyl)-N-((5-(2,6-dioxopiperidin-3-yl)-4-oxo-5,6-dihydro-4H-thieno[3,4-c]pyrrol-1-yl)methyl)-2-oxoacetamide I-24;

2-(4-((dimethylamino)methyl)phenyl)-N-((5-(2,6-dioxopiperidin-3-yl)-4-oxo-5,6-dihydro-4H-thieno[3,4-c]pyrrol-1-yl)methyl)-2-oxoacetamide I-25;

2-(4-(morpholinomethyl)phenyl)-N-((5-(2,6-dioxopiperidin-3-yl)-4-oxo-5,6-dihydro-4H-thieno[3,4-c]pyrrol-1-yl)methyl)-2-oxoacetamide I-26;

2-(3-methyl-4-(tert-butyl)phenyl)-N-((5-(2,6-dioxopiperidin-3-yl)-4-oxo-5,6-dihydro-4H-thieno[3,4-c]pyrrol-1-yl)methyl)-2-oxoacetamide I-27;

N-((5-(2,6-dioxopiperidin-3-yl)-4-oxo-5,6-dihydro-4H-thieno[3,4-c]pyrrol-1-yl)methyl)-2-(4-(1-methylpiperidin-4-yl)phenyl)-2-oxoacetamide I-31;

N-((5-(2,6-dioxopiperidin-3-yl)-4-oxo-5,6-dihydro-4H-thieno[3,4-c]pyrrol-1-yl)methyl)-2-oxo-2-(4-(1,1,1-trifluoropropan-2-yl)phenyl)acetamide I-36;

2-(4-(tert-butyl)phenyl)-N-((5-(2,6-dioxopiperidin-3-yl)-4-oxo-5,6-dihydro-4H-thieno[3,4-c]pyrrol-1-yl)methyl)-2-oxoacetamide I-40;

2-(4-(tert-butyl)phenyl)-N-(2-(5-(2,6-dioxopiperidin-3-yl)-4-oxo-5,6-dihydro-4H-thieno[3,4-c]pyrrol-1-yl)ethyl)-2-oxoacetamide I-41;

N-((5-(2,6-dioxopiperidin-3-yl)-4-oxo-5,6-dihydro-4H-thieno[3,4-c]pyrrol-1-yl)methyl)-2-(4-(1-methylcyclopropyl)phenyl)-2-oxoacetamide I-42;

N-((5-(2,6-dioxopiperidin-3-yl)-4-oxo-5,6-dihydro-4H-thieno[3,4-c]pyrrol-1-yl)methyl)-2-(4-(1-hydroxy-2-methylpropan-2-yl)phenyl)-2-oxoacetamide I-43;

2-(3-(dimethylamino)-4-methylphenyl)-N-((5-(2,6-dioxopiperidin-3-yl)-4-oxo-5,6-dihydro-4H-thieno[3,4-c]pyrrol-1-yl)methyl)-2-oxoacetamide I-44; or $N^1$-((5-(2,6-dioxopiperidin-3-yl)-4-oxo-5,6-dihydro-4H-thieno[3,4-c]pyrrol-1-yl)methyl)-$N^2$,$N^2$-dimethyloxalamide I-70;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is:

2-(4-(tert-butyl)phenyl)-N-((2-(2,6-dioxopiperidin-3-yl)-1-oxoisoindolin-5-yl)methyl)-2-oxoacetamide I-2;

N-((2-(2,6-dioxopiperidin-3-yl)-1-oxoisoindolin-5-yl)methyl)-2-oxo-2-(4-(1-(trifluoromethyl)cyclopropyl)phenyl)acetamide I-5;

(S)-2-(4-(tert-butyl)phenyl)-N-((2-(2,7-dioxoazepan-3-yl)-1-oxoisoindolin-5-yl)methyl)-2-oxoacetamide I-10;

2-(4-(tert-butyl)phenyl)-N-((2-(2,6-dioxopiperidin-3-yl)-1,3-dioxoisoindolin-5-yl)methyl)-2-oxoacetamide I-32;

2-(3-(tert-butyl)phenyl)-N-((2-(2,6-dioxopiperidin-3-yl)-1-oxoisoindolin-5-yl)methyl)-2-oxoacetamide I-33;

2-(4-(tert-butyl)phenyl)-N-((2-(2,6-dioxopiperidin-3-yl)-1-oxoisoindolin-5-yl)methyl)-N-methyl-2-oxoacetamide I-34;

N-((2-(2,6-dioxopiperidin-3-yl)-1-oxoisoindolin-5-yl)methyl)-2-(5-isopropylthiophen-2-yl)-2-oxoacetamide I-37;

N-(2-(2-(2,6-Dioxopiperidin-3-yl)-1-oxoisoindolin-5-yl)ethyl)-2-oxo-2-(4-(1-(trifluoromethyl)cyclopropyl)phenyl)acetamide I-52;

2-(3-chloro-4-methylphenyl)-N-((2-(2,6-dioxopiperidin-3-yl)-1-oxoisoindolin-5-yl)methyl)-2-oxoacetamide I-53;

2-(3-methyl-4-(tert-butyl)phenyl)-N-((2-(2,6-dioxopiperidin-3-yl)-1-oxoisoindolin-5-yl)methyl)-2-oxoacetamide I-55;

N-((2-(2,6-dioxopiperidin-3-yl)-4-methyl-1-oxoisoindolin-5-yl)methyl)-2-oxo-2-(4-(1-(trifluoromethyl)cyclopropyl)phenyl)acetamide I-60;

2-(4-(tert-butyl)piperidin-1-yl)-N-((2-(2,6-dioxopiperidin-3-yl)-1-oxoisoindolin-5-yl)methyl)-2-oxoacetamide I-62;

N-((2-(2,6-dioxopiperidin-3-yl)-1-oxoisoindolin-5-yl)methyl)-2-oxo-3-(4-(1-(trifluoromethyl)cyclopropyl)phenyl)propanamide I-63;

2-(4-(tert-butyl)cyclohexyl)-N-((2-(2,6-dioxopiperidin-3-yl)-1-oxoisoindolin-5-yl)methyl)-2-oxoacetamide I-68;

N-((2-(2,6-dioxopiperidin-3-yl)-1-oxoisoindolin-5-yl)methyl)-2-oxo-2-phenylacetamide I-83;

N-((2-(2,6-dioxopiperidin-3-yl)-1-oxoisoindolin-5-yl)methyl)-2-oxo-2-(2,4,6-trimethoxyphenyl)acetamide I-84;

N-((2-(2,6-dioxopiperidin-3-yl)-1-oxoisoindolin-5-yl)methyl)-2-oxo-2-(2,4,6-trimethylphenyl)acetamide I-85;

N-((2-(2,6-dioxopiperidin-3-yl)-1-oxoisoindolin-5-yl)methyl)-2-oxo-2-(2-fluorophenyl)acetamide I-86;

N-((2-(2,6-dioxopiperidin-3-yl)-1-oxoisoindolin-5-yl)methyl)-2-oxo-2-(4-trifluoromethylphenyl)acetamide I-87;

N-((2-(2,6-dioxopiperidin-3-yl)-1-oxoisoindolin-5-yl)methyl)-2-(4-methoxyphenyl)-2-oxoacetamide I-89;

2-(4-cyanophenyl)-N-((2-(2,6-dioxopiperidin-3-yl)-1-oxoisoindolin-5-yl)methyl)-2-oxoacetamide I-90;

2-(3-chlorophenyl)-N-((2-(2,6-dioxopiperidin-3-yl)-1-oxoisoindolin-5-yl)methyl)-2-oxoacetamide I-91;

2-(3,4-difluorophenyl)-N-((2-(2,6-dioxopiperidin-3-yl)-1-oxoisoindolin-5-yl)methyl)-2-oxoacetamide I-93;

N-((2-(2,6-dioxopiperidin-3-yl)-1-oxoisoindolin-5-yl)methyl)-2-(3-methoxyphenyl)-2-oxoacetamide I-95;

N-((2-(2,6-dioxopiperidin-3-yl)-1-oxoisoindolin-5-yl)methyl)-2-(naphthalen-2-yl)-2-oxoacetamide I-97;

2-(3,5-dimethylphenyl)-N-((2-(2,6-dioxopiperidin-3-yl)-1-oxoisoindolin-5-yl)methyl)-2-oxoacetamide I-99;

N-((2-(2,6-dioxopiperidin-3-yl)-1-oxoisoindolin-5-yl)methyl)-2-(3-fluorophenyl)-2-oxoacetamide I-100;

2-(3,4-dichlorophenyl)-N-((2-(2,6-dioxopiperidin-3-yl)-1-oxoisoindolin-5-yl)methyl)-2-oxoacetamide I-102;

N-((2-(2,6-dioxopiperidin-3-yl)-1-oxoisoindolin-5-yl)methyl)-2-oxo-2-(pyridin-4-yl)acetamide I-103; or 2-(4-(tert-butyl)-2,6-dimethylphenyl)-N-((2-(2,6-dioxopiperidin-3-yl)-1-oxoisoindolin-5-yl)methyl)-2-oxoacetamide I-104;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is:

2-(4-(tert-butyl)phenyl)-N-((2-(2,6-dioxopiperidin-3-yl)-1-oxoisoindolin-4-yl)methyl)-2-oxoacetamide I-28;

2-(4-(tert-butyl)phenyl)-N-((2-(2,6-dioxopiperidin-3-yl)-6-fluoro-1-oxoisoindolin-4-yl)methyl)-2-oxoacetamide I-29;

N-((2-(2,6-dioxopiperidin-3-yl)-1-oxoisoindolin-4-yl)methyl)-2-oxo-2-(4-(1-(trifluoromethyl)cyclopropyl)phenyl)acetamide I-30;

2-(3-(tert-butyl)phenyl)-N-((2-(2,6-dioxopiperidin-3-yl)-1-oxoisoindolin-4-yl)methyl)-2-oxoacetamide I-46;

2-(4-(tert-butyl)phenyl)-N-((2-(2,6-dioxopiperidin-3-yl)-1-oxoisoindolin-4-yl)methyl)-N-methyl-2-oxoacetamide I-47;

2-(4-(tert-butyl)phenyl)-N-((2-(2,6-dioxopiperidin-3-yl)-1,3-dioxoisoindolin-4-yl)methyl)-2-oxoacetamide I-48;

(2R)-(3-(4-((2-(4-(tert-butyl)phenyl)-2-oxoacetamido)methyl)-1-oxoisoindolin-2-yl)-2,6-dioxopiperidin-1-yl) methyl 2-amino-3-methylbutanoate I-49;

2-(4-(tert-butyl)phenyl)-N-((2-(2,6-dioxopiperidin-3-yl)-5-fluoro-1-oxoisoindolin-4-yl)methyl)-2-oxoacetamide I-50;

2-(4-(tert-butyl)phenyl)-N-((2-(2,6-dioxopiperidin-3-yl)-5,6-difluoro-1-oxoisoindolin-4-yl)methyl)-2-oxoacetamide I-51;

2-(3-methyl-4-(tert-butyl)phenyl)-N-((2-(2,6-dioxopiperidin-3-yl)-1-oxoisoindolin-4-yl)methyl)-2-oxoacetamide I-54;

2-(4-(tert-butyl)phenyl)-N-(2-(2,6-dioxopiperidin-3-yl)-1-oxoisoindolin-4-yl)-2-oxoacetamide I-56;

N-(2-(2,6-dioxopiperidin-3-yl)-1-oxoisoindolin-4-yl)-2-oxo-2-(4-(1-(trifluoromethyl)cyclopropyl)phenyl)acetamide I-57;

N-((2-(2,6-dioxopiperidin-3-yl)-1,3-dioxoisoindolin-4-yl)methyl)-2-oxo-2-(4-(1-(trifluoromethyl)cyclopropyl)phenyl)acetamide I-58;

N-((2-(2,6-dioxopiperidin-3-yl)-1-oxoisoindolin-4-yl)methyl)-2-(5-isopropylthiophen-2-yl)-2-oxoacetamide I-59;

2-(4-(tert-butyl)piperidin-1-yl)-N-((2-(2,6-dioxopiperidin-3-yl)-1-oxoisoindolin-4-yl)methyl)-2-oxoacetamide I-61;

(2,6-dioxo-3-(1-oxo-4-((2-oxo-2-(4-(1-(trifluoromethyl)cyclopropyl)-phenyl)acetamido)methyl)isoindolin-2-yl)piperidin-1-yl)methyl D-valinate I-64;

N-(2-(2-(2,6-dioxopiperidin-3-yl)-1-oxoisoindolin-4-yl)ethyl)-2-oxo-2-(4-(1-(trifluoromethyl)cyclopropyl)phenyl)acetamide I-65;

N-((2-(2,6-dioxopiperidin-3-yl)-1-oxoisoindolin-4-yl)methyl)-2-oxo-2-(4-(piperidin-4-yl)phenyl)acetamide I-66;

2-(4-(tert-butyl)cyclohexyl)-N-((2-(2,6-dioxopiperidin-3-yl)-1-oxoisoindolin-4-yl)methyl)-2-oxoacetamide I-67;

N-((2-(2,6-dioxopiperidin-3-yl)-1-oxoisoindolin-4-yl)methyl)-2-oxo-2-(p-tolyl)acetamide I-72;

2-(3,4-difluorophenyl)-N-((2-(2,6-dioxopiperidin-3-yl)-1-oxoisoindolin-4-yl)methyl)-2-oxoacetamide I-73;

N-((2-(2,6-dioxopiperidin-3-yl)-1-oxoisoindolin-4-yl)methyl)-2-oxo-2-phenylacetamide I-74;

N-((2-(2,6-dioxopiperidin-3-yl)-1-oxoisoindolin-4-yl)methyl)-2-oxo-2-(4-(trifluoromethyl)phenyl)acetamide I-75;

2-(4-cyanophenyl)-N-((2-(2,6-dioxopiperidin-3-yl)-1-oxoisoindolin-4-yl)methyl)-2-oxoacetamide I-76;

2-(4-chlorophenyl)-N-((2-(2,6-dioxopiperidin-3-yl)-1-oxoisoindolin-4-yl)methyl)-2-oxoacetamide I-77;

2-(4-methoxyphenyl)-N-((2-(2,6-dioxopiperidin-3-yl)-1-oxoisoindolin-4-yl)methyl)-2-oxoacetamide I-78;

2-(2,4,6-trimethoxyphenyl)-N-((2-(2,6-dioxopiperidin-3-yl)-1-oxoisoindolin-4-yl)methyl)-2-oxoacetamide I-79;

2-(2,4,6-trimethylphenyl)-N-((2-(2,6-dioxopiperidin-3-yl)-1-oxoisoindolin-4-yl)methyl)-2-oxoacetamide I-80;
2-(4-fluorophenyl)-N-((2-(2,6-dioxopiperidin-3-yl)-1-oxoisoindolin-4-yl)methyl)-2-oxoacetamide I-81;
2-(2-fluorophenyl)-N-((2-(2,6-dioxopiperidin-3-yl)-1-oxoisoindolin-4-yl)methyl)-2-oxoacetamide I-82;
2-(3-chlorophenyl)-N-((2-(2,6-dioxopiperidin-3-yl)-1-oxoisoindolin-4-yl)methyl)-2-oxoacetamide I-88;
2-(3-fluorophenyl)-N-((2-(2,6-dioxopiperidin-3-yl)-1-oxoisoindolin-4-yl)methyl)-2-oxoacetamide I-92;
2-(3-methoxyphenyl)-N-((2-(2,6-dioxopiperidin-3-yl)-1-oxoisoindolin-4-yl)methyl)-2-oxoacetamide I-94;
N-((2-(2,6-dioxopiperidin-3-yl)-1-oxoisoindolin-4-yl)methyl)-2-(naphthalen-2-yl)-2-oxoacetamide I-96;
2-(3,5-dimethylphenyl)-N-((2-(2,6-dioxopiperidin-3-yl)-1-oxoisoindolin-4-yl)methyl)-2-oxoacetamide I-98;
2-(3,4-dichlorophenyl)-N-((2-(2,6-dioxopiperidin-3-yl)-1-oxoisoindolin-4-yl)methyl)-2-oxoacetamide I-101;
2-(4-(tert-butyl)-2,6-dimethylphenyl)-N-((2-(2,6-dioxopiperidin-3-yl)-1-oxoisoindolin-4-yl)methyl)-2-oxoacetamide I-105; or
2-(4-bromophenyl)-N-((2-(2,6-dioxopiperidin-3-yl)-1-oxoisoindolin-4-yl)methyl)-2-oxoacetamide I-106;
or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In still another embodiment, provided herein is:
2-(4-(tert-butyl)phenyl)-N-((5-(2,6-dioxopiperidin-3-yl)-6-oxo-5,6-dihydro-4H-thieno[2,3-c]pyrrol-2-yl)methyl)-2-oxoacetamide I-35;
2-(4-(tert-butyl)phenyl)-N-((2-(2,6-dioxopiperidin-3-yl)-3-oxoisoindolin-4-yl)methyl)-2-oxoacetamide I-38;
2-(4-(tert-butyl)phenyl)-N-((5-(2,6-dioxopiperidin-3-yl)-6-oxo-5,6-dihydro-4H-thieno[2,3-c]pyrrol-3-yl)methyl)-2-oxoacetamide I-39;
2-(4-(tert-butyl)phenyl)-N-((5-(2,6-dioxopiperidin-3-yl)-6-oxo-5,6-dihydro-4H-thieno[2,3-c]pyrrol-2-yl)methyl)-2-oxoacetamide I-45;
N-((5-(2,6-dioxopiperidin-3-yl)-6-oxo-5,6-dihydro-4H-thieno[2,3-c]pyrrol-2-yl)methyl)-2-oxo-4-phenylbutanamide I-69; or
N$^1$-((5-(2,6-dioxopiperidin-3-yl)-6-oxo-5,6-dihydro-4H-thieno[2,3-c]pyrrol-2-yl)methyl)-N$^2$,N$^2$-dimethyloxalamide I-71;
or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

Compounds of Formulae (IIa), (IIb), and (IIc)

In one embodiment, provided herein is a compound of Formula (IIa), (IIb), or (IIc):

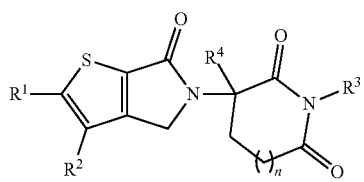
(IIa)

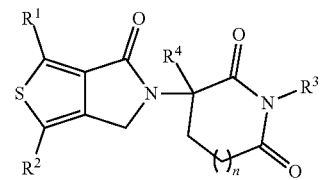
(IIb)

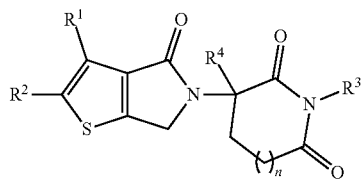
(IIc)

or a pharmaceutically acceptable salt thereof, wherein R$^1$, R$^2$, R$^3$, R$^4$, and n are each as described herein.

In certain embodiments, in Formula (IIa), one of R$^1$ and R$^2$ is H, n is 1 or 2, R$^3$ is H, R$^4$ is H, L is —CH$_2$—NH—C(=O)—NH—CH$_2$— or —CH$_2$—NH—C(=O)—NH—*, then ring A is not

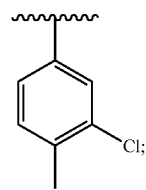 [SMILES: *c1ccc(C)c(Cl)c1]

wherein the symbol "*" indicates the attachment point to ring A. In certain embodiments, in Formula (IIb), R is H, n is 1 or 2, R$^3$ is H, R$^4$ is H, L is —NH—C(=O)—CH$_2$—*, —CH$_2$—NH—C(=O)—CH$_2$—*, or —CH$_2$—NH—C(=S)—NH—*, then ring A is not

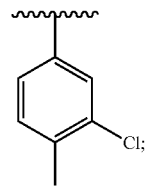 [SMILES: *c1ccc(C)c(Cl)c1]

wherein the symbol "*" indicates the attachment point to ring A. In certain embodiments, in Formula (IIb), R$^1$ is H, n is 1 or 2, R$^3$ is H, R$^4$ is H, L is —NH—C(=O)—NH—, —CH$_2$—NH—C(=O)—NH—CH$_2$—, or —CH$_2$—NH—C(=O)—NH—*, then ring A is not

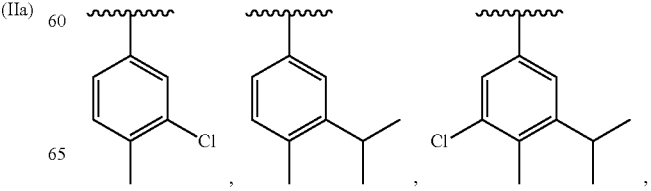

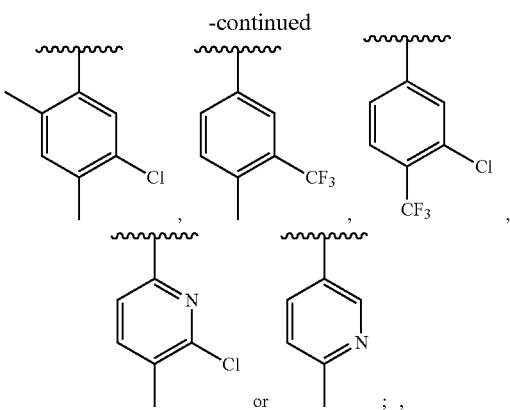

wherein the symbol "*" indicates the attachment point to ring A. In certain embodiments, in Formula (IIc), $R^1$ is H, n is 1, $R^3$ is H, $R^4$ is H, L is —$CH_2$—NH—C(=O)—NH—*, then ring A is not

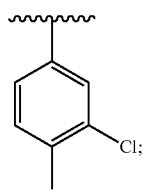

wherein the symbol "*" indicates the attachment point to ring A.

In certain embodiments, in Formula (IIa), (IIb), or (IIc), one of $R^1$ and $R^2$ is H. In certain embodiments, in Formula (IIa), (IIb) or (IIc), $R^1$ is H. In certain embodiments, in Formula (IIa), (IIb), or (IIc), $R^2$ is H.

In certain embodiments, in Formula (IIa), (IIb), or (IIc), n is 1. In certain embodiments, in Formula (IIa), (IIb), or (IIc), n is 2. In certain embodiments, in Formula (IIa), (IIb), or (IIc), n is 0.

In certain embodiments, in Formula (IIa), (IIb), or (IIc), $R^3$ is H. In certain embodiments, in Formula (IIa), (IIb), or (IIc), $R^3$ is $C_1$-$C_6$ alkyl, for example, methyl, ethyl, or isopropyl. In certain embodiments, in Formula (IIa), (IIb), or (IIc), $R^3$ is

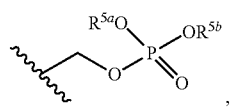

and wherein $R^{5a}$ and $R^{5b}$ are each independently H or $C_1$-$C_6$ alkyl. In certain embodiments, in Formula (IIa), (IIb), or (IIc), $R^3$ is

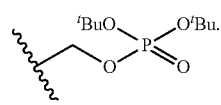

In certain embodiments, in Formula (IIa), (IIb), or (IIc), $R^3$ is

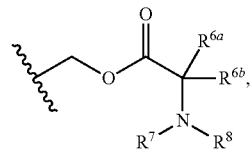

wherein $R^7$ and $R^8$ are each H, and $R^{6a}$ and $R^{6b}$ are each independently H or optionally substituted $C_1$-$C_6$ alkyl. In certain embodiments, in Formula (IIa), (IIb), or (IIc), $R^3$ is

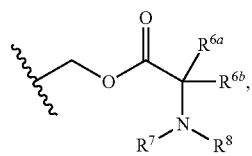

wherein $R^7$ and $R^8$ are each H; and $R^{6a}$ and $R^{6b}$ are each as defined herein. In certain embodiments, in Formula (IIa), (IIb), or (IIc), $R^3$ is

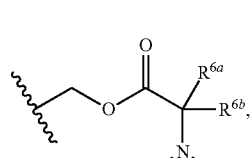

wherein $R^7$ and $R^8$ together with the nitrogen atom to which they are attached form optionally substituted 3 to 7 membered heterocyclyl; and $R^{6a}$ and $R^{6b}$ are each as defined herein. In certain embodiments, in Formula (IIa), (IIb), or (IIc), $R^3$ is valyloxymethyl. In one embodiment, $R^3$ is L-valyloxymethyl. In another embodiment, $R^3$ is D-valyloxymethyl.

In certain embodiments, in Formula (IIa), (IIb) or (IIc), $R^4$ is H. In certain embodiments, in Formula (IIa), (IIb) or (IIc), $R^4$ is $C_1$-$C_6$ alkyl, for example, methyl, ethyl, or isopropyl.

In certain embodiments, in Formula (IIa), (IIb) or (IIc), L is

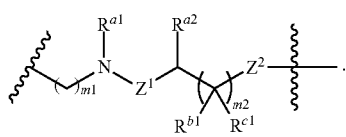

In certain embodiments, each $R^{a1}$ and $R^{a2}$ is independently H or $C_1$-$C_6$ alkyl, for example, methyl. In certain embodiments, $Z^2$ is a bond. In certain embodiments, $Z^2$ is O. In certain embodiments, one of $R^{b1}$ and $R^{c1}$ is H, halogen, $C_1$-$C_6$ alkyl, or $C_1$-$C_6$ haloalkyl; and the other one of $R^{b1}$ and $R^{c1}$ is halogen, $C_1$-$C_6$ alkyl, $C_1$-$C_6$ haloalkyl, $C_3$-$C_7$ cycloalkyl, —$NH_2$, —NH($C_1$-$C_4$ alkyl), —N($C_1$-$C_4$ alkyl)$_2$, or hydroxyl. In certain embodiments, $R^{b1}$ is H, and $R^{c1}$ is hydroxyl, trifluoromethyl, methyl, ethyl, isopropyl, cyclopropyl, methoxy, —$NH_2$, —$NHCH_3$, —$NHC_2H_5$, —$N(CH_3)_2$, or —$N(C_2H_5)_2$; or $R^{b1}$ is fluoro or trifluoromethyl, and $R^{c1}$ is fluoro or hydroxyl. In certain embodiments, $R^{b1}$ and $R^{c1}$ together with the carbon atom to which they are attached form a $C_3$-$C_7$ cycloalkyl optionally substituted with one or more $R^B$, for example, a cyclopropyl optionally substituted with a halogen or trifluoromethyl. In certain embodiments, both $R^{b1}$ and $R^{c1}$ are H, and L is

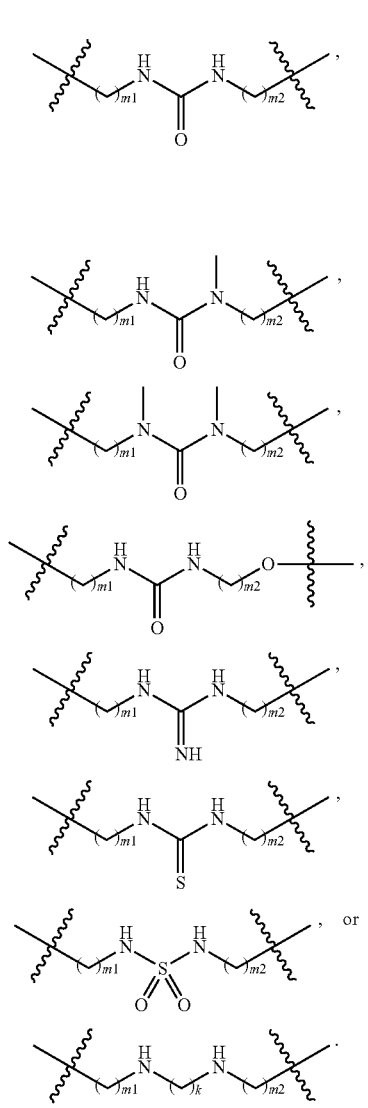

In one embodiment, L is

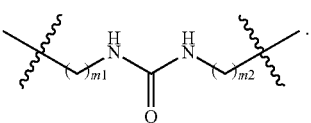

In another embodiment, L is

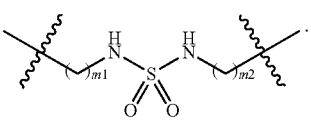

In yet another embodiment, L is

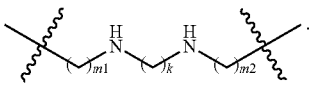

In certain embodiments, each m1 is independently 0, 1, or 2. In certain embodiments, each m2 is independently 0, 1, 2, or 3. For example, the combination of m1 and m2 may be 0 and 1; 1 and 0; 1 and 1; 2 and 1; 1 and 2; or 1 and 3. In certain embodiments, k is 3, 4, or 5. In certain embodiments, L is connected to ring A on the right side.

In certain embodiments, in Formula (IIa), (IIb), or (IIc), L is

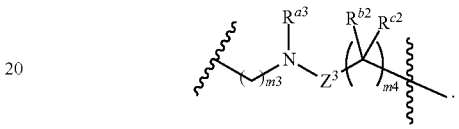

In certain embodiments, $R^{a3}$ is H or $C_1$-$C_6$ alkyl (for example, methyl). In certain embodiments, L is

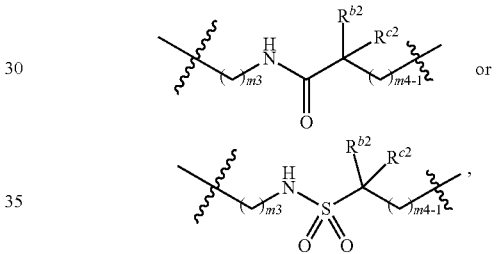

where the —($CH_2$)— on the right side of L has m4 minus 1 repeating units. In certain embodiments, each m3 is independently 0, 1, or 2. In certain embodiments, each m4 is independently 1, 2, or 3. For example, the combination of m3 and m4 may be 0 and 1; 1 and 1; 2 and 1; 1 and 2; or 1 and 3. In certain embodiments, both $R^{b2}$ and $R^{c2}$ are H. In certain embodiments, one of $R^{b2}$ and $R^{c2}$ is H, halogen, $C_1$-$C_6$ alkyl, or $C_1$-$C_6$ haloalkyl, and the other one of $R^{b2}$ and $R^{c2}$ is halogen, $C_1$-$C_6$ alkyl, $C_1$-$C_6$ haloalkyl, $C_3$-$C_7$ cycloalkyl, —$NH_2$, —NH($C_1$-$C_4$ alkyl), —N($C_1$-$C_4$ alkyl)$_2$, or hydroxyl. In certain embodiments, $R^{b2}$ is H and $R^{c2}$ is hydroxyl, trifluoromethyl, methyl, ethyl, isopropyl, cyclopropyl, methoxy, —$NH_2$, —$NHCH_3$, —$NHC_2H_5$, —$N(CH_3)_2$, or —$N(C_2H_5)_2$; or $R^{b2}$ is fluoro or trifluoromethyl, and $R^{c2}$ is fluoro or hydroxyl. In certain embodiments, $R^{b2}$ and $R^{c2}$ together with the carbon atom to which they are attached form a $C_3$-$C_7$ cycloalkyl optionally substituted with one or more $R^B$, for example, a cyclopropyl optionally substituted with a halogen or trifluoromethyl. In certain embodiments, L is connected to ring A on the right side.

In certain embodiments, in Formula (IIa), (IIb) or (IIc), ring A is phenyl, unsubstituted or substituted with one or more $R^A$. In certain embodiments, ring A is 5, 6, 9, or 10 membered heteroaryl containing 1, 2, or 3 heteroatoms selected from the group consisting of N, O, and S, for example, ring A is pyridyl, thienyl, furyl, pyrimidinyl, pyrazolyl, imidazolyl, thiazolyl, isothiazolyl, oxazolyl, isoxazolyl, or thiadiazolyl, each independently unsubstituted or substituted with one or more $R^A$. In one embodiment, ring A is thienyl, unsubstituted or substituted with one or more $R^A$. Other non-limiting examples of ring A may be selected from the group consisting of

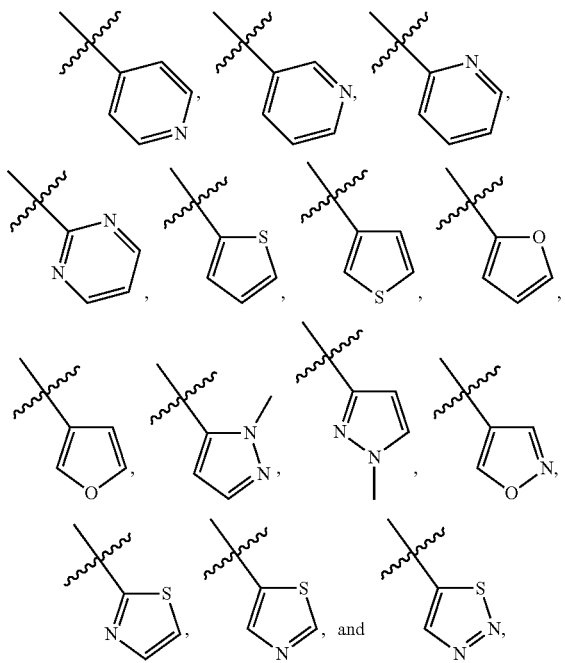

each of which is optionally substituted with one or more $R^A$. In certain embodiments, ring A is $C_3$-$C_7$ carbocyclyl, $C_3$-$C_7$ cycloalkyl, or $C_5$-$C_7$ cycloalkyl, for example, cyclopentyl or cyclohexyl, each independently unsubstituted or substituted with one or more $R^A$. In certain embodiments, ring A is 5, 6, 9, or 10 membered heterocyclyl containing 1, 2, or 3 heteroatoms selected from the group consisting of N, O, and S, for example, ring A is

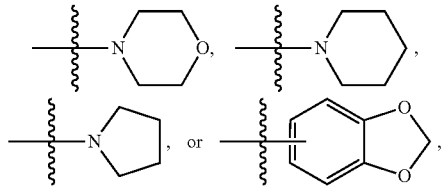

each of which is optionally substituted with one or more $R^A$. In certain embodiments, ring A is substituted with one, two, or three $R^A$. In certain embodiments, ring A is unsubstituted.

In certain embodiments, in Formula (IIa), (IIb) or (IIc), each $R^A$ is independently halogen, hydroxyl, $C_1$-$C_6$ alkyl, $C_1$-$C_6$ haloalkyl, $C_1$-$C_6$ haoalkoxy, —$(CH_2)_t$—$NR^{7a}R^{8a}$, —$O(CH_2)_t$—$NR^{7a}R^{8a}$, —$C(O)NR^{7b}R^{8b}$, —$C(O)OR^{10b}$, —$NR^{7d}C(O)R^{11b}$, phenyl, or $C_3$-$C_7$ cycloalkyl, wherein each phenyl and $C_3$-$C_7$ cycloalkyl is optionally substituted with one or more $R^B$. In certain embodiments, $R^A$ is —$(CH_2)_t$—$NR^{7a}R^{8a}$ or —$O(CH_2)_t$—$NR^{7a}R^{8a}$; t is 0 or 1; and each $R^{7a}$ and $R^{8a}$ is independently $C_1$-$C_6$ alkyl, or $R^{7a}$ and $R^{8a}$ together with the nitrogen atoms to which they are attached form a 5 or 6 membered heterocyclyl, for example,

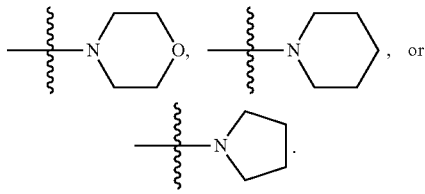

In certain embodiments, $R^A$ is —$C(O)NR^{7b}R^{8b}$; each $R^{7b}$ and $R^{8b}$ is independently $C_1$-$C_6$ alkyl, or $R^{7b}$ and $R^{8b}$ together with the nitrogen atoms to which they are attached form a 5 or 6 membered heterocyclyl, for example,

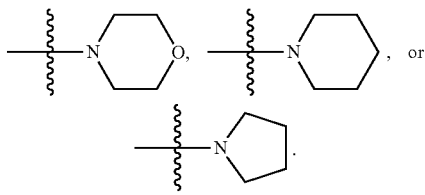

In certain embodiments, $R^A$ is —$C(O)OR^{10b}$, and $R^{10b}$ is $C_1$-$C_6$ alkyl, for example, methyl. In certain embodiments, $R^A$ is —$NR^{7d}C(O)R^{11b}$, $R^{7d}$ is H, and $R^{11b}$ is $C_1$-$C_6$ alkyl. In certain embodiments, $R^A$ is —$SR^{10a}$, and $R^{10a}$ is $C_1$-$C_6$ alkyl. In certain embodiments, each $R^A$ is independently halogen, methyl, isopropyl, t-butyl, isobutyl, hydroxyl, methoxy, ethoxy, propoxy, trifluoromethyl, trifluoromethoxy, —$S(C_3H_7)$, —$N(CH_3)_2$, —$N(C_2H_5)_2$, —NHC(=O)$CH_3$, —$CH_2N(CH_3)_2$, —$O(CH_2)_2N(CH_3)_2$, —$C(=O)NH_2$, —$C(=O)N(CH_3)_2$, cyclopropyl, cyclopentyl, cyclohexyl,

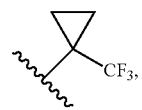 [SMILES: *C1(C(F)(F)F)CC1]

phenyl,

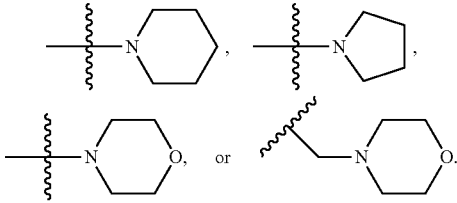

In certain embodiments, ring A is substituted with two substituents, such as $C_1$-$C_6$ alkyl and halogen; two $C_1$-$C_6$ alkyl (identical or different); two halogens (identical or different); halogen and $C_1$-$C_6$ alkoxy (e.g., methoxy, ethoxy, or isopropoxy); $C_1$-$C_6$ alkyl and $C_1$-$C_6$ haloalkyl; $C_1$-$C_6$ alkyl and mono-substituted amino (e.g., —NH($C_1$-$C_6$ alkyl), such as —$NHCH_3$ or —$NHC_2H_5$); $C_1$-$C_6$ alkyl and di-substituted amino (e.g., —N($C_1$-$C_6$ alkyl)$_2$, where the two $C_1$-$C_6$ alkyl may be identical or different, such as —$N(CH_3)_2$, —$N(CH_3)C_2H_5$, or —$N(C_2H_5)_2$); halogen and mono-substituted amino (e.g., —NH($C_1$-$C_6$ alkyl), such as —$NHCH_3$ or —$NHC_2H_5$); halogen and di-substituted amino (e.g., —N(C$_1$-C$_6$ alkyl)$_2$, where the two C$_1$-C$_6$ alkyl may be identical or different, such as —N(CH$_3$)$_2$, —N(CH$_3$)C$_2$H$_5$, or —N(C$_2$H$_5$)$_2$); C$_1$-C$_6$ haloalkyl and mono-substituted amino (e.g., —NH(C$_1$-C$_6$ alkyl), such as —NHCH$_3$ or —NHC$_2$H$_5$); C$_1$-C$_6$ haloalkyl and di-substituted amino (e.g., —N(C$_1$-C$_6$ alkyl)$_2$, where the two C$_1$-C$_6$ alkyl may be identical or different, such as —N(CH$_3$)$_2$, —N(CH$_3$)C$_2$H$_5$, or —N(C$_2$H$_5$)$_2$); C$_1$-C$_6$ alkyl and hydroxy; C$_1$-C$_6$ alkyl and C$_1$-C$_6$ alkoxy (e.g., methoxy, ethoxy, or isopropoxy); C$_1$-C$_6$ alkyl and —(CH$_2$)$_t$—NR$^{7a}$R$^{8a}$ (where t is 0 or 1; and each R$^{7a}$ and R$^{8a}$ is independently C$_1$-C$_6$ alkyl, or R$^{7a}$ and R$^{8a}$ together with the nitrogen atoms to which they are attached form a 5 or 6 membered heterocyclyl, such as

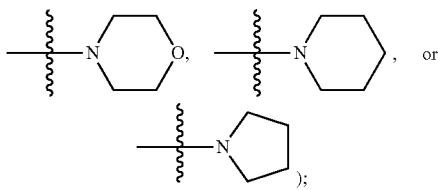

C$_1$-C$_6$ alkyl and —C(O)NR$^{7b}$R$^{8b}$; C$_1$-C$_6$ alkoxy and —C(O)NR$^{7b}$R$^{8b}$ (for —C(O)NR$^{7b}$R$^{8b}$, each R$^{7b}$ and R$^{8b}$ is independently C$_1$-C$_6$ alkyl, or R$^{7b}$ and R$^{8b}$ together with the nitrogen atoms to which they are attached form a 5 or 6 membered heterocyclyl, such as

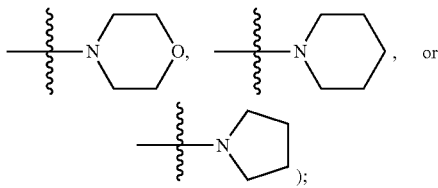

C$_1$-C$_6$ alkyl and —NR$^{7d}$C(O)R$^{11b}$ (where R$^{7d}$ is H and R$^{11b}$ is C$_1$-C$_6$ alkyl).

In one embodiment, provided herein is:
1-(3-(dimethylamino)-4-methylphenyl)-3-((5-(2,6-dioxopiperidin-3-yl)-6-oxo-5,6-dihydro-4H-thieno[2,3-c]pyrrol-2-yl)methyl)urea II-1;
1-(3-chloro-4-methylphenyl)-3-((5-(2,6-dioxopiperidin-3-yl)-6-oxo-5,6-dihydro-4H-thieno[2,3-c]pyrrol-3-yl)methyl)urea II-2;
(S)-1-(3-chloro-4-methylphenyl)-3-((5-(2,7-dioxoazepan-3-yl)-4-oxo-5,6-dihydro-4H-thieno[2,3-c]pyrrol-2-yl)methyl)urea II-3;
1-((5-(2,6-dioxopiperidin-3-yl)-4-oxo-5,6-dihydro-4H-thieno[3,4-c]pyrrol-1-yl)methyl)-3-(3-methoxy-4-methylphenyl)urea II-4;
1-(4-chloro-3-(trifluoromethoxy)phenyl)-3-((5-(2,6-dioxopiperidin-3-yl)-4-oxo-5,6-dihydro-4H-thieno[3,4-c]pyrrol-1-yl)methyl)urea II-5;
1-(3-chloro-4-methoxyphenyl)-3-((5-(2,6-dioxopiperidin-3-yl)-4-oxo-5,6-dihydro-4H-thieno[3,4-c]pyrrol-1-yl)methyl)urea II-6;
1-(benzo[d][1,3]dioxol-5-yl)-3-((5-(2,6-dioxopiperidin-3-yl)-4-oxo-5,6-dihydro-4H-thieno[3,4-c]pyrrol-1-yl)methyl)urea II-7;
1-(3-chloro-5-(trifluoromethyl)phenyl)-3-((5-(2,6-dioxopiperidin-3-yl)-4-oxo-5,6-dihydro-4H-thieno[3,4-c]pyrrol-1-yl)methyl)urea II-8;
1-(3,5-bis(trifluoromethyl)phenyl)-3-((5-(2,6-dioxopiperidin-3-yl)-4-oxo-5,6-dihydro-4H-thieno[3,4-c]pyrrol-1-yl)methyl)urea II-9;
1-(3-chloro-4-methylphenyl)-3-((5-(2,6-dioxopiperidin-3-yl)-4-oxo-5,6-dihydro-4H-thieno[3,4-c]pyrrol-1-yl)methyl)urea II-10;
1-(3-(dimethylamino)-4-methylphenyl)-3-((5-(2,6-dioxopiperidin-3-yl)-4-oxo-5,6-dihydro-4H-thieno[3,4-c]pyrrol-1-yl)methyl)urea II-11;
N-(5-(3-((5-(2,6-dioxopiperidin-3-yl)-4-oxo-5,6-dihydro-4H-thieno[3,4-c]pyrrol-1-yl)methyl)ureido)-2-methylphenyl)acetamide II-12;
1-(3-chloro-4-(dimethylamino)phenyl)-3-((5-(2,6-dioxopiperidin-3-yl)-4-oxo-5,6-dihydro-4H-thieno[3,4-c]pyrrol-1-yl)methyl)urea II-13;
N-(2-chloro-4-(3-((5-(2,6-dioxopiperidin-3-yl)-4-oxo-5,6-dihydro-4H-thieno[3,4-c]pyrrol-1-yl)methyl)ureido)phenyl)acetamide II-14;
1-(3-chloro-4-methylbenzyl)-3-((5-(2,6-dioxopiperidin-3-yl)-6-oxo-5,6-dihydro-4H-thieno[2,3-c]pyrrol-3-yl)methyl)urea II-15;
5-(3-((5-(2,6-dioxopiperidin-3-yl)-4-oxo-5,6-dihydro-4H-thieno[3,4-c]pyrrol-1-yl)methyl)ureido)-2-methylbenzamide II-16;
(S)-1-(3-chloro-4-methylphenyl)-3-((5-(2,7-dioxoazepan-3-yl)-4-oxo-5,6-dihydro-4H-thieno[3,4-c]pyrrol-1-yl)methyl)urea II-17;
N-((5-(2,6-dioxopiperidin-3-yl)-4-oxo-5,6-dihydro-4H-thieno[3,4-c]pyrrol-1-yl)methyl)-2,2-difluoro-2-(4-fluorophenyl)acetamide II-18;
(S)-1-(3-chloro-4-methylbenzyl)-3-((5-(2,7-dioxoazepan-3-yl)-4-oxo-5,6-dihydro-4H-thieno[2,3-c]pyrrol-2-yl)methyl)urea II-19;
1-(3-chloro-4-methylphenyl)-3-((5-(2,6-dioxopiperidin-3-yl)-4-oxo-5,6-dihydro-4H-thieno[3,4-c]pyrrol-1-yl)methyl)-1,3-dimethylurea II-20;
1-(3-chloro-4-methylbenzyl)-3-((5-(2,6-dioxopiperidin-3-yl)-4-oxo-5,6-dihydro-4H-thieno[2,3-c]pyrrol-2-yl)methyl)urea II-21;
1-(3-chloro-4-methylphenyl)-3-((5-(2,6-dioxopiperidin-3-yl)-4-oxo-5,6-dihydro-4H-thieno[3,4-c]pyrrol-1-yl)methyl)-1-methylurea II-22;
3-(1-(((3-((3-chloro-4-methylphenyl)amino)propyl)amino)methyl)-4-oxo-4H-thieno[3,4-c]pyrrol-5(6H)-yl)piperidine-2,6-dione II-23;
2-(3-chloro-4-methylphenyl)-N-((5-(2,6-dioxopiperidin-3-yl)-4-oxo-5,6-dihydro-4H-thieno[3,4-c]pyrrol-1-yl)methyl)acetamide II-24;
N-((5-(2,6-dioxopiperidin-3-yl)-4-oxo-5,6-dihydro-4H-thieno[3,4-c]pyrrol-1-yl)methyl)-2-(4-fluorophenyl)acetamide II-25;
1-((5-(2,6-dioxopiperidin-3-yl)-6-oxo-5,6-dihydro-4H-thieno[2,3-c]pyrrol-2-yl)methyl)-3-(3-methyl-4-morpholinophenyl)urea II-26;
1-((5-(2,6-dioxopiperidin-3-yl)-6-oxo-5,6-dihydro-4H-thieno[2,3-c]pyrrol-2-yl)methyl)-3-(3-methyl-4-(pyrrolidin-1-yl)phenyl)urea II-27;
2-(3-chloro-4-methylphenyl)-N-((5-(2,6-dioxopiperidin-3-yl)-4-oxo-5,6-dihydro-4H-thieno[3,4-c]pyrrol-1-yl)methyl)-2,2-difluoroacetamide II-28;
(S)-2-(3-chloro-4-methylphenyl)-N-((5-(2,7-dioxoazepan-3-yl)-4-oxo-5,6-dihydro-4H-thieno[3,4-c]pyrrol-1-yl)methyl)-2,2-difluoroacetamide II-29;
2-(3-chloro-4-methylphenyl)-N-((5-(2,6-dioxopiperidin-3-yl)-6-oxo-5,6-dihydro-4H-thieno[2,3-c]pyrrol-2-yl)methyl)acetamide II-30;

1-(3-chloro-4-methylphenyl)-3-(2-(5-(2,6-dioxopiperidin-3-yl)-4-oxo-5,6-dihydro-4H-thieno[3,4-c]pyrrol-1-yl)ethyl)urea II-31;

1-(3-chloro-4-methylbenzyl)-3-(2-(5-(2,6-dioxopiperidin-3-yl)-4-oxo-5,6-dihydro-4H-thieno[3,4-c]pyrrol-1-yl)ethyl)urea II-32;

3-(3-chloro-4-methylphenyl)-N-((5-(2,6-dioxopiperidin-3-yl)-6-oxo-5,6-dihydro-4H-thieno[2,3-c]pyrrol-2-yl)methyl)propenamide II-33;

3-(3-chloro-4-methylphenyl)-N-((5-(2,6-dioxopiperidin-3-yl)-4-oxo-5,6-dihydro-4H-thieno[3,4-c]pyrrol-1-yl)methyl)propenamide II-34;

3-{2-[(3-chloro-4-methylphenylsulfonylamino)methyl]-6-oxo-3-thia-7-azabicyclo[3.3.0]octa-1,4-dien-7-yl}-2,6-piperidinedione II-35;

1-(2,6-dichlorobenzyl)-3-((5-(2,6-dioxopiperidin-3-yl)-6-oxo-5,6-dihydro-4H-thieno[2,3-c]pyrrol-2-yl)methyl)urea II-36;

1-(2,6-dichlorobenzyl)-3-((5-(2,6-dioxopiperidin-3-yl)-4-oxo-5,6-dihydro-4H-thieno[3,4-c]pyrrol-1-yl)methyl)urea II-37;

2-(3-chloro-4-methylphenyl)-N-((5-(2,6-dioxopiperidin-3-yl)-6-oxo-5,6-dihydro-4H-thieno[2,3-c]pyrrol-2-yl)methyl)-2,2-difluoroacetamide II-38;

1-(3-chloro-4-methylphenyl)-3-((5-(2,6-dioxopiperidin-3-yl)-6-oxo-5,6-dihydro-4H-thieno[2,3-c]pyrrol-2-yl)methyl)thiourea II-39;

1-((5-(2,6-dioxopiperidin-3-yl)-4-oxo-5,6-dihydro-4H-thieno[3,4-c]pyrrol-1-yl)methyl)-3-(5-methyl-4-(trifluoromethyl)pyrimidin-2-yl)urea II-40;

4-(3-chloro-4-methylphenyl)-N-((5-(2,6-dioxopiperidin-3-yl)-4-oxo-5,6-dihydro-4H-thieno[3,4-c]pyrrol-1-yl)methyl)butanamide II-41;

1-(2,6-dichlorophenyl)-3-((5-(2,6-dioxopiperidin-3-yl)-6-oxo-5,6-dihydro-4H-thieno[2,3-c]pyrrol-2-yl)methyl)urea II-42;

1-(2,6-dichlorophenyl)-3-((5-(2,6-dioxopiperidin-3-yl)-4-oxo-5,6-dihydro-4H-thieno[3,4-c]pyrrol-1-yl)methyl)urea II-43;

3-{3-[(3-chloro-4-methylphenylsulfonylamino)methyl]-8-oxo-2-thia-7-azabicyclo[3.3.0]octa-1(5),3-dien-7-yl}-2,6-piperidinedione II-44;

1-(3-(dimethylamino)-4-fluorophenyl)-3-((5-(2,6-dioxopiperidin-3-yl)-6-oxo-5,6-dihydro-4H-thieno[2,3-c]pyrrol-2-yl)methyl)urea II-45;

1-((5-(2,6-dioxopiperidin-3-yl)-6-oxo-5,6-dihydro-4H-thieno[2,3-c]pyrrol-2-yl)methyl)-3-(3-hydroxy-4-methylphenyl)urea II-46;

1-(3-(diethylamino)-4-methylphenyl)-3-((5-(2,6-dioxopiperidin-3-yl)-6-oxo-5,6-dihydro-4H-thieno[2,3-c]pyrrol-2-yl)methyl)urea II-47;

1-(3-(dimethylamino)phenyl)-3-((5-(2,6-dioxopiperidin-3-yl)-6-oxo-5,6-dihydro-4H-thieno[2,3-c]pyrrol-2-yl)methyl)urea II-48;

1-(3-(dimethylamino)-5-methylphenyl)-3-((5-(2,6-dioxopiperidin-3-yl)-6-oxo-5,6-dihydro-4H-thieno[2,3-c]pyrrol-2-yl)methyl)urea II-49;

1-(3-(dimethylamino)-5-(trifluoromethyl)phenyl)-3-((5-(2,6-dioxopiperidin-3-yl)-6-oxo-5,6-dihydro-4H-thieno[2,3-c]pyrrol-2-yl)methyl)urea II-50;

1-(3-((dimethylamino)methyl)-4-methylphenyl)-3-((5-(2,6-dioxopiperidin-3-yl)-6-oxo-5,6-dihydro-4H-thieno[2,3-c]pyrrol-2-yl)methyl)urea II-51;

1-(4-(diethylamino)-3-methylphenyl)-3-((5-(2,6-dioxopiperidin-3-yl)-6-oxo-5,6-dihydro-4H-thieno[2,3-c]pyrrol-2-yl)methyl)urea II-52;

1-(3-((dimethylamino)methyl)phenyl)-3-((5-(2,6-dioxopiperidin-3-yl)-6-oxo-5,6-dihydro-4H-thieno[2,3-c]pyrrol-2-yl)methyl)urea II-53;

1-((5-(2,6-dioxopiperidin-3-yl)-6-oxo-5,6-dihydro-4H-thieno[2,3-c]pyrrol-2-yl)methyl)-3-(3-isopropyl-4-methylphenyl)urea II-54;

1-(3-(dimethylamino)-4-(trifluoromethyl)phenyl)-3-((5-(2,6-dioxopiperidin-3-yl)-6-oxo-5,6-dihydro-4H-thieno[2,3-c]pyrrol-2-yl)methyl)urea II-55;

1-((5-(2,6-dioxopiperidin-3-yl)-6-oxo-5,6-dihydro-4H-thieno[2,3-c]pyrrol-2-yl)methyl)-3-(3-(isopropyl(methyl)amino)phenyl)urea II-56;

2-(3-chloro-4-methylphenyl)-N-((5-(2,6-dioxopiperidin-3-yl)-6-oxo-5,6-dihydro-4H-thieno[2,3-c]pyrrol-3-yl)methyl)acetamide II-57;

1-((5-(2,6-dioxopiperidin-3-yl)-6-oxo-5,6-dihydro-4H-thieno[2,3-c]pyrrol-2-yl)methyl)-3-(3-methoxy-4-methylphenyl)urea II-58;

1-(4-(dimethylamino)-3-methylphenyl)-3-((5-(2,6-dioxopiperidin-3-yl)-6-oxo-5,6-dihydro-4H-thieno[2,3-c]pyrrol-2-yl)methyl)urea II-59;

1-(3-(dimethylamino)-5-isopropylphenyl)-3-((5-(2,6-dioxopiperidin-3-yl)-6-oxo-5,6-dihydro-4H-thieno[2,3-c]pyrrol-2-yl)methyl)urea II-60;

2-(4-(dimethylamino)phenyl)-N-((5-(2,6-dioxopiperidin-3-yl)-4-oxo-5,6-dihydro-4H-thieno[3,4-c]pyrrol-1-yl)methyl)acetamide II-61;

2-(4-(tert-butyl)phenyl)-N-((5-(2,6-dioxopiperidin-3-yl)-4-oxo-5,6-dihydro-4H-thieno[3,4-c]pyrrol-1-yl)methyl)acetamide II-62;

N-((5-(2,6-dioxopiperidin-3-yl)-4-oxo-5,6-dihydro-4H-thieno[3,4-c]pyrrol-1-yl)methyl)-2-(3-isopropyl-4-methoxyphenyl)acetamide II-63;

3-(1-(((5-((3-chloro-4-methylphenyl)amino)pentyl)amino)methyl)-4-oxo-4H-thieno[3,4-c]pyrrol-5(6H)-yl)piperidine-2,6-dione II-64;

3-(2-(((3-((3-chloro-4-methylphenyl)amino)propyl)amino)methyl)-6-oxo-4,6-dihydro-5H-thieno[2,3-c]pyrrol-5-yl)piperidine-2,6-dione II-65;

3-(2-(((3-((3-chloro-4-methylphenyl)amino)propyl)amino)methyl)-6-oxo-4,6-dihydro-5H-thieno[2,3-c]pyrrol-5-yl)piperidine-2,6-dione II-66;

2-(3-chloro-4-methylphenyl)-N-((5-(2,6-dioxopiperidin-3-yl)-4-oxo-5,6-dihydro-4H-thieno[3,4-c]pyrrol-1-yl)methyl)propenamide II-67;

2-(3-(dimethylamino)-4-methylphenyl)-N-((5-(2,6-dioxopiperidin-3-yl)-4-oxo-5,6-dihydro-4H-thieno[3,4-c]pyrrol-1-yl)methyl)acetamide II-68;

1-(3-chloro-4-methylphenyl)-N-((5-(2,6-dioxopiperidin-3-yl)-4-oxo-5,6-dihydro-4H-thieno[3,4-c]pyrrol-1-yl)methyl)methanesulfonamide II-69;

1-((5-(2,6-dioxopiperidin-3-yl)-6-oxo-5,6-dihydro-4H-thieno[2,3-c]pyrrol-2-yl)methyl)-3-(3-isopropylphenyl)urea II-70;

1-(3-(diethylamino)phenyl)-3-((5-(2,6-dioxopiperidin-3-yl)-6-oxo-5,6-dihydro-4H-thieno[2,3-c]pyrrol-2-yl)methyl)urea II-71;

1-(3-chloro-4-methylphenyl)-3-((5-(2,5-dioxopyrrolidin-3-yl)-6-oxo-5,6-dihydro-4H-thieno[2,3-c]pyrrol-2-yl)methyl)urea II-72;

1-(3-chloro-4-methylphenyl)-3-((5-(3-methyl-2,6-dioxopiperidin-3-yl)-6-oxo-5,6-dihydro-4H-thieno[2,3-c]pyrrol-2-yl)methyl)urea II-73;

N-((5-(2,6-dioxopiperidin-3-yl)-4-oxo-5,6-dihydro-4H-thieno[3,4-c]pyrrol-1-yl)methyl)-2-(4-isopropylphenyl)acetamide II-74;

N-((5-(2,6-dioxopiperidin-3-yl)-4-oxo-5,6-dihydro-4H-thieno[3,4-c]pyrrol-1-yl)methyl)-2-(4-methylcyclohexyl)acetamide II-75;

N-((5-(2,6-dioxopiperidin-3-yl)-4-oxo-5,6-dihydro-4H-thieno[3,4-c]pyrrol-1-yl)methyl)-2-(3-(piperidin-1-yl)phenyl)acetamide II-76;

2-(3-(2-(dimethylamino)ethoxy)phenyl)-N-((5-(2,6-dioxopiperidin-3-yl)-4-oxo-5,6-dihydro-4H-thieno[3,4-c]pyrrol-1-yl)methyl)acetamide II-77;

N-((5-(2,6-dioxopiperidin-3-yl)-4-oxo-5,6-dihydro-4H-thieno[3,4-c]pyrrol-1-yl)methyl)-2-morpholinoacetamide II-78;

2-(3-chloro-4-methylphenyl)-N-((5-(2,6-dioxopiperidin-3-yl)-4-oxo-5,6-dihydro-4H-thieno[2,3-c]pyrrol-2-yl)methyl)acetamide II-79;

2-(4-(2-(dimethylamino)ethoxy)phenyl)-N-((5-(2,6-dioxopiperidin-3-yl)-4-oxo-5,6-dihydro-4H-thieno[3,4-c]pyrrol-1-yl)methyl)acetamide II-80;

(3-(2-((3-(3-(dimethylamino)-4-methylphenyl)ureido)methyl)-6-oxo-4,6-dihydro-5H-thieno[2,3-c]pyrrol-5-yl)-2,6-dioxopiperidin-1-yl)methyl D-valinate II-81;

(3-(2-((3-(3-chloro-4-methylphenyl)ureido)methyl)-6-oxo-4,6-dihydro-5H-thieno[2,3-c]pyrrol-5-yl)-2,6-dioxopiperidin-1-yl)methyl D-valinate II-82;

N-((5-(2,6-dioxopiperidin-3-yl)-4-oxo-5,6-dihydro-4H-thieno[3,4-c]pyrrol-1-yl)methyl)-2-(4-morpholinophenyl)acetamide II-83;

4-(4-(tert-butyl)phenyl)-N-((5-(2,6-dioxopiperidin-3-yl)-4-oxo-5,6-dihydro-4H-thieno[3,4-c]pyrrol-1-yl)methyl)butanamide II-84;

4-(4-(dimethylamino)phenyl)-N-((5-(2,6-dioxopiperidin-3-yl)-4-oxo-5,6-dihydro-4H-thieno[3,4-c]pyrrol-1-yl)methyl)butanamide II-85;

4-(4-(tert-butyl)phenyl)-N-((5-(2,6-dioxopiperidin-3-yl)-4-oxo-5,6-dihydro-4H-thieno[3,4-c]pyrrol-1-yl)methyl)-2-methylbutanamide II-86;

2-(3-chloro-4-methylphenyl)-N-((5-(2,6-dioxopiperidin-3-yl)-4-oxo-5,6-dihydro-4H-thieno[3,4-c]pyrrol-1-yl)methyl)butanamide II-87;

2-amino-N-((5-(2,6-dioxopiperidin-3-yl)-4-oxo-5,6-dihydro-4H-thieno[3,4-c]pyrrol-1-yl)methyl)-2-(p-tolyl)acetamide II-88;

2-amino-2-(3-chlorophenyl)-N-((5-(2,6-dioxopiperidin-3-yl)-4-oxo-5,6-dihydro-4H-thieno[3,4-c]pyrrol-1-yl)methyl)acetamide II-89;

(S)-1-(3-chloro-4-methylphenyl)-3-((5-(2,6-dioxopiperidin-3-yl)-6-oxo-5,6-dihydro-4H-thieno[2,3-c]pyrrol-2-yl)methyl)urea II-90;

(R)-1-(3-chloro-4-methylphenyl)-3-((5-(2,6-dioxopiperidin-3-yl)-6-oxo-5,6-dihydro-4H-thieno[2,3-c]pyrrol-2-yl)methyl)urea II-91;

2-(4-(tert-butyl)phenyl)-N-((5-(2,6-dioxopiperidin-3-yl)-4-oxo-5,6-dihydro-4H-thieno[3,4-c]pyrrol-1-yl)methyl)propenamide II-92;

N-((5-(2,6-dioxopiperidin-3-yl)-4-oxo-5,6-dihydro-4H-thieno[3,4-c]pyrrol-1-yl)methyl)-2-(4-(pyrrolidin-1-yl)phenyl)acetamide II-93;

2-(4-(tert-butyl)phenyl)-N-((5-(2,6-dioxopiperidin-3-yl)-4-oxo-5,6-dihydro-4H-thieno[3,4-c]pyrrol-1-yl)methyl)-3-methylbutanamide II-94;

2-(3-chloro-4-methylphenyl)-N-((5-(2,6-dioxopiperidin-3-yl)-4-oxo-5,6-dihydro-4H-thieno[3,4-c]pyrrol-1-yl)methyl)-3-methylbutanamide II-95;

1-(3-(dimethylamino)-4-ethylphenyl)-3-((5-(2,6-dioxopiperidin-3-yl)-6-oxo-5,6-dihydro-4H-thieno[2,3-c]pyrrol-2-yl)methyl)urea II-96;

1-(3-(diethylamino)-4-fluorophenyl)-3-((5-(2,6-dioxopiperidin-3-yl)-6-oxo-5,6-dihydro-4H-thieno[2,3-c]pyrrol-2-yl)methyl)urea II-97;

1-((5-(2,6-dioxopiperidin-3-yl)-6-oxo-5,6-dihydro-4H-thieno[2,3-c]pyrrol-2-yl)methyl)-3-(4-methyl-3-(pyrrolidin-1-yl)phenyl)urea II-98;

1-((5-(2,6-dioxopiperidin-3-yl)-6-oxo-5,6-dihydro-4H-thieno[2,3-c]pyrrol-2-yl)methyl)-3-(3-(pyrrolidin-1-yl)phenyl)urea II-99;

1-((5-(2,6-dioxopiperidin-3-yl)-6-oxo-5,6-dihydro-4H-thieno[2,3-c]pyrrol-2-yl)methyl)-3-(3-(ethyl(methyl)amino)-4-methylphenyl)urea II-100;

4-(3-chloro-4-methylphenyl)-N-((5-(2,6-dioxopiperidin-3-yl)-4-oxo-5,6-dihydro-4H-thieno[3,4-c]pyrrol-1-yl)methyl)-2-methylbutanamide II-101;

(2S)-2-(3-chloro-4-methylphenyl)-N-((5-(2,6-dioxopiperidin-3-yl)-4-oxo-5,6-dihydro-4H-thieno[3,4-c]pyrrol-1-yl)methyl)propenamide II-102;

(2R)-2-(3-chloro-4-methylphenyl)-N-((5-(2,6-dioxopiperidin-3-yl)-4-oxo-5,6-dihydro-4H-thieno[3,4-c]pyrrol-1-yl)methyl)propenamide II-103;

(S)-4-(3-chloro-4-methylphenyl)-N-((5-(2,6-dioxopiperidin-3-yl)-4-oxo-5,6-dihydro-4H-thieno[3,4-c]pyrrol-1-yl)methyl)-2,2-dimethylbutanamide II-104;

di-tert-butyl ((3-(2-((3-(3-(dimethylamino)-4-methylphenyl)ureido)-methyl)-6-oxo-4,6-dihydro-5H-thieno[2,3-c]pyrrol-5-yl)-2,6-dioxopiperidin-1-yl)methyl) phosphate II-105;

N-((5-(2,6-dioxopiperidin-3-yl)-4-oxo-5,6-dihydro-4H-thieno[3,4-c]pyrrol-1-yl)methyl)-2-(4-isopropylphenyl)-3-methylbutanamide II-106;

N-((5-(2,6-dioxopiperidin-3-yl)-6-oxo-5,6-dihydro-4H-thieno[2,3-c]pyrrol-2-yl)methyl)-2-(perfluorophenyl)acetamide II-107;

2-(dimethylamino)-N-((5-(2,6-dioxopiperidin-3-yl)-4-oxo-5,6-dihydro-4H-thieno[3,4-c]pyrrol-1-yl)methyl)-2-(2-fluorophenyl)acetamide II-108;

N-((5-(2,6-dioxopiperidin-3-yl)-4-oxo-5,6-dihydro-4H-thieno[3,4-c]pyrrol-1-yl)methyl)-4-phenylbutanamide II-109;

1-((5-(2,6-dioxopiperidin-3-yl)-6-oxo-5,6-dihydro-4H-thieno[2,3-c]pyrrol-2-yl)methyl)-3-phenylthiourea II-110;

1-((5-(2,6-dioxopiperidin-3-yl)-4-oxo-5,6-dihydro-4H-thieno[3,4-c]pyrrol-1-yl)methyl)-3-(4-(trifluoromethoxy)phenyl)thiourea II-111;

2-amino-N-((5-(2,6-dioxopiperidin-3-yl)-4-oxo-5,6-dihydro-4H-thieno[3,4-c]pyrrol-1-yl)methyl)-2-(4-propoxyphenyl)acetamide II-112;

2-amino-N-((5-(2,6-dioxopiperidin-3-yl)-4-oxo-5,6-dihydro-4H-thieno[3,4-c]pyrrol-1-yl)methyl)-2-(4-hydroxyphenyl)acetamide II-113;

1-(3-(dimethylamino)-4-methylphenyl)-3-((5-(2,6-dioxopiperidin-3-yl)-4,6-dioxo-5,6-dihydro-4H-thieno[2,3-c]pyrrol-2-yl)methyl)urea II-114;

4-(4-(dimethylamino)-3-methylphenyl)-N-((5-(2,6-dioxopiperidin-3-yl)-4-oxo-5,6-dihydro-4H-thieno[3,4-c]pyrrol-1-yl)methyl)butanamide II-115;

N-((5-(2,6-dioxopiperidin-3-yl)-6-oxo-5,6-dihydro-4H-thieno[2,3-c]pyrrol-2-yl)methyl)-2-(3-fluoro-2-methoxyphenyl)acetamide II-116;

4-bromo-2,5-dichloro-N-((5-(2,6-dioxopiperidin-3-yl)-4-oxo-5,6-dihydro-4H-thieno[3,4-c]pyrrol-1-yl)methyl)thiophene-3-sulfonamide II-117;

methyl 5-chloro-3-(N-((5-(2,6-dioxopiperidin-3-yl)-4-oxo-5,6-dihydro-4H-thieno[3,4-c]pyrrol-1-yl)methyl)sulfamoyl)thiophene-2-carboxylate II-118;

N-((5-(2,6-dioxopiperidin-3-yl)-4-oxo-5,6-dihydro-4H-thieno[3,4-c]pyrrol-1-yl)methyl)-4-methyl-1,2,3-thiadiazole-5-carboxamide II-119;

N-(5-(N-((5-(2,6-dioxopiperidin-3-yl)-4-oxo-5,6-dihydro-4H-thieno[3,4-c]pyrrol-1-yl)methyl)sulfamoyl)-4-methylthiazol-2-yl)acetamide II-120;

N-((5-(2,6-dioxopiperidin-3-yl)-4-oxo-5,6-dihydro-4H-thieno[3,4-c]pyrrol-1-yl)methyl)-2,3,4,5,6-pentafluorobenzenesulfonamide II-121;

N-((5-(2,6-dioxopiperidin-3-yl)-4-oxo-5,6-dihydro-4H-thieno[3,4-c]pyrrol-1-yl)methyl)-1-methyl-1H-imidazole-4-sulfonamide II-122;

1-((5-(2,6-dioxopiperidin-3-yl)-4-oxo-5,6-dihydro-4H-thieno[3,4-c]pyrrol-1-yl)methyl)-3-(2,3,5,6-tetrachlorophenyl)thiourea II-123;

4-(tert-butyl)-N-((5-(2,6-dioxopiperidin-3-yl)-4-oxo-5,6-dihydro-4H-thieno[3,4-c]pyrrol-1-yl)methyl)benzenesulfonamide II-124;

methyl 3-(3-((5-(2,6-dioxopiperidin-3-yl)-4-oxo-5,6-dihydro-4H-thieno[3,4-c]pyrrol-1-yl)methyl)ureido)thiophene-2-carboxylate II-125;

N-((5-(2,6-dioxopiperidin-3-yl)-4-oxo-5,6-dihydro-4H-thieno[3,4-c]pyrrol-1-yl)methyl)thiazole-2-carboxamide II-126;

1-(4-(tert-butyl)phenyl)-N-((5-(2,6-dioxopiperidin-3-yl)-4-oxo-5,6-dihydro-4H-thieno[3,4-c]pyrrol-1-yl)methyl)cyclopropane-1-carboxamide II-127;

1-(4-(tert-butyl)phenyl)-N-((5-(2,6-dioxopiperidin-3-yl)-4-oxo-5,6-dihydro-4H-thieno[3,4-c]pyrrol-1-yl)methyl)methanesulfonamide II-128;

2-(4-(tert-butyl)phenyl)-N-((5-(2,6-dioxopiperidin-3-yl)-4-oxo-5,6-dihydro-4H-thieno[3,4-c]pyrrol-1-yl)methyl)-2,2-difluoroacetamide II-129;

N-((5-(2,6-dioxopiperidin-3-yl)-4-oxo-5,6-dihydro-4H-thieno[3,4-c]pyrrol-1-yl)methyl)furan-3-sulfonamide II-130;

4-(tert-butyl)-N-(2-(5-(2,6-dioxopiperidin-3-yl)-4-oxo-5,6-dihydro-4H-thieno[3,4-c]pyrrol-1-yl)ethyl)benzenesulfonamide II-131;

2-(4-(tert-butyl)phenyl)-N-((5-(2,6-dioxopiperidin-3-yl)-4-oxo-5,6-dihydro-4H-thieno[3,4-c]pyrrol-1-yl)methyl)-2-hydroxyacetamide II-132;

2-(4-(tert-butyl)phenyl)-N-((5-(2,6-dioxopiperidin-3-yl)-4-oxo-5,6-dihydro-4H-thieno[3,4-c]pyrrol-1-yl)methyl)-3,3,3-trifluoro-2-hydroxypropanamide II-133;

3-bromo-N-((5-(2,6-dioxopiperidin-3-yl)-6-oxo-5,6-dihydro-4H-thieno[2,3-c]pyrrol-2-yl)methyl)furan-2-carboxamide II-134;

4-bromo-N-((5-(2,6-dioxopiperidin-3-yl)-6-oxo-5,6-dihydro-4H-thieno[2,3-c]pyrrol-2-yl)methyl)-2-(trifluoromethoxy)benzenesulfonamide II-135;

2-chloro-N-((5-(2,6-dioxopiperidin-3-yl)-6-oxo-5,6-dihydro-4H-thieno[2,3-c]pyrrol-2-yl)methyl)thiazole-5-carboxamide II-136;

methyl 2-(3-((5-(2,6-dioxopiperidin-3-yl)-6-oxo-5,6-dihydro-4H-thieno[2,3-c]pyrrol-2-yl)methyl)ureido)thiophene-3-carboxylate II-137;

1-((5-(2,6-dioxopiperidin-3-yl)-6-oxo-5,6-dihydro-4H-thieno[2,3-c]pyrrol-2-yl)methyl)-3-(6-morpholinopyridin-3-yl)urea II-138;

1-(1,3-dimethyl-1H-pyrazol-5-yl)-3-((5-(2,6-dioxopiperidin-3-yl)-6-oxo-5,6-dihydro-4H-thieno[2,3-c]pyrrol-2-yl)methyl)urea II-139;

N-((5-(2,6-dioxopiperidin-3-yl)-6-oxo-5,6-dihydro-4H-thieno[2,3-c]pyrrol-2-yl)methyl)-3,5-dimethylisoxazole-4-carboxamide II-140;

N-(5-(N-((5-(2,6-dioxopiperidin-3-yl)-6-oxo-5,6-dihydro-4H-thieno[2,3-c]pyrrol-2-yl)methyl)sulfamoyl)-4-methylthiazol-2-yl)acetamide II-141;

N-((5-(2,6-dioxopiperidin-3-yl)-6-oxo-5,6-dihydro-4H-thieno[2,3-c]pyrrol-2-yl)methyl)-2,5-dimethylfuran-3-sulfonamide II-142;

5-(N-((5-(2,6-dioxopiperidin-3-yl)-6-oxo-5,6-dihydro-4H-thieno[2,3-c]pyrrol-2-yl)methyl)sulfamoyl)-2-methoxy-N,N-dimethylbenzamide II-143;

N-((5-(2,6-dioxopiperidin-3-yl)-6-oxo-5,6-dihydro-4H-thieno[2,3-c]pyrrol-2-yl)methyl)-2-(propylthio)nicotinamide II-144;

1-((5-(2,6-dioxopiperidin-3-yl)-4-oxo-5,6-dihydro-4H-thieno[3,4-c]pyrrol-1-yl)methyl)-3-(3-phenoxypropyl)urea II-145; or N-((5-(2,6-dioxopiperidin-3-yl)-4-oxo-5,6-dihydro-4H-thieno[3,4-c]pyrrol-1-yl)methyl)-4-(4-morpholinophenyl)butanamide II-146;

or a pharmaceutically acceptable salt thereof.

In another embodiment, provided herein is:

2-(4-(tert-butyl)phenyl)-N-((5-(2,6-dioxopiperidin-3-yl)-4-oxo-5,6-dihydro-4H-thieno[3,4-c]pyrrol-1-yl)methyl)-3,3,3-trifluoropropanamide II-147;

1-(4-(tert-butyl)phenyl)-3-((5-(2,6-dioxopiperidin-3-yl)-4-oxo-5,6-dihydro-4H-thieno[3,4-c]pyrrol-1-yl)methyl)urea II-148;

1-(2,3-dimethylphenyl)-3-((5-(2,6-dioxopiperidin-3-yl)-6-oxo-5,6-dihydro-4H-thieno[2,3-c]pyrrol-2-yl)methyl)urea II-150;

1-(2,4-dimethylphenyl)-3-((5-(2,6-dioxopiperidin-3-yl)-6-oxo-5,6-dihydro-4H-thieno[2,3-c]pyrrol-2-yl)methyl)urea II-151;

1-(2,5-dimethylphenyl)-3-((5-(2,6-dioxopiperidin-3-yl)-6-oxo-5,6-dihydro-4H-thieno[2,3-c]pyrrol-2-yl)methyl)urea II-152;

1-([1,1'-biphenyl]-4-yl)-3-((5-(2,6-dioxopiperidin-3-yl)-6-oxo-5,6-dihydro-4H-thieno[2,3-c]pyrrol-2-yl)methyl)urea II-153;

1-((5-(2,6-dioxopiperidin-3-yl)-6-oxo-5,6-dihydro-4H-thieno[2,3-c]pyrrol-2-yl)methyl)-3-(4-methoxyphenyl)urea II-154;

1-(4-cyanophenyl)-3-((5-(2,6-dioxopiperidin-3-yl)-6-oxo-5,6-dihydro-4H-thieno[2,3-c]pyrrol-2-yl)methyl)urea II-155;

1-(2,6-dimethylphenyl)-3-((5-(2,6-dioxopiperidin-3-yl)-6-oxo-5,6-dihydro-4H-thieno[2,3-c]pyrrol-2-yl)methyl)urea II-155;

1-((5-(2,6-dioxopiperidin-3-yl)-6-oxo-5,6-dihydro-4H-thieno[2,3-c]pyrrol-2-yl)methyl)-3-phenethylthiourea II-157;

1-(2-trifluoromethylphenyl)-3-((5-(2,6-dioxopiperidin-3-yl)-6-oxo-5,6-dihydro-4H-thieno[2,3-c]pyrrol-2-yl)methyl)urea II-158;

1-(3-cyanophenyl)-3-((5-(2,6-dioxopiperidin-3-yl)-6-oxo-5,6-dihydro-4H-thieno[2,3-c]pyrrol-2-yl)methyl)urea II-159;

1-(4-chloro-2-trifluoromethylphenyl)-3-((5-(2,6-dioxopiperidin-3-yl)-6-oxo-5,6-dihydro-4H-thieno[2,3-c]pyrrol-2-yl)methyl)urea II-160;

1-(2,4,6-trimethylphenyl)-3-((5-(2,6-dioxopiperidin-3-yl)-6-oxo-5,6-dihydro-4H-thieno[2,3-c]pyrrol-2-yl)methyl)urea II-161;

1-(3,5-dimethoxyphenyl)-3-((5-(2,6-dioxopiperidin-3-yl)-6-oxo-5,6-dihydro-4H-thieno[2,3-c]pyrrol-2-yl)methyl)urea II-162;

1-((5-(2,6-dioxopiperidin-3-yl)-6-oxo-5,6-dihydro-4H-thieno[2,3-c]pyrrol-2-yl)methyl)-3-(naphthalen-1-yl)urea II-163; or N-((5-(2,6-Dioxopiperidin-3-yl)-4-oxo-5,6-dihydro-4H-thieno[3,4-c]pyrrol-1-yl)methyl)-2,2-difluoro-2-(4-(1-(trifluoromethyl)cyclopropyl)phenyl)acetamide II-165;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

Compounds of Formula (IV)

In one embodiment, provided herein is a compound of Formula (IV):

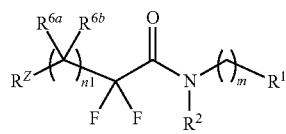
(IV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^{6a}$, $R^{6b}$, $R^Z$, m, and n1 are each as defined herein for Formula (III).

In certain embodiments, $R^Z$ is $-NR^{7a}R^{8a}$, wherein $R^{7a}$ and $R^{8a}$ are each as defined herein for Formula (I). In certain embodiments, $R^Z$ is $-NR^{7a}R^{8a}$, wherein $R^{7a}$ and $R^{8a}$ are each independently H or optionally substituted $C_1$-$C_6$ alkyl. In certain embodiments, $R^Z$ is $-NHCH_3$, $-NHC_2H_5$, $-N(CH_3)_2$, $-N(CH_3)C_2H_5$, or $-N(C_2H_5)_2$. In certain embodiments, $R^Z$ is dimethylamino. In certain embodiments, $R^Z$ is ring A as defined herein for Formula (I).

In one embodiment, provided herein is a compound of Formula (IVa):

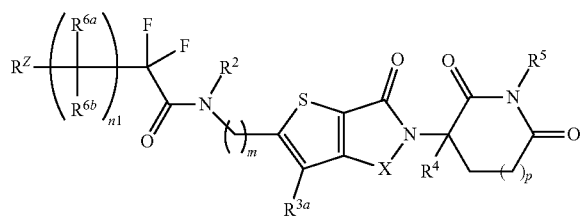
(IVa)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3a}$, $R^{6a}$, $R^{6b}$, $R^Z$, X, m, p, and n1 are each as defined herein.

In another embodiment, provided herein is a compound of Formula (IVb):

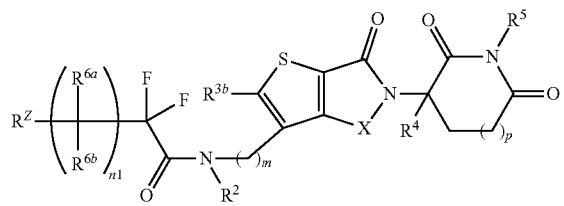
(IVb)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3b}$, $R^{6a}$, $R^{6b}$, $R^Z$, X, m, p, and n1 are each as defined herein.

In yet another embodiment, provided herein is a compound of Formula (IVc):

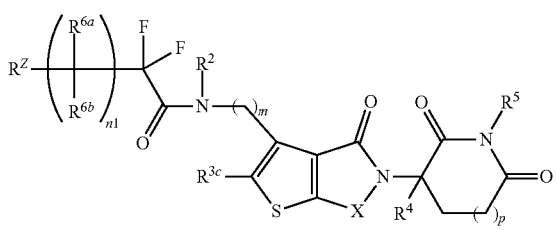
(IVc)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3c}$, $R^{6a}$, $R^{6b}$, $R^Z$, X, m, p, and n1 are each as defined herein.

In yet another embodiment, provided herein is a compound of Formula (IVd):

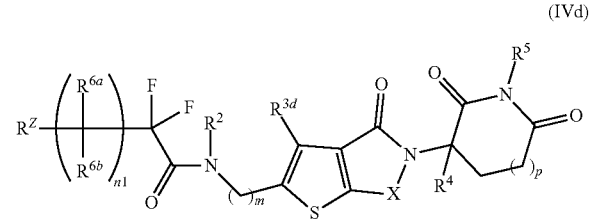
(IVd)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3d}$, $R^{6a}$, $R^{6b}$, $R^Z$, X, m, p, and n1 are each as defined herein.

In yet another embodiment, provided herein is a compound of Formula (IVe):

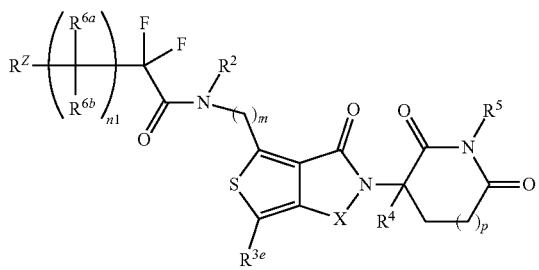

(IVe)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^3$, $R^{6a}$, $R^{6b}$, $R^Z$, X, m, p, and n1 are each as defined herein.

In still another embodiment, provided herein is a compound of Formula (IVf):

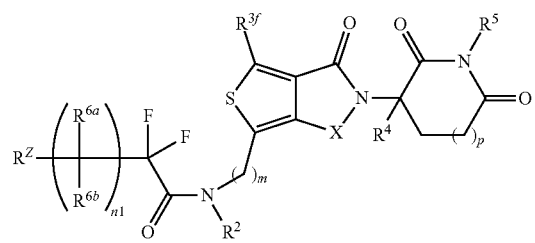

(IVf)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^3$, $R^{6a}$, $R^{6b}$, $R^Z$, X, m, p, and n1 are each as defined herein.

In one embodiment, in any one of Formulae (IVa) to (IVf),

X is $CH_2$ or $C(=O)$;

$R^Z$ is (a) amino, mono-substituted amino, or di-substituted amino; or (b) $C_6$-$C_{10}$ aryl, 5 to 10 membered heteroaryl, $C_3$-$C_8$ carbocyclyl, or 3 to 10 membered heterocyclyl, each of which is optionally substituted with one, two, or three substituents $R^A$, wherein each substituent $R^A$ is independently (i) halogen, cyano, hydroxyl, $C_1$-$C_6$ alkyl, $C_1$-$C_6$ alkoxy, $C_1$-$C_6$ haloalkyl, —$(CH_2)_t$—$NR^{7a}R^{8a}$, or —$NR^{7d}C(O)R^{11b}$, or (ii) phenyl, $C_3$-$C_8$ carbocyclyl, or 3 to 10 membered heterocyclyl, each of which is optionally substituted with one or more $R^B$;

$R^2$ is H or $C_1$-$C_6$ alkyl;

$R^4$ is H or $C_1$-$C_6$ alkyl;

$R^5$ is H or

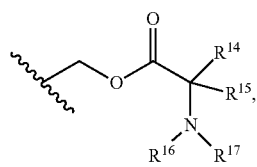

where $R^{14}$, $R^{15}$, $R^{16}$, and $R^{17}$ are each as defined herein;

$R^{3a}$, $R^{3b}$, $R^{3c}$, $R^{3d}$, $R^{3e}$, or $R^{3f}$, if present, is H;

each $R^{6a}$ and $R^{6b}$ is independently H or $C_1$-$C_6$ alkyl;

m is an integer of 0, 1, or 2;

p is an integer of 0, 1, or 2; and n1 is an integer of 0, 1, 2, or 3.

In another embodiment, in any one of Formulae (IVa) to (IVf),

X is $CH_2$ or $C(=O)$;

$R^Z$ is (a) mono-substituted amino or di-substituted amino; or (b) phenyl, naphthyl, thienyl, pyridyl, piperidinyl, or cyclohexyl, each of which is optionally substituted with one, two, or three substituents $R^A$, wherein each substituent $R^A$ is independently halogen, cyano, hydroxyl, $C_1$-$C_6$ alkyl, $C_1$-$C_6$ alkoxy, $C_1$-$C_6$ haloalkyl, —$(CH_2)$—$NR^{7a}R^{8a}$, —$NR^{7d}C(O)R^{11b}$, phenyl, $C_3$-$C_8$ carbocyclyl, or 3 to 10 membered heterocyclyl, wherein each of phenyl, 5 to 10 membered heteroaryl, $C_3$-$C_8$ carbocyclyl, and 3 to 10 membered heterocyclyl is optionally substituted with one or more $R^B$;

$R^2$ is H or methyl;

$R^4$ is H;

$R^5$ is H or valyloxymethyl;

$R^{3a}$, $R^{3b}$, $R^{3c}$, $R^{3d}$, $R^{3e}$, or $R^{3f}$, if present, is H;

each $R^{6a}$ and $R^{6b}$ is independently H or methyl;

m is an integer of 0, 1, or 2;

p is an integer of 0, 1 or 2; and n1 is an integer of 0, 1, 2, or 3,

In yet another embodiment, in any one of Formulae (IVa) to (IVf),

X is $CH_2$ or $C(=O)$;

$R^Z$ is (a) dimethylamino; or (b) phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, propyl, butyl, hydroxyl-butyl, cyclopropyl, methylcyclopropyl, trifluoromethyl-cyclopropyl, phenyl, methyl-piperidinyl, hydroxyl, methoxy, dimethylamino, or acetamido;

$R^2$ is H or methyl;

$R^4$ is H;

$R^5$ is H or D-valyloxymethyl;

$R^{3a}$, $R^{3b}$, $R^{3c}$, $R^{3d}$, $R^{3e}$, or $R^{3f}$, if present, is H;

each $R^{6a}$ and $R^{6b}$ is H;

m is an integer of 0, 1, or 2;

p is an integer of 1 or 2; and n1 is an integer of 0, 1, 2, or 3.

In yet another embodiment, in any one of Formulae (IVa) to (IVf),

X is $CH_2$ or $C(=O)$;

$R^Z$ is dimethylamino, phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, isopropyl, sec-butyl, tert-butyl, hydroxyl-tert-butyl, cyclopropyl, methylcyclopropyl, trifluoromethyl-cyclopropyl, phenyl, methyl-piperidinyl, hydroxyl, methoxy, dimethylamino, or acetamido;

$R^2$ is H or methyl;

$R^4$ is H;

$R^5$ is H or D-valyloxymethyl;

$R^{3a}$, $R^{3b}$, $R^{3c}$, $R^{3d}$, $R^{3e}$, or $R^{3f}$, if present, is H;

each $R^{6a}$ and $R^{6b}$ is H;

m is an integer of 0, 1, or 2;

p is an integer of 1 or 2; and n1 is an integer of 0, 1, 2, or 3.

In yet another embodiment, in any one of Formulae (IVa) to (IVf),

X is CH$_2$ or C(=O);

R$^Z$ is dimethylamino, phenyl, cyanophenyl, fluorophenyl, chlorophenyl, bromophenyl, methylphenyl, (1-trifluoromethylethyl)phenyl, trifluoromethylphenyl, dimethylaminomethylphenyl, morpholin-4-ylmethylphenyl, isopropylphenyl, sec-butylphenyl, tert-butylphenyl, (hydroxyl-tert-butyl)phenyl, cyclopropylphenyl, (1-methylcyclopropyl)phenyl, (1-trifluoromethylcyclopropyl)-phenyl, phenylphenyl, (1-methylpiperidin-4-yl)phenyl, hydroxylphenyl, methoxyphenyl, dimethylaminophenyl, acetamidophenyl, difluorophenyl, dichlorophenyl, chloro-methylphenyl, methyl-tert-butylphenyl, dimethylphenyl, trimethylphenyl, trimethoxyphenyl, dimethyl-tert-butylphenyl, dimethylamino-methylphenyl, naphthyl, thienyl, isopropylthienyl, pyridyl, tert-butylcyclohexyl, piperidinyl, or tert-butylpiperidinyl;

R$^2$ is H or methyl;

R$^4$ is H;

R$^5$ is H or D-valyloxymethyl;

R$^{3a}$, R$^{3b}$, R$^{3c}$, R$^{3d}$, R$^{3e}$, or R$^{3f}$, if present, is H;

each R$^{6a}$ and R$^{6b}$ is H;

m is an integer of 0, 1, or 2;

p is an integer of 1 or 2; and n1 is an integer of 0, 1, or 2.

In still another embodiment, in any one of Formulae (IVa) to (IVf),

X is CH$_2$ or C(=O);

R$^Z$ is dimethylamino, phenyl, 4-cyanophenyl, 2-fluorophenyl, 3-fluorophenyl, 4-fluorophenyl, 3-chlorophenyl, 4-chlorophenyl, 4-bromophenyl, 4-methylphenyl, 4-(1-trifluoromethylethyl)phenyl, 4-trifluoromethylphenyl, 4-dimethylaminomethylphenyl, 4-morpholin-4-ylmethylphenyl, 4-isopropylphenyl, 4-sec-butylphenyl, 3-tert-butylphenyl, 4-tert-butylphenyl, 4-(hydroxyl-tert-butyl)phenyl, 4-cyclopropylphenyl, 4-(1-methylcyclopropyl)phenyl, 4-(1-trifluoromethylcyclopropyl)phenyl, 4-phenylphenyl, 4-(1-methylpiperidin-4-yl)phenyl, 4-hydroxylphenyl, 3-methoxyphenyl, 4-methoxyphenyl, 4-dimethylaminophenyl, 4-acetamidophenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 3-dimethylamino-4-methylphenyl, 2-naphthyl, thien-2-yl, 5-isopropylthien-2-yl, 4-pyridyl, 4-tert-butylcyclohexyl, piperidin-4-yl, or 4-tert-butylpiperidin-1-yl;

R$^2$ is H or methyl;

R$^4$ is H;

R$^5$ is H or D-valyloxymethyl;

R$^{3a}$, R$^{3b}$, R$^{3c}$, R$^{3d}$, R$^{3e}$, or R$^{3f}$, if present, is H;

each R$^{6a}$ and R$^{6b}$ is H;

m is an integer of 0, 1, or 2;

p is an integer of 1 or 2; and n1 is an integer of 0, 1, or 2.

In one embodiment, provided herein is a compound of Formula (IVg):

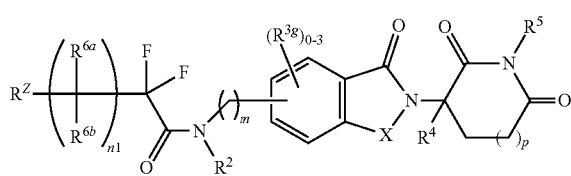

(IVg)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein R$^2$, R$^4$, R$^5$, R$^{3g}$, R$^{6a}$, R$^{6b}$, R$^Z$, X, m, p, and n1 are each as defined herein.

In another embodiment, provided herein is a compound of Formula (IVh):

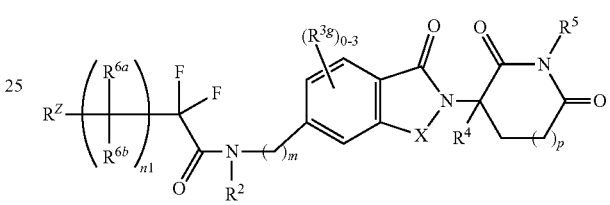

(IVh)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein R$^2$, R$^4$, R$^5$, R$^{3g}$, R$^{6a}$, R$^{6b}$, R$^Z$, X, m, p, and n1 are each as defined herein.

In yet another embodiment, provided herein is a compound of Formula (IVi):

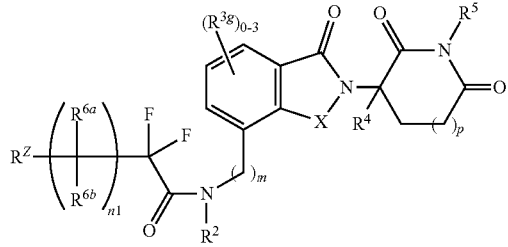

(IVi)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein R$^2$, R$^4$, R$^5$, R$^{3g}$, R$^{6a}$, R$^{6b}$, R$^Z$, X, m, p, and n1 are each as defined herein.

In one embodiment, in any one of Formulae (IVg) to (IVi),

X is CH$_2$ or C(=O);

R$^Z$ is (a) amino, mono-substituted amino, or di-substituted amino; or (b) C$_6$-C$_{10}$ aryl, 5 to 10 membered heteroaryl, C$_3$-C$_8$ carbocyclyl, or 3 to 10 membered heterocyclyl, each of which is optionally substituted with one, two, or three substituents R$^A$, wherein each substituent R$^A$ is independently (i) halogen, cyano, hydroxyl, C$_1$-C$_6$ alkyl, $C_1$-$C_6$ alkoxy, $C_1$-$C_6$ haloalkyl, —$(CH_2)_t$—$NR^{7a}R^{8a}$, or —$NR^{7d}C(O)R^{11b}$, or (ii) phenyl, $C_3$-$C_8$ carbocyclyl, or 3 to 10 membered heterocyclyl, each of which is optionally substituted with one or more $R^B$;
$R^2$ is H or $C_1$-$C_6$ alkyl;
$R^4$ is H or $C_1$-$C_6$ alkyl;
$R^5$ is H or

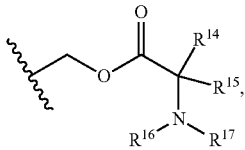

where $R^{14}$, $R^{15}$, $R^{16}$, and $R^{17}$ are each as defined herein;
$R^{3g}$ is halogen or $C_1$-$C_6$ alkyl;
each $R^{6a}$ and $R^{6b}$ is independently H or $C_1$-$C_6$ alkyl;
m is an integer of 0, 1, or 2;
p is an integer of 0, 1, or 2; and
n1 is an integer of 0, 1, 2, or 3.

In another embodiment, in any one of Formulae (IVg) to (IVi),
X is $CH_2$ or $C(=O)$;
$R^Z$ is (a) mono-substituted amino or di-substituted amino; or (b) phenyl, naphthyl, thienyl, pyridyl, piperidinyl, or cyclohexyl, each of which is optionally substituted with one, two, or three substituents $R^A$, wherein each substituent $R^A$ is independently halogen, cyano, hydroxyl, $C_1$-$C_6$ alkyl, $C_1$-$C_6$ alkoxy, $C_1$-$C_6$ haloalkyl, —$(CH_2)$—$NR^{7a}R^{8a}$, —$NR^{7d}C(O)R^{11b}$, phenyl, $C_3$-$C_8$ carbocyclyl, or 3 to 10 membered heterocyclyl, wherein each of phenyl, 5 to 10 membered heteroaryl, $C_3$-$C_8$ carbocyclyl, and 3 to 10 membered heterocyclyl is optionally substituted with one or more $R^B$;
$R^2$ is H or methyl;
$R^4$ is H;
$R^5$ is H or valyloxymethyl;
$R^{3g}$ is fluoro or methyl;
each $R^{6a}$ and $R^{6b}$ is independently H or methyl;
m is an integer of 0, 1, or 2;
p is an integer of 0, 1 or 2; and
n1 is an integer of 0, 1, 2, or 3, In yet another embodiment, in any one of Formulae (IVg) to (IVi),
X is $CH_2$ or $C(=O)$;
$R^Z$ is (a) dimethylamino; or (b) phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethylethyl, trifluoromethyl, dimethylaminomethyl, morpholinylmethyl, propyl, butyl, hydroxyl-butyl, cyclopropyl, methylcyclopropyl, trifluoromethylcyclopropyl, phenyl, methyl-piperidinyl, hydroxyl, methoxy, dimethylamino, or acetamido;
$R^2$ is H or methyl;
$R^4$ is H;
$R^5$ is H or D-valyloxymethyl;
$R^{3g}$ is fluoro or methyl;
each $R^{6a}$ and $R^{6b}$ is H;
m is an integer of 0, 1, or 2;
p is an integer of 1 or 2; and
n1 is an integer of 0, 1, 2, or 3.

In yet another embodiment, in any one of Formulae (IVg) to (IVi),

X is $CH_2$ or $C(=O)$;
$R^Z$ is dimethylamino, phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, isopropyl, sec-butyl, tert-butyl, hydroxyl-tert-butyl, cyclopropyl, methylcyclopropyl, trifluoromethyl-cyclopropyl, phenyl, methyl-piperidinyl, hydroxyl, methoxy, dimethylamino, or acetamido;
$R^2$ is H or methyl;
$R^4$ is H;
$R^5$ is H or D-valyloxymethyl;
$R^{3g}$ is fluoro or methyl;
each $R^{6a}$ and $R^{6b}$ is H;
m is an integer of 0, 1, or 2;
p is an integer of 1 or 2; and
n1 is an integer of 0, 1, 2, or 3.

In yet another embodiment, in any one of Formulae (IVg) to (IVi),
X is $CH_2$ or $C(=O)$;
$R^Z$ is dimethylamino, phenyl, cyanophenyl, fluorophenyl, chlorophenyl, bromophenyl, methylphenyl, (1-trifluoromethylethyl)phenyl, trifluoromethylphenyl, dimethylaminomethylphenyl, morpholin-4-ylmethylphenyl, isopropylphenyl, sec-butylphenyl, tert-butylphenyl, (hydroxyl-tert-butyl)phenyl, cyclopropylphenyl, (1-methylcyclopropyl)phenyl, (1-trifluoromethylcyclopropyl)-phenyl, phenylphenyl, (1-methylpiperidin-4-yl)phenyl, hydroxylphenyl, methoxyphenyl, dimethylaminophenyl, acetamidophenyl, difluorophenyl, dichlorophenyl, chloro-methylphenyl, methyl-tert-butylphenyl, dimethylphenyl, trimethylphenyl, trimethoxyphenyl, dimethyl-tert-butylphenyl, dimethylamino-methylphenyl, naphthyl, thienyl, isopropylthienyl, pyridyl, tert-butylcyclohexyl, piperidinyl, or tert-butylpiperidinyl;
$R^2$ is H or methyl;
$R^4$ is H;
$R^5$ is H or D-valyloxymethyl;
$R^{3g}$ is fluoro or methyl;
each $R^{6a}$ and $R^{6b}$ is H;
m is an integer of 0, 1, or 2;
p is an integer of 1 or 2; and
n1 is an integer of 0, 1, or 2.

In yet another embodiment, in any one of Formulae (IVg) to (IVi),
X is $CH_2$ or $C(=O)$;
$R^Z$ is dimethylamino, phenyl, 4-cyanophenyl, 2-fluorophenyl, 3-fluorophenyl, 4-fluorophenyl, 3-chlorophenyl, 4-chlorophenyl, 4-bromophenyl, 4-methylphenyl, 4-(1-trifluoromethylethyl)phenyl, 4-trifluoromethylphenyl, 4-dimethylaminomethylphenyl, 4-morpholin-4-ylmethylphenyl, 4-isopropylphenyl, 4-sec-butylphenyl, 3-tert-butylphenyl, 4-tert-butylphenyl, 4-(hydroxyl-tert-butyl)phenyl, 4-cyclopropylphenyl, 4-(1-methylcyclopropyl)phenyl, 4-(1-trifluoromethylcyclopropyl)phenyl, 4-phenylphenyl, 4-(1-methylpiperidin-4-yl)phenyl, 4-hydroxylphenyl, 3-methoxyphenyl, 4-methoxyphenyl, 4-dimethylaminophenyl, 4-acetamidophenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 3-dimethylamino-4-methylphenyl, 2-naphthyl, thien-2-yl, 5-isopropylthien-2-yl, 4-pyridyl, 4-tert-butylcyclohexyl, piperidin-4-yl, or 4-tert-butylpiperidin-1-yl;

$R^2$ is H or methyl;

$R^4$ is H;

$R^5$ is H or D-valyloxymethyl;

$R^{3g}$ is methyl;

each $R^{6a}$ and $R^{6b}$ is H;

m is an integer of 0, 1, or 2;

p is an integer of 1 or 2; and n1 is an integer of 0, 1, or 2.

In still another embodiment, in Formula (IVg) to (IVi),

X is $CH_2$ or $C(=O)$;

$R^Z$ is dimethylamino, phenyl, 4-cyanophenyl, 2-fluorophenyl, 3-fluorophenyl, 3-chlorophenyl, 4-trifluoromethylphenyl, 3-tert-butylphenyl, 4-tert-butylphenyl, 4-(1-trifluoromethylcyclopropyl)phenyl, 3-methoxyphenyl, 4-methoxyphenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 2-naphthyl, 5-isopropylthien-2-yl, 4-pyridyl, 4-tert-butylcyclohexyl, or 4-tert-butylpiperidin-1-yl;

$R^2$ is H or methyl;

$R^4$ is H;

$R^5$ is H or D-valyloxymethyl;

$R^{3g}$ is methyl;

m is an integer of 1 or 2;

p is an integer of 1 or 2; and n1 is an integer of 0, 1, or 2.

In one embodiment, provided herein is:

N-((5-(2,6-dioxopiperidin-3-yl)-4-oxo-5,6-dihydro-4H-thieno[3,4-c]pyrrol-1-yl)methyl)-2,2-difluoro-2-(4-fluorophenyl)acetamide II-18;

2-(3-chloro-4-methylphenyl)-N-((5-(2,6-dioxopiperidin-3-yl)-4-oxo-5,6-dihydro-4H-thieno[3,4-c]pyrrol-1-yl)methyl)-2,2-difluoroacetamide II-28;

(S)-2-(3-chloro-4-methylphenyl)-N-((5-(2,7-dioxoazepan-3-yl)-4-oxo-5,6-dihydro-4H-thieno[3,4-c]pyrrol-1-yl)methyl)-2,2-difluoroacetamide II-29;

2-(3-chloro-4-methylphenyl)-N-((5-(2,6-dioxopiperidin-3-yl)-6-oxo-5,6-dihydro-4H-thieno[2,3-c]pyrrol-2-yl)methyl)-2,2-difluoroacetamide II-38;

2-(4-(tert-butyl)phenyl)-N-((5-(2,6-dioxopiperidin-3-yl)-4-oxo-5,6-dihydro-4H-thieno[3,4-c]pyrrol-1-yl)methyl)-2,2-difluoroacetamide II-129;

N-((2-(2,6-dioxopiperidin-3-yl)-1-oxoisoindolin-5-yl)methyl)-2,2-difluoro-2-(4-(1-(trifluoromethyl)cyclopropyl)phenyl)acetamide II-164; or N-((5-(2,6-dioxopiperidin-3-yl)-4-oxo-5,6-dihydro-4H-thieno[3,4-c]pyrrol-1-yl)methyl)-2,2-difluoro-2-(4-(1-(trifluoromethyl)cyclopropyl)phenyl)acetamide II-165;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

Compounds of Formula (V)

In one embodiment, provided herein is a compound of Formula (V):

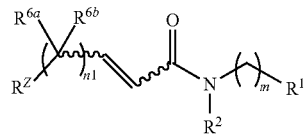

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^{6a}$, $R^{6b}$, $R^Z$, m, and n1 are each as defined herein for Formula (III).

In another embodiment, provided herein is a compound of Formula (Va):

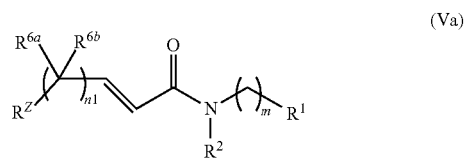

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; $R^1$, $R^2$, $R^{6a}$, $R^{6b}$, $R^Z$, m, and n1 are each as defined herein for Formula (III).

In certain embodiments, $R^Z$ is $—NR^{7a}R^{8a}$, wherein $R^{7a}$ and $R^{8a}$ are each as defined herein for Formula (I). In certain embodiments, R is $—NR^{7a}R^{8a}$, wherein $R^{7a}$ and $R^{8a}$ are each independently H or optionally substituted $C_1$-$C_6$ alkyl. In certain embodiments, $R^Z$ is $—NHCH_3$, $—NHC_2H_5$, $—N(CH_3)_2$, $—N(CH_3)C_2H_5$, or $—N(C_2H_5)_2$. In certain embodiments, $R^Z$ is dimethylamino. In certain embodiments, $R^Z$ is ring A as defined herein for Formula (I).

In one embodiment, provided herein is a compound of Formula (Vb):

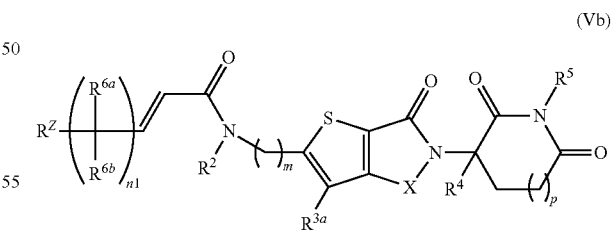

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3a}$, $R^{6a}$, $R^{6b}$, $R^Z$, X, m, p, and n1 are each as defined herein.

In another embodiment, provided herein is a compound of Formula (Vc):

(Vc)

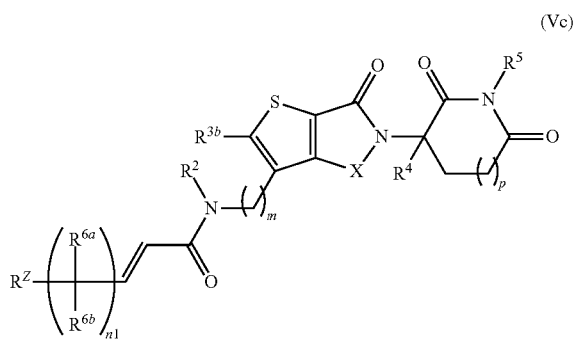

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3b}$, $R^{6a}$, $R^{6b}$, $R^Z$, X, m, p, and n1 are each as defined herein.

In yet another embodiment, provided herein is a compound of Formula (Vd):

(Vd)

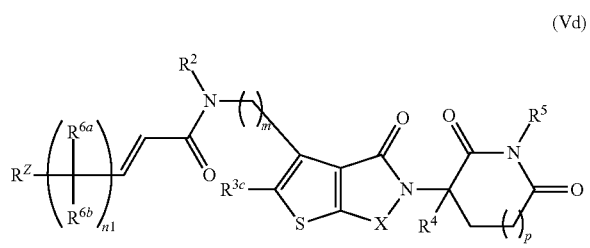

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^3$, $R^{6a}$, $R^{6b}$, $R^Z$, X, m, p, and n1 are each as defined herein.

In yet another embodiment, provided herein is a compound of Formula (Ve):

(Ve)

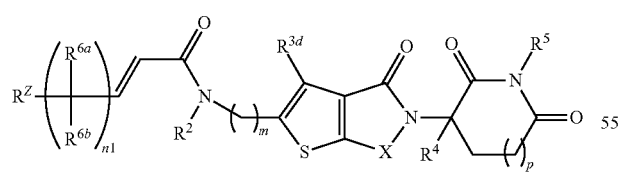

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3d}$, $R^{6a}$, $R^{6b}$, $R^Z$, X, m, p, and n1 are each as defined herein.

In yet another embodiment, provided herein is a compound of Formula (Vf):

(Vf)

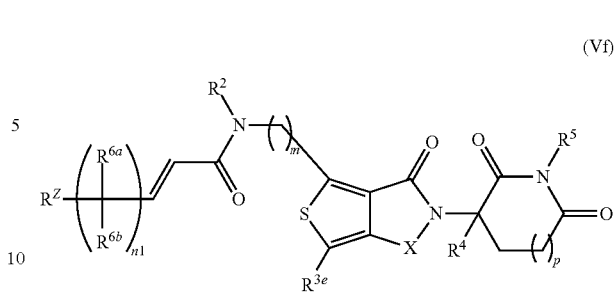

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^3$, $R^{6a}$, $R^{6b}$, $R^Z$, X, m, p, and n1 are each as defined herein.

In still another embodiment, provided herein is a compound of Formula (IVg):

(Vg)

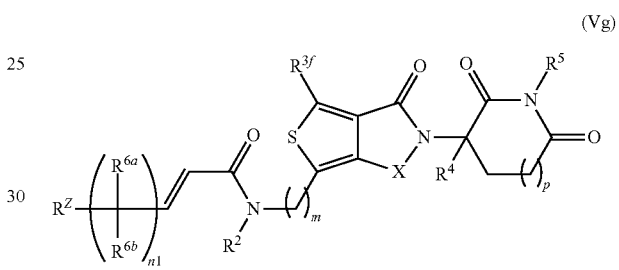

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^3$, $R^{6a}$, $R^{6b}$, $R^Z$, X, m, p, and n1 are each as defined herein.

In one embodiment, in any one of Formulae (Vb) to (Vg),
X is $CH_2$ or C(=O);
$R^Z$ is (a) amino, mono-substituted amino, or di-substituted amino; or (b) $C_6$-$C_{10}$ aryl, 5 to 10 membered heteroaryl, $C_3$-$C_8$ carbocyclyl, or 3 to 10 membered heterocyclyl, each of which is optionally substituted with one, two, or three substituents $R^A$, wherein each substituent $R^A$ is independently (i) halogen, cyano, hydroxyl, $C_1$-$C_6$ alkyl, $C_1$-$C_6$ alkoxy, $C_1$-$C_6$ haloalkyl, —$(CH_2)_t$—$NR^{7a}R^{8a}$, or —$NR^{7d}C(O)R^{11b}$, or (ii) phenyl, $C_3$-$C_8$ carbocyclyl, or 3 to 10 membered heterocyclyl, each of which is optionally substituted with one or more $R^B$;
$R^2$ is H or $C_1$-$C_6$ alkyl;
$R^4$ is H or $C_1$-$C_6$ alkyl;
$R^5$ is H or

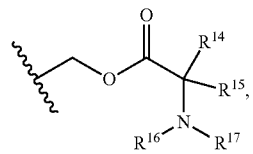

where $R^{14}$, $R^{15}$, $R^{16}$, and $R^{17}$ are each as defined herein;
$R^{3a}$, $R^{3b}$, $R^{3c}$, $R^{3d}$, $R^{3e}$, or $R^{3f}$, if present, is H;
each $R^{6a}$ and $R^{6b}$ is independently H or $C_1$-$C_6$ alkyl;

m is an integer of 0, 1, or 2;
p is an integer of 0, 1, or 2; and
n1 is an integer of 0, 1, 2, or 3.

In another embodiment, in any one of Formulae (Vb) to (Vg),

X is $CH_2$ or $C(=O)$;

$R^Z$ is (a) mono-substituted amino or di-substituted amino; or (b) phenyl, naphthyl, thienyl, pyridyl, piperidinyl, or cyclohexyl, each of which is optionally substituted with one, two, or three substituents $R^A$, wherein each substituent $R^A$ is independently halogen, cyano, hydroxyl, $C_1$-$C_6$ alkyl, $C_1$-$C_6$ alkoxy, $C_1$-$C_6$ haloalkyl, —$(CH_2)$—$NR^{7a}R^{8a}$, —$NR^{7d}C(O)R^{11b}$, phenyl, $C_3$-$C_8$ carbocyclyl, or 3 to 10 membered heterocyclyl, wherein each of phenyl, 5 to 10 membered heteroaryl, $C_3$-$C_8$ carbocyclyl, and 3 to 10 membered heterocyclyl is optionally substituted with one or more $R^B$;

$R^2$ is H or methyl;

$R^4$ is H;

$R^5$ is H or valyloxymethyl;

$R^{3a}$, $R^{3b}$, $R^{3c}$, $R^{3d}$, $R^{3e}$, or $R^{3f}$, if present, is H;

each $R^{6a}$ and $R^{6b}$ is independently H or methyl;

m is an integer of 0, 1, or 2;

p is an integer of 0, 1 or 2; and n1 is an integer of 0, 1, 2, or 3.

In yet another embodiment, in any one of Formulae (Vb) to (Vg),

X is $CH_2$ or $C(=O)$;

$R^Z$ is (a) dimethylamino; or (b) phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethylethyl, trifluoromethyl, dimethylaminomethyl, morpholinylmethyl, propyl, butyl, hydroxyl-butyl, cyclopropyl, methylcyclopropyl, trifluoromethylcyclopropyl, phenyl, methyl-piperidinyl, hydroxyl, methoxy, dimethylamino, or acetamido;

$R^2$ is H or methyl;

$R^4$ is H;

$R^5$ is H or D-valyloxymethyl;

$R^{3a}$, $R^{3b}$, $R^{3c}$, $R^{3d}$, $R^{3e}$, or $R^{3f}$, if present, is H;

each $R^{6a}$ and $R^{6b}$ is H;

m is an integer of 0, 1, or 2;

p is an integer of 1 or 2; and n1 is an integer of 0, 1, 2, or 3.

In yet another embodiment, in any one of Formulae (Vb) to (Vg),

X is $CH_2$ or $C(=O)$;

$R^Z$ is dimethylamino, phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, isopropyl, sec-butyl, tert-butyl, hydroxyl-tert-butyl, cyclopropyl, methylcyclopropyl, trifluoromethyl-cyclopropyl, phenyl, methyl-piperidinyl, hydroxyl, methoxy, dimethylamino, or acetamido;

$R^2$ is H or methyl;

$R^4$ is H;

$R^5$ is H or D-valyloxymethyl;

$R^{3a}$, $R^{3b}$, $R^{3c}$, $R^{3d}$, $R^{3e}$, or $R^{3f}$, if present, is H;

each $R^{6a}$ and $R^{6b}$ is H;

m is an integer of 0, 1, or 2;

p is an integer of 1 or 2; and n1 is an integer of 0, 1, 2, or 3.

In yet another embodiment, in any one of Formulae (Vb) to (Vg),

X is $CH_2$ or $C(=O)$;

$R^Z$ is dimethylamino, phenyl, cyanophenyl, fluorophenyl, chlorophenyl, bromophenyl, methylphenyl, (1-trifluoromethylethyl)phenyl, trifluoromethylphenyl, dimethylaminomethylphenyl, morpholin-4-ylmethylphenyl, isopropylphenyl, sec-butylphenyl, tert-butylphenyl, (hydroxyl-tert-butyl)phenyl, cyclopropylphenyl, (1-methylcyclopropyl)phenyl, (1-trifluoromethylcyclopropyl)-phenyl, phenylphenyl, (1-methylpiperidin-4-yl)phenyl, hydroxylphenyl, methoxyphenyl, dimethylaminophenyl, acetamidophenyl, difluorophenyl, dichlorophenyl, chloro-methylphenyl, methyl-tert-butylphenyl, dimethylphenyl, trimethylphenyl, trimethoxyphenyl, dimethyl-tert-butylphenyl, dimethylamino-methylphenyl, naphthyl, thienyl, isopropylthienyl, pyridyl, tert-butylcyclohexyl, piperidinyl, or tert-butylpiperidinyl;

$R^2$ is H or methyl;

$R^4$ is H;

$R^5$ is H or D-valyloxymethyl;

$R^{3a}$, $R^{3b}$, $R^{3c}$, $R^{3d}$, $R^{3e}$, or $R^{3f}$, if present, is H;

each $R^{6a}$ and $R^{6b}$ is H;

m is an integer of 0, 1, or 2;

p is an integer of 1 or 2; and n1 is an integer of 0, 1, or 2.

In still another embodiment, in any one of Formulae (Vb) to (Vg),

X is $CH_2$ or $C(=O)$;

$R^Z$ is dimethylamino, phenyl, 4-cyanophenyl, 2-fluorophenyl, 3-fluorophenyl, 4-fluorophenyl, 3-chlorophenyl, 4-chlorophenyl, 4-bromophenyl, 4-methylphenyl, 4-(1-trifluoromethylethyl)phenyl, 4-trifluoromethylphenyl, 4-dimethylaminomethylphenyl, 4-morpholin-4-ylmethylphenyl, 4-isopropylphenyl, 4-sec-butylphenyl, 3-tert-butylphenyl, 4-tert-butylphenyl, 4-(hydroxyl-tert-butyl)phenyl, 4-cyclopropylphenyl, 4-(1-methylcyclopropyl)phenyl, 4-(1-trifluoromethylcyclopropyl)phenyl, 4-phenylphenyl, 4-(1-methylpiperidin-4-yl)phenyl, 4-hydroxylphenyl, 3-methoxyphenyl, 4-methoxyphenyl, 4-dimethylaminophenyl, 4-acetamidophenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 3-dimethylamino-4-methylphenyl, 2-naphthyl, thien-2-yl, 5-isopropylthien-2-yl, 4-pyridyl, 4-tert-butylcyclohexyl, piperidin-4-yl, or 4-tert-butylpiperidin-1-yl;

$R^2$ is H or methyl;

$R^4$ is H;

$R^5$ is H or D-valyloxymethyl;

$R^{3a}$, $R^{3b}$, $R^{3c}$, $R^{3d}$, $R^{3e}$, or $R^{3f}$, if present, is H;

each $R^{6a}$ and $R^{6b}$ is H;

m is an integer of 0, 1, or 2;

p is an integer of 1 or 2; and n1 is an integer of 0, 1, or 2.

In one embodiment, provided herein is a compound of Formula (Vh):

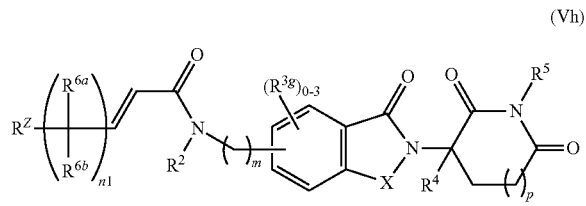

(Vh)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3g}$, $R^{6a}$, $R^{6b}$, $R^Z$, X, m, p, and n1 are each as defined herein.

In another embodiment, provided herein is a compound of Formula (Vi):

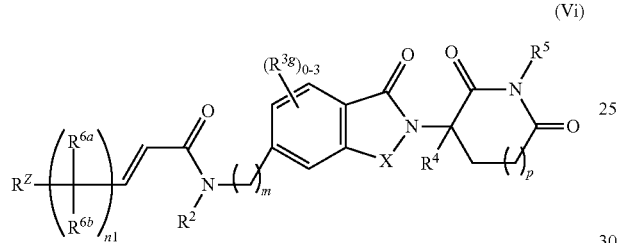

(Vi)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3g}$, $R^{6a}$, $R^{6b}$, $R^Z$, X, m, p, and n1 are each as defined herein.

In yet another embodiment, provided herein is a compound of Formula (Vj):

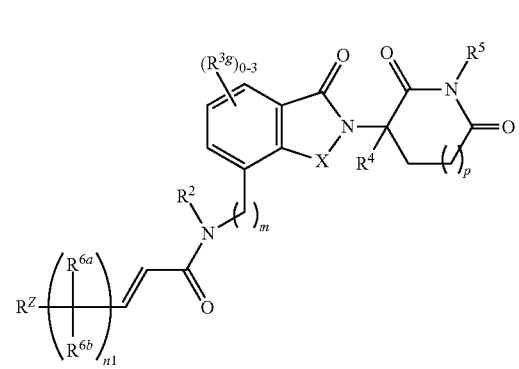

(Vj)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^4$, $R^5$, $R^{3g}$, $R^{6a}$, $R^{6b}$, $R^Z$, X, m, p, and n1 are each as defined herein.

In one embodiment, in any one of Formulae (Vh) to (Vj),
X is $CH_2$ or C(=O);
$R^Z$ is (a) amino, mono-substituted amino, or di-substituted amino; or (b) $C_6$-$C_{10}$ aryl, 5 to 10 membered heteroaryl, $C_3$-$C_8$ carbocyclyl, or 3 to 10 membered heterocyclyl, each of which is optionally substituted with one, two, or three substituents $R^A$, wherein each substituent $R^A$ is independently (i) halogen, cyano, hydroxyl, $C_1$-$C_6$ alkyl, $C_1$-$C_6$ alkoxy, $C_1$-$C_6$ haloalkyl, —$(CH_2)_t$—$NR^{7a}R^{8a}$, or —$NR^{7d}C(O)R^{11b}$, or (ii) phenyl, $C_3$-$C_8$ carbocyclyl, or 3 to 10 membered heterocyclyl, each of which is optionally substituted with one or more $R^B$;
$R^2$ is H or $C_1$-$C_6$ alkyl;
$R^4$ is H or $C_1$-$C_6$ alkyl;
$R^5$ is H or

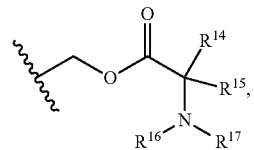

where $R^{14}$, $R^{15}$, $R^{16}$, and $R^{17}$ are each as defined herein;
$R^{3g}$ is halogen or $C_1$-$C_6$ alkyl;
each $R^{6a}$ and $R^{6b}$ is independently H or $C_1$-$C_6$ alkyl;
m is an integer of 0, 1, or 2;
p is an integer of 0, 1, or 2; and
n1 is an integer of 0, 1, 2, or 3.

In another embodiment, in any one of Formulae (Vh) to (Vj),
X is $CH_2$ or C(=O);
$R^Z$ is (a) mono-substituted amino or di-substituted amino; or (b) phenyl, naphthyl, thienyl, pyridyl, piperidinyl, or cyclohexyl, each of which is optionally substituted with one, two, or three substituents $R^A$, wherein each substituent $R^A$ is independently halogen, cyano, hydroxyl, $C_1$-$C_6$ alkyl, $C_1$-$C_6$ alkoxy, $C_1$-$C_6$ haloalkyl, —$(CH_2)$—$NR^{7a}R^{8a}$, —$NR^{7d}C(O)R^{11b}$, phenyl, $C_3$-$C_8$ carbocyclyl, or 3 to 10 membered heterocyclyl, wherein each of phenyl, 5 to 10 membered heteroaryl, $C_3$-$C_8$ carbocyclyl, and 3 to 10 membered heterocyclyl is optionally substituted with one or more $R^B$;
$R^2$ is H or methyl;
$R^4$ is H;
$R^5$ is H or valyloxymethyl;
$R^{3g}$ is fluoro or methyl;
each $R^{6a}$ and $R^{6b}$ is independently H or methyl;
m is an integer of 0, 1, or 2;
p is an integer of 0, 1 or 2; and
n1 is an integer of 0, 1, 2, or 3, In yet another embodiment, in any one of Formulae (Vh) to (Vj),
X is $CH_2$ or C(=O);
$R^Z$ is (a) dimethylamino; or (b) phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethylethyl, trifluoromethyl, dimethylaminomethyl, morpholinylmethyl, propyl, butyl, hydroxyl-butyl, cyclopropyl, methylcyclopropyl, trifluoromethylcyclopropyl, phenyl, methyl-piperidinyl, hydroxyl, methoxy, dimethylamino, or acetamido;
$R^2$ is H or methyl;
$R^4$ is H;
$R^5$ is H or D-valyloxymethyl;
$R^{3g}$ is fluoro or methyl;
each $R^{6a}$ and $R^{6b}$ is H;
m is an integer of 0, 1, or 2;

p is an integer of 1 or 2; and
n1 is an integer of 0, 1, 2, or 3.

In yet another embodiment, in any one of Formulae (Vh) to (Vj),

X is $CH_2$ or $C(=O)$;
$R^Z$ is dimethylamino, phenyl, naphthyl, thienyl, pyridyl, piperidinyl, or cyclohexyl, each of which is optionally substituted with one, two, or three substituents $R^A$, wherein each substituent $R^A$ is independently cyano, fluoro, chloro, bromo, methyl, trifluoromethyl-ethyl, trifluoromethyl, dimethylaminomethyl, morpholinylmethyl, isopropyl, sec-butyl, tert-butyl, hydroxyl-tert-butyl, cyclopropyl, methylcyclopropyl, trifluoromethyl-cyclopropyl, phenyl, methyl-piperidinyl, hydroxyl, methoxy, dimethylamino, or acetamido;
$R^2$ is H or methyl;
$R^4$ is H;
$R^5$ is H or D-valyloxymethyl;
$R^{3g}$ is fluoro or methyl;
each $R^{6a}$ and $R^{6b}$ is H;
m is an integer of 0, 1, or 2;
p is an integer of 1 or 2; and
n1 is an integer of 0, 1, 2, or 3.

In yet another embodiment, in any one of Formulae (Vh) to (Vj),

X is $CH_2$ or $C(=O)$;
$R^Z$ is dimethylamino, phenyl, cyanophenyl, fluorophenyl, chlorophenyl, bromophenyl, methylphenyl, (1-trifluoromethylethyl)phenyl, trifluoromethylphenyl, dimethylaminomethylphenyl, morpholin-4-ylmethylphenyl, isopropylphenyl, sec-butylphenyl, tert-butylphenyl, (hydroxyl-tert-butyl)phenyl, cyclopropylphenyl, (1-methylcyclopropyl)phenyl, (1-trifluoromethylcyclopropyl)-phenyl, phenylphenyl, (1-methylpiperidin-4-yl)phenyl, hydroxylphenyl, methoxyphenyl, dimethyl-aminophenyl, acetamidophenyl, difluorophenyl, dichlorophenyl, chloro-methylphenyl, methyl-tert-butylphenyl, dimethylphenyl, trimethylphenyl, trimethoxyphenyl, dimethyl-tert-butylphenyl, dimethylamino-methylphenyl, naphthyl, thienyl, isopropylthienyl, pyridyl, tert-butylcyclohexyl, piperidinyl, or tert-butylpiperidinyl;
$R^2$ is H or methyl;
$R^4$ is H;
$R^5$ is H or D-valyloxymethyl;
$R^{3g}$ is fluoro or methyl;
each $R^{6a}$ and $R^{6b}$ is H;
m is an integer of 0, 1, or 2;
p is an integer of 1 or 2; and
n1 is an integer of 0, 1, or 2.

In yet another embodiment, in any one of Formulae (Vh) to (Vj),

X is $CH_2$ or $C(=O)$;
$R^Z$ is dimethylamino, phenyl, 4-cyanophenyl, 2-fluorophenyl, 3-fluorophenyl, 4-fluorophenyl, 3-chlorophenyl, 4-chlorophenyl, 4-bromophenyl, 4-methylphenyl, 4-(1-trifluoromethylethyl)phenyl, 4-trifluoromethylphenyl, 4-dimethylaminomethylphenyl, 4-morpholin-4-ylmethylphenyl, 4-isopropylphenyl, 4-sec-butylphenyl, 3-tert-butylphenyl, 4-tert-butylphenyl, 4-(hydroxyl-tert-butyl)phenyl, 4-cyclopropylphenyl, 4-(1-methylcyclopropyl)phenyl, 4-(1-trifluoromethylcyclopropyl)phenyl, 4-phenylphenyl, 4-(1-methylpiperidin-4-yl)phenyl, 4-hydroxylphenyl, 3-methoxyphenyl, 4-methoxyphenyl, 4-dimethylaminophenyl, 4-acetamidophenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 3-dimethylamino-4-methylphenyl, 2-naphthyl, thien-2-yl, 5-isopropylthien-2-yl, 4-pyridyl, 4-tert-butylcyclohexyl, piperidin-4-yl, or 4-tert-butylpiperidin-1-yl;
$R^2$ is H or methyl;
$R^4$ is H;
$R^5$ is H or D-valyloxymethyl;
$R^{3g}$ is methyl;
each $R^{6a}$ and $R^{6b}$ is H;
m is an integer of 0, 1, or 2;
p is an integer of 1 or 2; and
n1 is an integer of 0, 1, or 2.

In still another embodiment, in Formula (Vh) to (Vj),

X is $CH_2$ or $C(=O)$;
$R^Z$ is dimethylamino, phenyl, 4-cyanophenyl, 2-fluorophenyl, 3-fluorophenyl, 3-chlorophenyl, 4-trifluoromethylphenyl, 3-tert-butylphenyl, 4-tert-butylphenyl, 4-(1-trifluoromethylcyclopropyl)phenyl, 3-methoxyphenyl, 4-methoxyphenyl, 3,4-difluorophenyl, 3,4-dichlorophenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 2-naphthyl, 5-isopropylthien-2-yl, 4-pyridyl, 4-tert-butylcyclohexyl, or 4-tert-butylpiperidin-1-yl;
$R^2$ is H or methyl;
$R^4$ is H;
$R^5$ is H or D-valyloxymethyl;
$R^{3g}$ is methyl;
m is an integer of 1 or 2;
p is an integer of 1 or 2; and
n1 is an integer of 0, 1, or 2.

In one embodiment, provided herein is (E)-N-((2-(2,6-dioxopiperidin-3-yl)-1-oxoisoindolin-5-yl)methyl)-3-(4-(1-(trifluoromethyl)cyclopropyl)phenyl)acrylamide II-149; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In any embodiments of the compounds described herein, when a substituent is selected from a carbocyclyl (e.g., $C_3$-$C_8$ carbocyclyl), it includes $C_3$-$C_8$ cycloalkyl. When a substituent is select from 3 to 7 membered heterocyclyl, it includes 3 to 7 membered monocyclic heterocycle rings with no double or triple bond within the ring structure.

In certain embodiments, the compound provided herein is formed as a pharmaceutically acceptable salt. In certain embodiments, the compound provided herein or a pharmaceutically acceptable salt thereof is racemic. In certain embodiments, the compound provided herein or a pharmaceutically acceptable salt thereof has an S-configuration at the carbon atom with an asterisk

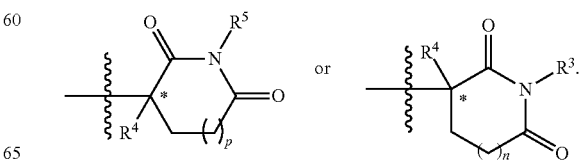

In certain embodiments, the compound provided herein or a pharmaceutically acceptable salt thereof has an R-configuration at the carbon atom with an asterisk

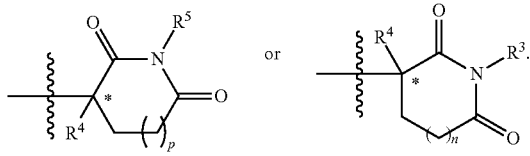

In some embodiments, the compound provided herein or a pharmaceutically acceptable salt thereof is enriched in one enantiomer over another enantiomer, for example, enriched by about 10%, 20%, 30%, 40%, 50%, 60%, 70%, 80%, 90%, 95%, or 99%, or any value in between. In certain embodiments, the compound provided herein or a pharmaceutically acceptable salt thereof is enriched in one diastereomer over another diastereomer, for example, enriched by about 10%, 20%, 30%, 40%, 50%, 60%, 70%, 80%, 90%, 95%, or 99%, or any value in between. In certain embodiments, the compound provided herein is a pharmaceutically acceptable salt. In some embodiments, the compound provided herein or a pharmaceutically acceptable salt thereof is a pharmaceutically acceptable solvate.

Methods of Treatment/Uses

In certain embodiments, provided herein is a method of treating, ameliorating, or preventing a disease, disorder, or condition associated with GSPT1 in a subject, comprising administering to the subject a therapeutically effective amount of a compound provided herein, or a pharmaceutically acceptable salt thereof, or a pharmaceutical composition comprising a compound provided herein. In certain embodiments, the disease, disorder, or condition is associated with GSPT1 malfunction. In certain embodiments, the disease, disorder, or condition is inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, or cancer. In certain embodiments, the disease, disorder, or condition is cancer. Non-limiting examples of cancer include breast cancer, melanoma, renal cancer, prostate cancer, colon cancer, lung cancer, bladder cancer, brain cancer, cervical cancer, head and neck cancer, esophageal and gastric cancers, osteosarcoma, multiple myeloma, leukemia, lymphoma, neuroendocrine cancer, hepatocellular carcinoma, renal cell cancer, pancreatic cancer, thyroid cancer, glioblastoma, ovarian, endometrial cancer, and astrogliosis. In certain embodiments, the disease, disorder, or condition is a breast cancer, lung cancer, leukemia, lymphoma, hepatocellular carcinoma, gastric cancer, or prostate cancer and astrogliosis. In certain embodiments, the disease, disorder, or condition is leukemia, acute myelogenous leukemia, acute myeloid leukemia, lymphoma, or hepatocellular carcinoma. In certain embodiments, the subject possesses wild-type GSPT1 or aberrant GSPT1. In certain embodiments, the subject overexpresses GSPT1.

In certain embodiments, provided herein is a method of inhibiting GSPT1 activity in a cell, or a method of decreasing a cellular level of GSPT1 in a cell, comprising contacting the cell with an effective amount of a compound provided herein or a pharmaceutically acceptable salt thereof. In certain embodiments, the cell is a breast cancer cell, a lung cancer cell, a leukemia cell, a lymphoma cell, a hepatocellular carcinoma cell, a gastric cancer cell, or a prostate cancer cell. In certain embodiments, the cell is a leukemia cell, a lymphoma cell, or a hepatocellular carcinoma cell. In certain, the cell possesses wild-type GSPT1 or aberrant GSPT1, or overexpresses GSPT1.

In certain embodiments, provided herein is a method of treating, ameliorating, or preventing a disease, disorder, or condition associated with a protein in a subject, comprising administering to the subject a therapeutically effective amount of a compound provided herein or a pharmaceutically acceptable salt thereof, or a pharmaceutical composition comprising a compound provided herein; wherein the protein is a cytokine, aiolos, ikaros, helios, or CK1α. In certain embodiments, the protein is a cytokine. In certain embodiments, the cytokine is IL-1β, IL-6, TNFα, or IL-2. In certain embodiments, the cytokine is a pro-inflammatory cytokine. In certain embodiments, the protein is aiolos, ikaros, or helios. In certain embodiments, the protein is CK1α. In certain embodiments, the disease, disorder, or condition is inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, or cancer. In certain embodiments, the disease, disorder, or condition is cancer. In certain embodiments, the disease, disorder, or condition is a leukemia, a lymphoma, or a hepatocellular carcinoma.

In one embodiment, the subject is a mammalian. In another embodiment, the subject is a human.

In certain embodiments, provided herein is a method of modulating (such as inhibiting or stimulating) protein activity, comprising contacting a cell with a compound provided herein or a pharmaceutically acceptable salt thereof; wherein the protein is a cytokine, aiolos, ikaros, helios, or CK1α. In certain embodiments, the method is to inhibit a cytokine activity, wherein the cytokine is a pro-inflammatory cytokine selected from a group consisting of IL-1β, IL-6, and TNFα. In certain embodiments, the method is to stimulate cytokine activity, wherein the cytokine is an anti-inflammatory cytokine, such as IL-2. In certain embodiments, the method is to inhibit aiolos activity. In certain embodiments, the method is to inhibit ikaros activity. In certain embodiments, the method is to inhibit helios activity. In certain embodiments, the method is to inhibit CK1α activity.

In certain embodiments, provided herein is a method for treating, ameliorating, or preventing a skin disorder, disease, or condition in a subject, comprising administering to the subject a therapeutically effective amount of a compound provided herein or a pharmaceutically acceptable salt thereof, or a pharmaceutical composition comprising a compound provided herein. In certain embodiments, the skin disorder is skin cancer.

In certain embodiments, a compound provided herein is in the form of a pharmaceutically acceptable salt, solvate, active metabolite, tautomer, or prodrug thereof. In certain embodiments, the pharmaceutical composition provided herein contains at least one pharmaceutically acceptable inactive ingredient. The pharmaceutical composition can be formulated for intravenous injection, subcutaneous injection, oral administration, buccal administration, inhalation, nasal administration, topical administration, transdermal administration, ophthalmic administration, or otic administration. The pharmaceutical composition can be in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

The pharmaceutical composition provided herein can further comprise an additional therapeutically active agent other than a compound provided herein. Such a agent can include, but are not limited to, an anti-inflammatory agent, anti-cancer agent, immunostimulatory agent, or immunosuppressive agent.

Pharmaceutical Compositions

In certain embodiments, provided herein is a pharmaceutical composition comprising a compound provided herein or a pharmaceutically acceptable salt thereof; and a pharmaceutically acceptable excipient.

As used herein, an "excipient" refers to an essentially inert substance that is added to a pharmaceutical composition to provide, without limitation, bulk, consistency, stability, binding ability, lubrication, disintegrating ability etc., to the composition. For example, stabilizers such as anti-oxidants and metal-chelating agents are excipients. Excipients also include ingredients in a pharmaceutical composition that lack appreciable pharmacological activity but may be pharmaceutically necessary or desirable. For example, to increase the bulk of a potent drug which mass is too small for manufacture and/or administration. It may also be a liquid for the dissolution of a drug to be administered by injection, ingestion, or inhalation. For example, a buffered aqueous solution, such as, without limitation, phosphate buffered saline that mimics the pH and isotonicity of the human blood.

The pharmaceutical compositions described herein can be administered to a human patient per se, or in pharmaceutical compositions where they are mixed with other active ingredients, as in combination therapy, or excipients, or combinations thereof. Proper formulation is dependent upon the route of administration chosen. Techniques for formulation and administration of the compounds described herein are known to those skilled in the art.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In certain embodiments, a compound provided herein or a pharmaceutically acceptable salt thereof, or a pharmaceutical composition thereof is administered orally or topically.

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such a notice, for example, may be the labeling approved by the U.S. Food and Drug Administration for prescription drugs, or the approved product insert. Compositions that can include a compound and/or salt described herein formulated in a compatible pharmaceutical excipient may also be prepared, placed in an appropriate container, and labeled for treatment of an indicated condition.

The disclosure will be further understood by the following non-limiting examples.

EXAMPLES

As used herein, the symbols and conventions used in these processes, schemes, and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry.

For all of the following examples, standard work-up and purification methods known to those skilled in the art can be utilized. Unless otherwise indicated, all temperatures are expressed in ° C. (degrees Centigrade). All reactions are conducted at room temperature unless otherwise specified. Synthetic methodologies illustrated herein are intended to exemplify the applicable chemistry through the use of specific examples and are not indicative of the scope of the disclosure.

The starting materials (e.g., compound 3) used in the following examples were commercially available or prepared, for example, according to the procedures described in US 2019/0322683 A1, US 2019/0365775, and US 2020/0009120 A1, the disclosure of each of which is incorporated herein by reference in its entirety.

Example 1

Compound I-1: 2-(4-(Tert-butyl)phenyl)-N-((5-(2,6-dioxopiperidin-3-yl)-4-oxo-5,6-dihydro-4H-thieno[3,4-c]pyrrol-1-yl)methyl)-2-oxoacetamide

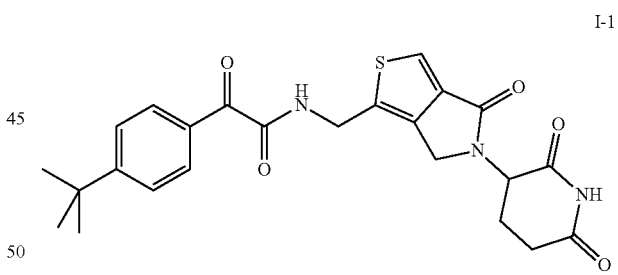

Compound I-1 was synthesized as shown in Scheme 1.

Scheme 1

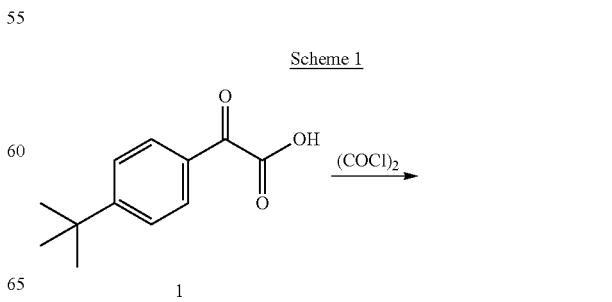

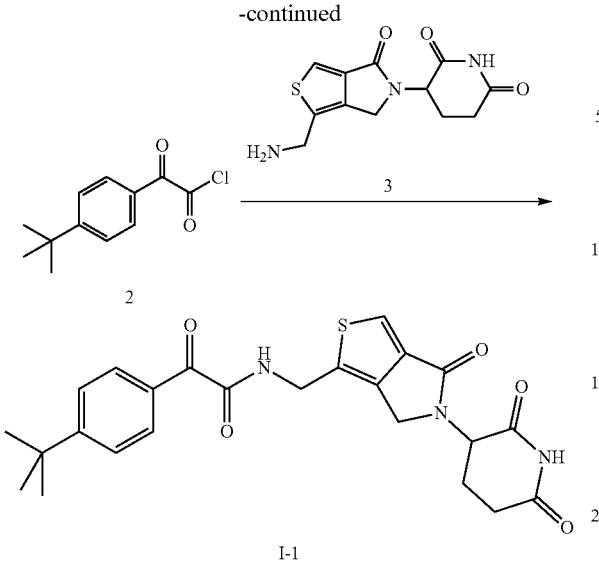

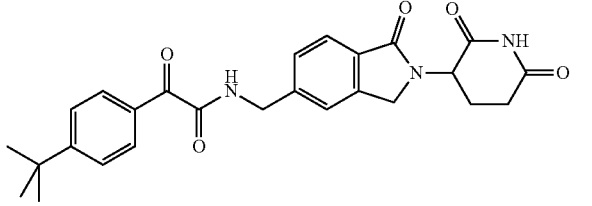

I-1

To a solution of 2-(4-(tert-butyl)phenyl)-2-oxoacetic acid 1 (3.38 g, 16 mmol) in DCM (25 mL) at RT was added oxalyl chloride (4.17 g, 33 mmol) and one drop of DMF. After stirring at RT for 18 h, the reaction was concentrated to give 2-(4-(tert-butyl)phenyl)-2-oxoacetyl chloride 2 (3.8 g, 100% yield) as an oil.

To a solution of 3-(1-(aminomethyl)-4-oxo-4H-thieno[3,4-c]pyrrol-5(6H)-yl)piperidine-2,6-dione 3 (2.0 g, 5.2 mmol) in DCM (20 mL) was added TEA (1.58 g, 15.6 mmol) and 2-(4-(tert-butyl)phenyl)-2-oxoacetyl chloride 2 (1.4 g, 6.3 mmol). After stirring at RT for 3 h, the mixture was concentrated and the residue was purified using silica gel eluting with DCM/MeOH (10:1) to give compound I-1 (1.1 g) in 45% yield. MS (ESI) m/z: 468.1 [M+1]$^+$; $^1$H NMR (400 MHz, DMSO-d$_6$) δ 10.98 (s, 1H), 9.57 (t, J=6.0 Hz, 1H), 7.94-7.92 (m, 3H), 7.60 (d, J=8.4 Hz, 1H), 5.05-5.01 (m, 1H), 4.59 (d, J=6.0 Hz, 2H), 4.37-4.22 (m, 4H), 3.67 (d, J=5.6 Hz, 2H), 2.91-2.85 (m, 1H), 2.67-2.57 (m, 1H), 2.34-2.25 (m, 1H), 2.02-1.97 (m, 1H), 1.31 (s, 9H).

Example 2

Compound I-2: 2-(4-(Tert-butyl)phenyl)-N-((2-(2,6-dioxopiperidin-3-yl)-1-oxoisoindolin-5-yl)methyl)-2-oxoacetamide

I-2

Compound I-2 was synthesized as shown in Scheme 2.

To a solution of methyl 4-cyano-2-methylbenzoate 4 (4.00 g, 22.8 mmol) in CCl$_4$ (150 mL) at RT was added NBS (4.88 g, 27.4 mmol), and the suspension was heated at 80° C. for 5 min. AIBN (1.88 g, 11.4 mmol) was added, and the mixture was heated at 80° C. for 16 h and then cooled to RT and filtered. The filtrate was concentrated and the residue was purified using silica gel eluting with EA/PE from 0% to 5% to give methyl 2-(bromomethyl)-4-cyanobenzoate 5 (3.84 g, 67% yield).

To a solution of methyl 2-(bromomethyl)-4-cyanobenzoate 5 (729 mg, 2.7 mmol) and 3-aminopiperidine-2,6-dione (532 mg, 3.2 mmol) in DMF (12 mL) at RT was added TEA (1.2 mL, 8.1 mmol). The reaction mixture was heated at 85° C. for 4 h and then concentrated. The residue was purified using silica gel eluting with DCM/MeOH (100:1 to 50:1) to afford 2-(2,6-dioxopiperidin-3-yl)-1-oxoisoindoline-5-carbonitrile 6 (320 mg) in 44% yield. MS (ESI) m/z: 270.0 [M+H]$^+$; $^1$H NMR (300 MHz, DMSO-d6) δ 11.03 (s, 1H), 8.16 (s, 1H), 7.99 (d, J=7.8 Hz, 1H), 7.91 (d, J=7.8 Hz, 1H), 5.18-5.12 (m, 1H), 4.58-4.39 (m, 2H), 2.92-2.62 (m, 1H), 2.57 (d, J=2.1 Hz, 1H), 2.45-2.40 (m, 1H), 2.05-2.00 (m, 1H).

Scheme 2

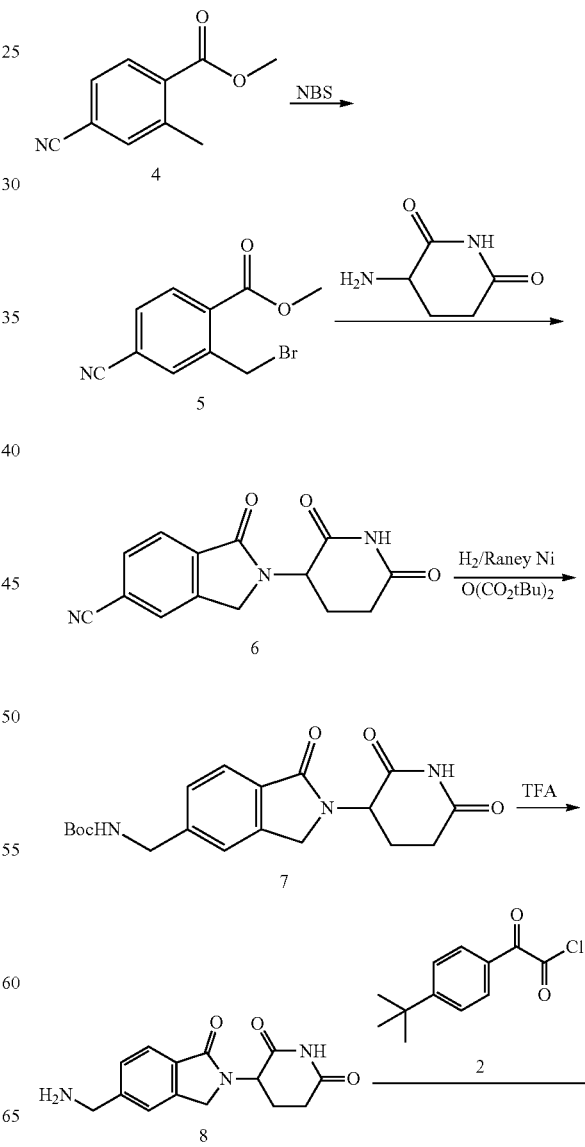

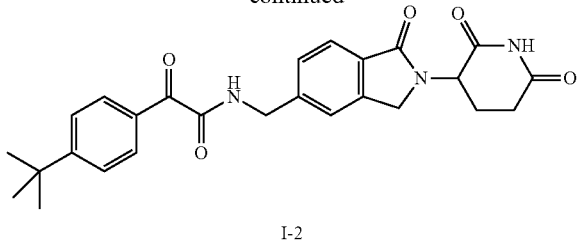

I-2

To a solution of 2-(2,6-dioxopiperidin-3-yl)-1-oxoisoindoline-5-carbonitrile 6 (320 mg, 1.18 mmol) in MeOH (16 mL) at RT was added Raney Ni (180 mg), followed by the addition of di-tert-butyl dicarbonate (514 mg, 2.36 mmol). The suspension was stirred at RT for 14 h under $H_2$, and then filtered and concentrated. The residue was purified using silica gel eluting with DCM/MeOH (100:1 to 50:1) to give tert-butyl ((2-(2,6-dioxopiperidin-3-yl)-1-oxoisoindolin-5-yl)methyl)carbamate 7 (280 mg) in 63% yield. MS (ESI) m/z: 374.1 $[M+H]^+$.

To a solution of tert-butyl ((2-(2,6-dioxopiperidin-3-yl)-1-oxoisoindolin-5-yl)methyl)-carbamate 7 (160 mg, 0.42 mmol) in DCM (6 mL) at RT was added TFA (1.5 mL). The mixture was stirred for 3 h and then concentrated to give 3-(5-(aminomethyl)-1-oxoisoindolin-2-yl)piperidine-2,6-dione TFA 8 (190 mg). MS (ESI) m/z: 274.1 $[M+H]^+$.

To a solution of 2-(4-(tert-butyl)phenyl)-2-oxoacetyl chloride 2 (109 mg crude, 0.485 mmol) in DCM (5 mL) at RT was added TEA (98 mg, 0.97 mmol), followed by the addition of 3-(5-(aminomethyl)-1-oxoisoindolin-2-yl)piperidine-2,6-dione 8 (132 mg, 0.485 mmol). The mixture was stirred at RT for 3 h and then concentrated. The residue was purified using prep-HPLC eluting with ACN/$H_2$O (0.1% TFA) from 10% to 95% to give compound I-2 (35 mg) in 16% yield. MS (ESI) m/z: 462.1 $[M+1]^+$; $^1$H NMR (400 MHz, DMSO-$d_6$) δ 10.97 (s, 1H), 9.51 (t, J=6.0 Hz, 1H), 7.95 (d, J=8.4 Hz, 2H), 7.74 (d, J=8.0 Hz, 1H), 7.62 (d, J=8.4 Hz, 3H), 7.48 (d, J=7.6 Hz, 1H), 5.11 (dd, J=4.8, 13.2 Hz, 1H), 4.57 (d, J=6.0 Hz, 2H), 4.49-4.31 (m, 2H), 2.96-2.88 (m, 1H), 2.66-2.57 (m, 1H), 2.41-2.32 (m, 1H), 2.02-1.99 (m, 1H), 1.31 (s, 9H).

Example 3

Compound I-3: N-((5-(2,6-Dioxopiperidin-3-yl)-4-oxo-5,6-dihydro-4H-thieno[3,4-c]pyrrol-1-yl)methyl)-2-oxo-2-(4-(1-(trifluoromethyl)cyclopropyl)phenyl)acetamide

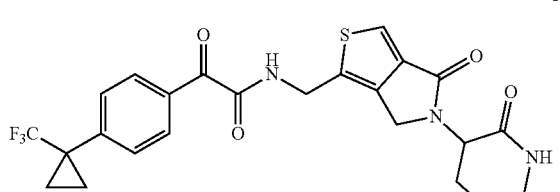

I-3

Compound I-3 was synthesized as shown in Scheme 3.

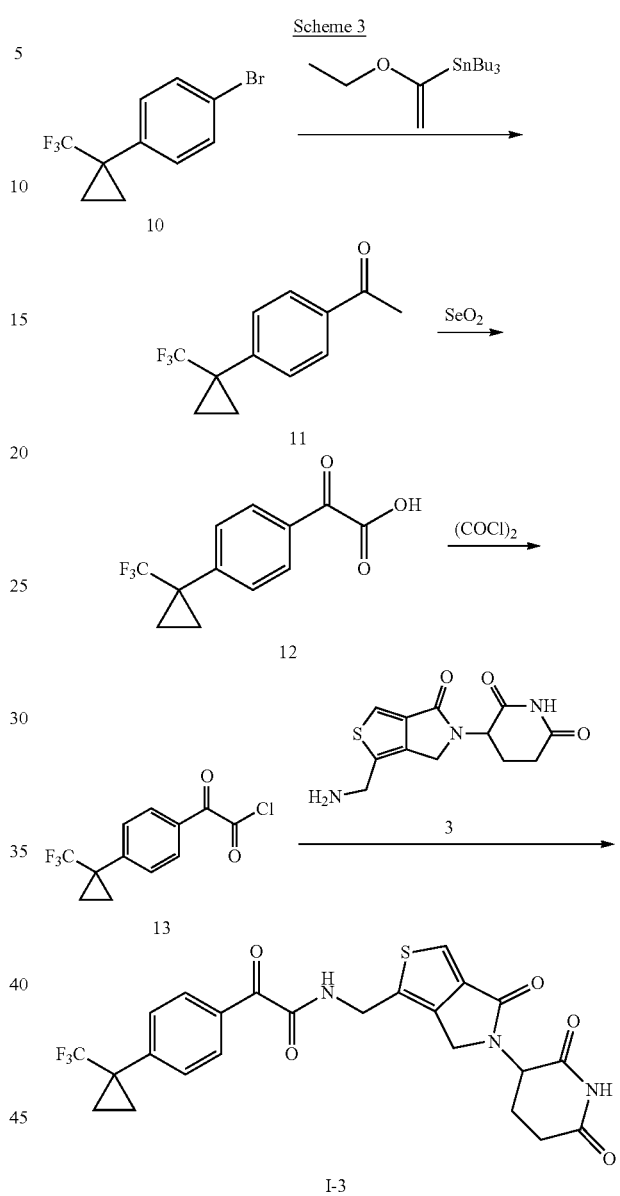

To a solution of 1-bromo-4-(1-(trifluoromethyl)cyclopropyl)benzene 10 (368 mg, 1.39 mmol) in 1,4-dioxane (10 mL) at RT was added tributyl(1-ethoxyvinyl)stannane (762 mg, 2.11 mmol) and Pd(PPh$_3$)$_4$ (321 mg, 0.278 mmol). The mixture was purged with $N_2$ and then stirred at 100° C. overnight. The mixture was filtered and concentrated. After the residue was dissolved in THF, HCl (1N) was added at RT and the mixture was stirred for 10 min. The mixture was washed with NaHCO$_3$ (aq.) and extracted with EA. The combined organic layers were washed with brine, dried over Na$_2$SO$_4$, filtered, and concentrated. The crude product was purified using silica gel column eluting with DCM/MeOH (10:1) to give 1-(4-(1-(trifluoromethyl)cyclopropyl)phenyl)ethanone 11 (270 mg) in 76% yield.

To a solution of 1-(4-(1-(trifluoromethyl)cyclopropyl)phenyl)ethanone 11 (165 mg, 0.724 mmol) in pyridine (8 mL) at RT was added SeO$_2$ (160.6 mg, 1.447 mmol). After stirring at 90° C. for 2 h, the mixture was concentrated, diluted with water, and extracted with EA. The combine organic layers were washed with HCl (2N), dried over Na₂SO₄, filtered, and concentrated to afford 2-oxo-2-(4-(1-(trifluoromethyl)cyclopropyl)phenyl)acetic acid 12 (150 mg), which was used in the next step without further purification.

To a solution of 2-oxo-2-(4-(1-(trifluoromethyl)cyclopropyl)phenyl)acetic acid 12 (150 mg crude, 0.581 mmol) in DCM (8 mL) at RT was added oxalyl chloride (147.6 mg, 1.163 mmol) and DMF (2 drops). The mixture was stirred at RT for 1 h and then concentrated to afford 2-oxo-2-(4-(1-(trifluoromethyl)cyclopropyl)phenyl)acetyl chloride 13 (158 mg), which was used in the next step without further purification.

To a solution of 3-(1-(aminomethyl)-4-oxo-4H-thieno[3,4-c]pyrrol-5(6H)-yl)piperidine-2,6-dione 3 (80 mg, 0.286 mmol) in DCM (8 mL) at 0° C. was added Et₃N (57.9 mg, 0.573 mmol). After stirring for 2 min, 2-oxo-2-(4-(1-(trifluoromethyl)cyclopropyl)phenyl)acetyl chloride 13 (158 mg crude, 0.573 mmol) was added and the mixture was stirred at RT for 2 h. After concentration, the residue was purified by prep-HPLC eluting with ACN/H₂O (0.1% TFA) from 10% to 95% to afford compound I-3 (33.6 mg, 23% yield). MS (ESI) m/z: 520.0 [M+H]⁺; ¹H NMR (400 MHz, DMSO-d₆) δ 10.98 (s, 1H), 9.62 (t, J=5.6 Hz, 1H), 8.02-7.65 (m, 5H), 5.03 (dd, J=5.2 Hz, 13.6 Hz, 1H), 4.60 (d, J=6.0 Hz, 2H), 4.33 (q, J=15.6 Hz, 2H), 2.92-2.84 (m, 1H), 2.61-2.56 (m, 1H), 2.32-2.28 (m, 1H), 2.01-1.97 (m, 1H), 1.42-1.39 (m, 2H), 1.23-1.20 (m, 2H).

Example 4

Compound I-4: N-((5-(2,6-Dioxopiperidin-3-yl)-4-oxo-5,6-dihydro-4H-thieno[3,4-c]pyrrol-1-yl)methyl)-2-(5-isopropylthiophen-2-yl)-2-oxoacetamide

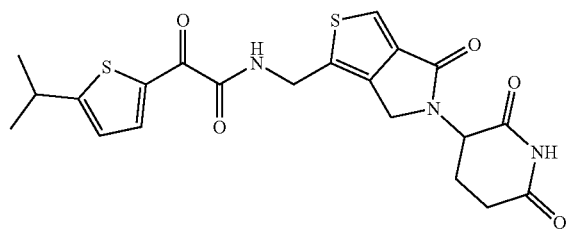

I-4

Compound I-4 was synthesized as shown in Scheme 4.

To a solution of ethyl 2-(5-bromothiophen-2-yl)-2-oxoacetate 15 (400 mg, 1.520 mmol) in toluene/H₂O (10 mL:1 mL) at RT was added 4,4,5,5-tetramethyl-2-(prop-1-en-2-yl)-1,3,2-dioxaborolane (332 mg, 1.98 mmol) and K₃PO₄ (967 mg, 4.56 mmol). After the mixture was purged with N₂, Pd(PPh₃)₂Cl₂ (214 mg, 0.304 mmol) was added, and the mixture was stirred at 100° C. for 16 h and then cooled to RT. The mixture was filtered and the filtrate was concentrated. The residue was purified using silica gel eluting with EA/PE from 0% to 9% to give ethyl 2-oxo-2-(5-(prop-1-en-2-yl)thiophen-2-yl)acetate 16 (125 mg) in 38% yield.

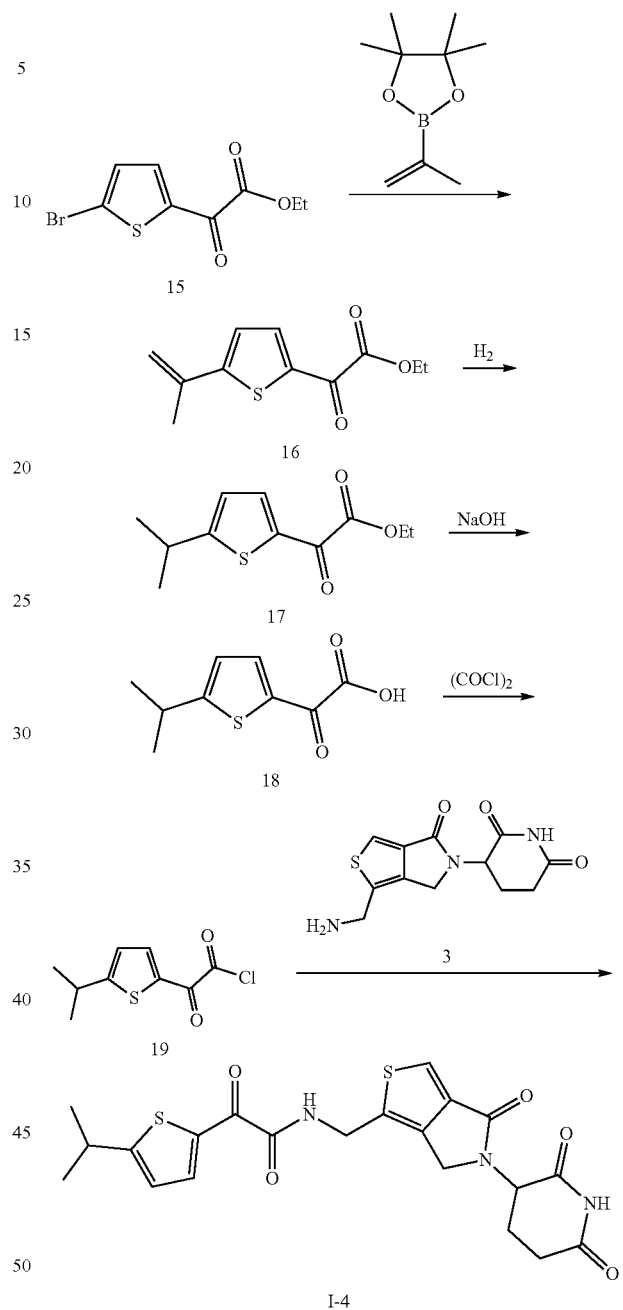

Scheme 4

To a solution of ethyl 2-oxo-2-(5-(prop-1-en-2-yl)thiophen-2-yl)acetate 16 (125 mg, 0.558 mmol) in THF (6 mL) at RT was added Pd/C (100 mg). The mixture was degassed and purged with H₂ several times. The mixture was stirred at RT for 18 h and then filtered and concentrated. The crude product was purified using silica gel eluting with EA/PE from 0% to 9% to give ethyl 2-(5-isopropylthiophen-2-yl)-2-oxoacetate 17 (72 mg) in 57% yield.

To a solution of ethyl 2-(5-isopropylthiophen-2-yl)-2-oxoacetate 17 (72 mg, 0.318 mmol) in EtOH (4 mL) was added NaOH (aq., 5 M). The mixture was stirred at RT for 1 h and then concentrated. The residue was acidified with HCl (4 N) to pH=3 and extracted with EA. The combined organic layers were dried over Na₂SO₄, filtered, and concentrated to give 2-(5-isopropylthiophen-2-yl)-2-oxoacetic acid 18 (63 mg), which was used in next step without further purification.

To a solution of 2-(5-isopropylthiophen-2-yl)-2-oxoacetic acid 18 (63 mg, 0.32 mmol) in DCM (5 mL) at RT was added oxalyl chloride (80.9 mg, 0.637 mmol) and DMF (2 drops). The resulting mixture was stirred at RT for 1 h and then concentrated to give 2-(5-isopropylthiophen-2-yl)-2-oxoacetyl chloride 19 (77.5 mg), which was used in the next step without further purification.

To a solution of 3-(1-(aminomethyl)-4-oxo-4H-thieno[3,4-c]pyrrol-5(6H)-yl)piperidine-2,6-dione 3 (50 mg, 0.179 mmol) in DCM (5 mL) at 0° C. was added TEA (36.2 mg, 0.358 mmol). After 2 min, 2-(5-isopropylthiophen-2-yl)-2-oxoacetyl chloride 19 (77.5 mg crude, 0.358 mmol) was added, and the mixture was stirred at RT for 1.5 h. After concentration, the residue was diluted with water and extracted with EA. The combined organic layers were concentrated and purified using prep-HPLC eluting with ACN/H$_2$O (0.1% TFA) from 10% to 95% to afford compound I-4 (27 mg, 33% yield). MS (ESI) m/z: 460.0 [M+H]$^+$; $^1$H NMR (400 MHz, DMSO-d$_6$) δ 10.99 (s, 1H), 9.62 (t, J=8.0 Hz, 1H), 8.06-7.91 (m, 2H), 7.11 (s, 1H), 5.04-5.00 (m, 1H), 4.53-4.51 (m, 2H), 4.35 (q, J=15.6 Hz, 44 Hz, 2H), 2.92-2.83 (m, 1H), 2.31-2.25 (m, 2H), 1.99-1.96 (m, 2H), 1.31 (d, J=6.4 Hz, 6H).

To a solution of 3-(5-(aminomethyl)-1-oxoisoindolin-2-yl)piperidine-2,6-dione 8 (80 mg, 0.258 mmol) in DCM (4 mL) at 0° C. was added TEA (52.2 mg, 0.516 mmol). After stirring for 2 min, 2-oxo-2-(4-(1-(trifluoromethyl)cyclopropyl)phenyl)acetyl chloride 13 (71.3 mg, 0.258 mmol) was added and the mixture was stirred at RT for 2 h. After concentration, the residue was purified using prep-HPLC eluting with ACN/H$_2$O (0.1% TFA) from 10% to 95% to afford compound I-5 (16.1 mg) in 12% yield. MS (ESI) m/z: 514.0 [M+H]$^+$; $^1$H NMR (400 MHz, DMSO-d$_6$) δ 10.98 (s, 1H), 9.57 (t, J=6.0 Hz, 1H), 8.03-8.01 (m, 2H), 7.74-7.48 (m, 7H), 5.13-5.09 (m, 1H), 4.59-4.57 (m, 2H), 4.49-4.31 (m, 2H), 2.95-2.87 (m, 1H), 2.63-2.58 (m, 1H), 2.45-2.38 (m, 1H), 2.03-1.99 (m, 1H), 1.43-1.40 (m, 2H), 1.24-1.21 (m, 2H).

Example 5

Compound I-5: N-((2-(2,6-Dioxopiperidin-3-yl)-1-oxoisoindolin-5-yl)methyl)-2-oxo-2-(4-(1-(trifluoromethyl)cyclopropyl)phenyl)acetamide Example 6

Compound I-28: 2-(4-(Tert-butyl)phenyl)-N-((2-(2,6-dioxopiperidin-3-yl)-1-oxoisoindolin-4-yl)methyl)-2-oxoacetamide

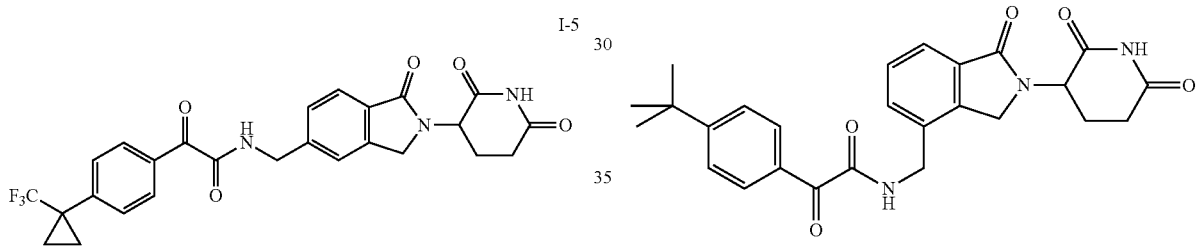

Compound I-5 was synthesized as shown in Scheme 5.

Scheme 5

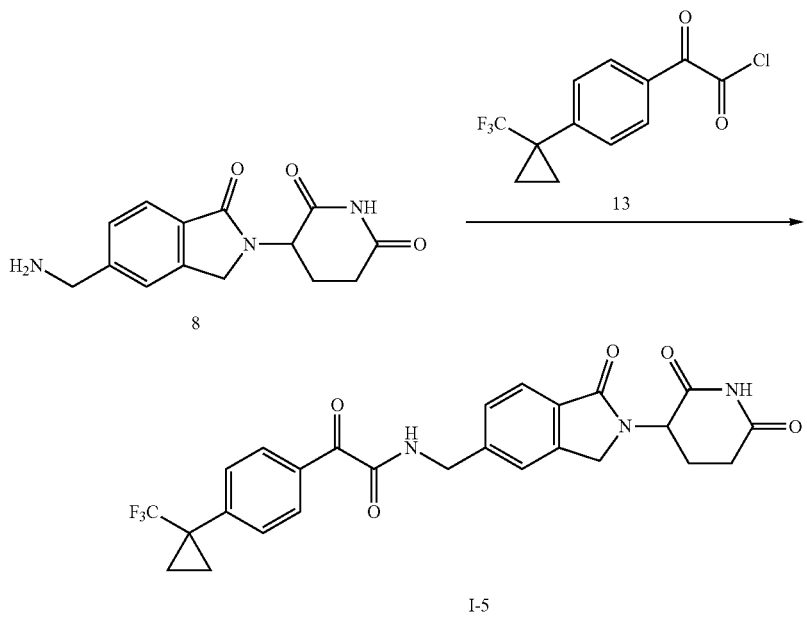

Compound I-28 was synthesized as shown in Scheme 6.

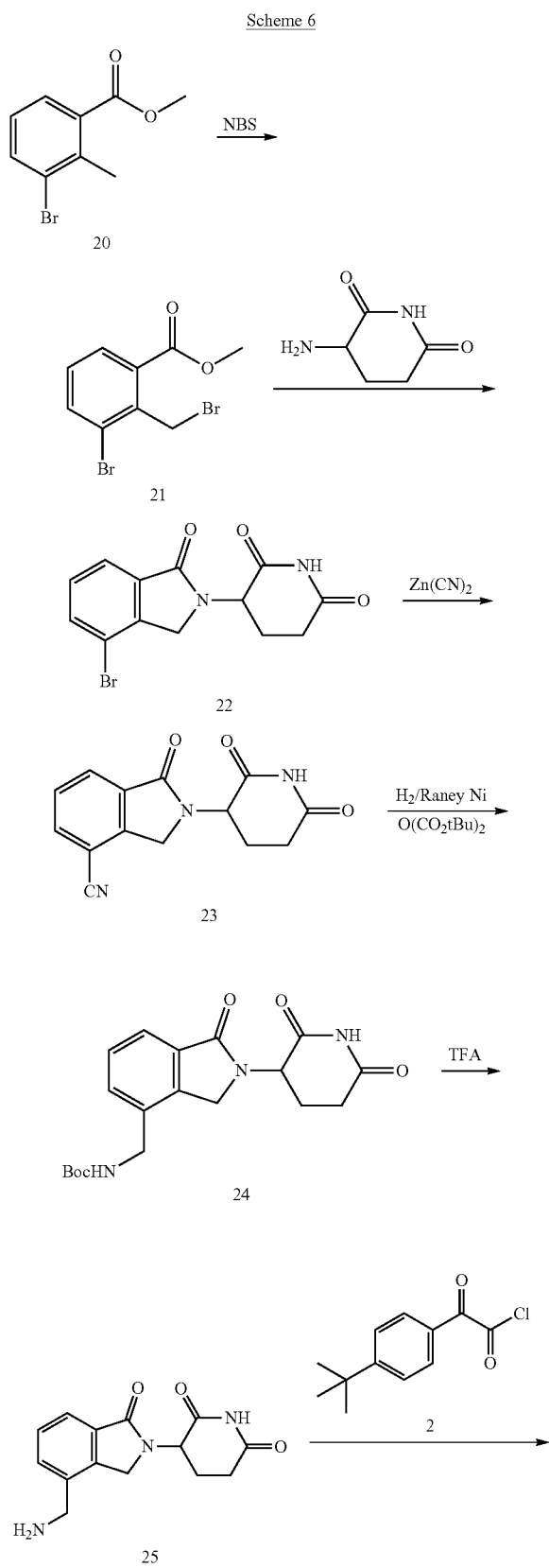

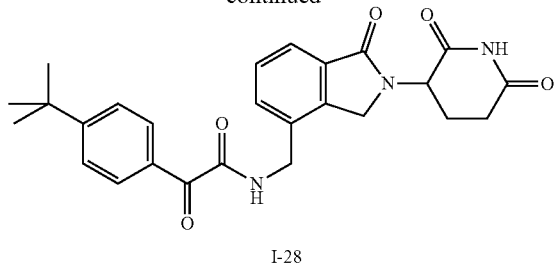

To a solution of methyl 3-bromo-2-methylbenzoate 20 (22.9 g, 10 mmol) in CCl$_4$ (200 mL) was added NBS (21.4 g, 12 mmol) and AIBN (1.64 g, 1 mmol). The mixture was stirred at 85° C. overnight, and then concentrated and purified using silica gel eluting with PE/EA (10:1) to give methyl 3-bromo-2-(bromomethyl)benzoate 21 (24 g) in 78% yield.

To a solution of methyl 3-bromo-2-(bromomethyl)benzoate 21 (6.0 g, 19.5 mmol) in ACN (60 mL) was added 3-aminopiperidine-2,6-dione HCl salt (3.8 g, 23.4 mmol) and DIEA (12.5 g, 97.4 mmol). The mixture was stirred at 90° C. overnight, and then cooled to 40° C., filtered, and washed with tert-butyl methyl ether to give 3-(4-bromo-1-oxoisoindolin-2-yl)piperidine-2,6-dione 22 (5.5 g) in 87% yield. MS (ESI) m/z: 323.0, 325.0 [M+H]$^+$.

To a solution of 3-(4-bromo-1-oxoisoindolin-2-yl)piperidine-2,6-dione 22 (1.5 g, 4.64 mmol) in DMF (10 mL) was added Zn(CN)$_2$ (0.54 g, 4.64 mmol), dppf (0.52 g, 0.93 mmol), and Pd$_2$(dba)$_3$ (0.44 g, 0.46 mmol). The mixture was heated at 150° C. for 2 h under microwave, and then concentrated and purified using silica gel eluting with DCM/MeOH from 50:1 to 30:1 to give 2-(2,6-dioxopiperidin-3-yl)-1-oxoisoindoline-4-carbonitrile 23 (990 mg) in 79% yield. MS (ESI) m/z: 270.0 [M+H]$^+$.

To a solution of 2-(2,6-dioxopiperidin-3-yl)-1-oxoisoindoline-4-carbonitrile 23 (0.3 g, 1.1 mmol) in MeOH (20 mL) was added Boc$_2$O (365 mg, 1.7 mmol) and Raney Ni (0.05 mg). The suspension was stirred under H$_2$ for 48 h. The mixture was filtered then the filtrate was concentrated and purified using silica gel eluting with DCM/MeOH from 50:1 to 30:1 to give tert-butyl ((2-(2,6-dioxopiperidin-3-yl)-1-oxoisoindolin-4-yl)methyl)carbamate 24 (110 mg) in 26% yield. MS (ESI) m/z: 374.1 [M+H]$^+$.

To a solution of 2-(4-(tert-butyl)phenyl)-2-oxoacetic acid (206 mg, 1.0 mmol) in dioxane (5 mL) at 0° C. was added SOCl$_2$ (1.19 g, 10 mmol), and the mixture was stirred at 90° C. for 3 h and then concentrated to give 2-(4-(tert-butyl)phenyl)-2-oxoacetyl chloride 2 (crude).

To a solution of tert-butyl ((2-(2,6-dioxopiperidin-3-yl)-1-oxoisoindolin-4-yl)methyl)carbamate 24 (110 mg, 0.42 mmol) in DCM (3 mL) at 0° C. was added TFA (1 mL). The mixture was stirred for 2 h and then concentrated. The residue (compound 25) (100 mg) was dissolved in DCM (5 mL) and cooled to 0° C. and then TEA (59 mg, 0.59 mmol) was added. The mixture was stirred at 0° C. for 5 min and then a solution of 2-(4-(tert-butyl)phenyl)-2-oxoacetyl chloride 2 (1.0 mmol, crude) in DCM (5 mL) was added. The mixture was stirred at RT overnight and then concentrated and purified by prep-HPLC using 0.1% TFA in water and 0.1% TFA in ACN with a gradient of 95% to 5% in 0.1% TFA water to afford compound I-28 (50 mg) in 37% yield. MS (ESI) m/z: 462.1 [M+H]$^+$; $^1$H NMR (DMSO-d$_6$, 400 MHz) δ 11.03 (s, 1H), 9.49 (s, 1H), 7.92 (d, J=7.6 Hz, 2H), 7.68-7.53 (m, 5H), 5.16 (dd, J=5.2, 13.2 Hz, 1H), 4.60-4.42

(m, 4H), 2.93-2.89 (m, 1H), 2.67-2.59 (m, 1H), 2.37-2.33 (m, 1H), 2.05-2.01 (m, 1H), 1.31 (s, 9H).

Example 7

Compound I-32: 2-(4-(Tert-butyl)phenyl)-N-((2-(2,6-dioxopiperidin-3-yl)-1,3-dioxoisoindolin-5-yl)methyl)-2-oxoacetamide

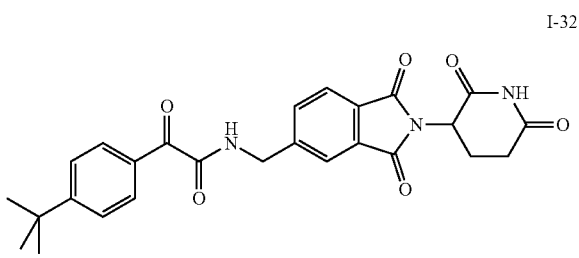 [SMILES: CC(C)(C)c1ccc(C(=O)C(=O)NCc2ccc3c(c2)C(=O)N(C2CCC(=O)NC2=O)C3=O)cc1]

I-32

Compound I-32 was synthesized as shown in Scheme 7.

To a solution of 5-bromoisobenzofuran-1,3-dione 30 (2.0 g, 8.8 mmol) in AcOH (25 mL) was added 3-aminopiperidine-2,6-dione (1.4 g, 8.8 mmol) and sodium acetate (1.4 g, 17.6 mmol). The mixture was stirred at 120° C. for 5 h and then concentrated. The residue was washed with H₂O, MeOH, and DCM to give 5-bromo-2-(2,6-dioxopiperidin-3-yl)isoindoline-1,3-dione 31 (2.7 g) in 90% yield. MS (ESI) m/z: 359.0 [M+Na]⁺.

To a solution of 5-bromo-2-(2,6-dioxopiperidin-3-yl)isoindoline-1,3-dione 31 (1.0 g, 3.0 mmol) in 1-methyl-2-pyrrolidinone (8 mL) was added CuCN (0.8 g, 9.0 mmol). The mixture was stirred at 180° C. for 2 h under microwave and then filtered. The filtrate was diluted with H₂O and extracted with EA. The combined organic layers were washed with brine, dried over Na₂SO₄, filtered, and concentrated. The residue was triturated with MeOH/DCM (1:10) to give 2-(2,6-dioxopiperidin-3-yl)-1,3-dioxoisoindoline-5-carbonitrile 32 (600 mg) in 71% yield. MS (ESI) m/z: 306.0 [M+Na]⁺.

Scheme 7

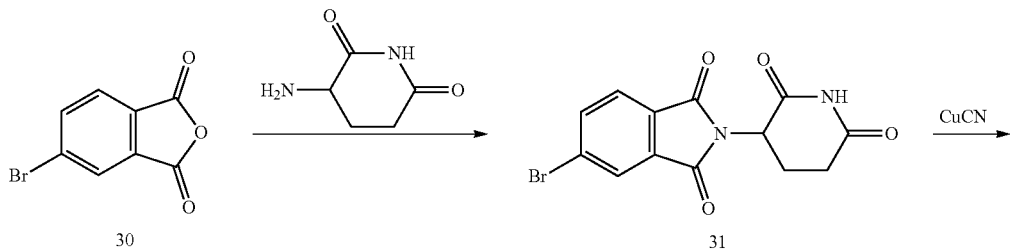

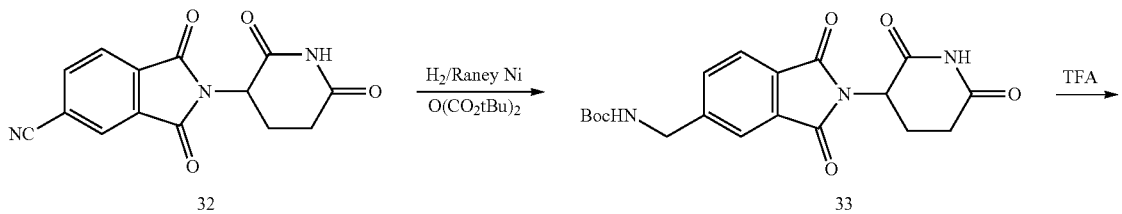

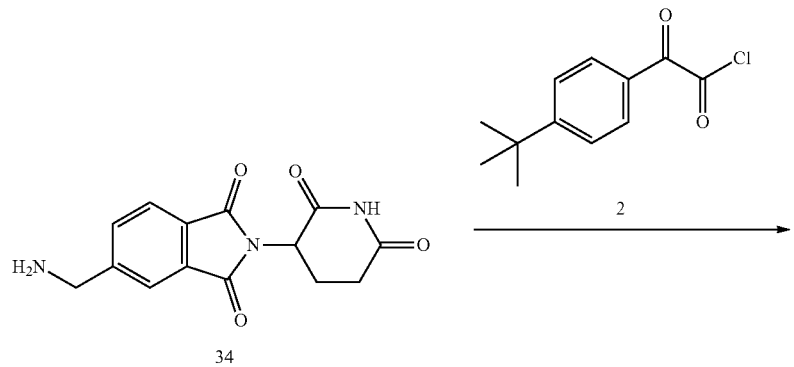

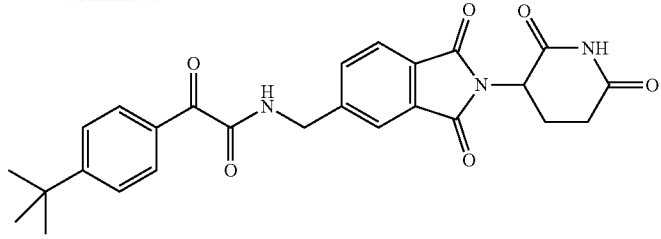

I-32

To a solution of 2-(2,6-dioxopiperidin-3-yl)-1,3-dioxoisoindoline-5-carbonitrile 32 (0.21 g, 0.75 mmol) in MeOH (20 mL) was added Boc₂O (0.24 mg, 1.12 mmol) and Raney Ni (0.06 mg). The mixture was stirred under H₂ for 2 d and then filtered, and the filtrate was concentrated. The residue was purified using silica gel eluting with DCM/MeOH from 50:1 to 30:1 to give tert-butyl ((2-(2,6-dioxopiperidin-3-yl)-1,3-dioxoisoindolin-5-yl)methyl)carbamate 33 (80 mg) in 28% yield. MS (ESI) m/z: 405.2 [M+NH₄⁺].

To a solution of tert-butyl ((2-(2,6-dioxopiperidin-3-yl)-1,3-dioxoisoindolin-5-yl)methyl)carbamate 33 (80 mg, 0.20 mmol) in DCM (3 mL) was added TFA (1 mL). The mixture was stirred for 1 h and then concentrated and triturated with methyl tert-butyl ether to give 5-(aminomethyl)-2-(2,6-dioxopiperidin-3-yl)isoindoline-1,3-dione TFA salt 34 (80 mg, crude). MS (ESI) m/z: 288.0 [M+H]⁺.

To a solution of 5-(aminomethyl)-2-(2,6-dioxopiperidin-3-yl)isoindoline-1,3-dione TFA salt 34 (80 mg) in DCM (5 mL) at 0° C. was added TEA (42 mg, 0.42 mmol), followed by addition of 2-(4-(tert-butyl)phenyl)-2-oxoacetyl chloride 2 (0.21 mmol). The mixture was stirred at RT overnight and then concentrated. The residue was purified by prep-HPLC using conditions to afford compound I-32. MS (ESI) m/z: 476.1 [M+H]⁺; ¹H NMR (DMSO-d₆, 400 MHz) δ 11.11 (s, 1H), 9.58 (t, J=6.4 Hz, 1H), 7.95-7.82 (m, 5H), 7.61 (d, J=8.4 Hz, 2H), 5.16 (dd, J=5.2, 12.8 Hz, 1H), 4.64 (d, J=6.4 Hz, 2H), 2.90-2.86 (m, 1H), 2.67-2.52 (m, 2H), 2.08-2.04 (m, 1H), 1.31 (s, 9H).

Example 8

Compound I-38: 2-(4-(Tert-butyl)phenyl)-N-((2-(2,6-dioxopiperidin-3-yl)-3-oxoisoindolin-4-yl)methyl)-2-oxoacetamide

I-38

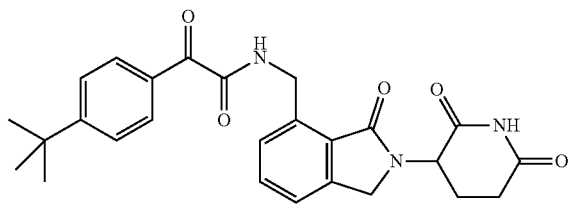

Compound I-38 was synthesized as shown in Scheme 8.
To a solution of methyl 2-bromo-6-methylbenzoate 35 (5.0 g, 21.8 mmol) in DMF (40 mL) was added CuCN (2.35 g, 26.2 mmol) and CuI (415.7 mg, 2.18 mmol). The mixture was stirred at 130° C. for 16 h under N₂ and then cooled 20° C., diluted with methyl tert-butyl ether (30 mL), and filtered. The filtrate was diluted with H₂O (20 mL) and extracted with methyl tert-butyl ether (30 mL×2). The combined organic layers were concentrated and the residue was purified using silica gel eluting with EA in PE from 2% to 10% to give methyl 2-cyano-6-methylbenzoate 36 (2.8 g) in 73% yield.

Scheme 8

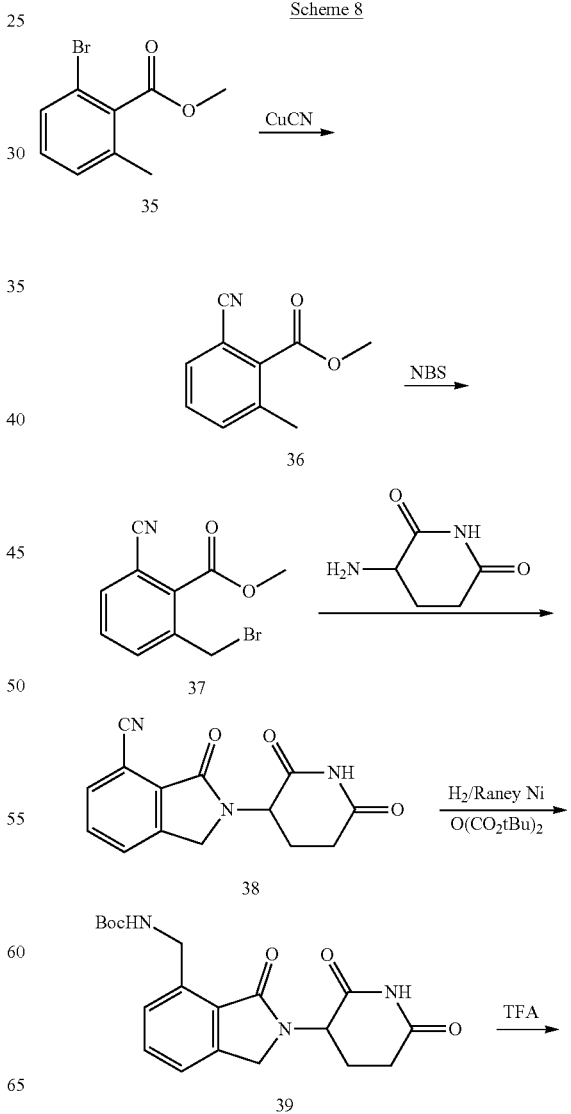

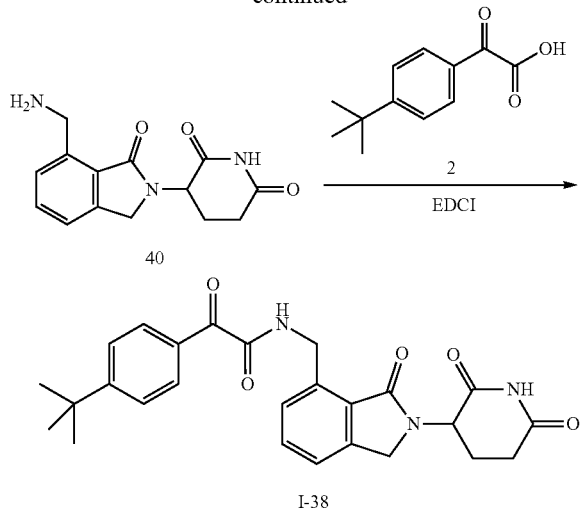

1H), 5.13 (dd, J=4.8, 13.2 Hz, 1H), 4.98 (d, J=5.6 Hz, 2H), 4.49-4.32 (m, 2H), 2.92-2.87 (m, 1H), 2.63-2.59 (m, 1H), 2.43-2.39 (m, 1H), 2.02-1.99 (m, 1H), 1.31 (s, 9H).

Example 9

Compound I-47: 2-(4-(Tert-butyl)phenyl)-N-((2-(2, 6-dioxopiperidin-3-yl)-1-oxoisoindolin-4-yl) methyl)-N-methyl-2-oxoacetamide

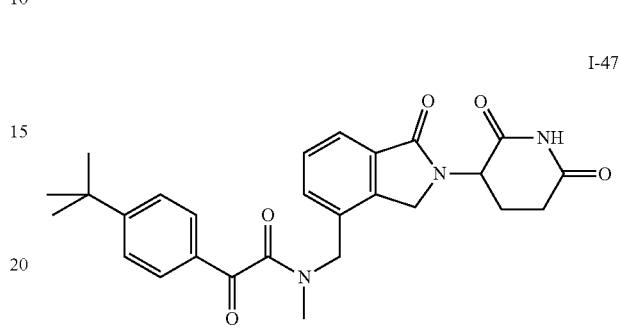

Compound I-47 was synthesized as shown in Scheme 9.

To a solution of methyl 3-bromo-2-(bromomethyl)benzoate 21 (4.10 g, 13.3 mmol, crude) in DMF (30 mL) was added tert-butyl 4,5-diamino-5-oxopentanoate (3.19 g, 13.31 mmol) and K$_2$CO$_3$ (7.62 g, 75 mmol). The mixture was stirred for 20 min and then heated to 50° C. for 2 h and heated to 80° C. for 1 h. The solution was cooled to RT, diluted with H$_2$O, and extracted with EA. The combined organic layers were washed with brine, dried over Na$_2$SO$_4$, filtered, and concentrated. The residue was triturated with methyl tert-butyl ether to give tert-butyl 5-amino-4-(4-bromo-1-oxoisoindolin-2-yl)-5-oxopentanoate 41 (2.44 g) in 46% yield.

To a solution of tert-butyl 5-amino-4-(4-bromo-1-oxoisoindolin-2-yl)-5-oxopentanoate 41 (1.24 g, 3.12 mmol) in DMF (10 mL) was added Zn(CN)$_2$ (263 mg, 2.24 mmol), Pd$_2$(dba)$_3$ (295 mg, 0.32 mmol), and dppf (344 mg, 0.62 mmol). The mixture was heated at 150° C. under microwave for 2 h and then concentrated. The residue was purified using silica gel eluting with EA in PE from 30% to 100% to give tert-butyl 5-amino-4-(4-cyano-1-oxoisoindolin-2-yl)-5-oxopentanoate 42 (754 mg) in 70% yield.

To a solution of methyl 2-cyano-6-methylbenzoate 36 (2.8 g, 15.98 mmol) in CCl$_4$ (30 mL) was added NBS (2.84 g, 15.98 mmol) and 2,2'-azoisobutyronitrile (787 mg, 4.79 mmol). The mixture was stirred at 85° C. for 16 h and then cooled to RT, filtered, and concentrated. The residue was purified using silica gel eluting with EA in PE from 10% to 20% to give methyl 2-(bromomethyl)-6-cyanobenzoate 37 (3.0 g, 74% yield).

To a solution of methyl 2-(bromomethyl)-6-cyanobenzoate 37 (1.25 g, 4.92 mmol) in DMF (20 mL) was added 3-aminopiperidine-2,6-dione hydrochloride (971.7 mg, 5.90 mmol) and TEA (1.49 g, 14.8 mmol). The mixture was stirred at 85° C. for 16 h and then concentrated. The residue was triturated with ACN to give 2-(2,6-dioxopiperidin-3-yl)-3-oxoisoindoline-4-carbonitrile 38 (1.0 g) in 75% yield. MS (ESI) m/z: 270.1 [M+H]$^+$.

To a solution of 2-(2,6-dioxopiperidin-3-yl)-3-oxoisoindoline-4-carbonitrile 38 (500 mg, 1.86 mmol) in MeOH (20 mL) was added di-tert-butyl pyrocarbonate (607.92 mg, 2.79 mmol) and Raney Ni (100 mg). The mixture was stirred under H$_2$ overnight and then filtered and concentrated. The residue was purified using silica gel eluting with EA in PE from 50% to 100% and then eluting with MeOH/DCM (1:10) to give tert-butyl ((2-(2,6-dioxopiperidin-3-yl)-3-oxoisoindolin-4-yl)methyl)carbamate 39 (360 mg) in 52% yield. MS (ESI) m/z: 318.1 [M−56]$^+$.

To a solution of tert-butyl ((2-(2,6-dioxopiperidin-3-yl)-3-oxoisoindolin-4-yl)methyl)carbamate 39 (110 mg, 0.295 mmol) in DCM (10 mL) was added TFA (2 mL). The mixture was stirred at 20° C. for 2 h and then concentrated to give 3-(7-(aminomethyl)-1-oxoisoindolin-2-yl)piperidine-2,6-dione 40 (80 mg, crude).

To a solution of 3-(7-(aminomethyl)-1-oxoisoindolin-2-yl)piperidine-2,6-dione 40 (80.0 mg, crude) in DMF (20 mL) was added 2-(4-(tert-butyl)phenyl)-2-oxoacetic acid 1 (60.4 mg, 0.293 mmol), HOBt (59.3 mg, 0.439 mmol), EDCI (84.2 mg, 0.439 mmol), and DIEA (113.5 mg, 0.878 mmol). The mixture was stirred at 20° C. for 16 h and then diluted with H$_2$O and extracted with DCM. The combined organic layers were dried over Na$_2$SO$_4$, filtered, and concentrated. The residue was purified by prep-HPLC to afford compound I-38 (24.9 mg) in 18% yield. MS (ESI) m/z: 462.2 [M+H]$^+$; $^1$H NMR (400 MHz, DMSO-d$_6$) δ 11.00 (s, 1H), 9.37 (t, J=6.0 Hz, 1H), 7.96 (d, J=8.4 Hz, 2H), 7.64-7.60 (m, 3H), 7.52 (d, J=7.6 Hz, 1H), 7.41 (d, J=7.2 Hz, Scheme 9

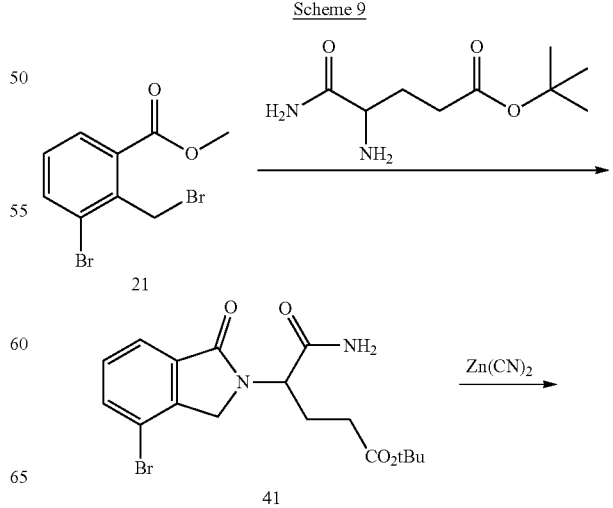

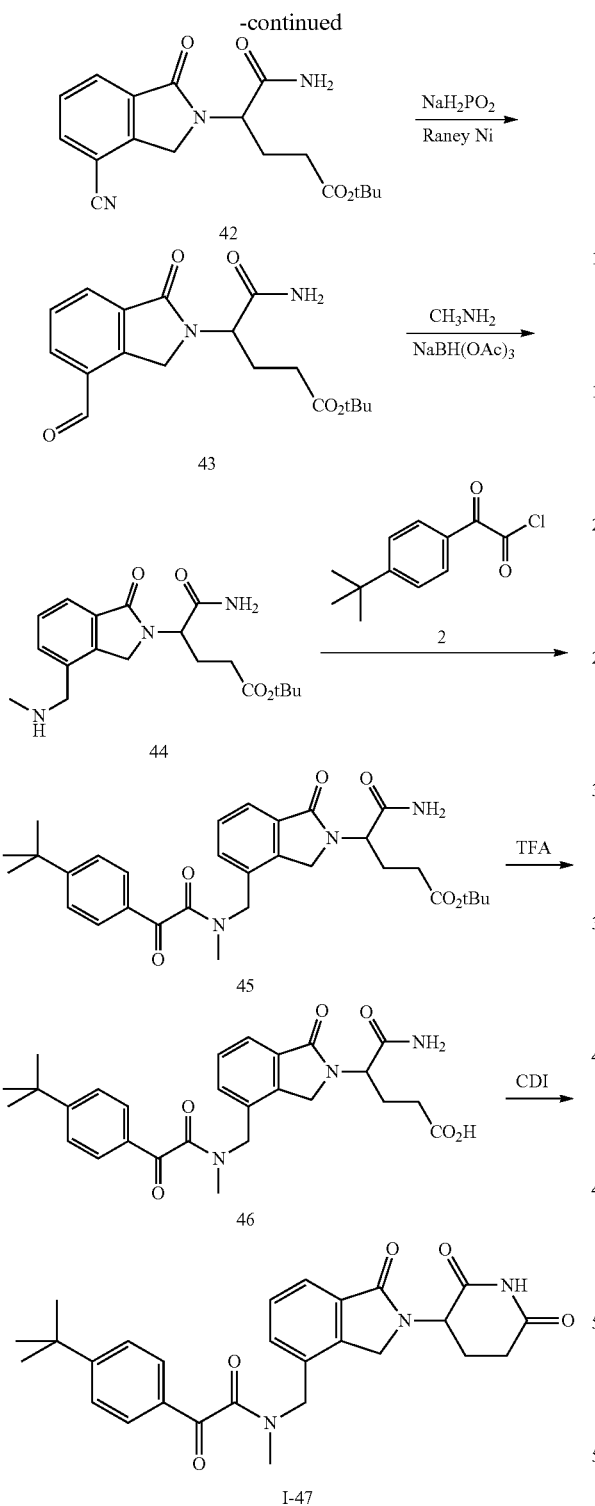

43

44

45

46

I-47

To a solution of tert-butyl 5-amino-4-(4-cyano-1-oxoisoindolin-2-yl)-5-oxopentanoate 42 (754 mg, 2.19 mmol) in AcOH/pyridine/H₂O (6 mL/12 mL/6 mL) was added NaH₂PO₂ (962 mg, 10.93 mmol) and Raney Ni (0.4 g). The mixture was stirred for 3 h and then filtered, and the filtrate was extracted with EA. The combined organic layers were washed with 1N HCl, dried over Na₂SO₄, filtered, and concentrated. The residue was purified using silica gel eluting with EA in PE from 30% to 100% and give tert-butyl 5-amino-4-(4-formyl-1-oxoisoindolin-2-yl)-5-oxopentanoate 43 (426 mg) in 55% yield.

To a solution of tert-butyl 5-amino-4-(4-formyl-1-oxoisoindolin-2-yl)-5-oxopentanoate 43 (426 mg, 1.23 mmol) in DCM (25 mL) was added methylamine (192 mg, 6.19 mmol) and NaBH(OAc)₃ (1.31 g, 6.19 mmol). The mixture was stirred overnight and then NaBH₃CN (155 mg, 2.47 mmol) was added. The mixture was stirred for 1 h and then concentrated. The residue was purified using silica gel eluting with EA in PE from 50% to 100% to give tert-butyl 5-amino-4-(4-((methylamino)methyl)-1-oxoisoindolin-2-yl)-5-oxopentanoate 44 (200 mg) in 45% yield.

To a solution of tert-butyl 5-amino-4-(4-((methylamino)methyl)-1-oxoisoindolin-2-yl)-5-oxopentanoate 44 (200 mg, 0.55 mmol) in DCM (10 mL) was added TEA (0.15 mL), followed by addition of a solution of 2-(4-(tert-butyl)phenyl)-2-oxoacetyl chloride 2 (204 mg, crude) in DCM (4 mL). The mixture was stirred for 1 h, and then diluted with H₂O and extracted with DCM. The combined organic layers were washed with brine, dried over Na₂SO₄, filtered, and concentrated. The residue was purified using silica gel eluting with EA in PE from 30% to 90% to give tert-butyl 5-amino-4-(4-((2-(4-(tert-butyl)phenyl)-N-methyl-2-oxoacetamido)methyl)-1-oxoisoindolin-2-yl)-5-oxopentanoate 45 (132 mg) in 43% yield.

To a solution of tert-butyl 5-amino-4-(4-((2-(4-(tert-butyl)phenyl)-N-methyl-2-oxoacetamido)methyl)-1-oxoisoindolin-2-yl)-5-oxopentanoate 45 (132 mg, 0.24 mmol) in DCM (6 mL) was added TFA (53.6 mg, 0.47 mmol). The mixture was stirred for 1 h and then concentrated. The residue was purified by prep-TLC eluting with EA in PE from 30% to 100% to give 5-amino-4-(4-((2-(4-(tert-butyl)phenyl)-N-methyl-2-oxoacetamido)methyl)-1-oxoisoindolin-2-yl)-5-oxopentanoic acid 46 (94 mg) in 79% yield.

To a solution of 5-amino-4-(4-((2-(4-(tert-butyl)phenyl)-N-methyl-2-oxoacetamido)-methyl)-1-oxoisoindolin-2-yl)-5-oxopentanoic acid 46 (94 mg, 0.20 mmol) in ACN (6 mL) was added CDI (118 mg, 0.73 mmol). The mixture was stirred at 95° C. for 1.5 h and then concentrated. The residue was purified by prep-HPLC to afford compound I-47 (20.4 mg) in 23% yield. MS (ESI) m/z: 476.1 [M+H]⁺; ¹HNMR (DMSO-d₆, 400 MHz) δ 11.02 (d, J=14.0 Hz, 1H), 7.85-7.44 (m, 7H), 5.20-5.08 (m, 1H), 4.80 (s, 1H), 4.56-4.26 (m, 3H), 2.99-2.85 (m, 4H), 2.66-2.59 (m, 1H), 2.51-2.41 (m, 1H), 2.30-1.97 (m, 1H), 1.26 (d, J=10.0 Hz, 9H).

Example 10

Compound I-49: (2R)-(3-(4-((2-(4-(Tert-butyl)phenyl)-2-oxoacetamido)methyl)-1-oxoisoindolin-2-yl)-2,6-dioxopiperidin-1-yl)methyl 2-amino-3-methylbutanoate

I-49

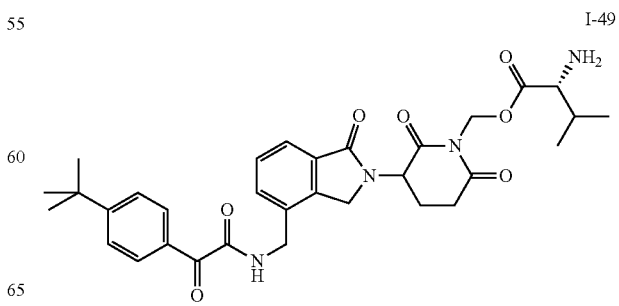

Compound I-49 was synthesized as shown in Scheme 10.
Scheme 10
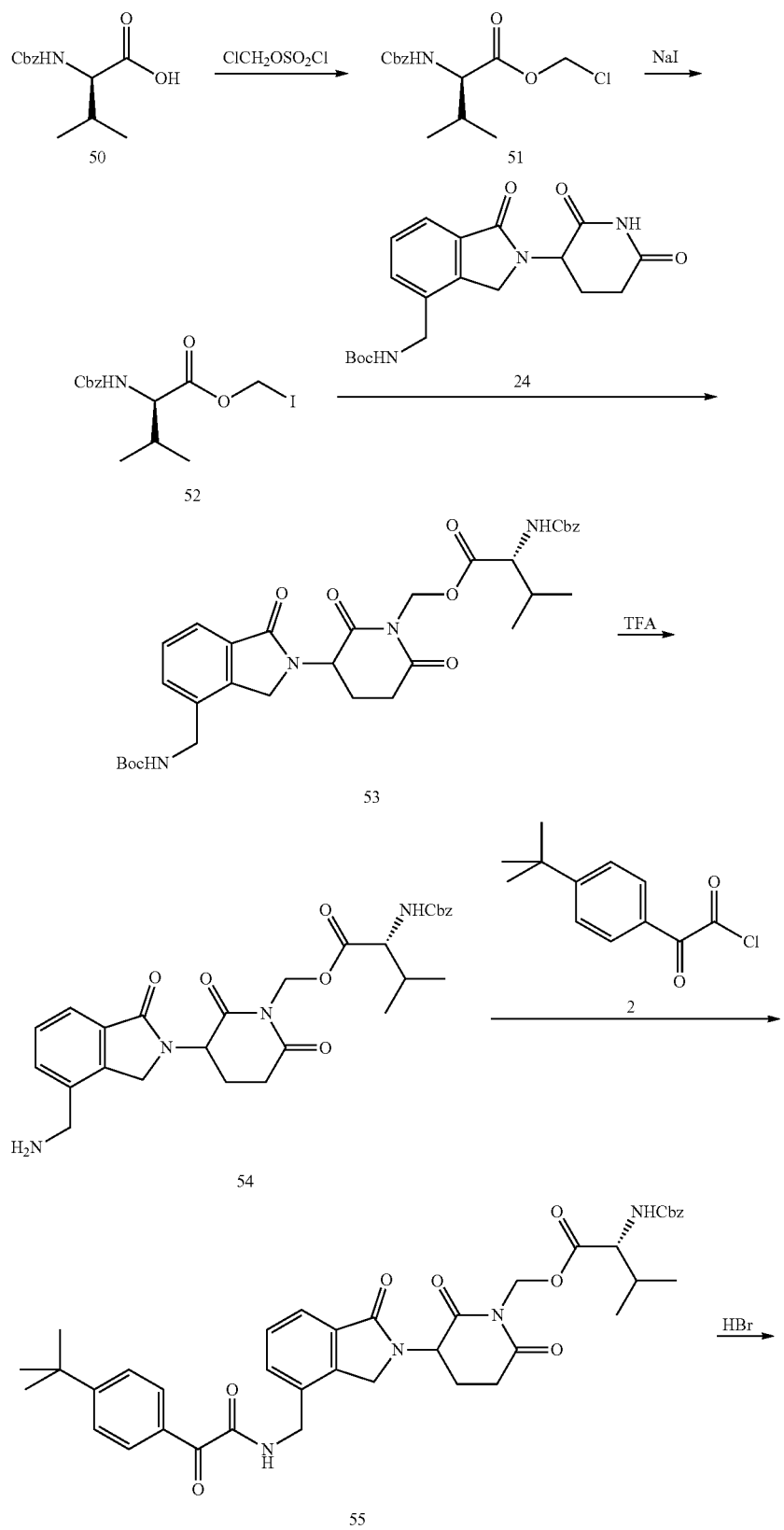

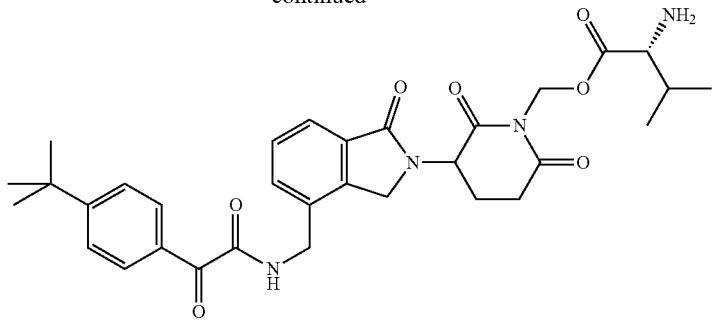

I-49

To a solution of (R)-2-(((benzyloxy)carbonyl)amino)-3-methylbutanoic acid 50 (0.9 g, 3.6 mmol) in DCM/H₂O (10 mL/1 mL) at 0° C. was added NaHCO₃ (1.2 g, 14.4 mmol), followed by addition of Bu₄NHSO₄ (122 mg, 0.1 mmol). After 10 min, chloromethyl sulfochloridate (0.70 g, 4.32 mmol) was added. The mixture was stirred for 4 h. The mixture was diluted with H₂O and extracted with DCM. The combined organic layers were dried over Na₂SO₄, filtered, and concentrated. The residue was purified using silica gel eluting with MeOH in DCM from 0% to 1% to give (R)-chloromethyl 2-(((benzyloxy)carbonyl)amino)-3-methylbutanoate 51 (0.83 g) in 77% yield. MS (ESI) m/z: 300[M+H]⁺.

To a solution of (R)-chloromethyl 2-(((benzyloxy)carbonyl)amino)-3-methylbutanoate 51 (232 mg, 0.776 mmol) in ACN (5 mL) was added sodium iodide (140 mg, 0.931 mmol). The mixture was stirred overnight and then filtered, and the filtrate was concentrated. The residue was purified using silica gel eluting with EA in PE from 0% to 10% to give (R)-iodomethyl 2-(((benzyloxy)carbonyl)amino)-3-methylbutanoate 52 (250 mg) in 83% yield. MS (ESI) m/z: 392 [M+H]⁺.

To a solution of tert-butyl ((2-(2,6-dioxopiperidin-3-yl)-1-oxoisoindolin-4-yl)methyl)carbamate 24 (132 mg, 0.355 mmol) in DMF (4 mL) at 0° C. was added sodium hydride (17 mg, 0.71 mmol). The mixture was stirred at RT for 30 min and then (R)-iodomethyl 2-(((benzyloxy)carbonyl)amino)-3-methylbutanoate (250 mg, 0.639 mmol) 52 was added. The mixture was stirred at RT for 1 h, and then diluted with H₂O and extracted with DCM. The combined organic layers were dried over Na₂SO₄, filtered, and concentrated. The residue was purified using silica gel eluting with MeOH in DCM from 0% to 5% to give (2R)-(3-(4-(((tert-butoxycarbonyl)amino)methyl)-1-oxoisoindolin-2-yl)-2,6-dioxopiperidin-1-yl)methyl 2-(((benzyloxy)carbonyl)amino)-3-methylbutanoate 53 (165 mg) in 36% yield. MS (ESI) m/z: 637 [M+H]⁺.

To a solution of (2R)-(3-(4-(((tert-butoxycarbonyl)amino)methyl)-1-oxoisoindolin-2-yl)-2,6-dioxopiperidin-1-yl)methyl 2-(((benzyloxy)carbonyl)amino)-3-methylbutanoate 53 (165 mg, 0.259 mmol) in DCM (4 mL) was added TFA (1 mL). The mixture was stirred for 2 h and then concentrated to give (2R)-(3-(4-(aminomethyl)-1-oxoisoindolin-2-yl)-2,6-dioxopiperidin-1-yl)methyl 2-(((benzyloxy)carbonyl)amino)-3-methylbutanoate TFA salt 54 (139 mg, crude). MS (ESI) m/z: 537 [M+H]⁺.

To a solution of (2R)-(3-(4-(aminomethyl)-1-oxoisoindolin-2-yl)-2,6-dioxopiperidin-1-yl)methyl 2-(((benzyloxy)carbonyl)amino)-3-methylbutanoate 54 (139 mg, 0.26 mmol) in DCM (5 mL) was added TEA (65 mg, 0.65 mmol), followed by addition of 2-(4-(tert-butyl)phenyl)-2-oxoacetyl chloride 2 (87.5 mg, 0.39 mmol). The mixture was stirred for 4 h and then concentrated. The residue was purified using silica gel eluting with MeOH in DCM from 0% to 8% to give (2R)-(3-(4-((2-(4-(tert-butyl)phenyl)-2-oxoacetamido)methyl)-1-oxoisoindolin-2-yl)-2,6-dioxopiperidin-1-yl) methyl 2-(((benzyloxy)carbonyl)amino)-3-methylbutanoate 55 (125 mg, 67% yield). MS (ESI) m/z: 725 [M+H]⁺.

To a solution of (2R)-(3-(4-((2-(4-(tert-butyl)phenyl)-2-oxoacetamido)methyl)-1-oxoisoindolin-2-yl)-2,6-dioxopiperidin-1-yl)methyl 2-(((benzyloxy)carbonyl)amino)-3-methylbutanoate 55 (120 mg, 0.166 mmol) in AcOH (1.5 mL) was added HBr (33% in AcOH, 1.5 mL). The mixture was stirred for 1 h and then concentrated. The residue was dissolved in DMF (2 mL) and adjusted to pH=7 with TEA. After concentration, the residue was purified by prep-HPLC to give (2R)-(3-(4-((2-(4-(tert-butyl)phenyl)-2-oxoacetamido)methyl)-1-oxoisoindolin-2-yl)-2,6-dioxopiperidin-1-yl)methyl 2-amino-3-methylbutanoate I-49 (12.8 mg) in 13% yield. MS (ESI) m/z: 591.2 [M+H]⁺; ¹HNMR (DMSO-d₆, 400 MHz) δ 9.50 (t, J=6.0 Hz, 1H), 8.32 (br s, 3H), 7.92 (d, J=8.0 Hz, 2H), 7.70-7.68 (m, 1H), 7.62-7.57 (m, 4H), 5.86-5.72 (m, 2H), 5.35-5.32 (m, 1H), 4.65-4.39 (m, 4H), 3.96 (s, 1H), 3.18-3.11 (m, 1H), 2.92-2.87 (m, 1H), 2.51-2.40 (m, 2H), 2.15-2.10 (m, 2H), 1.31 (s, 9H), 0.94-0.92 (m, 6H).

Example 11

Compound I-52: N-(2-(2-(2,6-Dioxopiperidin-3-yl)-1-oxoisoindolin-5-yl)ethyl)-2-oxo-2-(4-(1-(trifluoromethyl)cyclopropyl)phenyl)acetamide

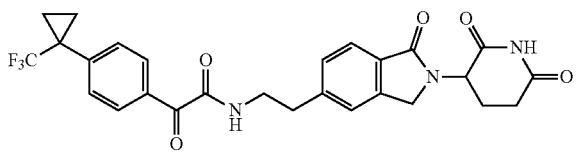

I-52

Compound I-52 was synthesized as shown in Scheme 11.

To a stirred solution of methyl 2-(bromomethyl)-4-cyanobenzoate 5 (2.04 g, 8.05 mmol) and tert-butyl 4,5-diamino-5-oxopentanoate hydrochloride (1.95 g, 9.66 mmol) in DMF (20 mL) was added TEA (2.44 g, 24.14 mmol). The mixture was stirred at 40° C. overnight and then concentrated. The residue was dissolved in EA, washed with water, filtered, and concentrates to give tert-butyl 5-amino-4-(5-cyano-1-oxoisoindolin-2-yl)-5-oxopentanoate 60 (1.8 g) in 65.3% yield. MS (ESI) m/z: 343.2 [M+H]+.

To a stirred solution of tert-butyl 5-amino-4-(5-cyano-1-oxoisoindolin-2-yl)-5-oxopentanoate 60 (1.8 g, 5.25 mmol) in AcOH (20 mL), pyridine (40 mL), and water (20 mL) was added sodium hypophosphite (2.3 g, 26.2 mmol) and Raney Ni. The mixture was stirred for 2 h and then filtered and concentrates. The residue was dissolved in DCM and 1 N HCl was added. The organic layer was separated and concentrated. The residue was triturated with tert-butyl methyl ether to give tert-butyl 5-amino-4-(5-formyl-1-oxoisoindo-lin-2-yl)-5-oxopentanoate 61 (1.27 g) in 70% yield. MS (ESI) m/z: 347.1 [M+H]+.

To a stirred solution of tert-butyl 5-amino-4-(5-formyl-1-oxoisoindolin-2-yl)-5-oxopentanoate 61 (1.27 g, 3.67 mmol) in MeOH (30 mL) was added sodium borohydride (84 mg, 2.2 mmol) at 0° C. The mixture was stirred at 0° C. for 10 min and then RT for 3 h. Water was added and the mixture was extracted with EA. The organic layer was washed with brine, dried over Na2SO4, filtered, and concentrates to give tert-butyl 5-amino-4-(5-(hydroxymethyl)-1-oxoisoindolin-2-yl)-5-oxopentanoate 62 (960 mg) in 75% yield. MS (ESI) m/z: 349.1 [M+H]+.

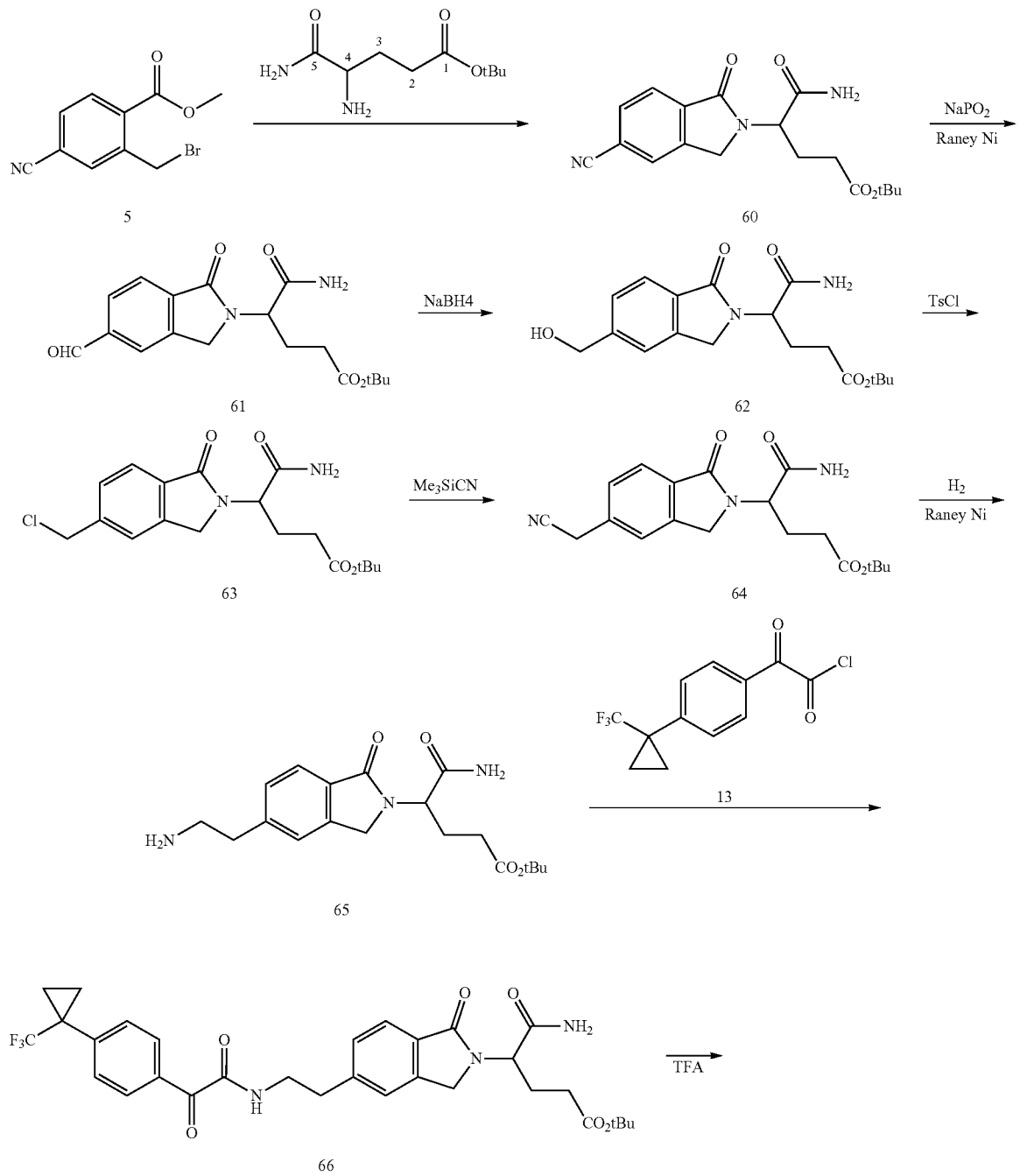

Scheme 11

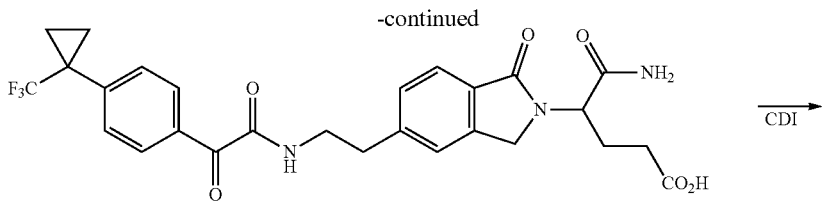

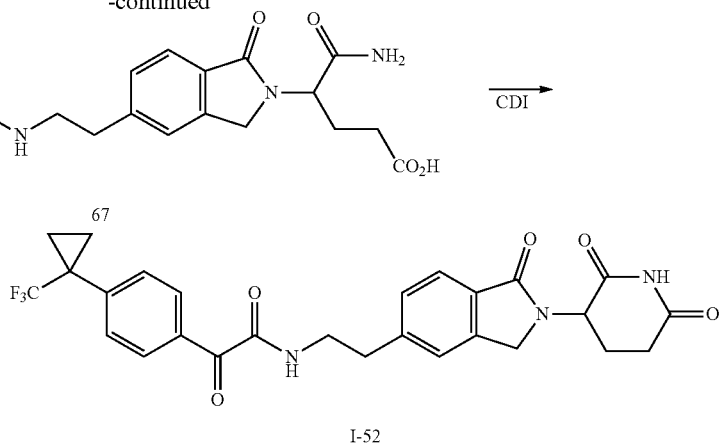

To a stirred solution of tert-butyl 5-amino-4-(5-(hydroxymethyl)-1-oxoisoindolin-2-yl)-5-oxopentanoate 62 (960 mg, 2.76 mmol), 4-dimethylaminopyridine (35 mg, 0.28 mmol), and TEA (558 mg, 5.52 mmol) in DCM (20 mL) was added tosyl chloride (1.05 g, 5.52 mmol). The mixture was stirred for 3 h, and then concentrated and purified using silica gel eluting with PE/EA (1:2) to give tert-butyl 5-amino-4-(5-(chloromethyl)-1-oxoisoindolin-2-yl)-5-oxopentanoate 63 (640 mg) in 64% yield. MS (ESI) m/z: 367.1 [M+H]$^+$.

To a stirred solution tert-butyl 5-amino-4-(5-(chloromethyl)-1-oxoisoindolin-2-yl)-5-oxopentanoate 63 (640 mg, 1.75 mmol) in THF (15 mL) was added trimethylsilyl cyanide (525 mg, 5.25 mmol) and tetrabutylammonium fluoride (5.25 mL) was then added dropwise. The mixture was stirred at 35° C. for 3 h, and then concentrated and purified using silica gel eluting with PE/EA (1:2) to give tert-butyl 5-amino-4-(5-(cyanomethyl)-1-oxoisoindolin-2-yl)-5-oxopentanoate 64 (450 mg) in 72% yield. MS (ESI) m/z: 358.2 [M+H]$^+$.

To a stirred solution of tert-butyl 5-amino-4-(5-(cyanomethyl)-1-oxoisoindolin-2-yl)-5-oxopentanoate 64 (400 mg, 1.12 mmol) in THF (20 mL) was added Raney Ni. The mixture was stirred for 3 h under H$_2$, and then filtered and concentrates to give tert-butyl 5-amino-4-(5-(2-aminoethyl)-1-oxoisoindolin-2-yl)-5-oxopentanoate 65 (400 mg, crude). MS (ESI) m/z: 362.2 [M+H]$^+$.

To a stirred solution of tert-butyl 5-amino-4-(5-(2-aminoethyl)-1-oxoisoindolin-2-yl)-5-oxopentanoate 65 (400 mg, 1.12 mmol) in THF (20 mL) was added TEA (340 mg, 3.36 mmol) and a solution of 2-oxo-2-(4-(1-(trifluoromethyl)cyclopropyl)phenyl)acetyl chloride 11 (1.55 mmol) in DCM (5 mL) at 0° C. The mixture was stirred at 0° C. for 10 min and RT for 3 h, and then concentrated. The residue was purified by prep-TLC (EA) to give tert-butyl 5-amino-5-oxo-4-(1-oxo-5-(2-(2-oxo-2-(4-(1-(trifluoromethyl)cyclopropyl)phenyl)acetamido)ethyl)isoindolin-2-yl)pentanoate 66 (400 mg) in 59% yield. MS (ESI) m/z: 602.2 [M+H]$^+$.

To a stirred solution of tert-butyl 5-amino-5-oxo-4-(1-oxo-5-(2-(2-oxo-2-(4-(1-(trifluoromethyl)cyclopropyl)phenyl)acetamido)ethyl)isoindolin-2-yl)pentanoate 66 (107 mg, 0.178 mmol) in DCM (3 mL) was added TFA (3 mL). The mixture was stirred for 2 h and then concentrated to give 5-amino-5-oxo-4-(1-oxo-5-(2-(2-oxo-2-(4-(1-(trifluoromethyl)cyclopropyl)-phenyl)acetamido)ethyl)isoindolin-2-yl)pentanoic acid 67 (110 mg, crude). MS (ESI) m/z: 546.2 [M+H]$^+$.

To a stirred solution 5-amino-5-oxo-4-(1-oxo-5-(2-(2-oxo-2-(4-(1-(trifluoromethyl)-cyclopropyl)phenyl)acetamido)ethyl)isoindolin-2-yl)pentanoic acid 67 (0.178 mmol) in ACN (5 mL) was added CDI (145 mg, 0.89 mmol). The mixture was stirred at 95° C. overnight, and then concentrated and purified by prep-TLC eluting with PE/EA (1:2) and then by prep-HPLC to give compound I-52 (27.8 mg) in 30% yield. MS (ESI) m/z: 528.1 [M+H]$^+$; $^1$H NMR (400 MHz, DMSO-d$_6$) δ 10.97 (s, 1H), 9.01 (t, J=6.0 Hz, 1H), 7.81-7.83 (m, 2H), 7.66 (d, J=8.0 Hz, 1H), 7.59-7.61 (m, 2H), 7.51 (s, 1H), 7.40 (d, J=8.0 Hz, 1H), 5.10 (dd, J=4.8, 13.2 Hz, 1H), 4.28-4.44 (m, 2H), 3.55-3.57 (m, 2H), 2.97 (t, J=6.8 Hz, 2H), 2.88-2.92 (m, 1H), 2.57-2.62 (m, 1H), 2.38-2.42 (m, 1H), 1.98-2.01 (m, 1H), 1.39-1.42 (m, 2H), 1.17-1.19 (m, 2H).

Example 12

Compound I-61: 2-(4-(Tert-butyl)piperidin-1-yl)-N-((2-(2,6-dioxopiperidin-3-yl)-1-oxoisoindolin-4-yl)methyl)-2-oxoacetamide

I-61

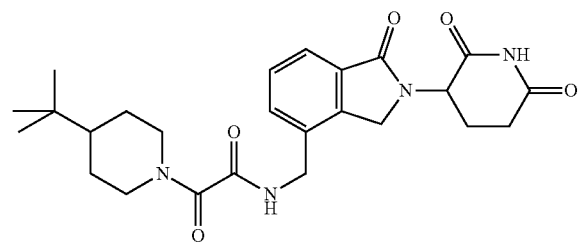

Compound I-61 was synthesized as shown in Scheme 12.

Scheme 12

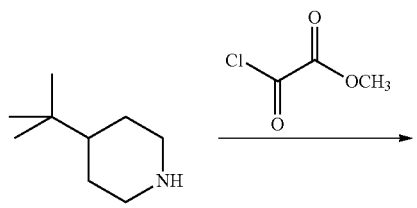

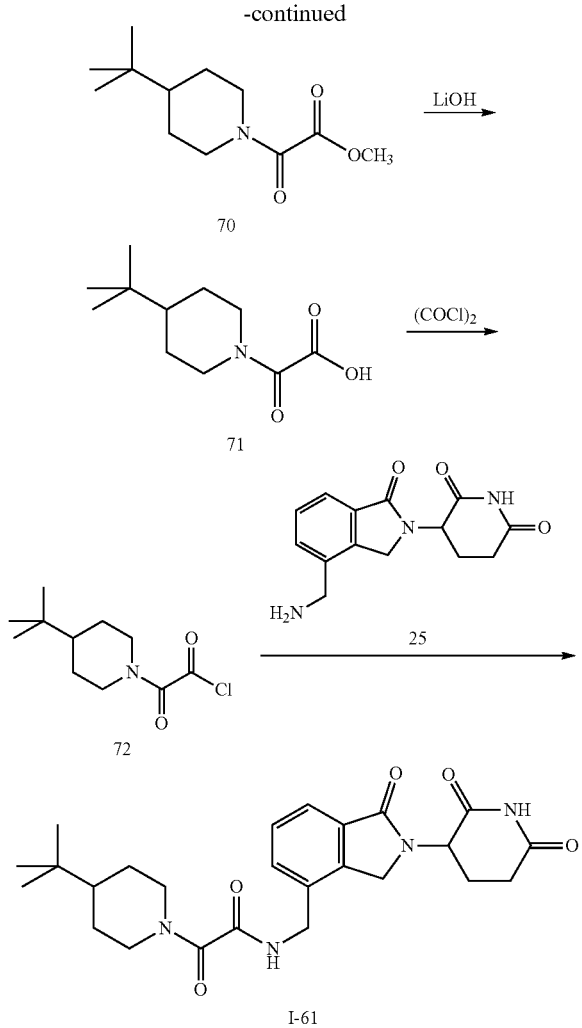

To a solution of methyl 2-(4-(tert-butyl)piperidin-1-yl)-2-oxoacetate 70 (130 mg, 0.57 mmol) in THF/H$_2$O (4 mL/1 mL) was added LiOH (48 mg, 1.12 mmol). The mixture was stirred at 25° C. for 16 h and then concentrated. The residue was adjusted to pH=5 using 1N HCl and then extracted with EA. The combined organic layers were dried over Na$_2$SO$_4$, filtered, and concentrated. The residue was purified using silica gel eluting with MeOH in DCM from 10% to 20% to give 2-(4-(tert-butyl)piperidin-1-yl)-2-oxoacetic acid 71 (130 mg) in 99% yield. MS (ESI) m/z: 214.1 [M+H]$^+$.

To a solution of methyl 2-(4-(tert-butyl)piperidin-1-yl)-2-oxoacetic acid 71 (52 mg, 0.24 mmol) in DCM (3 mL) was added oxalyl dichloride (46 mg, 0.36 mmol) at 0° C., followed by addition of DMF (1 drop). The mixture was stirred at 25° C. for 1 h and then concentrated to give 2-(4-(tert-butyl)piperidin-1-yl)-2-oxoacetyl chloride 72 (60 mg) in 98% yield.

To a solution of 2-(4-(tert-butyl)piperidin-1-yl)-2-oxoacetyl chloride 72 (114 mg, 0.31 mmol) in DCM (4 mL) was added TEA (63 mg, 0.62 mmol) and 3-(4-(aminomethyl)-1-oxoisoindolin-2-yl)piperidine-2,6-dione 25 (72 mg, 0.31 mmol). The mixture was stirred for 1 h, and then concentrated and purified by prep-HPLC to give compound I-61 (49.9 mg) in 44% yield. MS (ESI) m/z: 469.2[M+H]$^+$; $^1$H NMR (400 MHz, DMSO-d$_6$) δ 11.00 (s, 1H), 9.24 (d, J=4.0 Hz, 1H), 7.65 (s, 1H), 7.52 (d, J=4.4 Hz, 2H), 5.16 (dd, J=3.6, 12.4 Hz, 1H), 4.57-4.35 (m, 5H), 3.75 (t, J=12.8 Hz, 1H), 2.98-2.90 (m, 2H), 2.65-2.56 (m, 2H), 2.42-2.34 (m, 1H), 2.04-2.01 (m, 1H), 1.73-1.66 (m, 2H), 1.28-1.23 (m, 1H), 1.11-1.01 (m, 2H), 0.83 (s, 9H).

Example 13

Compound I-63: N-((2-(2,6-Dioxopiperidin-3-yl)-1-oxoisoindolin-5-yl)methyl)-2-oxo-3-(4-(1-(trifluoromethyl)cyclopropyl)phenyl)propanamide

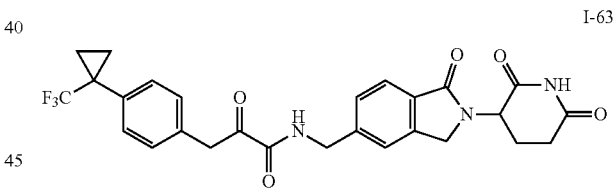

Compound I-63 was synthesized as shown in Scheme 13.

To a solution of 4-(tert-butyl)piperidine hydrochloride (150 mg, 0.85 mmol) in DCM (6 mL) was added TEA (171 mg, 1.7 mmol) and methyl 2-chloro-2-oxoacetate (124 mg, 1.02 mmol). The mixture was stirred for 30 min and then concentrated. The residue was purified using silica gel eluting with EA in PE from 30% to 50% to give methyl 2-(4-(tert-butyl)piperidin-1-yl)-2-oxoacetate 70 (130 mg) in 68% yield. MS (ESI) m/z: 228.2 [M+H]$^+$.

Scheme 13

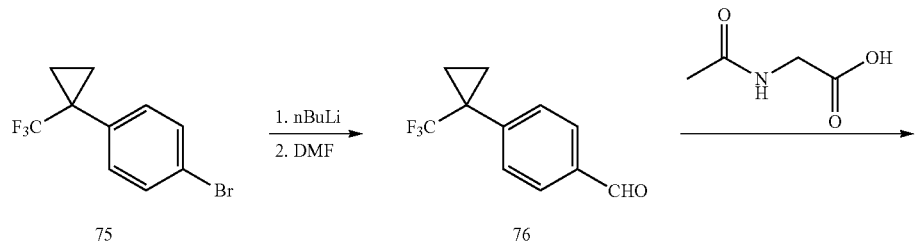

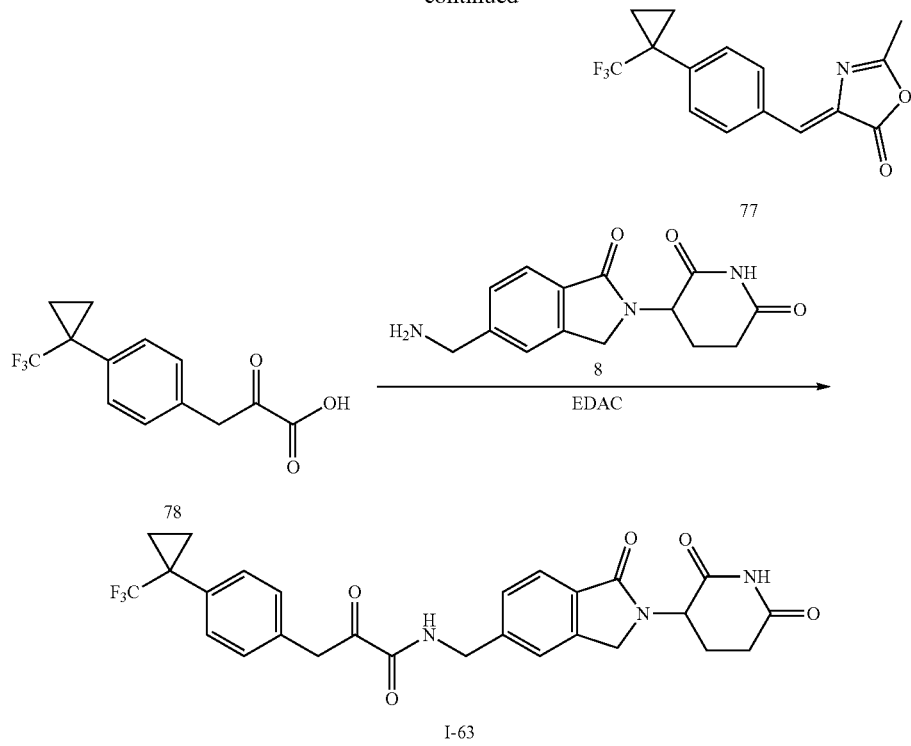

To a stirred solution of 1-bromo-4-(1-(trifluoromethyl) cyclopropyl)benzene 75 (2.3 g, 8.68 mmol) in THF (20 mL) was dropwise added n-butyllithium (2.5 M solution in hexane, 5.2 mL) at −78° C. under $N_2$. After stirring for 1 h at −78° C., DMF (2 mL) was added and the mixture was stirred at −78° C. for 1 h. The mixture was quenched with saturated ammonium chloride and extracted with EA. The organic layer was washed with brine, dried over $Na_2SO_4$, filtered, and concentrates to give 4-(1-(trifluoromethyl)cyclopropyl)benzaldehyde 76 (1.8 g) in 97% yield. $^1$H NMR (400 MHz, $CDCl_3$) δ 10.02 (s, 1H), 7.86 (d, J=8.0 Hz, 2H), 7.63 (d, J=8.0 Hz, 2H), 1.41-1.43 (m, 2H), 1.06-1.08 (m, 2H).

To a stirred solution of 4-(1-(trifluoromethyl)cyclopropyl) benzaldehyde 76 (500 mg, 2.34 mmol) in acetic anhydride (5 mL) was added 2-acetamidoacetic acid (410 mg, 3.5 mmol) and sodium acetate trihydrate (287 mg, 3.5 mmol). The mixture was stirred at 120° C. overnight, and then cooled to RT, poured into ice-water, and extracted with EA. The organic layer was washed with brine, dried over $Na_2SO_4$, concentrates, and purified using silica gel (PE/EA (4:1) to give (Z)-2-methyl-4-(4-(1-(trifluoromethyl)cyclopropyl)benzylidene)oxazol-5(4H)-one 77 (180 mg, crude). MS (ESI) m/z: 296.1 [M+H]$^+$; $^1$H NMR (400 MHz, $CDCl_3$) δ 8.04 (d, J=8.0 Hz, 2H), 7.52 (d, J=8.0 Hz, 2H), 7.12 (s, 1H), 2.41 (s, 3H), 1.41-1.43 (m, 2H), 1.06-1.08 (m, 2H).

A solution of (Z)-2-methyl-4-(4-(1-(trifluoromethyl)cyclopropyl)benzylidene)oxazol-5(4H)-one 77 (180 mg, 0.61 mmol) in 4 N HCl (8 mL) was stirred at 100° C. for 2 h and then filtered and purified by prep-HPLC to give 2-oxo-3-(4-(1-(trifluoromethyl)cyclopropyl)phenyl)propanoic acid 78. MS (ESI) m/z: 271.1 [M−H]$^+$.

To a stirred solution 3-(5-(aminomethyl)-1-oxoisoindolin-2-yl)piperidine-2,6-dione hydrochloride 8 (47 mg, 0.15 mmol) and 2-oxo-3-(4-(1-(trifluoromethyl)cyclopropyl)phenyl)-propanoic acid 78 (40 mg, 0.15 mmol) in DMF (2 mL) was added DIEA (106 mg, 0.5 mmol), 1-hydroxybenzotriazole (40 mg, 0.3 mmol), and EDAC-HCl (58 mg, 0.3 mmol). The mixture was stirred for 2 h and then concentrated. The residue was purified by prep-HPLC to give compound I-63 (2.9 mg). MS (ESI) m/z: 527.9 [M+H]$^+$; $^1$H NMR (400 MHz, DMSO-d6) δ 10.96 (s, 1H), 8.76 (t, J=6.0 Hz, 1H), 7.69-7.70 (m, 1H), 7.60-7.58 (m, 1H), 7.51-7.43 (m, 5H), 6.73-6.69 (m, 1H), 5.10 (dd, J=5.2, 13.2 Hz, 1H), 4.52-4.29 (m, 4H), 2.95-2.87 (m, 1H), 2.62-2.57 (m, 1H), 2.40-2.36 (m, 1H), 2.01-1.98 (m, 1H), 1.35-1.33 (m, 2H), 1.14-1.12 (m, 2H).

Example 14

Compound I-70: $N^1$-((5-(2,6-Dioxopiperidin-3-yl)-4-oxo-5,6-dihydro-4H-thieno[3,4-c]pyrrol-1-yl) methyl)-$N^2$,$N^2$-dimethyloxalamide

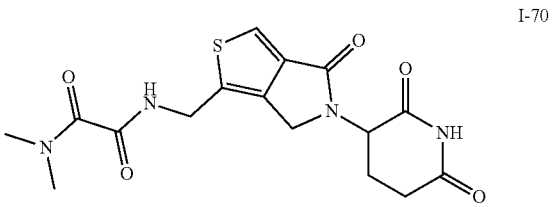 [SMILES: CN(C)C(=O)C(=O)NCc1scc2c1CN(C1CCC(=O)NC1=O)C2=O]

Compound I-70 was synthesized as shown in Scheme 14.

Scheme 14

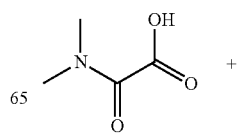

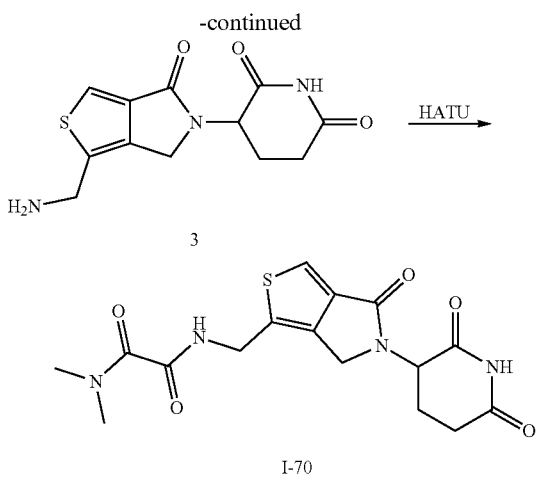

To a solution of 2-(dimethylamino)-2-oxoacetic acid (30 mg, 0.26 mmol) in DMF (1.5 mL) was added 3-(1-(aminomethyl)-4-oxo-4H-thieno[3,4-c]pyrrol-5(6H)-yl)piperidine-2,6-dione (80 mg, 0.26 mmol), HATU (148 mg, 0.39 mmol), and DIEA (105 mg, 0.78 mmol). The mixture was stirred for 1 h and then concentrated. The residue was purified by prep-HPLC to give compound I-70 (32 mg) in 32% yield. MS (ESI) m/z: 379.2 [M+H]⁺.

The following compounds were prepared according to a synthetic procedure described herein.

Compound I-6: 2-(3-chloro-4-methylphenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 460.1 [M+1]⁺.

Compound I-7: 2-(4-dimethylaminophenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 455.1 [M+1]⁺.

Compound I-8: 2-phenyl-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 412.0 [M+1]⁺.

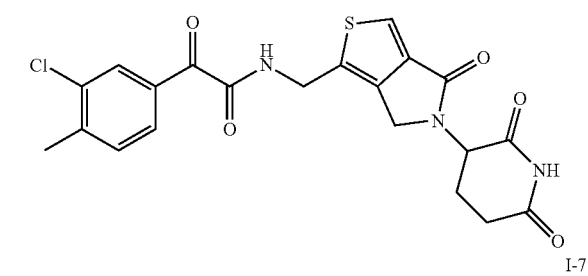

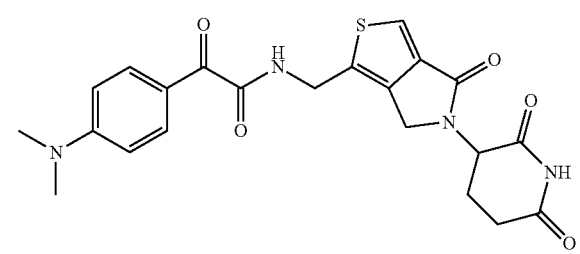

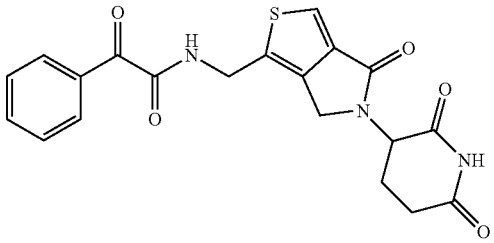

Compound I-9: N-((5-(2,6-dioxopiperidin-3-yl)-4-oxo-5,6-dihydro-4H-thieno[3,4-c]pyrrol-1-yl)methyl)-2-(thiophen-2-yl)-2-oxoacetamide. MS (ESI) m/z: 418.0 [M+1]⁺.

Compound I-10: (S)-2-(4-(tert-butyl)phenyl)-N-((2-(2,7-dioxoazepan-3-yl)-1-oxoisoindolin-5-yl)methyl)-2-oxoacetamide. MS (ESI) m/z: 476.2 [M+1]⁺.

Compound I-11: 2-(4-methoxyphenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 442.0 [M+1]⁺.

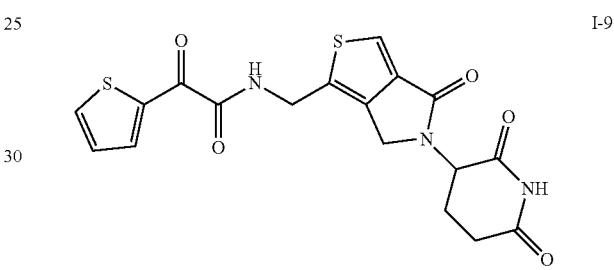

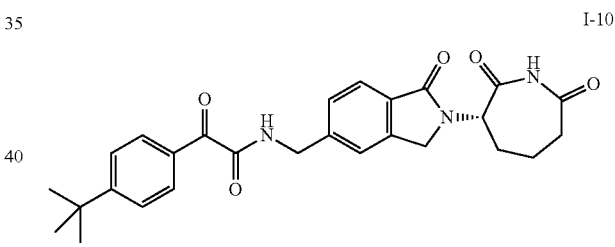

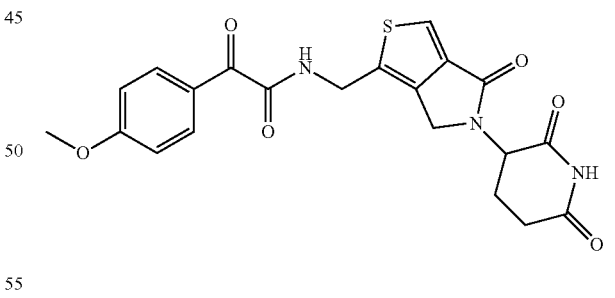

Compound I-12: 2-(4-cyclopropylphenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 452.1 [M+1]⁺.

Compound I-13: 2-(4-(tert-butyl)phenyl)-N-((5-(2,6-dioxopiperidin-3-yl)-4,6-dioxo-5,6-dihydro-4H-thieno[3,4-c]pyrrol-1-yl)methyl)-2-oxoacetamide. MS (ESI) m/z: 482.1 [M+H]⁺.

Compound I-14: 2-(4-isopropylphenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 454.1 [M+1]⁺.

I-12

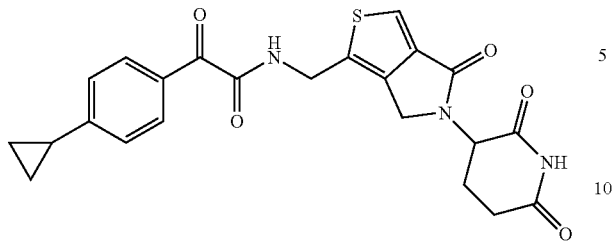

I-13

I-14

Compound I-15: 2-(4-(sec-butyl)phenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 468.1 [M+1]⁺.

Compound I-16: 2-(4-hydroxyphenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 428.1 [M+1]⁺.

Compound I-17: 2-(4-methylphenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 426.5 [M+1]⁺.

I-15

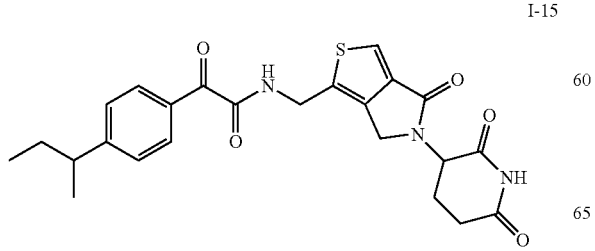

I-16

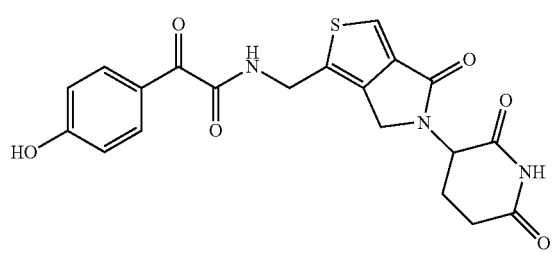

I-17

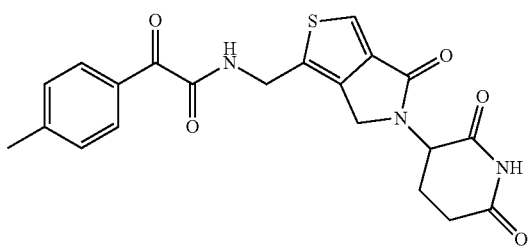

Compound I-18: 2-(4-chlorophenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 446.0 [M+1]⁺.

Compound I-19: 2-(3-tert-butylphenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 468.1 [M+1]⁺.

Compound I-20: 2-(4-acetamidophenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 469.1 [M+1]⁺.

I-18

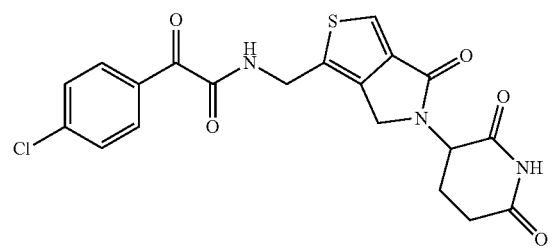

I-19

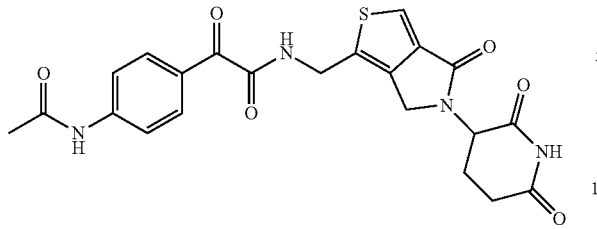

I-20

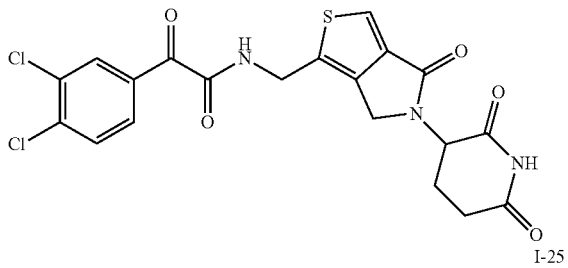

I-24

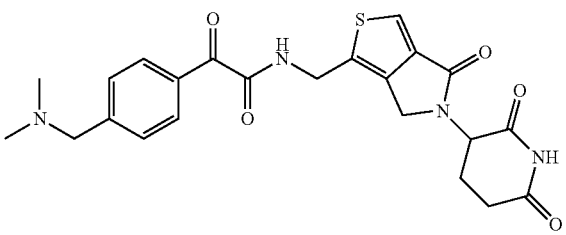

I-25

Compound I-21: 2-([1,1'-biphenyl]-4-yl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 488.1 [M+1]⁺.

Compound I-22: 2-(4-fluorophenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 430.5 [M+1]⁺.

Compound I-23: 2-(4-trifluoromethylphenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 480.0 [M+1]⁺.

Compound I-26: 2-(4-(morpholinomethyl)phenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 511.1 [M+1]⁺.

Compound I-27: 2-(3-methyl-4-(tert-butyl)phenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 482.1 [M+1]⁺.

I-21

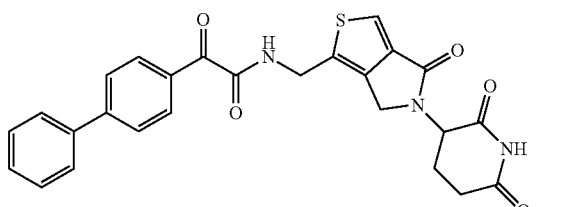

I-22

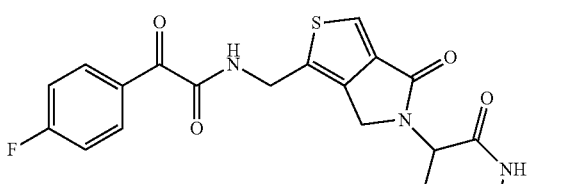

I-23

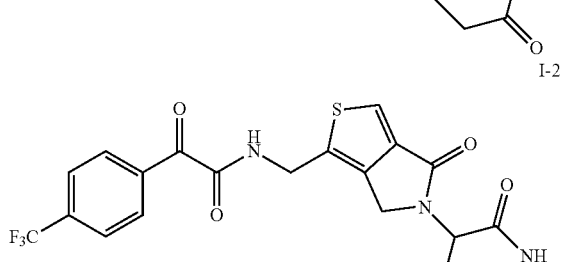

I-26

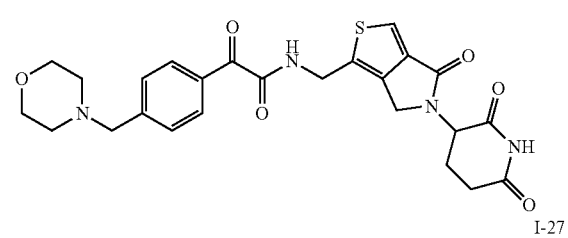

I-27

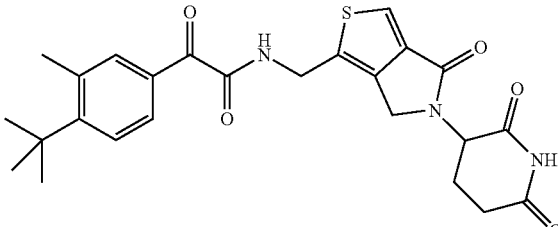

Compound I-24: 2-(3,4-dichlorophenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 481.0 [M+1]⁺.

Compound I-25: 2-(4-((dimethylamino)methyl)phenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 469.1 [M+1]⁺.

Compound I-29: 2-(4-(tert-butyl)phenyl)-N-((2-(2,6-dioxopiperidin-3-yl)-6-fluoro-1-oxoisoindolin-4-yl)methyl)-2-oxoacetamide. MS (ESI) m/z: 480.1 [M+H]⁺; ¹H NMR (DMSO-d₆, 400 MHz) δ 11.03 (s, 1H), 9.50 (t, J=6.0 Hz, 1H), 7.94 (d, J=7.6 Hz, 2H), 7.61 (d, J=8.4 Hz, 2H), 7.48 (dd, J=2.4, 7.6 Hz, 1H), 7.41 (dd, J=2.4, 10.0 Hz, 1H), 5.16 (dd, J=5.2, 13.2 Hz, 1H), 4.59-4.41 (m, 4H), 2.98-2.88 (m, 1H), 2.67-2.60 (m, 1H), 2.43-2.33 (m, 1H), 2.07-2.02 (m, 1H), 1.31 (s, 9H).

Compound I-30: N-((2-(2,6-dioxopiperidin-3-yl)-1-oxoisoindolin-4-yl)methyl)-2-oxo-2-(4-(1-(trifluoromethyl)cyclopropyl)phenyl)acetamide. MS (ESI) m/z: 514.2 [M+H]⁺;

$^1$H NMR (DMSO-d$_6$, 400 MHz) δ 11.02 (s, 1H), 9.53 (t, J=5.2 Hz, 1H), 7.99 (d, J=7.6 Hz, 2H), 7.67-7.52 (m, 5H), 5.16 (dd, J=5.6, 13.2 Hz 1H), 4.60-4.42 (m, 4H), 2.96-2.89 (m, 1H), 2.66-2.58 (m, 1H), 2.31-2.26 (m, 1H), 2.04-1.99 (m, 1H), 1.40 (s, 2H), 1.17 (s, 2H).

I-29

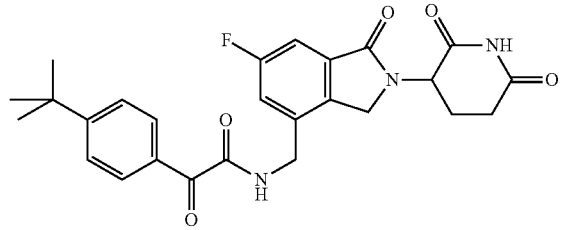

I-30

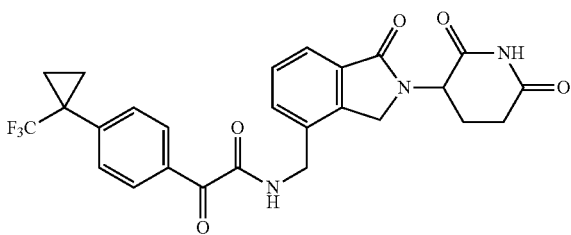

Compound I-31: N-((5-(2,6-dioxopiperidin-3-yl)-4-oxo-5,6-dihydro-4H-thieno[3,4-c]pyrrol-1-yl)methyl)-2-(4-(1-methylpiperidin-4-yl)phenyl)-2-oxoacetamide. MS (ESI) m/z: 509.2 [M+1]$^+$; $^1$H NMR (400 MHz, DMSO-d$_6$) δ 10.98 (s, 1H), 9.60 (t, J=5.6 Hz, 2H), 7.98 (d, J=8.4 Hz, 2H), 7.94 (s, 1H), 7.46 (d, J=8.4 Hz, 2H), 5.03 (dd, J=5.2, 13.2 Hz, 1H), 4.60 (d, J=6.0 Hz, 2H), 4.38-4.22 (m, 2H), 3.55-3.52 (m, 2H), 3.09-3.06 (m, 2H), 2.92-2.88 (m, 2H), 2.86-2.82 (m, 3H), 2.61-2.50 (m, 1H), 2.05-2.02 (m, 1H), 1.99-1.98 (m, 3H), 1.87-1.84 (m, 2H).

Compound I-33: 2-(3-(tert-butyl)phenyl)-N-((2-(2,6-dioxopiperidin-3-yl)-1-oxoisoindolin-5-yl)methyl)-2-oxoacetamide. MS (ESI) m/z: 462.1 [M+1]$^+$; $^1$H NMR (400 MHz, DMSO-d$_6$) δ 10.98 (s, 1H), 9.54 (t, J=6.0 Hz, 1H), 7.92 (t, J=1.6 Hz, 1H), 7.81-7.78 (m, 1H), 7.73 (d, J=7.6 Hz, 1H), 7.58 (s, 1H), 7.54-7.49 (m, 2H), 5.12 (dd, J=5.2, 13.6 Hz, 1H), 4.58 (d, J=6.0 Hz, 2H), 4.48-4.31 (m, 2H), 2.95-2.87 (m, 1H), 2.67-2.58 (m, 1H), 2.42-2.33 (m, 1H), 2.03-1.98 (m, 1H), 1.27 (s, 9H).

I-31

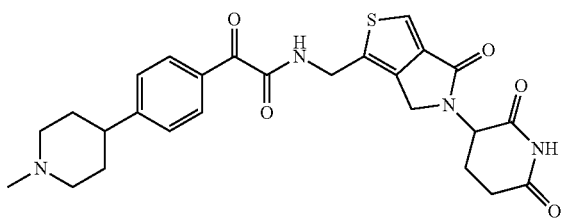

I-33

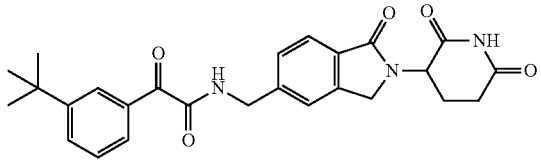

Compound I-34: 2-(4-(tert-butyl)phenyl)-N-((2-(2,6-dioxopiperidin-3-yl)-1-oxoisoindolin-5-yl)methyl)-N-methyl-2-oxoacetamide. MS (ESI) m/z: 476.2 [M+1]$^+$; $^1$H NMR (400 MHz, DMSO-d6) δ 10.98 (s, 1H), 7.83-7.38 (m, 7H), 5.14-5.08 (m, 1H), 4.81-4.33 (m, 4H), 2.95-2.83 (m, 4H), 2.62-2.58 (m, 1H), 2.49-2.40 (m, 1H), 2.02-1.99 (m, 1H), 1.31 (s, 9H).

Compound I-35: 2-(4-(tert-butyl)phenyl)-N-((5-(2,6-dioxopiperidin-3-yl)-6-oxo-5,6-dihydro-4H-thieno[2,3-c]pyrrol-2-yl)methyl)-2-oxoacetamide. MS (ESI) m/z=468.1 [M+H]$^+$; $^1$H NMR (400 MHz, DMSO-d$_6$) δ 10.95 (s, 1H), 9.65 (t, J=5.6 Hz, 1H), 7.87 (s, 1H), 7.93 (d, J=8.8 Hz, 2H), 7.62 (d, J=8.8 Hz, 2H), 7.19 (s, 1H), 4.99 (dd, J=5.2, 13.6 Hz, 1H), 4.69 (d, J=7.0 Hz, 2H), 4.39-4.21 (m, 2H), 2.92-2.84 (m, 1H), 2.60-2.56 (m, 1H), 2.37-2.32 (m, 1H), 2.02-1.97 (m, 1H), 1.31 (s, 9H).

I-34

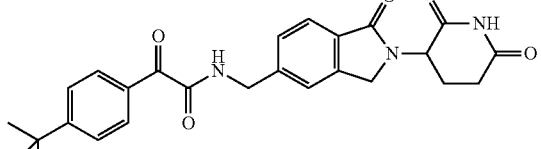

I-35

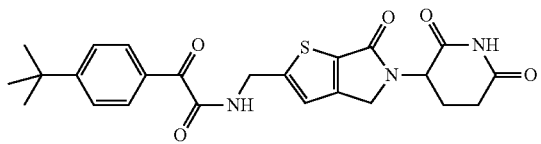

Compound I-36: N-((5-(2,6-dioxopiperidin-3-yl)-4-oxo-5,6-dihydro-4H-thieno[3,4-c]pyrrol-1-yl)methyl)-2-oxo-2-(4-(1,1,1-trifluoropropan-2-yl)phenyl)acetamide. MS (ESI) m/z: 508.0 [M+1]$^+$; $^1$H NMR (400 MHz, DMSO-d$_6$) δ 10.98 (s, 1H), 9.62 (t, J=6.4 Hz, 1H), 8.01 (d, J=8.4 Hz, 2H), 7.93 (s, 1H), 7.62 (d, J=8.0 Hz, 2H), 5.03 (dd, J=4.8, 13.2 Hz, 1H), 4.60 (d, J=6.0 Hz, 2H), 4.37-4.22 (m, 2H), 4.02-3.93 (m, 1H), 2.93-2.84 (m, 1H), 2.61-2.51 (m, 1H), 2.35-2.25 (m, 1H), 2.01-1.98 (m, 1H), 1.48 (d, J=7.2 Hz, 2H).

Compound I-37: N-((2-(2,6-dioxopiperidin-3-yl)-1-oxoisoindolin-5-yl)methyl)-2-(5-isopropylthiophen-2-yl)-2-oxoacetamide. MS (ESI) m/z: 454.1 [M+1]$^+$; $^1$H NMR (400 MHz, DMSO-d$_6$) δ 10.97 (s, 1H), 9.56 (t, J=6.4 Hz, 1H), 8.08 (d, J=4.0 Hz, 1H), 7.70 (d, J=8.0 Hz, 1H), 7.53 (s, 1H), 7.46 (d, J=7.6 Hz, 1H), 7.11 (d, J=4.0 Hz, 1H), 5.11 (dd, J=5.2, 13.6 Hz, 1H), 4.52 (d, J=6.4 Hz, 2H), 4.48-4.30 (m, 2H), 3.28-3.23 (m, 1H), 2.92-2.86 (m, 1H), 2.62-2.57 (m, 1H), 2.40-2.33 (m, 1H), 2.02-1.98 (m, 1H), 1.32 (d, J=6.8 Hz, 6H).

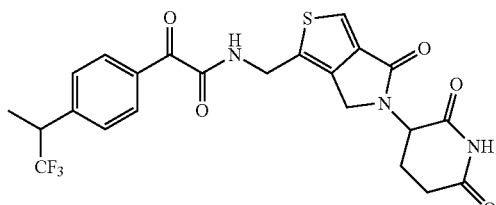

I-36

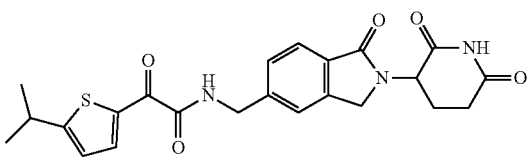

I-37

Compound I-39: 2-(4-(tert-butyl)phenyl)-N-((5-(2,6-dioxopiperidin-3-yl)-6-oxo-5,6-dihydro-4H-thieno[2,3-c]pyrrol-3-yl)methyl)-2-oxoacetamide. MS (ESI) m/z=468.0 [M+H]⁺; ¹H NMR (400 MHz, DMSO-d₆) δ 10.97 (s, 1H), 9.41 (t, J=6.0 Hz, 1H), 7.93 (d, J=8.4 Hz, 2H), 7.85 (s, 1H), 7.60 (d, J=8.4 Hz, 2H), 5.02 (dd, J=5.2, 13.2 Hz, 1H), 4.48 (d, J=6.0 Hz, 2H), 4.43-4.28 (m, 2H), 2.93-2.86 (m, 1H), 2.67-2.60 (m, 1H), 2.33-2.30 (m, 1H), 2.05-2.00 (m, 1H), 1.31 (s, 9H).

Compound I-40: 2-(4-(tert-butyl)phenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 482.1 [M+1]⁺; ¹H NMR (400 MHz, DMSO-d₆) δ 10.98 (s, 1H), 8.02 (s, 1H), 7.81-7.78 (m, 2H), 7.65-7.58 (m, 2H), 5.04 (dd, J=5.2, 13.2 Hz, 1H), 4.89-4.61 (m, 2H), 4.41-4.15 (m, 2H), 3.03-2.88 (m, 4H), 2.61-2.57 (m, 1H), 2.34-2.27 (m, 1H), 2.03-1.98 (m, 1H), 1.30 (s, 9H).

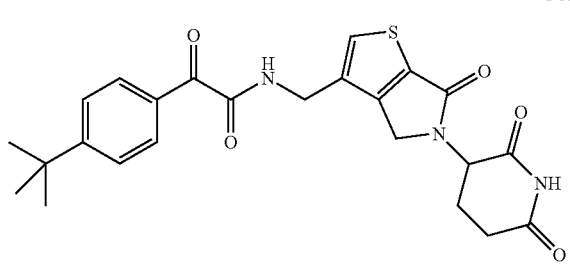

I-39

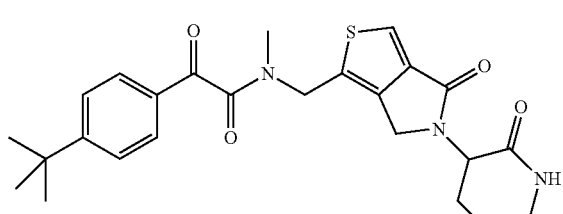

I-40

Compound I-41: 2-(4-(tert-butyl)phenyl)-N-(2-(5-(2,6-dioxopiperidin-3-yl)-4-oxo-5,6-dihydro-4H-thieno[3,4-c]pyrrol-1-yl)ethyl)-2-oxoacetamide. MS (ESI) m/z=482.1 [M+H]⁺; ¹H NMR (400 MHz, DMSO-d₆) δ 10.95 (s, 1H), 9.03 (t, J=5.6 Hz, 1H), 7.88 (s, 1H), 7.77 (d, J=8.4 Hz, 2H), 7.54 (d, J=8.4 Hz, 2H), 4.99 (dd, J=5.2, 13.2 Hz, 1H), 4.30 (d, J=15.6 Hz, 1H), 4.16 (d, J=15.2 Hz, 1H), 3.53-3.55 (m, 2H), 3.05 (t, J=6.8 Hz, 2H), 2.90-2.80 (m, 1H), 2.57-2.54 (m, 1H), 2.28-2.17 (m, 1H), 1.82-1.79 (m, 1H), 1.30 (s, 9H).

Compound I-42: N-((5-(2,6-dioxopiperidin-3-yl)-4-oxo-5,6-dihydro-4H-thieno[3,4-c]pyrrol-1-yl)methyl)-2-(4-(1-methylcyclopropyl)phenyl)-2-oxoacetamide. MS (ESI) m/z: 466.1 [M+1]⁺; ¹H NMR (400 MHz, DMSO-d₆) δ 10.98 (s, 1H), 9.56 (t, J=5.6 Hz, 1H), 7.93 (s, 1H), 7.90 (d, J=8.4 Hz, 2H), 7.37 (d, J=8.4 Hz, 2H), 5.02 (dd, J=4.8, 13.2 Hz, 1H), 4.59 (d, J=5.6 Hz, 2H), 4.36-4.21 (m, 2H), 2.88-2.85 (m, 1H), 2.60-2.56 (m, 1H), 2.31-2.27 (m, 1H), 2.00-1.97 (m, 1H), 1.42 (s, 3H), 0.96-0.94 (m, 2H), 0.90-0.87 (m, 2H).

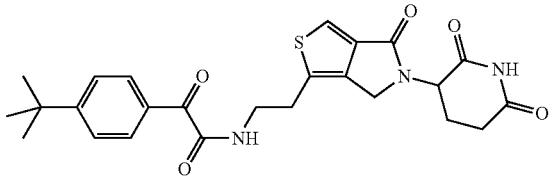

I-41

I-42

Compound I-43: N-((5-(2,6-dioxopiperidin-3-yl)-4-oxo-5,6-dihydro-4H-thieno[3,4-c]pyrrol-1-yl)methyl)-2-(4-(1-hydroxy-2-methylpropan-2-yl)phenyl)-2-oxoacetamide. MS(ESI) m/z: 484.0 [M+1]⁺; ¹H NMR (400 MHz, DMSO-d₆) δ 11.02 (s, 1H), 9.61 (t, J=8.0 Hz, 1H), 7.97 (s, 1H), 7.94 (d, J=11.2 Hz, 2H), 7.60 (d, J=11.6 Hz, 2H), 5.07 (dd, J=6.8, 10.0 Hz, 1H), 4.79 (t, J=7.2 Hz, 1H), 4.63 (d, J=7.6 Hz, 2H), 4.42-4.24 (m, 2H), 3.49 (d, J=7.2 Hz, 2H), 2.98-2.86 (m, 1H), 2.76-2.64 (m, 1H), 2.46-2.27 (m, 1H), 2.04-1.97 (m, 1H), 1.28 (s, 6H).

Compound I-44: 2-(3-(dimethylamino)-4-methylphenyl)-N-((5-(2,6-dioxopiperidin-3-yl)-4-oxo-5,6-dihydro-4H-thieno[3,4-c]pyrrol-1-yl)methyl)-2-oxoacetamide. MS (ESI) m/z: 469.1 [M+1]⁺; ¹H NMR (400 MHz, DMSO-d₆) δ 10.98 (s, 1H), 9.55 (t, J=6.4 Hz, 1H), 7.94 (s, 1H), 7.56-7.54 (m, 2H), 7.34 (d, J=7.6 Hz, 1H), 5.02 (dd, J=5.2, 13.2 Hz, 1H), 4.59 (d, J=6.0 Hz, 2H), 4.37-4.22 (m, 2H), 2.93-2.84 (m, 1H), 2.63 (s, 6H), 2.61-2.54 (m, 1H), 2.34 (s, 3H), 2.31-2.27 (m, 1H), 2.03-1.97 (m, 1H).

I-43

I-44

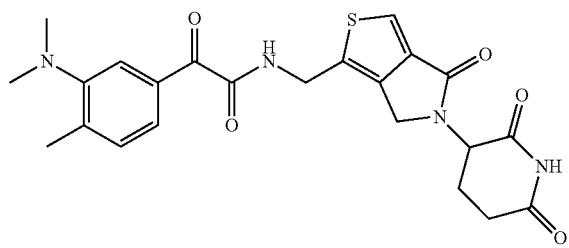

Compound I-45: 2-(4-(tert-butyl)phenyl)-N-((5-(2,6-dioxopiperidin-3-yl)-6-oxo-5,6-dihydro-4H-thieno[2,3-c]pyrrol-2-yl)methyl)-2-oxoacetamide. MS (ESI) m/z=468.1 [M+H]$^+$; $^1$H NMR (400 MHz, DMSO-d$_6$) δ 10.95 (s, 1H), 9.62 (t, J=5.6 Hz, 1H), 7.93 (d, J=8.4 Hz, 2H), 7.61 (d, J=8.0 Hz, 2H), 7.14 (s, 1H), 4.99 (dd, J=5.2, 13.2 Hz, 1H), 4.64 (d, J=4.8 Hz, 2H), 4.53-4.36 (m, 2H), 2.88-2.84 (m, 1H), 2.67-2.58 (m, 1H), 2.39-2.30 (m, 1H), 2.00-1.97 (m, 1H), 1.31 (s, 9H).

Compound I-46: 2-(3-(tert-butyl)phenyl)-N-((2-(2,6-dioxopiperidin-3-yl)-1-oxoisoindolin-4-yl)methyl)-2-oxoacetamide. MS (ESI) m/z: 462.2 [M+H]$^+$; $^1$H NMR (DMSO-d$_6$, 400 MHz) δ 11.05 (s, 1H), 9.55 (t, J=7.2 Hz, 1H), 7.94 (t, J=10.4 Hz, 1H), 7.82 (dd, J=2.0, 10.4 Hz, 2H), 7.71 (d, J=9.6 Hz, 1H), 7.64-7.52 (m, 3H), 5.20 (dd, J=6.4, 18.0 Hz, 1H), 4.65-4.44 (m, 4H), 3.00-2.90 (m, 1H), 2.75-2.61 (m, 1H), 2.44-2.37 (m, 1H), 2.07-2.01 (m, 1H), 1.30 (s, 9H).

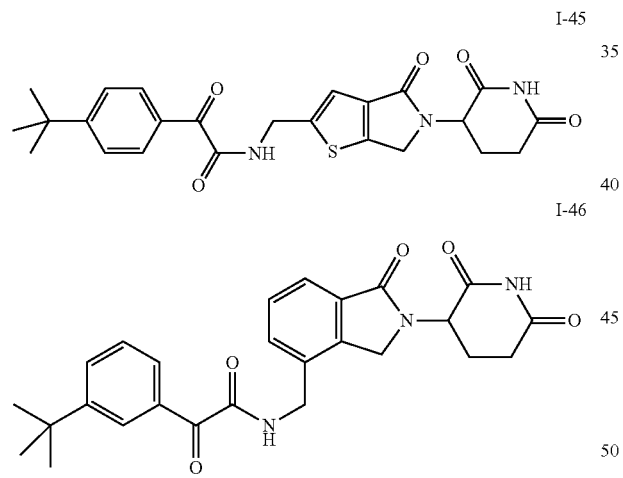

Compound I-48: 2-(4-(tert-butyl)phenyl)-N-((2-(2,6-dioxopiperidin-3-yl)-1,3-dioxoisoindolin-4-yl)methyl)-2-oxoacetamide. MS (ESI) m/z: 476.1 [M+H]$^+$; $^1$H NMR (DMSO-d$_6$, 400 MHz) δ 11.15 (s, 1H), 9.52 (t, J=5.6 Hz, 1H), 7.96 (d, J=8.4 Hz, 2H), 7.92-7.85 (m, 2H), 7.78 (d, J=8.0 Hz, 1H), 7.62 (d, J=8.4 Hz, 2H), 5.17 (dd, J=5.2, 12.8 Hz, 1H), 4.91 (dd, J=2.0, 5.6 Hz, 1H), 2.92-2.86 (m, 1H), 2.60-2.56 (m, 1H), 2.54-2.53 (m, 1H), 2.06-2.05 (m, 1H), 1.31 (s, 9H).

Compound I-50: 2-(4-(tert-butyl)phenyl)-N-((2-(2,6-dioxopiperidin-3-yl)-5-fluoro-1-oxoisoindolin-4-yl)methyl)-2-oxoacetamide. MS (ESI) m/z: 480.2 [M+H]$^+$; $^1$H NMR (DMSO-d$_6$, 400 MHz) δ 11.02 (s, 1H), 9.44 (t, J=6.0 Hz, 1H), 7.87 (d, J=8.4 Hz, 2H), 7.74 (dd, J=4.8, 8.4 Hz, 1H), 7.59 (d, J=8.4 Hz, 2H), 7.41 (dd, J=8.8, 10.0 Hz, 1H), 5.14 (dd, J=4.8, 12.8 Hz, 1H), 4.66-4.49 (m, 4H), 2.95-2.87 (m, 1H), 2.63-2.59 (m, 1H), 2.38-2.33 (m, 1H), 2.02-1.97 (m, 1H), 1.30 (s, 9H).

Compound I-51: 2-(4-(tert-butyl)phenyl)-N-((2-(2,6-dioxopiperidin-3-yl)-5,6-difluoro-1-oxoisoindolin-4-yl)methyl)-2-oxoacetamide. MS (ESI) m/z: 498.1 [M+H]$^+$; $^1$H NMR (DMSO-d$_6$, 400 MHz) δ 11.04 (s, 1H), 9.51 (t, J=5.6 Hz, 1H), 7.89 (d, J=8.4 Hz, 2H), 7.78 (t, J=7.8 Hz, 1H), 7.60 (d, J=8.4 Hz, 2H), 5.15 (dd, J=5.2, 13.2 Hz, 1H), 4.66-4.47 (m, 4H), 2.98-2.87 (m, 1H), 2.66-2.59 (m, 1H), 2.36 (qd, J=4.4, 13.2 Hz, 1H), 2.08-1.96 (m, 1H), 1.30 (s, 9H).

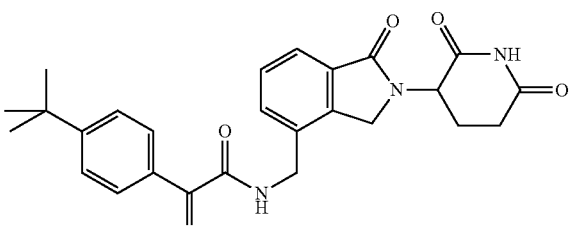

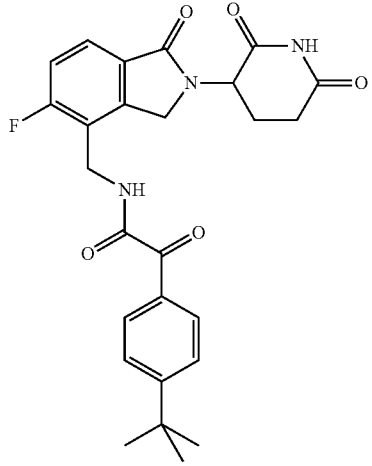

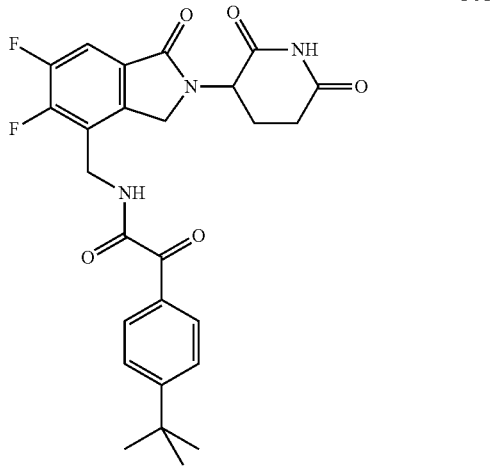

Compound I-53: 2-(3-chloro-4-methylphenyl)-N-((2-(2,6-dioxopiperidin-3-yl)-1-oxoisoindolin-5-yl)methyl)-2-oxoacetamide. MS (ESI) m/z: 454.0 [M+1]$^+$; $^1$H NMR (400 MHz, DMSO-d$_6$) δ 10.98 (s, 1H), 9.58 (t, J=6.4 Hz, 1H), 8.00 (d, J=1.6 Hz, 1H), 7.89 (dd, J=1.6, 8.0 Hz, 1H), 7.72 (d, J=7.6 Hz, 1H), 7.58 (d, J=8.0 Hz, 1H), 7.56 (s, 1H), 7.48 (d, J=8.4 Hz, 1H), 5.11 (dd, J=5.2, 13.2 Hz, 1H), 4.57 (d, J=6.0 Hz, 2H), 4.49-4.31 (m, 2H), 2.96-2.67 (m, 1H), 2.62-2.57 (m, 1H), 2.43 (s, 1H), 2.02-1.98 (m, 1H).

Compound I-54: 2-(3-methyl-4-(tert-butyl)phenyl)-N-((2-(2,6-dioxopiperidin-3-yl)-1-oxoisoindolin-4-yl)methyl)-2-oxoacetamide. MS (ESI) m/z: 476.0 [M+H]$^+$; $^1$H NMR (DMSO-d$_6$, 400 MHz) δ 11.01 (s, 1H), 9.47 (t, J=5.6 Hz, 1H), 7.73 (d, J=8.8 Hz, 1H), 7.68 (d, J=4.4 Hz, 2H), 7.60-7.51 (m, 3H), 5.18 (dd, J=4.8, 12.8 Hz, 1H), 4.63-4.45 (m, 4H), 2.97-2.89 (m, 1H), 2.64-2.60 (m, 1H), 2.54 (s, 3H), 2.46-2.33 (m, 1H), 2.07-1.90 (m, 1H), 1.38 (s, 9H).

I-53

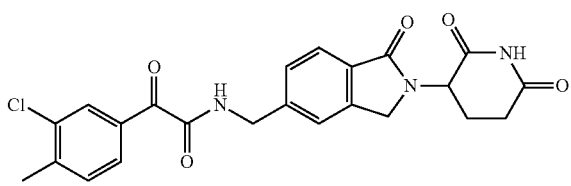

I-54

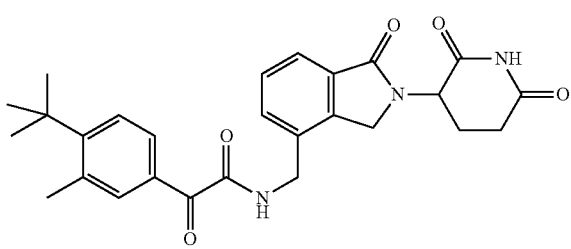

Compound I-55: 2-(3-methyl-4-(tert-butyl)phenyl)-N-((2-(2,6-dioxopiperidin-3-yl)-1-oxoisoindolin-5-yl)methyl)-2-oxoacetamide. MS (ESI) m/z: 476.1 [M+1]$^+$; $^1$H NMR (400 MHz, DMSO-d$_6$) δ 10.97 (s, 1H), 9.50 (t, J=5.6 Hz, 1H), 7.76-7.70 (m, 3H), 7.56-7.48 (m, 3H), 5.11 (dd, J=5.2, 13.2 Hz, 1H), 4.56 (d, J=6.0 Hz, 2H), 4.49-4.31 (m, 2H), 2.92-2.87 (m, 1H), 2.67-2.62 (m, 1H), 2.56 (s, 3H), 2.34-2.32 (m, 1H), 2.03-1.90 (m, 1H), 1.39 (s, 9H).

Compound I-56: 2-(4-(tert-butyl)phenyl)-N-(2-(2,6-dioxopiperidin-3-yl)-1-oxoisoindolin-4-yl)-2-oxoacetamide. MS (ESI) m/z: 448.5 [M+H]$^+$; $^1$H NMR (DMSO-d$_6$, 400 MHz) (10.95 (s, 1H), 8.20-9.51 (m, 7H), 5.16 (dd, 1H), 4.48 (q, 2H), 2.91 (m, 1H), 2.60 (m, 1H), 2.42 (m, 1H), 2.04 (m, 1H), 1.32 (s, 9H).

I-55

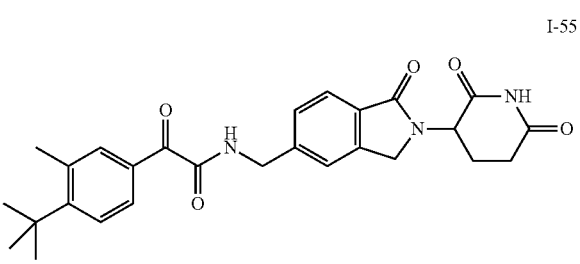

I-56

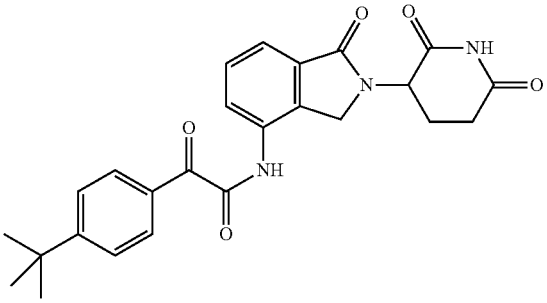

Compound I-57: N-(2-(2,6-dioxopiperidin-3-yl)-1-oxoisoindolin-4-yl)-2-oxo-2-(4-(1-(trifluoromethyl)cyclopropyl)phenyl)acetamide. MS (ESI) m/z: 500.4 [M+H]$^+$; $^1$H NMR (DMSO-d$_6$, 400 MHz) δ 11.00 (d, 1H), 7.64-8.10 (m, 7H), 5.14 (dd, 1H), 4.49 (q, 2H), 2.92 (m, 1H), 2.58 (m, 1H), 2.40 (m, 1H), 2.04 (m, 1H), 1.43 (m, 2H), 1.22 (m, 2H).

Compound I-58: N-((2-(2,6-dioxopiperidin-3-yl)-1,3-dioxoisoindolin-4-yl)methyl)-2-oxo-2-(4-(1-(trifluoromethyl)cyclopropyl)phenyl)acetamide. MS (ESI) m/z: 527.4 [M+H]$^+$; $^1$H NMR (DMSO-d$_6$, 400 MHz) δ 11.14 (s, 1H), 9.55-9.58 (t, 1H), 8.03-8.07 (d, 2H), 7.85-7.90 (m, 3H), 7.78-7.81 (d, 2H), 5.16-5.19 (m, 1H), 4.88-4.97 (m, 2H), 2.87-2.95 (m, 1H), 2.51-2.64 (m, 2H), 2.04-2.09 (m, 1H), 1.81-1.45 (m, 2H), 1.16-1.25 (m, 3H).

I-57

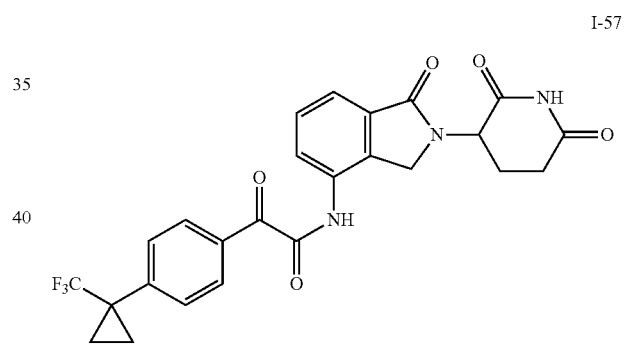

I-58

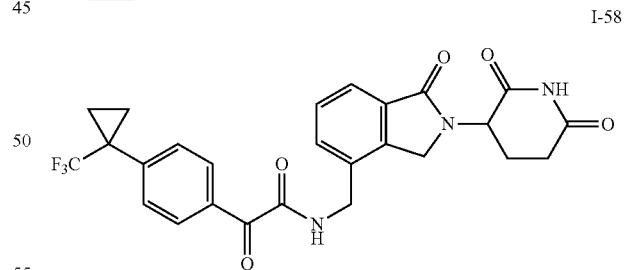

Compound I-59: N-((2-(2,6-dioxopiperidin-3-yl)-1-oxoisoindolin-4-yl)methyl)-2-(5-isopropylthiophen-2-yl)-2-oxoacetamide. MS (ESI) m/z: 453.9 [M+H]$^+$; $^1$H NMR (DMSO-d$_6$, 400 MHz) δ 11.01 (s, 1H), 9.54 (t, J=5.6 Hz, 1H), 8.05 (d, J=3.6 Hz, 1H), 7.66 (d, J=6.8 Hz, 1H), 7.57-7.49 (m, 2H), 7.10 (d, J=3.6 Hz, 1H), 5.15 (dd, J=4.4, 12.8 Hz, 1H), 4.58-4.41 (m, 4H), 3.28-3.22 (m, 1H), 2.96-2.88 (m, 1H), 2.64-2.60 (m, 1H), 2.40-2.36 (m, 1H), 2.05-2.02 (m, 1H), 1.31 (d, J=6.4 Hz, 6H).

Compound I-60: N-((2-(2,6-dioxopiperidin-3-yl)-4-methyl-1-oxoisoindolin-5-yl)methyl)-2-oxo-2-(4-(1-(trifluoromethyl)cyclopropyl)phenyl)acetamide. MS (ESI) m/z: 527.9 [M+H]$^+$; $^1$H NMR (400 MHz, DMSO-d$_6$) δ 10.98 (s, 1H), 9.47 (t, J=5.6 Hz, 1H), 7.99 (d, J=8.4 Hz, 2H), 7.68 (d, J=8.4 Hz, 2H), 7.58 (d, J=7.6 Hz, 1H), 7.46 (d, J=7.6 Hz, 1H), 5.13 (dd, J=5.2, 13.2 Hz, 1H), 4.57 (d, J=6.0 Hz, 2H), 4.48-4.26 (m, 2H), 2.98-2.90 (m, 1H), 2.63-2.59 (m, 1H), 2.47-2.40 (m, 1H), 2.33 (s, 3H), 2.02-1.99 (m, 1H), 1.41 (t, J=4.8 Hz, 2H), 1.22 (t, J=4.8 Hz, 2H).

I-59

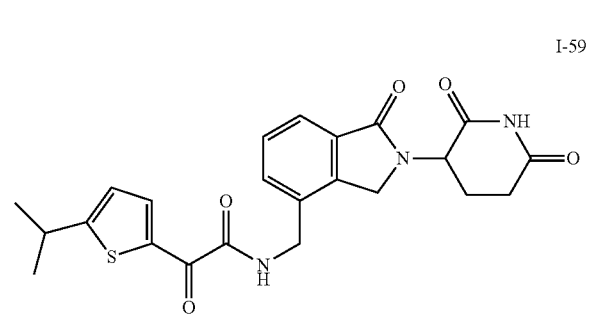

I-60

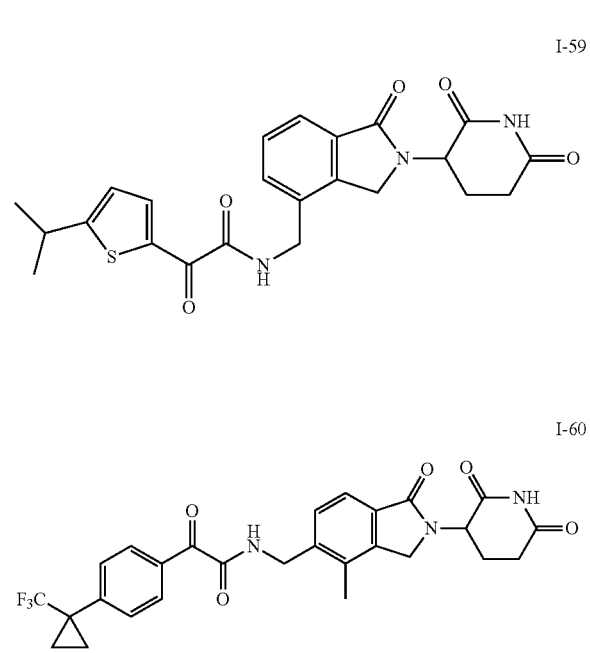

Compound I-62: 2-(4-(tert-butyl)piperidin-1-yl)-N-((2-(2,6-dioxopiperidin-3-yl)-1-oxoisoindolin-5-yl)methyl)-2-oxoacetamide. MS (ESI) m/z: 469.2[M+H]$^+$; $^1$H NMR (400 MHz, DMSO-d) δ 10.95 (s, 1H), 9.28 (t, J=6.0 Hz, 1H), 7.70 (d, J=7.6 Hz, 1H), 7.49 (s, 1H), 7.42 (d, J=8.0 Hz, 1H), 5.10 (dd, J=4.8, 13.2 Hz, 1H), 4.29-4.35 (m, 4H), 4.35-3.77 (m, 1H), 3.79 (d, J=11.6 Hz, 1H), 3.00-2.86 (m, 2H), 2.62-2.56 (m, 2H), 2.49-2.37 (m, 1H), 2.01-1.98 (m, 1H), 1.74-1.65 (m, 2H), 1.30-1.23 (m, 1H), 1.16-1.04 (m, 2H), 0.84 (s, 9H).

Compound I-63: N-((2-(2,6-dioxopiperidin-3-yl)-4-methyl-1-oxoisoindolin-5-yl)methyl)-2-oxo-2-(4-(1-(trifluoromethyl)cyclopropyl)phenyl)acetamide. MS (ESI) m/z: 527.9 [M+H]$^+$; $^1$H NMR (400 MHz, DMSO-d$_6$) δ 10.96 (s, 1H), 8.76 (t, J=6.0 Hz, 1H), 7.69-7.70 (m, 1H), 7.60-7.58 (m, 1H), 7.51-7.43 (m, 5H), 6.73-6.69 (m, 1H), 5.10 (dd, J=5.2, 13.2 Hz, 1H), 4.52-4.29 (m, 4H), 2.95-2.87 (m, 1H), 2.62-2.57 (m, 1H), 2.40-2.36 (m, 1H), 2.01-1.98 (m, 1H), 1.35-1.33 (m, 2H), 1.14-1.12 (m, 2H).

I-62

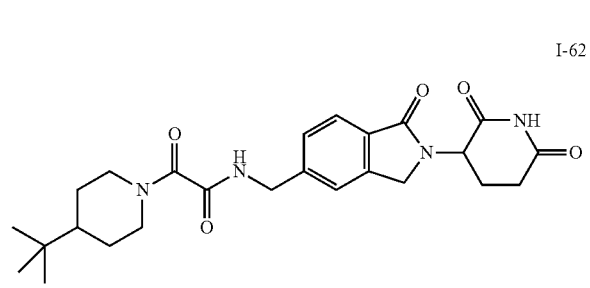

I-63

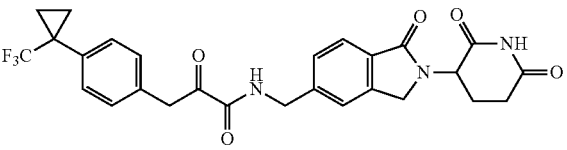

Compound I-64: (2,6-dioxo-3-(1-oxo-4-((2-oxo-2-(4-(1-(trifluoromethyl)cyclopropyl)-phenyl)acetamido)methyl)isoindolin-2-yl)piperidin-1-yl)methyl D-valinate. MS (ESI) m/z: 643.1 [M+H]$^+$; $^1$H NMR (DMSO-d$_6$, 400 MHz) 9.58 (t, J=6.0 Hz, 1H), 7.99 (d, J=8.0 Hz, 2H), 7.68-7.56 (m, 5H), 5.73-5.62 (m, 2H), 5.36-5.32 (m, 1H), 4.65-4.39 (m, 4H), 3.32 (s, 1H), 3.22-3.08 (m, 1H), 2.88-2.84 (m, 1H), 2.51-2.42 (m, 1H), 2.10-2.07 (m, 1H), 1.85-1.83 (m, 1H), 1.43-1.40 (m, 2H), 1.24-1.20 (m, 2H), 0.86-0.78 (m, 6H).

Compound I-65: N-(2-(2-(2,6-dioxopiperidin-3-yl)-1-oxoisoindolin-4-yl)ethyl)-2-oxo-2-(4-(1-(trifluoromethyl)cyclopropyl)phenyl)acetamide. MS (ESI) m/z: 528.1 [M+H]$^+$; $^1$H NMR (DMSO-d$_6$, 400 MHz) (10.98 (s, 1H), 9.03 (t, J=5.6 Hz, 1H), 7.79 (d, J=5.2 Hz, 2H), 7.65-7.58 (m, 3H), 7.54-7.48 (m, 2H), 5.12 (dd, J=5.2, 13.2 Hz, 1H), 4.53-4.33 (m, 2H), 3.61-3.59 (m, 2H), 2.93-2.87 (m, 3H), 2.61-2.51 (m, 1H), 2.40-2.29 (m, 1H), 1.91-1.87 (m, 1H), 1.42-1.39 (m, 2H), 1.19 (s, 2H).

I-64

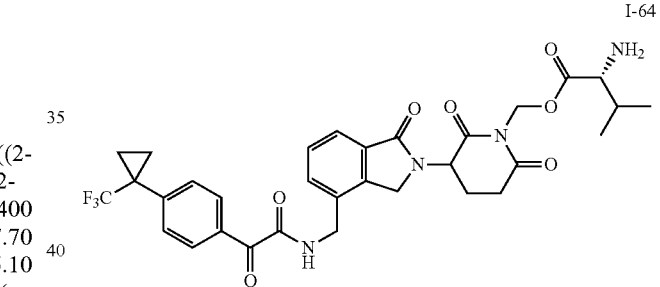

I-65

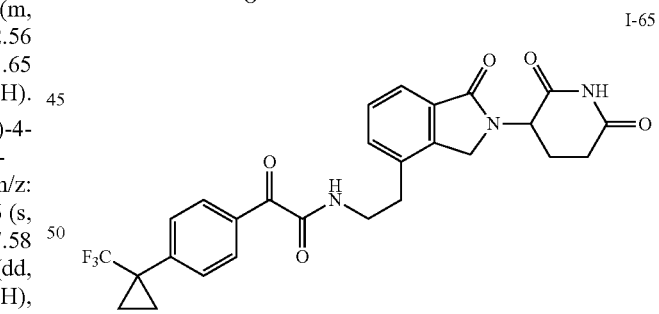

Compound I-66: N-((2-(2,6-dioxopiperidin-3-yl)-1-oxoisoindolin-4-yl)methyl)-2-oxo-2-(4-(piperidin-4-yl)phenyl)acetamide. MS (ESI) m/z: 489.2 [M+H]$^+$; $^1$H NMR (DMSO-d$_6$, 400 MHz) δ 10.98 (s, 1H), 9.56 (d, J=6.0 Hz, 1H), 8.80 (d, J=63.2 Hz, 2H), 7.98 (d, J=8.4 Hz, 2H), 7.73 (d, J=7.6 Hz, 1H), 7.56 (s, 1H), 7.50-7.44 (m, 3H), 5.12 (dd, J=5.2, 13.2 Hz, 1H), 4.57-4.31 (m, 2H), 3.04-2.92 (m, 5H), 2.73 (d, J=4.4 Hz, 3H), 2.63-2.58 (m, 1H), 2.45-2.38 (m, 1H), 2.03-1.85 (m, 5H).

Compound I-67: 2-(4-(tert-butyl)cyclohexyl)-N-((2-(2,6-dioxopiperidin-3-yl)-1-oxoisoindolin-4-yl)methyl)-2-oxoacetamide. MS (ESI) m/z: 468.2 [M+H]$^+$; $^1$H NMR (DMSO-d$_6$, 400 MHz) δ 11.01 (s, 1H), 9.22 (t, J=6.0 Hz, 1H), 7.62-7.65 (m, 1H), 7.50-7.49 (m, 2H), 5.14 (dd, J=5.2, 13.2 Hz, 1H), 4.55-4.37 (m, 4H), 3.10-3.08 (m, 1H), 2.93-2.89 (m, 1H), 2.65-2.60 (m, 1H), 2.38-2.35 (m, 1H), 2.07-2.01 (m, 1H), 1.90-1.87 (m, 2H), 1.80-1.78 (m, 2H), 1.16-0.94 (m, 5H), 0.83 (s, 9H).

I-66

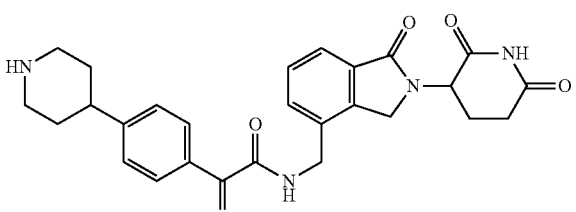

I-67

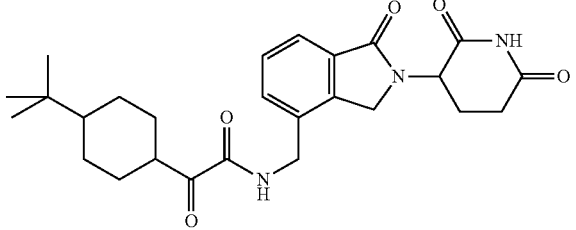

Compound I-68: 2-(4-(tert-butyl)cyclohexyl)-N-((2-(2,6-dioxopiperidin-3-yl)-1-oxoisoindolin-5-yl)methyl)-2-oxoacetamide. MS (ESI) m/z: 468.2 [M+1]$^+$; $^1$H NMR (400 MHz, DMSO-d$_6$) δ 10.97 (s, 1H), 9.23 (t, J=6.4 Hz, 1H), 7.68 (d, J=7.6 Hz, 1H), 7.47 (s, 1H), 7.40 (d, J=8.0 Hz, 1H), 5.10 (dd, J=5.2, 13.2 Hz, 1H), 4.46-4.28 (m, 4H), 3.14-3.07 (m, 1H), 2.95-2.86 (m, 1H), 2.62-2.57 (m, 1H), 2.44-2.32 (m, 1H), 2.02-1.97 (m, 1H), 1.91-1.89 (m, 2H), 1.81-1.78 (m, 2H), 1.21-0.92 (m, 5H), 0.83 (s, 9H).

Compound I-69: N-((5-(2,6-dioxopiperidin-3-yl)-6-oxo-5,6-dihydro-4H-thieno[2,3-c]pyrrol-2-yl)methyl)-2-oxo-4-phenylbutanamide. MS (ESI) m/z=440.1 [M+H]$^+$.

I-68

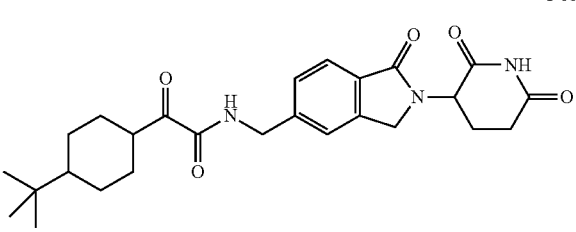

I-69

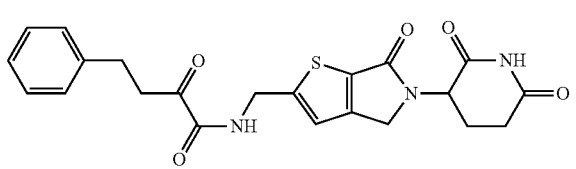

Compound I-71: N-((5-(2,6-dioxopiperidin-3-yl)-6-oxo-5,6-dihydro-4H-thieno[2,3-c]pyrrol-2-yl)methyl)-N$^2$,N$^2$-dimethyloxalamide. MS (ESI) m/z=379.1 [M+H]$^+$.

Compound I-72: N-((2-(2,6-dioxopiperidin-3-yl)-1-oxoisoindolin-4-yl)methyl)-2-oxo-2-(p-tolyl)acetamide. MS (ESI) m/z: 420.4 [M+H]$^+$; $^1$H NMR (DMSO-d$_6$, 400 MHz) δ 11.02 (s, 1H), 9.48 (t, 1H), 7.38-7.89 (m, 7H), 5.17 (dd, 1H), 4.42-4.59 (m, 4H), 2.93 (m, 1H), 2.60 (m, 1H), 2.36 (m, 4H), 2.02 (m, 1H).

Compound I-73: 2-(3,4-difluorophenyl)-N-((2-(2,6-dioxopiperidin-3-yl)-1-oxoisoindolin-4-yl)methyl)-2-oxoacetamide. MS (ESI) m/z: 442.4 [M+H]$^+$; $^1$H NMR (DMSO-d$_6$, 400 MHz) δ 11.02 (s, 1H), 9.59 (t, 1H), 7.52-8.08 (m, 6H), 5.15 (dd, 1H), 4.42-4.59 (m, 4H), 2.93 (m, 1H), 2.60 (m, 1H), 2.40 (m, 1H), 2.03 (m, 1H).

I-71

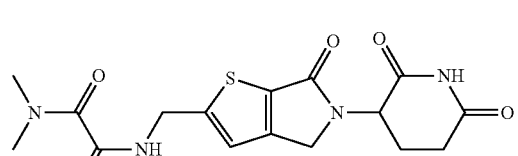

I-72

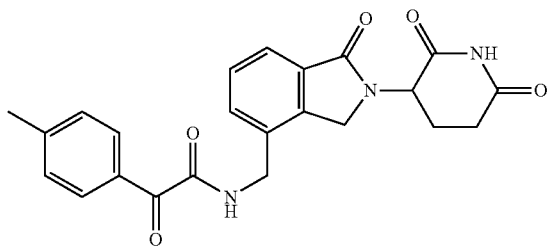

I-73

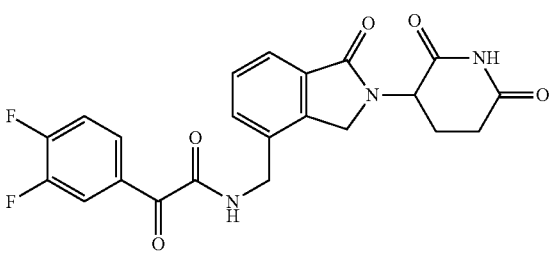

Compound I-74: N-((2-(2,6-dioxopiperidin-3-yl)-1-oxoisoindolin-4-yl)methyl)-2-oxo-2-phenylacetamide. MS (ESI) m/z: 405.3 [M+H]$^+$; $^1$H NMR (DMSO-d$_6$, 400 MHz) δ 11.02 (s, 1H), 9.52-9.56 (t, 1H), 7.95-8.0 (m, 2H), 7.68-7.99 (d, 2H), 7.53-7.60 (m, 4H), 5.14-5.18 (d, 2H), 4.55-4.60 (m, 3H), 4.43-4.47 (d, 1H), 3.55-3.62 (m, 1H), 3.10-3.15 (m, 1H), 2.92-2.98 (m, 1H).

Compound I-75: N-((2-(2,6-dioxopiperidin-3-yl)-1-oxoisoindolin-4-yl)methyl)-2-oxo-2-(4-(trifluoromethyl)phenyl)acetamide. MS (ESI) m/z: 474.4 [M+H]$^+$; $^1$H NMR (DMSO-d$_6$, 400 MHz) (11.03 (s, 1H), 9.61 (t, 1H), 7.54-8.21 (m, 7H), 5.17 (dd, 1H), 4.44-4.60 (m, 4H), 2.92 (m, 1H), 2.64 (m, 1H), 2.40 (m, 1H), 2.03 (m, 1H).

Compound I-76: 2-(4-cyanophenyl)-N-((2-(2,6-dioxopiperidin-3-yl)-1-oxoisoindolin-4-yl)methyl)-2-oxoacetamide. MS (ESI) m/z: 431.4 [M+H]$^+$; $^1$H NMR (DMSO-d$_6$, 400 MHz) δ11.04 (s, 1H), 9.60 (t, 1H), 7.52-8.17 (m, 7H), 5.17 (dd, 1H), 4.43-4.60 (m, 4H), 2.92 (m, 1H), 2.64 (m, 1H), 2.40 (m, 1H), 2.03 (m, 1H).

I-74

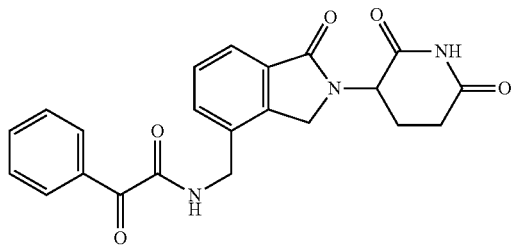

I-78

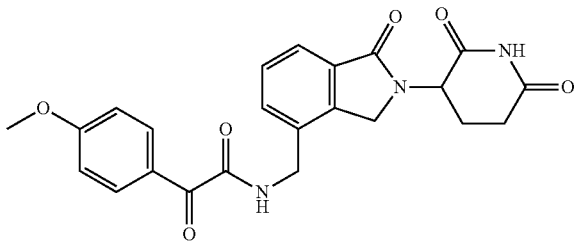

I-75

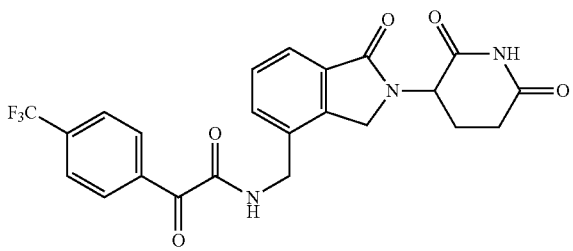

I-79

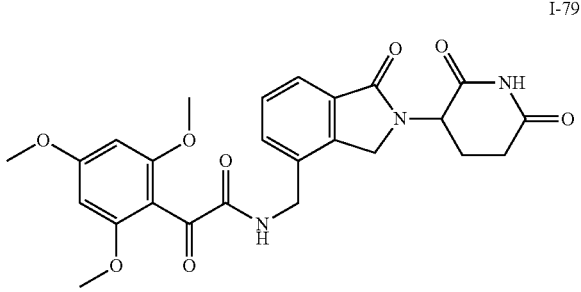

I-76

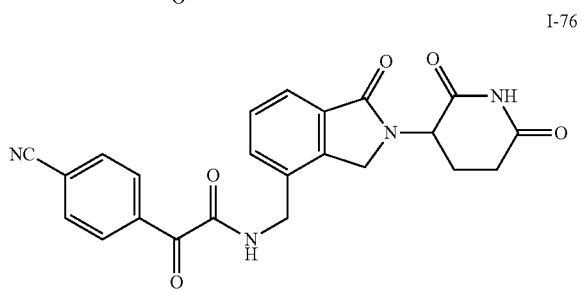

Compound I-77: 2-(4-chlorophenyl)-N-((2-(2,6-dioxopiperidin-3-yl)-1-oxoisoindolin-4-yl)methyl)-2-oxoacetamide. MS (ESI) m/z: 440.8 [M+H]$^+$; $^1$H NMR (DMSO-d$_6$, 400 MHz) δ11.03 (s, 1H), 9.55 (t, 1H), 7.65-8.01 (m, 7H), 5.17 (dd, 1H), 4.46-4.56 (m, 4H), 2.92 (m, 1H), 2.64 (m, 1H), 2.40 (m, 1H), 2.03 (m, 1H).

Compound I-78: 2-(4-methoxyphenyl)-N-((2-(2,6-dioxopiperidin-3-yl)-1-oxoisoindolin-4-yl)methyl)-2-oxoacetamide. MS (ESI) m/z: 436.4 [M+H]$^+$; $^1$H NMR (DMSO-d$_6$, 400 MHz) δ11.03 (s, 1H), 9.45 (t, 1H), 7.09-7.99 (m, 7H), 5.17 (dd, 1H), 4.42-4.60 (m, 4H), 3.87 (s, 3H), 2.92 (m, 1H), 2.64 (m, 1H), 2.40 (m, 1H), 2.03 (m, 1H).

Compound I-79: 2-(2,4,6-trimethoxyphenyl)-N-((2-(2,6-dioxopiperidin-3-yl)-1-oxoisoindolin-4-yl)methyl)-2-oxoacetamide. MS (ESI) m/z: 496.5 [M+H]$^+$; $^1$H NMR (DMSO-d$_6$, 400 MHz) δ 11.02 (s, 1H), 9.54 (t, 1H), 7.25-7.67 (m, 5H), 5.15 (dd, 1H), 4.44-4.61 (m, 4H), 3.77 (m, 9H), 2.92 (m, 1H), 2.61 (m, 1H), 2.38 (m, 1H), 2.03 (m, 1H).

Compound I-80: 2-(2,4,6-trimethylphenyl)-N-((2-(2,6-dioxopiperidin-3-yl)-1-oxoisoindolin-4-yl)methyl)-2-oxoacetamide. MS (ESI) m/z: 448.5 [M+H]$^+$; $^1$H NMR (DMSO-d$_6$, 400 MHz) δ 11.02 (s, 1H), 9.56 (t, 1H), 7.51-7.67 (m, 3H), 6.90 (s, 2H), 5.15 (dd, 1H), 4.39-4.57 (m, 4H), 2.93 (m, 1H), 2.61 (m, 1H), 2.36 (m, 1H), 2.25 (s, 3H), 2.08 (s, 6H), 2.03 (m, 1H).

Compound I-81: 2-(4-fluorophenyl)-N-((2-(2,6-dioxopiperidin-3-yl)-1-oxoisoindolin-4-yl)methyl)-2-oxoacetamide. MS (ESI) m/z: 423.4 [M+H]$^+$; $^1$H NMR (DMSO-d$_6$, 400 MHz) δ 11.03 (s, 1H), 9.52-9.55 (t, 1H), 8.08-8.11 (m, 2H), 7.65-7.68 (m, 1H), 7.53-7.60 (m, 2H), 7.40-7.44 (t, 2H), 5.14-5.18 (m, 1H), 4.53-4.60 (m, 3H), 4.43-4.49 (d, 1H), 2.90-2.96 (m, 1H), 2.61-2.67 (m, 1H), 2.37-2.44 (m, 1H), 1.91-2.02 (m, 1H).

Compound I-82: 2-(2-fluorophenyl)-N-((2-(2,6-dioxopiperidin-3-yl)-1-oxoisoindolin-4-yl)methyl)-2-oxoacetamide. MS (ESI) m/z: 423.4 [M+H]$^+$; $^1$H NMR (DMSO-d$_6$, 400 MHz) δ 11.02 (s, 1H), 9.49 (t, 1H), 7.83-7.89 (m, 1H), 7.77-7.82 (m, 1H), 7.67-7.70 (m, 1H), 7.53-7.60 (m, 2H), 7.35-7.41 (m, 2H), 5.13-5.17 (m, 1H), 4.52-4.59 (m, 3H), 4.42-4.48 (d, 1H), 2.90-2.96 (m, 1H), 2.60-2.65 (m, 1H), 2.34-2.40 (m, 1H), 2.00-2.05 (m, 1H).

I-77

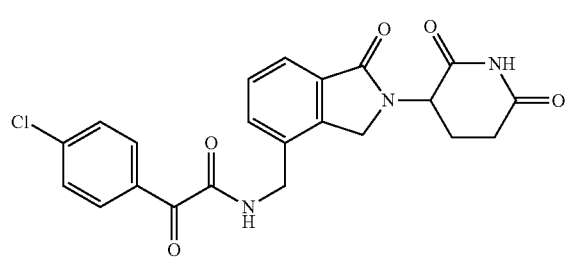

I-80

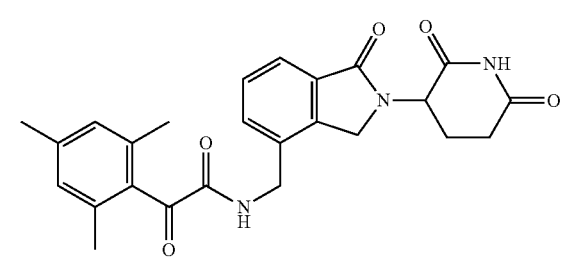

I-81

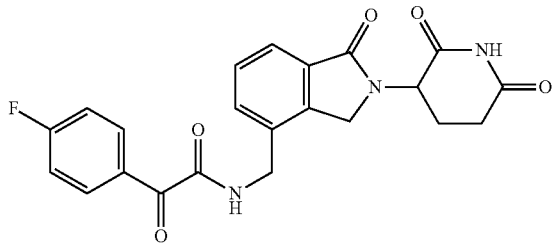

I-82

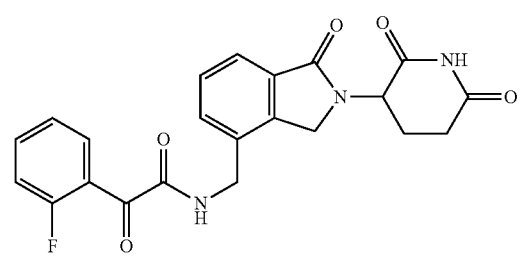

Compound I-83: N-((2-(2,6-dioxopiperidin-3-yl)-1-oxoisoindolin-5-yl)methyl)-2-oxo-2-phenylacetamide. MS (ESI) m/z: 405.8 [M+H]+; $^1$H NMR (DMSO-d$_6$, 400 MHz) δ 10.99 (s, 1H), 9.57 (t, 1H), 7.99-8.02 (m, 2H), 7.76-7.84 (m, 2H), 7.57-7.61 (m, 3H), 7.48-7.50 (m, 1H), 5.10-5.14 (m, 1H), 4.58-4.61 (m, 2H), 4.46-4.49 (m, 1H), 4.35-4.37 (m, 1H), 2.87-2.95 (m, 1H), 2.59-2.63 (m, 1H), 2.35-2.44 (m, 1H), 1.99-2.05 (m, 1H).

Compound I-84: N-((2-(2,6-dioxopiperidin-3-yl)-1-oxoisoindolin-5-yl)methyl)-2-oxo-2-(2,4,6-trimethoxyphenyl)acetamide. MS (ESI) m/z: 496.5 [M+1]+; $^1$H NMR (400 MHz, DMSO-d6) δ 10.99 (s, 1H), 9.56 (s, 1H), 7.74 (d, 1H), 7.72 (s, 1H), 7.58 (d, 1H), 7.27 (s, 2H), 5.12 (dd, 1H), 4.58 (d, 2H), 4.34-4.44 (d, 1H), 4.34-4.30 (d, 1H), 3.78 (s, 9H), 2.53-2.88 (m, 1H), 2.62-2.59 (d, 1H), 2.44-2.36 (m, 1H), 2.31 (s, 3H), 2.02-1.99 (m, 1H).

I-83

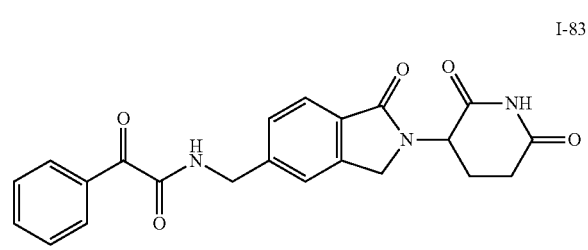

I-84

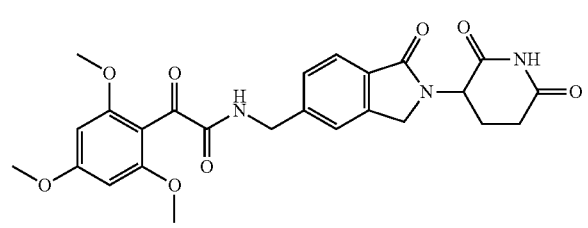

Compound I-85: N-((2-(2,6-dioxopiperidin-3-yl)-1-oxoisoindolin-5-yl)methyl)-2-oxo-2-(2,4,6-trimethylphenyl)acetamide. MS (ESI) m/z: 448.5 [M+1]+; $^1$H NMR (400 MHz, DMSO-d$_6$) δ 10.98 (s, 1H), 9.57 (s, 1H), 7.70 (d, 1H), 7.51 (s, 1H), 7.46 (d, 1H), 6.90 (s, 2H), 5.13-5.09 (dd, 1H), 4.50 (d, 2H), 4.44 (d, 1H), 4.33 (d, 1H), 2.95-2.98 (m, 1H), 2.62 (d, 1H), 2.44-2.37 (mm, 1H), 2.26 (s, 3H), 2.11 (s, 6H), 2.02-1.99 (m, 1H).

Compound I-86: N-((2-(2,6-dioxopiperidin-3-yl)-1-oxoisoindolin-5-yl)methyl)-2-oxo-2-(2-fluorophenyl)acetamide. MS (ESI) m/z: 424.5 [M+1]+; $^1$H NMR (400 MHz, DMSO-d6) δ 10.99 (s, 1H), 9.52 (s, 1H), 7.86 (m, 1H), 7.83 (m, 1H), 7.72 (s, 1H), 7.55 (m, 1H), 7.47-7.40 (m, 1H), 7.29 (m, 2H), 5.18-5.10 (m, 1H), 4.56 (d, 2H), 4.45 (d, 1H), 4.31 (d, 1H), 2.95-288 (m, 1H), 2.62-2.51 (d, 1H), 2.44-2.38 (m, 1H), 2.03-1.99 (m, 1H).

I-85

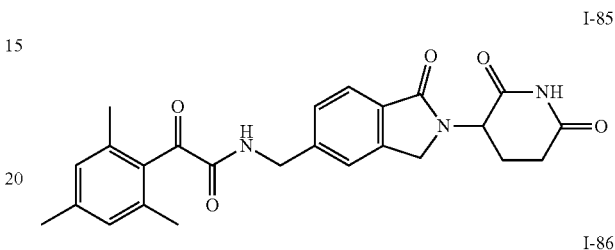

I-86

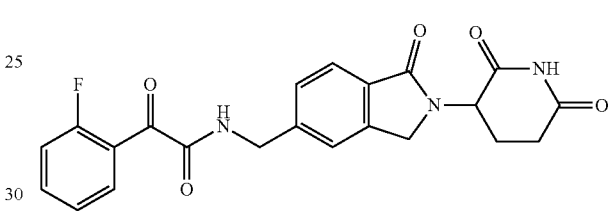

Compound I-87: N-((2-(2,6-dioxopiperidin-3-yl)-1-oxoisoindolin-5-yl)methyl)-2-oxo-2-(4-trifluoromethylphenyl)acetamide. MS (ESI) m/z: 474.4 [M+1]+; $^1$H NMR (400 MHz, DMSO-d6) δ 10.98 (s, 1H), 9.65 (t, 1H), 7.57-8.23 (m, 7H), 5.12 (dd, 1H), 4.35-4.60 (m, 4H), 2.92 (m, 1H), 2.64 (m, 1H), 2.40 (m, 1H), 2.03 (m, 1H).

Compound I-88: 2-(3-chlorophenyl)-N-((2-(2,6-dioxopiperidin-3-yl)-1-oxoisoindolin-4-yl)methyl)-2-oxoacetamide. MS (ESI) m/z: 440.8 [M+H]+; $^1$H NMR (DMSO-d$_6$, 400 MHz) δ10.98 (s, 1H), 9.65 (t, 1H), 7.57-8.23 (m, 7H), 5.11 (dd, 1H), 4.35-4.60 (m, 4H), 2.92 (m, 1H), 2.64 (m, 1H), 2.40 (m, 1H), 2.03 (m, 1H).

I-87

I-88

Compound I-89: N-((2-(2,6-dioxopiperidin-3-yl)-1-oxoisoindolin-5-yl)methyl)-2-(4-methoxyphenyl)-2-oxoacetamide. MS (ESI) m/z: 435.1 [M+1]⁺; ¹H NMR (400 MHz, DMSO-d₆) δ 10.99 (s, 1H), 9.49 (t, 1H), 7.99-8.01 (m, 2H), 7.72-7.76 (m, 1H), 7.52 (s, 1H), 7.44-7.49 (m, 1H), 7.10-7.14 (m, 2H), 5.08-5.15 (m, 1H), 4.52-4.56 (m, 2H), 4.45-4.49 (m, 1H), 4.31-4.35 (m, 1H), 3.87 (s, 3H), 2.90-2.97 (m, 1H), 2.55-2.64 (m, 1H), 2.36-2.45 (m, 1H), 1.99-2.06 (m, 1H).

Compound I-90: 2-(4-cyanophenyl)-N-((2-(2,6-dioxopiperidin-3-yl)-1-oxoisoindolin-5-yl)methyl)-2-oxoacetamide. MS (ESI) m/z: 431.4 [M+1]⁺; ¹H NMR (400 MHz, DMSO-d₆) δ 10.98 (s, 1H), 9.64 (t, 1H), 7.57-8.18 (m, 7H), 5.10 (dd, 1H), 4.35-4.59 (m, 4H), 2.92 (m, 1H), 2.64 (m, 1H), 2.40 (m, 1H), 2.03 (m, 1H).

I-89

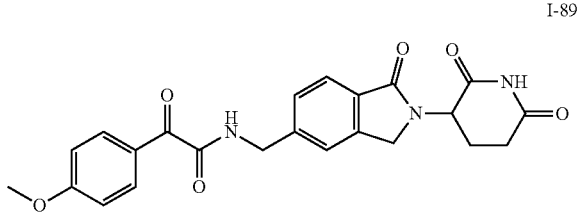

I-90

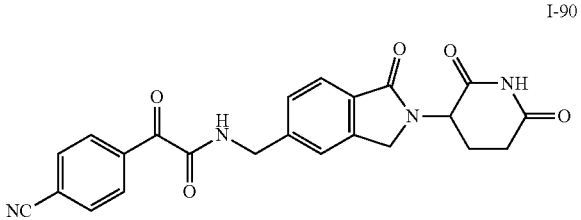

Compound I-91: 2-(3-chlorophenyl)-N-((2-(2,6-dioxopiperidin-3-yl)-1-oxoisoindolin-5-yl)methyl)-2-oxoacetamide. MS (ESI) m/z: 440.8 [M+1]⁺; ¹H NMR (400 MHz, DMSO-d₆) δ 10.98 (s, 1H), 9.62 (t, 1H), 7.50-8.15 (m, 7H), 5.11 (dd, 1H), 4.31-4.58 (m, 4H), 2.92 (m, 1H), 2.64 (m, 1H), 2.40 (m, 1H), 2.03 (m, 1H).

Compound I-92: 2-(3-fluorophenyl)-N-((2-(2,6-dioxopiperidin-3-yl)-1-oxoisoindolin-4-yl)methyl)-2-oxoacetamide. MS (ESI) m/z: 423.7 [M+H]⁺; ¹H NMR (DMSO-d₆, 400 MHz) δ 11.02 (s, 1H), 9.57 (t, 1H), 7.82-7.86 (m, 1H), 7.74-7.78 (m, 1H), 7.59-7.68 (m, 4H), 7.53-7.56 (m, 1H), 5.14-5.18 (m, 1H), 4.54-4.60 (m, 2H), 4.43-4.47 (m, 1H), 3.15-3.18 (d, 1H), 2.90-2.97 (m, 1H), 2.61-2.65 (m, 1H), 2.35-2.41 (m, 1H), 2.02-2.05 (m, 1H).

I-91

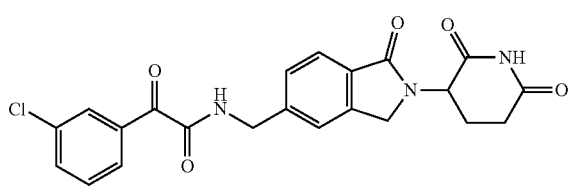

I-92

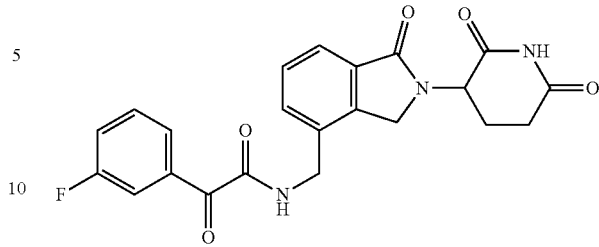

Compound I-93: 2-(3,4-difluorophenyl)-N-((2-(2,6-dioxopiperidin-3-yl)-1-oxoisoindolin-5-yl)methyl)-2-oxoacetamide. MS (ESI) m/z: 441.7 [M+1]⁺; ¹H NMR (400 MHz, DMSO-d₆) δ 10.98 (s, 1H), 9.62 (t, 1H), 8.10-8.15 (m, 1H), 7.92-7.98 (m, 1H), 7.67-7.73 (m, 2H), 7.55 (s, 1H), 7.46-7.49 (d, 1H), 5.10-5.14 (m, 1H), 4.56-4.59 (m, 2H), 4.44-4.48 (m, 1H), 4.31-4.34 (m, 1H), 2.83-2.87 (m, 1H), 2.49-2.52 (m, 1H), 2.41-2.45 (m, 1H), 1.98-2.02 (m, 1H).

Compound I-94: 2-(3-methoxyphenyl)-N-((2-(2,6-dioxopiperidin-3-yl)-1-oxoisoindolin-4-yl)methyl)-2-oxoacetamide. MS (ESI) m/z: 435.8 [M+H]⁺; ¹H NMR (DMSO-d₆, 400 MHz) δ 11.02 (s, 1H), 9.52 (t, 1H), 7.66-7.68 (m, 1H), 7.50-7.60 (m, 4H), 7.45-7.49 (m, 1H), 7.30-7.33 (m, 1H), 5.14-5.18 (m, 1H), 4.54-4.60 (m, 2H), 4.43-4.46 (m, 1H), 3.80 (s, 3H), 2.86-2.97 (m, 2H), 2.57-2.65 (m, 1H), 2.34-2.40 (m, 1H), 1.99-2.04 (m, 1H).

I-93

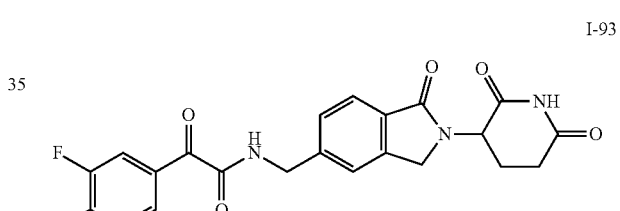

I-94

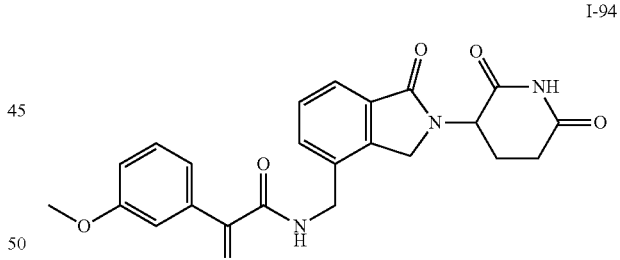

Compound I-95: N-((2-(2,6-dioxopiperidin-3-yl)-1-oxoisoindolin-5-yl)methyl)-2-(3-methoxyphenyl)-2-oxoacetamide. MS (ESI) m/z: 435.8 [M+1]⁺; ¹H NMR (400 MHz, DMSO-d₆) δ 10.98 (s, 1H), 9.56 (t, 1H), 7.72-7.76 (d, 1H), 7.51-7.59 (m, 2H), 7.46-7.50 (m, 3H), 7.28-7.32 (m, 1H), 5.10-5.13 (m, 1H), 4.56-4.59 (m, 2H), 4.41-4.46 (m, 1H), 4.35-4.39 (m, 1H), 3.80 (s, 3H), 2.88-2.94 (m, 1H), 2.52-2.59 (m, 1H), 2.36-2.44 (m, 1H), 2.00-2.03 (m, 1H).

Compound I-96: N-((2-(2,6-dioxopiperidin-3-yl)-1-oxoisoindolin-4-yl)methyl)-2-(naphthalen-2-yl)-2-oxoacetamide. MS (ESI) m/z: 456.5 [M+H]⁺; ¹H NMR (DMSO-d₆, 400 MHz) δ 11.02 (s, 1H), 9.59 (t, 1H), 7.56-8.15 (m, 10H), 5.16 (dd, 1H), 4.47-4.63 (m, 4H), 2.92 (m, 1H), 2.64 (m, 1H), 2.40 (m, 1H), 2.02 (m, 1H).

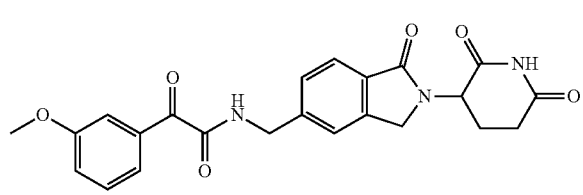

I-95

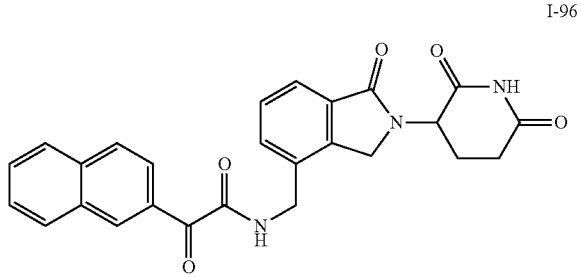

I-96

Compound I-97: N-((2-(2,6-dioxopiperidin-3-yl)-1-oxoisoindolin-5-yl)methyl)-2-(naphthalen-2-yl)-2-oxoacetamide. MS (ESI) m/z: 456.5 [M+1]$^+$; $^1$H NMR (400 MHz, DMSO-d$_6$) δ 10.99 (s, 1H), 9.63 (t, 1H), 7.53-8.69 (m, 10H), 5.16 (dd, 1H), 4.33-4.64 (m, 4H), 2.92 (m, 1H), 2.64 (m, 1H), 2.40 (m, 1H), 2.02 (m, 1H).

Compound I-98: 2-(3,5-dimethylphenyl)-N-((2-(2,6-dioxopiperidin-3-yl)-1-oxoisoindolin-4-yl)methyl)-2-oxoacetamide. MS (ESI) m/z: 434.4 [M+H]$^+$; $^1$H NMR (DMSO-d$_6$, 400 MHz) δ 11.02 (s, 1H), 9.50 (t, 1H), 7.37-7.69 (m, 6H), 5.15 (dd, 1H), 4.30-4.60 (m, 4H), 2.93 (m, 1H), 2.61 (m, 1H), 2.41 (m, 1H), 2.38 (s, 6H), 2.03 (m, 1H).

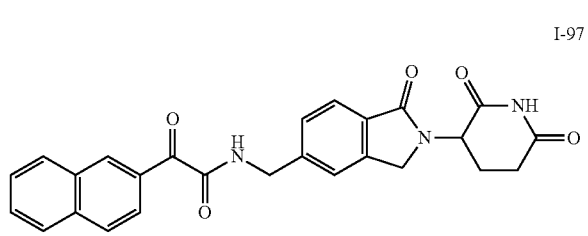

I-97

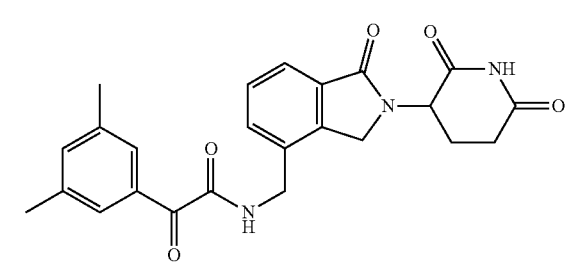

I-98

Compound I-99: 2-(3,5-dimethylphenyl)-N-((2-(2,6-dioxopiperidin-3-yl)-1-oxoisoindolin-5-yl)methyl)-2-oxoacetamide. MS (ESI) m/z: 434.4 [M+1]$^+$; $^1$H NMR (400 MHz, DMSO-d6) δ 10.99 (s, 1H), 9.52 (t, 1H), 7.37-7.75 (m, 6H), 5.13 (dd, 1H), 4.32-4.58 (m, 4H), 2.93 (m, 1H), 2.61 (m, 1H), 2.41 (m, 1H), 2.38 (s, 6H), 2.03 (m, 1H).

Compound I-100: N-((2-(2,6-dioxopiperidin-3-yl)-1-oxoisoindolin-5-yl)methyl)-2-(3-fluorophenyl)-2-oxoacetamide. MS (ESI) m/z: 423.8 [M+1]$^+$; $^1$H NMR (400 MHz, DMSO-d6) δ 10.98 (s, 1H), 9.61 (t, 1H), 7.88-7.95 (d, 1H), 7.73-7.80 (m, 1H), 7.65-7.70 (d, 1H), 7.57-7.63 (m, 2H), 7.57 (s, 1H), 7.50-7.55 (m, 1H), 5.08-5.13 (m, 1H), 4.56-4.59 (d, 2H), 4.45-4.50 (m, 1H), 4.31-4.37 (m, 1H), 2.88-2.96 (m, 1H), 2.58-2.64 (m, 1H), 2.36-2.45 (m, 1H), 1.99-2.06 (m, 1H).

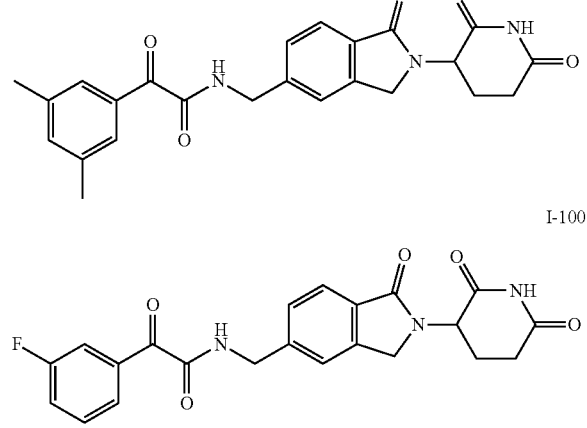

I-99

I-100

Compound I-101: 2-(3,4-dichlorophenyl)-N-((2-(2,6-dioxopiperidin-3-yl)-1-oxoisoindolin-4-yl)methyl)-2-oxoacetamide. MS (ESI) m/z: 473.6 [M+H]$^+$; $^1$H NMR (DMSO-d$_6$, 400 MHz) δ 11.02 (s, 1H), 9.60 (t, 1H), 8.22-8.25 (m, 1H), 7.96-8.01 (m, 1H), 7.85-7.89 (d, 1H), 7.64-7.68 (m, 1H), 7.55-7.60 (m, 1H), 7.51-7.54 (m, 1H), 5.14-5.19 (m, 1H), 4.55-4.60 (d, 1H), 4.51-4.55 (m, 2H), 4.43-4.47 (m, 1H), 2.89-2.96 (m, 1H), 2.58-2.65 (m, 1H), 2.35-2.43 (m, 1H), 1.99-2.05 (m, 1H).

Compound I-102: 2-(3,4-dichlorophenyl)-N-((2-(2,6-dioxopiperidin-3-yl)-1-oxoisoindolin-5-yl)methyl)-2-oxoacetamide. MS (ESI) m/z: 473.8 [M+1]$^+$; $^1$H NMR (400 MHz, DMSO-d$_6$) δ 10.98 (s, 1H), 9.63 (t, 1H), 8.23 (s, 1H), 8.00-8.05 (m, 1H), 7.88-7.95 (d, 1H), 7.70-7.75 (d, 1H), 7.57 (s, 1H), 7.46-7.50 (m, 1H), 5.09-5.15 (m, 1H), 4.56-4.60 (d, 2H), 4.43-4.45 (m, 1H), 4.31-4.36 (m, 1H), 2.90-2.95 (m, 1H), 2.56-2.62 (m, 1H), 2.38-2.44 (m, 1H), 1.99-2.04 (m, 1H).

I-101

I-102

Compound I-103: N-((2-(2,6-dioxopiperidin-3-yl)-1-oxoisoindolin-5-yl)methyl)-2-oxo-2-(pyridin-4-yl)acetamide. MS (ESI) m/z: 407.4 [M+1]+; 1H NMR (400 MHz, DMSO-d6) δ 10.97 (s, 1H), 9.43 (s, 1H), 8.74 (s, 2H), 7.81 (d, 2H), 7.70 (d, 1H), 7.55 (s, 1H), 7.46 (d, 1H), 5.12-5.08 (dd, 1H), 4.60 (d, 2H), 4.61-4.42 (d, 1H), 4.32-4.29 (d, 1H), 2.90-2.87 (m, 1H), 2.62-2.59 (bd, 1H), 2.39-2.36 (m, 1H), 2.01-1.99 (m, 1H).

Compound I-104: 2-(4-(tert-butyl)-2,6-dimethylphenyl)-N-((2-(2,6-dioxopiperidin-3-yl)-1-oxoisoindolin-5-yl)methyl)-2-oxoacetamide. MS (ESI) m/z: 490.5 [M+1]+; 1H NMR (400 MHz, DMSO-d6) δ 13.86 (s, 1H), 10.98 (s, 1H), 9.60 (s, 1H), 7.71 (d, 1H), 7.51 (s, 1H), 7.44 (m, 1H), 7.09 (s, 2H), 5.12-5.09 (dd, 1H), 4.48 (d, 2H), 4.47-4.44 (d, 1H), 4.33-4.29 (d, 1H), 2.95-2.87 (m, 1H), 2.61 (bd, 1H), 2.41-2.35 (m, 1H), 2.13 (s, 6H), 2.01-1.99 (m, 1H), 1.26 (s, 9H).

I-103

I-104

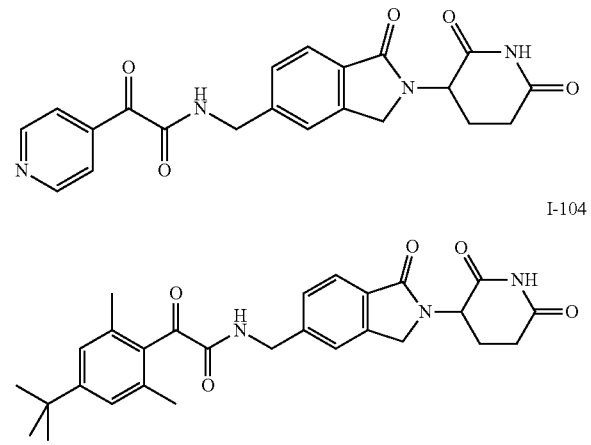

Compound I-105: 2-(4-(tert-butyl)-2,6-dimethylphenyl)-N-((2-(2,6-dioxopiperidin-3-yl)-1-oxoisoindolin-4-yl)methyl)-2-oxoacetamide. MS (ESI) m/z: 490.5 [M+1]+; 1H NMR (400 MHz, DMSO-d6) δ 11.01 (s, 1H), 9.58 (s, 1H), 7.65 (s, 1H), 7.54 (m, 2H), 7.09 (s, 2H), 5.17-5.13 (dd, 1H), 4.57-4.53 (d, 1H), 4.51 (d, 2H), 4.43-4.39 (d, 1H), 2.96-2.89 (m, 1H), 2.50 (bd, 1H), 2.37-2.33 (m, 1H), 2.11 (s, 6H), 2.04-1.99 (m, 1H), 1.26 (s, 9H).

Compound I-106: 2-(4-bromophenyl)-N-((2-(2,6-dioxopiperidin-3-yl)-1-oxoisoindolin-4-yl)methyl)-2-oxoacetamide. MS (ESI) m/z: 485.4 [M+1]+; 1H NMR (400 MHz, DMSO-d6) δ 11.02 (s, 1H), 9.54 (s, 1H), 7.95 (d, 2H), 7.68 (d, 1H), 7.55 (d, 1H), 7.52 (d, 1H), 5.18-5.14 (dd, 1H), 4.60 (d, 2H), 4.56-4.54 (m, 2H), 4.46 (d, 1H), 2.97-2.89 (m, 1H), 2.64-2.51 (bd, 1H), 2.49-2.36 (m, 1H), 2.04-1.91 (m, 1H).

I-105

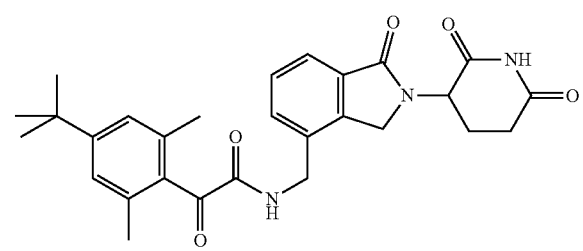

I-106

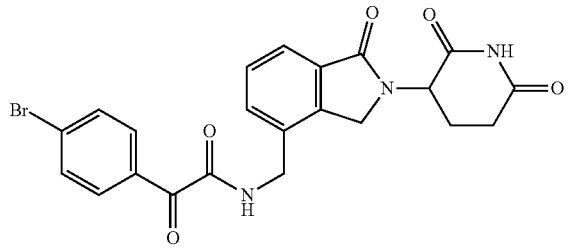

Example 15

Compound II-1: 1-(3-(Dimethylamino)-4-methylphenyl)-3-((5-(2,6-dioxopiperidin-3-yl)-6-oxo-5,6-dihydro-4H-thieno[2,3-c]pyrrol-2-yl)methyl)urea

II-1

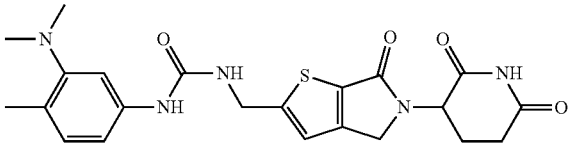

Compound II-1 was synthesized as shown in Scheme 15.

To a solution of triphosgene (119 mg, 0.40 mmol) in DCM (5 mL) was added dropwise a solution of N1,N1,6-trimethylbenzene-1,3-diamine (150 mg, 1.0 mmol) in DCM (5 mL) and TEA (200 mg, 2.0 mmol) at 0° C. for 30 min. The mixture was concentrated to give 5-isocyanato-N,N,2-trimethylaniline 80 (176 mg), which was used directly in the next step without further purification.

Scheme 15

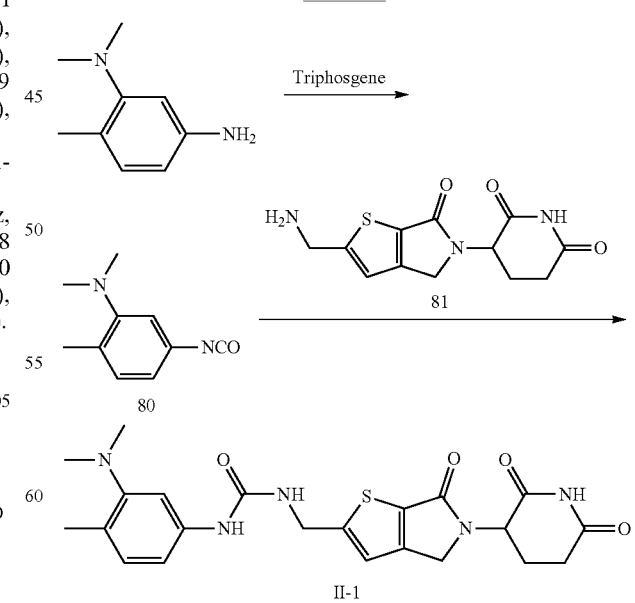

To a solution of 3-(2-(aminomethyl)-6-oxo-4H-thieno[2,3-c]pyrrol-5(6H)-yl)piperidine-2,6-dione TFA 81 (51.5 mg, 0.185 mmol) in THF (6 mL) at RT was added 5-isocyanato-N,N,2-trimethylaniline 80 (32.5 mg, 0.185 mmol), followed by addition of TEA (37.4 mg, 0.371 mmol). After stirred at RT for 2 h, the mixture was concentrated and purified using silica gel eluting with MeOH/DCM from 0% to 6% to give compound II-1 (40.4 mg) in 48% yield. MS (ESI) m/z: 455.8 [M+H]$^+$; $^1$H NMR (400 MHz, DMSO-d$_6$) δ 10.97 (s, 1H), 8.57 (s, 1H), 7.14-7.11 (m, 2H), 6.96-6.95 (m, 2H), 6.73 (t, J=6.0 Hz, 1H), 4.98 (dd, J=8.0, 13.2 Hz, 1H), 4.52 (d, J=5.6 Hz, 2H), 4.36-4.18 (m, 2H), 2.92-2.84 (m, 1H), 2.58-2.56 (m, 7H), 2.41-2.28 (m, 1H), 2.16 (s, 3H), 1.99-1.97 (m, 1H).

Example 16

Compound II-149: (E)-N-((2-(2,6-Dioxopiperidin-3-yl)-1-oxoisoindolin-5-yl)methyl)-3-(4-(1-(trifluoromethyl)cyclopropyl)phenyl)acrylamide

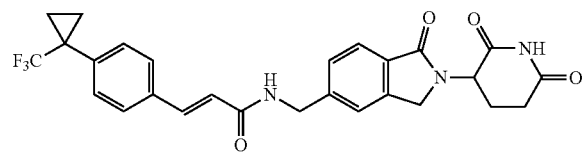

II-149

Compound II-149 was synthesized as shown in Scheme 16.

To a stirred solution of (Z)-2-methyl-4-(4-(1-(trifluoromethyl)cyclopropyl)-benzylidene)oxazol-5(4H)-one 85 (0.6 mmol) in 1,4-dioxane (4 mL) was added 4 N HCl (4 mL). The mixture was stirred at 100° C. for 4 h, and then concentrated and purified by prep-TLC eluting with DCM/MeOH (10:1) to give (E)-3-(4-(1-(trifluoromethyl)cyclopropyl)-phenyl)acrylic acid 86 (40 mg). MS (ESI) m/z: 255.1 [M−H]$^+$.

To a stirred solution 3-(5-(aminomethyl)-1-oxoisoindolin-2-yl)piperidine-2,6-dione 8 (60 mg, 0.156 mmol) and (E)-3-(4-(1-(trifluoromethyl)cyclopropyl)phenyl)acrylic acid 86 (40 mg, 0.156 mmol) in DMF (2 mL) was added DIEA (60 mg, 0.45 mmol), HOBt (43 mg, 0.32 mmol), and EDAC-HCl (62 mg, 0.32 mmol). The mixture was stirred for 2 h, and then concentrated and purified by prep-HPLC to give compound II-149 (8.1 mg). MS (ESI) m/z: 511.9 [M+H]$^+$; $^1$H NMR (400 MHz, DMSO-d$_6$) δ 10.96 (s, 1H), 8.76 (t, J=6.0 Hz, 1H), 7.69-7.70 (m, 1H), 7.60-7.58 (m, 1H), 7.51-7.43 (m, 5H), 6.73-6.69 (m, 1H), 5.10 (dd, J=5.2, 13.2 Hz, 1H), 4.52-4.29 (m, 4H), 2.95-2.87 (m, 1H), 2.62-2.57 (m, 1H), 2.40-2.36 (m, 1H), 2.01-1.98 (m, 1H), 1.35-1.33 (m, 2H), 1.14-1.12 (m, 2H).

Scheme 16

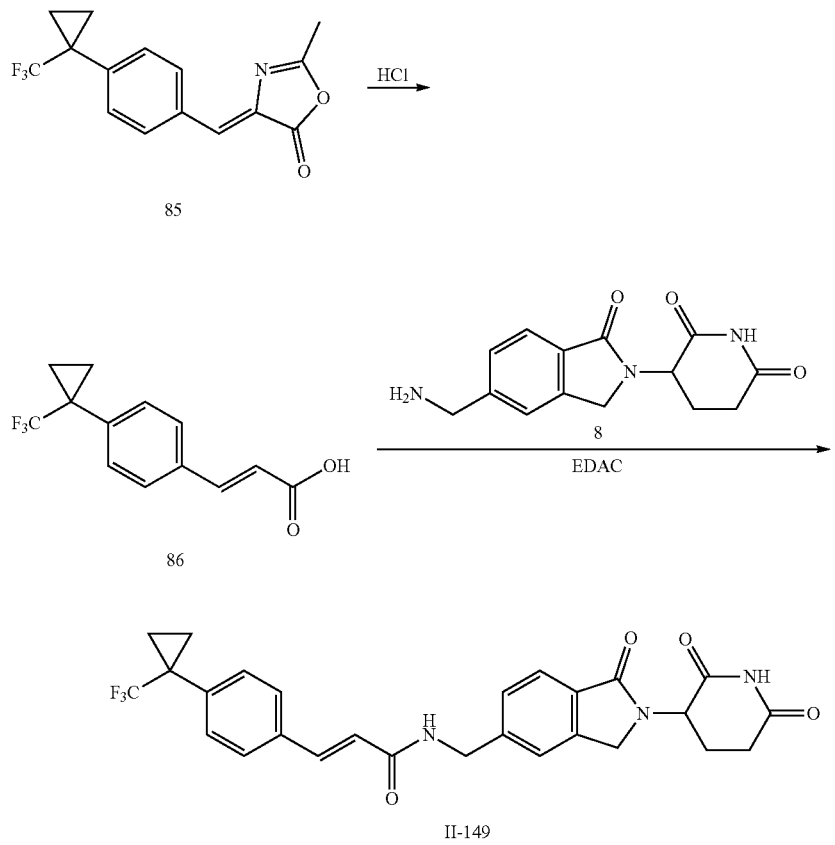

Example 17

Compound II-165: N-((5-(2,6-Dioxopiperidin-3-yl)-4-oxo-5,6-dihydro-4H-thieno[3,4-c]pyrrol-1-yl)methyl)-2,2-difluoro-2-(4-(1-(trifluoromethyl)cyclopropyl)phenyl)acetamide

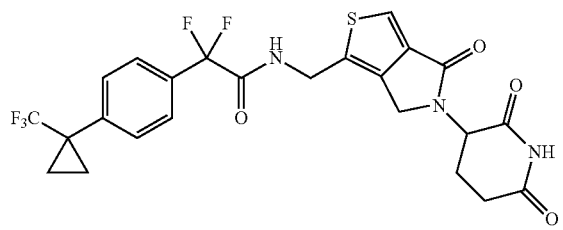

II-165

Compound II-165 was synthesized as shown in Scheme 17.

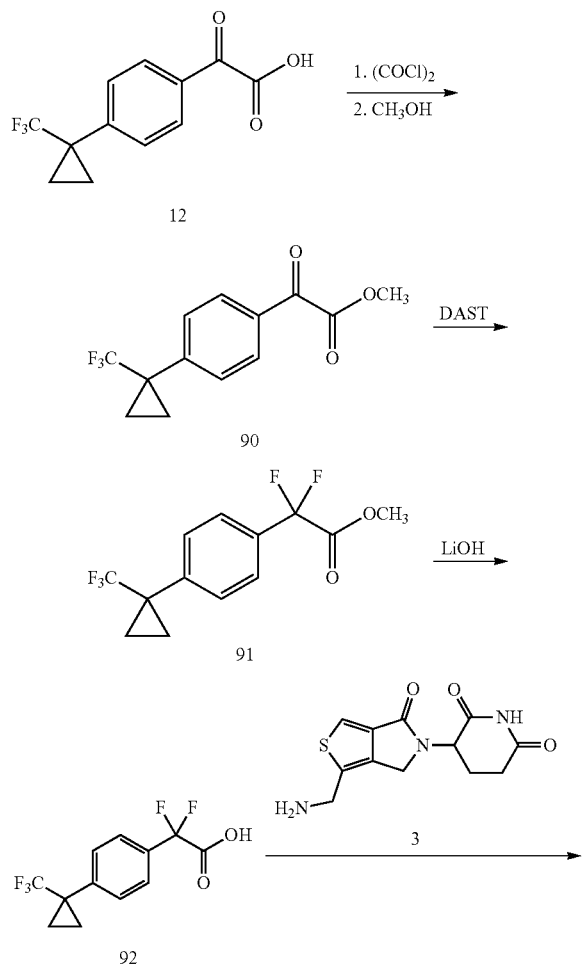

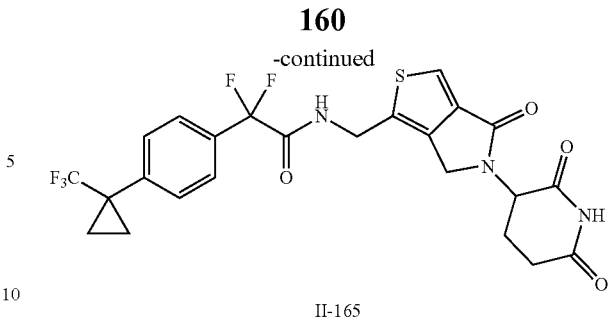

II-165

To a suspension of 2-oxo-2-(4-(1-(trifluoromethyl)cyclopropyl)phenyl)acetic acid 12 (500 mg, 1.9 mmol) in DCM (4 mL) was added (COCl)$_2$ (369 mg, 2.9 mmol) and DMF (0.1 mL) and the mixture was stirred for 1 h. MeOH (3 mL) was then added and the mixture was stirred for 10 m and then concentrated. The residue was purified using silica gel eluting with EA in PE from 0% to 10% to give methyl 2-oxo-2-(4-(1-(trifluoromethyl)cyclopropyl)phenyl)acetate 90 (480 mg) in 93% yield.

To a solution of methyl 2-oxo-2-(4-(1-(trifluoromethyl)cyclopropyl)phenyl)acetate 90 (480 mg, 1.76 mmol) in DCM (5 mL) at 0° C. was added DAST (1.28 g, 8.82 mmol). The mixture was stirred at RT for overnight. The reaction was quenched by addition of saturated aqueous NH$_4$Cl and the mixture was then extracted with DCM. The combined organic layers were dried over Na$_2$SO$_4$, filtered, and concentrated. The residue was purified using silica gel eluting with EA in petroleum from 0% to 20% to give methyl 2,2-difluoro-2-(4-(1-(trifluoromethyl)cyclopropyl)phenyl)acetate 91 (450 mg) in 87% yield.

To a solution of methyl 2,2-difluoro-2-(4-(1-(trifluoromethyl)cyclopropyl)phenyl)-acetate 91 (450 mg, 1.53 mmol) in THF/H$_2$O (10 mL/2 mL) at 0° C. was added LiOH.H$_2$O (128 mg, 3.06 mmol). The mixture was stirred at RT for 4 h, and then acidified with HCl (1N) (2 mL) and extracted with DCM. The combined organic layers were dried over Na$_2$SO$_4$, filtered, and concentrated. The residue was purified using silica gel eluting with MeOH in DCM from 0% to 10% to give 2,2-difluoro-2-(4-(1-(trifluoromethyl)cyclopropyl)phenyl)acetic acid 92 (250 mg) in 58% yield. MS (ESI) m/z: 281[M+H]$^+$.

To a solution of 3-(1-(aminomethyl)-4-oxo-4H-thieno[3,4-c]pyrrol-5(6H)-yl)piperidine-2,6-dione 3 (73 mg, 0.26 mmol) in DCM (2 mL) was added TEA (78 mg, 0.78 mmol), followed by addition of 2,2-difluoro-2-(4-(1-(trifluoromethyl)cyclopropyl)phenyl)acetic acid 92 (65 mg, 0.31 mmol) and T$_3$P (197 mg, 0.62 mmol, 50% in EA). The mixture was stirred for overnight and then concentrated. The residue was purified by prep-TLC eluting with DCM/MeOH (10:1) to give compound II-165 (7.4 mg) in 9% yield. MS (ESI) m/z: 542.1 [M+1]$^+$; $^1$HNMR (400 MHz, DMSO-d) 10.99 (s, 1H), 9.72 (t, J=5.6 Hz, 1H), 7.90 (s, 1H), 7.63-7.57 (m, 4H), 5.01 (dd, J=5.2, 13.2 Hz, 1H), 4.47 (d, J=6.0 Hz, 2H), 4.29-4.17 (m, 2H), 2.93-2.84 (m, 1H), 2.61-2.57 (m, 1H), 2.35-2.24 (m, 1H), 2.01-1.96 (m, 1H), 1.39-1.36 (m, 2H), 1.17 (s, 2H).

The following compounds were prepared according to a synthetic procedure described herein.

Compound II-2: 1-(3-chloro-4-methylphenyl)-3-((5-(2,6-dioxopiperidin-3-yl)-6-oxo-5,6-dihydro-4H-thieno[2,3-c]pyrrol-3-yl)methyl)urea. MS (ESI) m/z: 446.7 [M+H]$^+$.

Compound II-3: (S)-1-(3-chloro-4-methylphenyl)-3-((5-(2,7-dioxoazepan-3-yl)-4-oxo-5,6-dihydro-4H-thieno[2,3-c]pyrrol-2-yl)methyl)urea. MS (ESI) m/z: 461.1 [M+H]$^+$.

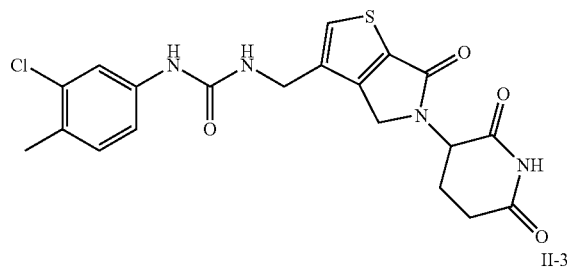
II-2

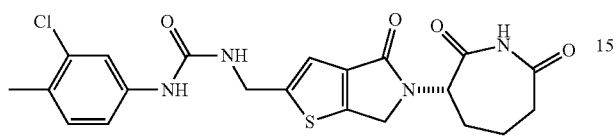
II-3

Compound II-4: 1-((5-(2,6-dioxopiperidin-3-yl)-4-oxo-5,6-dihydro-4H-thieno[3,4-c]pyrrol-1-yl)methyl)-3-(3-methoxy-4-methylphenyl)urea. MS (ESI) m/z: 442.8 [M+H]$^+$.

Compound II-5: 1-(4-chloro-3-(trifluoromethoxy)phenyl)-3-((5-(2,6-dioxopiperidin-3-yl)-4-oxo-5,6-dihydro-4H-thieno[3,4-c]pyrrol-1-yl)methyl)urea. MS (ESI) m/z: 517.0 [M+H]$^+$.

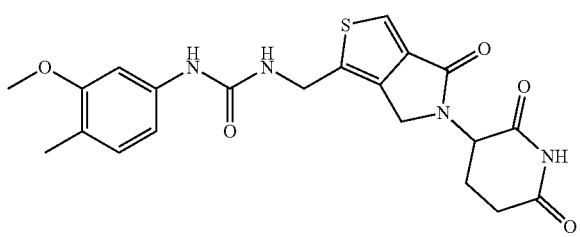
II-4

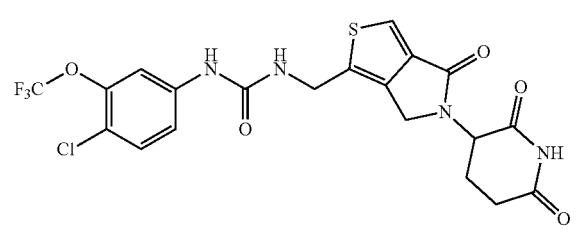
II-5

Compound II-6: 1-(3-chloro-4-methoxyphenyl)-3-((5-(2,6-dioxopiperidin-3-yl)-4-oxo-5,6-dihydro-4H-thieno[3,4-c]pyrrol-1-yl)methyl)urea. MS (ESI) m/z: 463.1 [M+H]$^+$.

Compound II-7: 1-(benzo[d][1,3]dioxol-5-yl)-3-((5-(2,6-dioxopiperidin-3-yl)-4-oxo-5,6-dihydro-4H-thieno[3,4-c]pyrrol-1-yl)methyl)urea. MS (ESI) m/z: 443.1 [M+H]$^+$.

Compound II-8: 1-(3-chloro-5-(trifluoromethyl)phenyl)-3-((5-(2,6-dioxopiperidin-3-yl)-4-oxo-5,6-dihydro-4H-thieno[3,4-c]pyrrol-1-yl)methyl)urea. MS (ESI) m/z: 501.0 [M+H]$^+$.

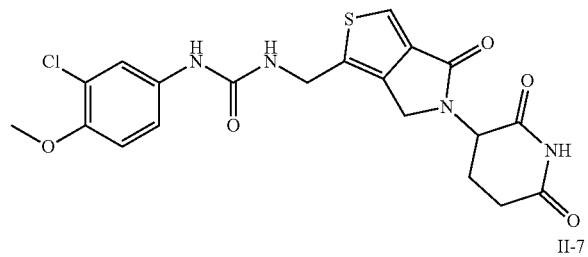
II-6

II-7

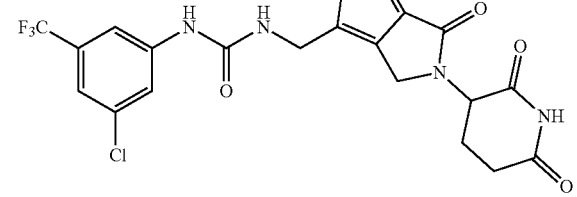
II-8

Compound II-9: 1-(3,5-bis(trifluoromethyl)phenyl)-3-((5-(2,6-dioxopiperidin-3-yl)-4-oxo-5,6-dihydro-4H-thieno[3,4-c]pyrrol-1-yl)methyl)urea. MS (ESI) m/z: 535.1 [M+H]$^+$.

Compound II-10: 1-(3-chloro-4-methylphenyl)-3-((5-(2,6-dioxopiperidin-3-yl)-4-oxo-5,6-dihydro-4H-thieno[3,4-c]pyrrol-1-yl)methyl)urea. MS (ESI) m/z: 447.1 [M+H]$^+$.

Compound II-11: 1-(3-(dimethylamino)-4-methylphenyl)-3-((5-(2,6-dioxopiperidin-3-yl)-4-oxo-5,6-dihydro-4H-thieno[3,4-c]pyrrol-1-yl)methyl)urea. MS (ESI) m/z: 456.1 [M+H]$^+$.

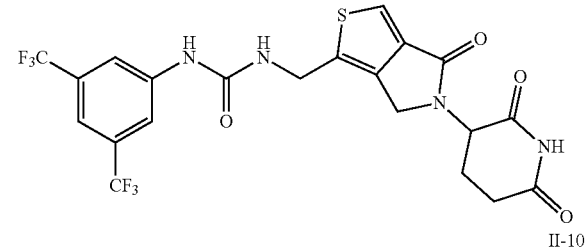
II-9

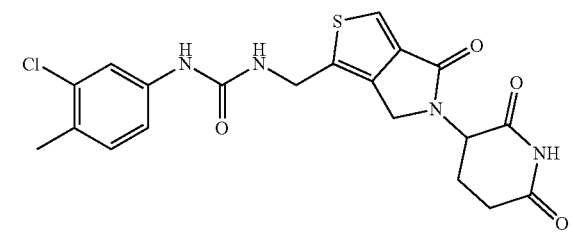
II-10

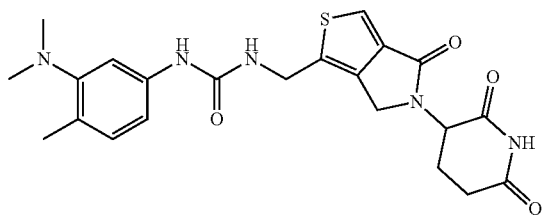

II-11

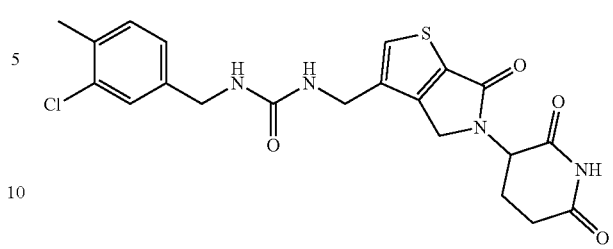

II-15

Compound II-12: N-(5-(3-((5-(2,6-dioxopiperidin-3-yl)-4-oxo-5,6-dihydro-4H-thieno[3,4-c]pyrrol-1-yl)methyl)ureido)-2-methylphenyl)acetamide. MS (ESI) m/z: 470.2 [M+H]$^+$.

Compound II-13: 1-(3-chloro-4-(dimethylamino)phenyl)-3-((5-(2,6-dioxopiperidin-3-yl)-4-oxo-5,6-dihydro-4H-thieno[3,4-c]pyrrol-1-yl)methyl)urea. MS (ESI) m/z: 476.1 [M+H]$^+$.

Compound II-16: 5-(3-((5-(2,6-dioxopiperidin-3-yl)-4-oxo-5,6-dihydro-4H-thieno[3,4-c]pyrrol-1-yl)methyl)ureido)-2-methylbenzamide. MS (ESI) m/z: 456.1 [M+H]$^+$.

Compound II-17: (S)-1-(3-chloro-4-methylphenyl)-3-((5-(2,7-dioxoazepan-3-yl)-4-oxo-5,6-dihydro-4H-thieno[3,4-c]pyrrol-1-yl)methyl)urea. MS (ESI) m/z: 459.8 [M+H]$^+$.

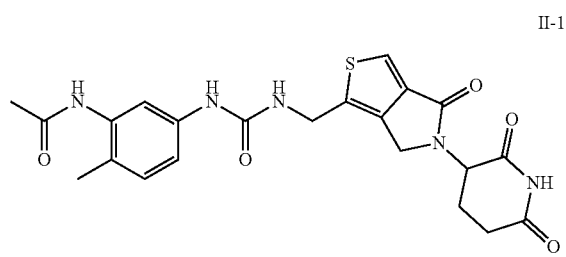

II-12

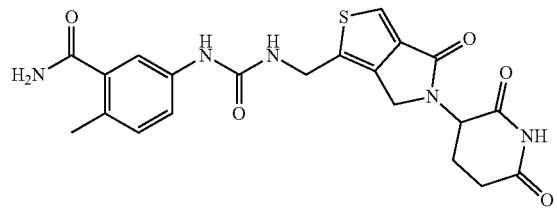

II-16

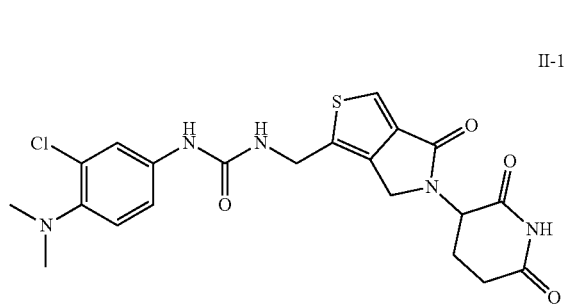

II-13

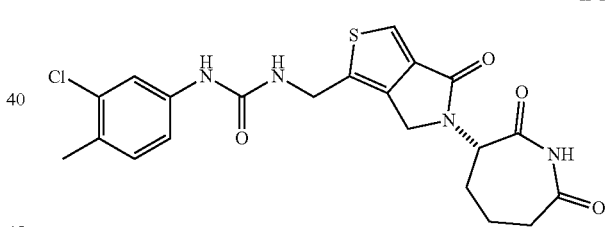

II-17

Compound II-14: N-(2-chloro-4-(3-((5-(2,6-dioxopiperidin-3-yl)-4-oxo-5,6-dihydro-4H-thieno[3,4-c]pyrrol-1-yl)methyl)ureido)phenyl)acetamide. MS (ESI) m/z: 490.1 [M+H]$^+$.

Compound II-15: 1-(3-chloro-4-methylbenzyl)-3-((5-(2,6-dioxopiperidin-3-yl)-6-oxo-5,6-dihydro-4H-thieno[2,3-c]pyrrol-3-yl)methyl)urea. MS (ESI) m/z: 461.1 [M+H]$^+$.

Compound II-18: N-((5-(2,6-dioxopiperidin-3-yl)-4-oxo-5,6-dihydro-4H-thieno[3,4-c]pyrrol-1-yl)methyl)-2,2-difluoro-2-(4-fluorophenyl)acetamide. MS (ESI) m/z: 452.1 [M+H]$^+$.

Compound II-19: (S)-1-(3-chloro-4-methylbenzyl)-3-((5-(2,7-dioxoazepan-3-yl)-4-oxo-5,6-dihydro-4H-thieno[2,3-c]pyrrol-2-yl)methyl)urea. MS (ESI) m/z: 475.1 [M+H]$^+$.

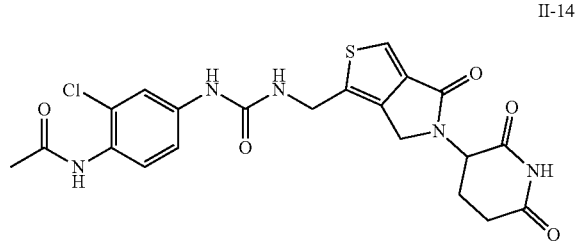

II-14

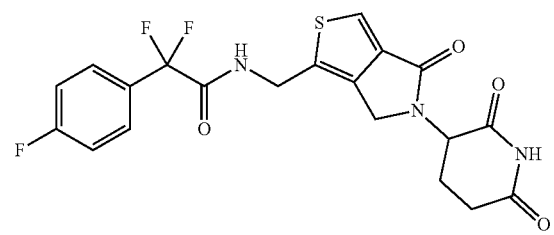

II-18

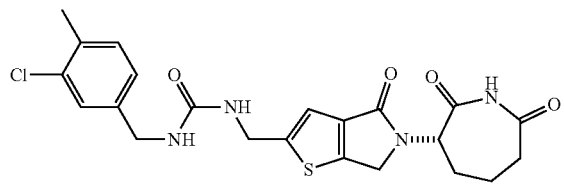

Compound II-20: 1-(3-chloro-4-methylphenyl)-3-((5-(2,6-dioxopiperidin-3-yl)-4-oxo-5,6-dihydro-4H-thieno[3,4-c]pyrrol-1-yl)methyl)-1,3-dimethylurea. MS (ESI) m/z: 475.1 [M+H]⁺.

Compound II-21: 1-(3-chloro-4-methylbenzyl)-3-((5-(2,6-dioxopiperidin-3-yl)-4-oxo-5,6-dihydro-4H-thieno[2,3-c]pyrrol-2-yl)methyl)urea. MS (ESI) m/z: 461.1 [M+H]⁺.

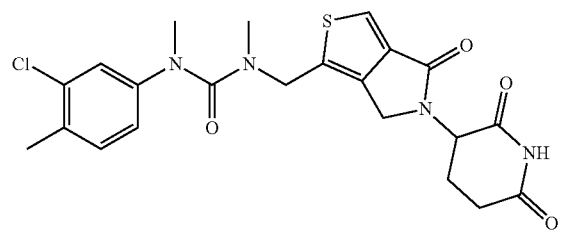

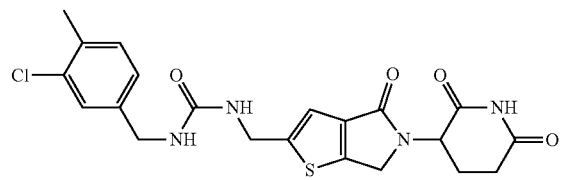

Compound II-22: 1-(3-chloro-4-methylphenyl)-3-((5-(2,6-dioxopiperidin-3-yl)-4-oxo-5,6-dihydro-4H-thieno[3,4-c]pyrrol-1-yl)methyl)-1-methylurea. MS (ESI) m/z: 461.1 [M+H]⁺.

Compound II-23: 3-(1-(((3-((3-chloro-4-methylphenyl)amino)propyl)amino)methyl)-4-oxo-4H-thieno[3,4-c]pyrrol-5(6H)-yl)piperidine-2,6-dione. MS (ESI) m/z: 460.8 [M+H]⁺.

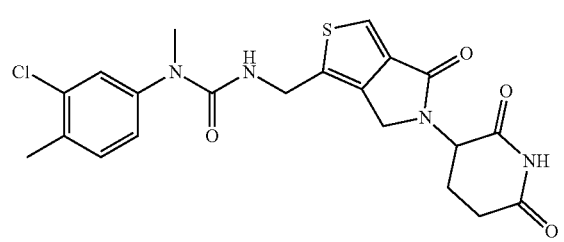

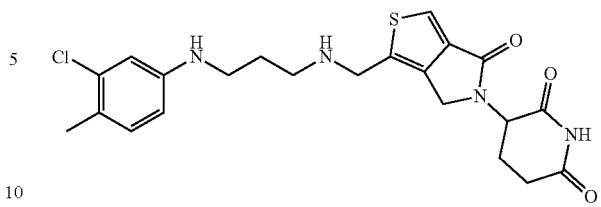

Compound II-24: 2-(3-chloro-4-methylphenyl)-N-((5-(2,6-dioxopiperidin-3-yl)-4-oxo-5,6-dihydro-4H-thieno[3,4-c]pyrrol-1-yl)methyl)acetamide. MS (ESI) m/z: 446.1 [M+H]⁺.

Compound II-25: N-((5-(2,6-dioxopiperidin-3-yl)-4-oxo-5,6-dihydro-4H-thieno[3,4-c]pyrrol-1-yl)methyl)-2-(4-fluorophenyl)acetamide. MS (ESI) m/z: 416.1 [M+H]⁺.

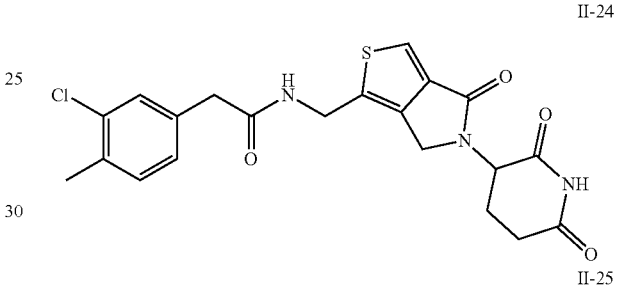

Compound II-26: 1-((5-(2,6-dioxopiperidin-3-yl)-6-oxo-5,6-dihydro-4H-thieno[2,3-c]pyrrol-2-yl)methyl)-3-(3-methyl-4-morpholinophenyl)urea. MS (ESI) m/z: 498.2 [M+H]⁺.

Compound II-27: 1-((5-(2,6-dioxopiperidin-3-yl)-6-oxo-5,6-dihydro-4H-thieno[2,3-c]pyrrol-2-yl)methyl)-3-(3-methyl-4-(pyrrolidin-1-yl)phenyl)urea. MS (ESI) m/z: 482.2 [M+H]⁺.

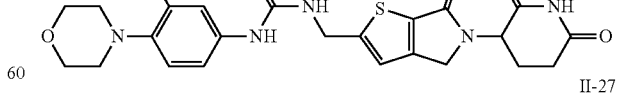

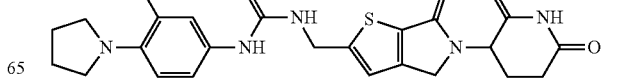

Compound II-28: 2-(3-chloro-4-methylphenyl)-N-((5-(2,6-dioxopiperidin-3-yl)-4-oxo-5,6-dihydro-4H-thieno[3,4-c]pyrrol-1-yl)methyl)-2,2-difluoroacetamide. MS (ESI) m/z: 482.1 [M+H]⁺.

Compound II-29: (S)-2-(3-chloro-4-methylphenyl)-N-((5-(2,7-dioxoazepan-3-yl)-4-oxo-5,6-dihydro-4H-thieno[3,4-c]pyrrol-1-yl)methyl)-2,2-difluoroacetamide. MS (ESI) m/z: 496.1 [M+H]⁺.

II-28

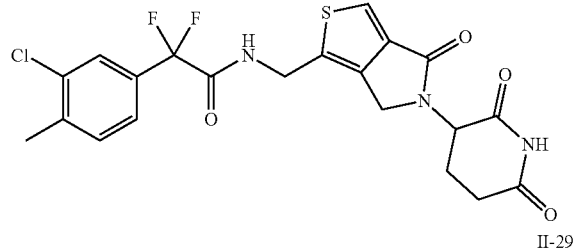

II-29

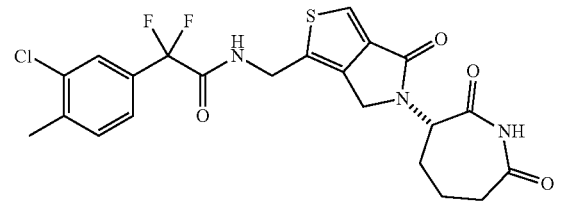

Compound II-30: 2-(3-chloro-4-methylphenyl)-N-((5-(2,6-dioxopiperidin-3-yl)-6-oxo-5,6-dihydro-4H-thieno[2,3-c]pyrrol-2-yl)methyl)acetamide. MS (ESI) m/z: 446.1 [M+H]⁺.

Compound II-31: 1-(3-chloro-4-methylphenyl)-3-(2-(5-(2,6-dioxopiperidin-3-yl)-4-oxo-5,6-dihydro-4H-thieno[3,4-c]pyrrol-1-yl)ethyl)urea. MS (ESI) m/z: 461.1 [M+H]⁺.

II-30

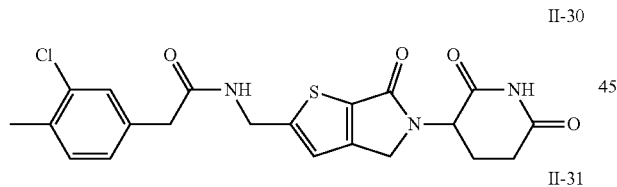

II-31

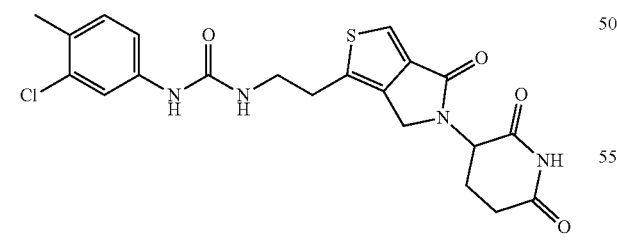

Compound II-32: 1-(3-chloro-4-methylbenzyl)-3-(2-(5-(2,6-dioxopiperidin-3-yl)-4-oxo-5,6-dihydro-4H-thieno[3,4-c]pyrrol-1-yl)ethyl)urea. MS (ESI) m/z: 475.1 [M+H]⁺.

Compound II-33: 3-(3-chloro-4-methylphenyl)-N-((5-(2,6-dioxopiperidin-3-yl)-6-oxo-5,6-dihydro-4H-thieno[2,3-c]pyrrol-2-yl)methyl)propanamide. MS (ESI) m/z: 460.1 [M+H]⁺.

II-32

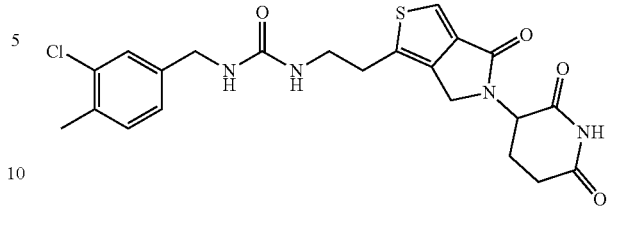

II-33

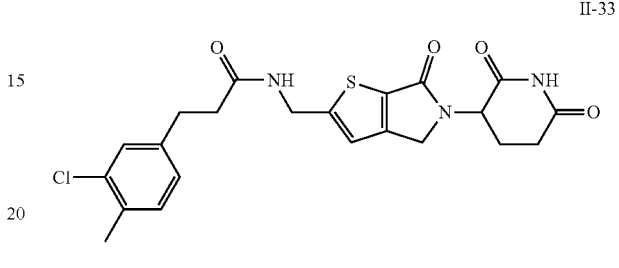

Compound II-34: 3-(3-chloro-4-methylphenyl)-N-((5-(2,6-dioxopiperidin-3-yl)-4-oxo-5,6-dihydro-4H-thieno[3,4-c]pyrrol-1-yl)methyl)propanamide. MS (ESI) m/z: 460.1 [M+H]⁺.

Compound II-35: 3-{2-[(3-chloro-4-methylphenylsulfonylamino)methyl]-6-oxo-3-thia-7-azabicyclo[3.3.0]octa-1,4-dien-7-yl}-2,6-piperidinedione. MS (ESI) m/z: 483.0 [M+H]⁺.

II-34

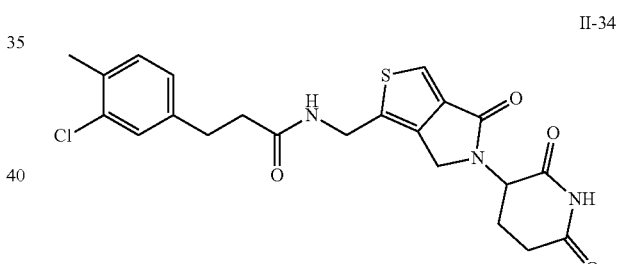

II-35

Compound II-36: 1-(2,6-dichlorobenzyl)-3-((5-(2,6-dioxopiperidin-3-yl)-6-oxo-5,6-dihydro-4H-thieno[2,3-c]pyrrol-2-yl)methyl)urea. MS (ESI) m/z: 481.0 [M+H]⁺.

Compound II-37: 1-(2,6-dichlorobenzyl)-3-((5-(2,6-dioxopiperidin-3-yl)-4-oxo-5,6-dihydro-4H-thieno[3,4-c]pyrrol-1-yl)methyl)urea. MS (ESI) m/z: 481.0 [M+H]⁺.

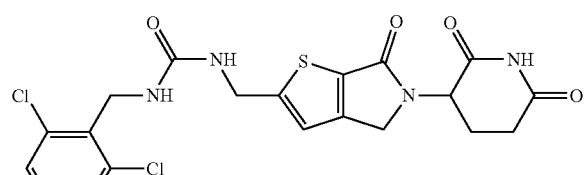

II-36

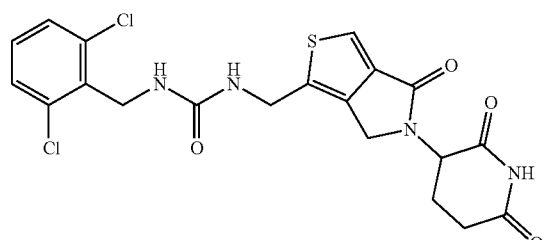

II-37

Compound II-38: 2-(3-chloro-4-methylphenyl)-N-((5-(2,6-dioxopiperidin-3-yl)-6-oxo-5,6-dihydro-4H-thieno[2,3-c]pyrrol-2-yl)methyl)-2,2-difluoroacetamide. MS (ESI) m/z: 482.0 [M+H]+.

Compound II-39: 1-(3-chloro-4-methylphenyl)-3-((5-(2,6-dioxopiperidin-3-yl)-6-oxo-5,6-dihydro-4H-thieno[2,3-c]pyrrol-2-yl)methyl)thiourea. MS (ESI) m/z: 463.0 [M+H]+.

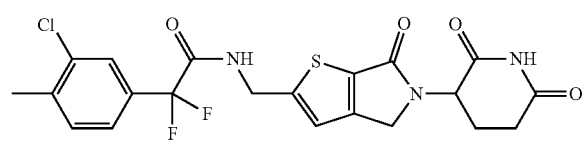

II-38

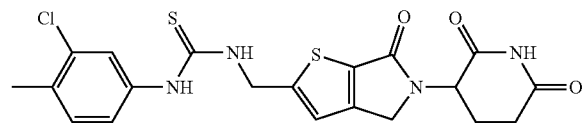

II-39

Compound II-40: 1-((5-(2,6-dioxopiperidin-3-yl)-4-oxo-5,6-dihydro-4H-thieno[3,4-c]pyrrol-1-yl)methyl)-3-(5-methyl-4-(trifluoromethyl)pyrimidin-2-yl)urea. MS (ESI) m/z: 483.1 [M+H]+.

Compound II-41: 4-(3-chloro-4-methylphenyl)-N-((5-(2,6-dioxopiperidin-3-yl)-4-oxo-5,6-dihydro-4H-thieno[3,4-c]pyrrol-1-yl)methyl)butanamide. MS (ESI) m/z: 474.1 [M+H]+.

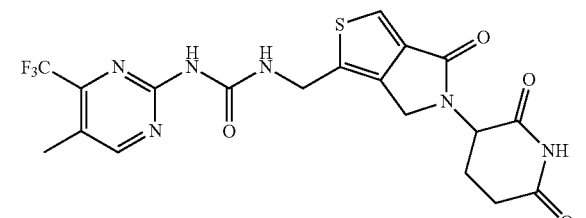

II-40

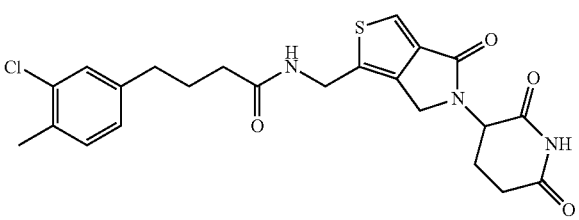

II-41

Compound II-42: 1-(2,6-dichlorophenyl)-3-((5-(2,6-dioxopiperidin-3-yl)-6-oxo-5,6-dihydro-4H-thieno[2,3-c]pyrrol-2-yl)methyl)urea. MS (ESI) m/z: 467.0 [M+H]+.

Compound II-43: 1-(2,6-dichlorophenyl)-3-((5-(2,6-dioxopiperidin-3-yl)-4-oxo-5,6-dihydro-4H-thieno[3,4-c]pyrrol-1-yl)methyl)urea. MS (ESI) m/z: 467.0 [M+H]+.

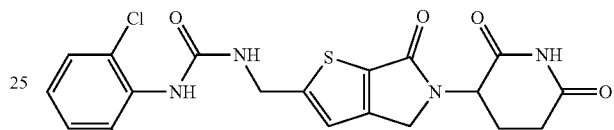

II-42

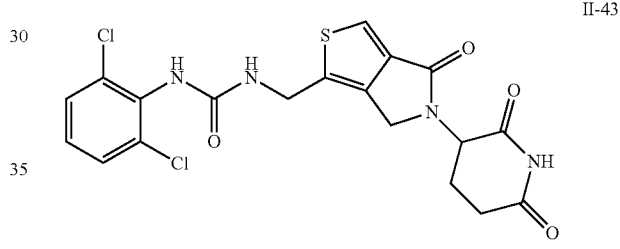

II-43

Compound II-44: 3-{3-[(3-chloro-4-methylphenylsulfonylamino)methyl]-8-oxo-2-thia-7-azabicyclo[3.3.0]octa-1(5),3-dien-7-yl}-2,6-piperidinedione. MS (ESI) m/z: 483.1 [M+H]+.

Compound II-45: 1-(3-(dimethylamino)-4-fluorophenyl)-3-((5-(2,6-dioxopiperidin-3-yl)-6-oxo-5,6-dihydro-4H-thieno[2,3-c]pyrrol-2-yl)methyl)urea. MS (ESI) m/z: 460.1 [M+H]+.

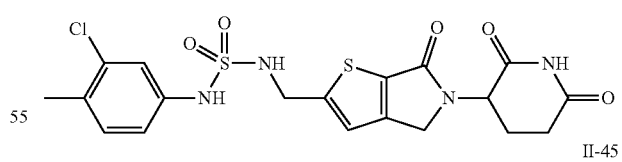

II-44

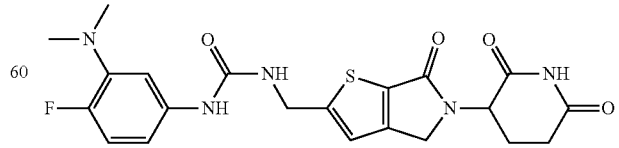

II-45

Compound II-46: 1-((5-(2,6-dioxopiperidin-3-yl)-6-oxo-5,6-dihydro-4H-thieno[2,3-c]pyrrol-2-yl)methyl)-3-(3-hydroxy-4-methylphenyl)urea. MS (ESI) m/z: 429.1 [M+H]+.

Compound II-47: 1-(3-(diethylamino)-4-methylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 484.2 [M+H]+.

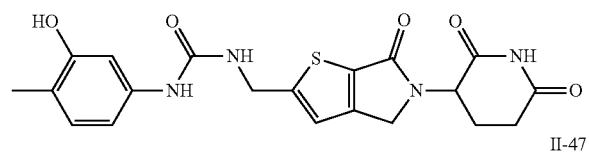

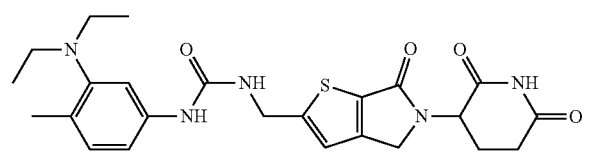

Compound II-48: 1-(3-(dimethylamino)phenyl)-3-((5-(2,6-dioxopiperidin-3-yl)-6-oxo-5,6-dihydro-4H-thieno[2,3-c]pyrrol-2-yl)methyl)urea. MS (ESI) m/z: 442.1 [M+H]+.

Compound II-49: 1-(3-(dimethylamino)-5-methylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 456.2 [M+H]+.

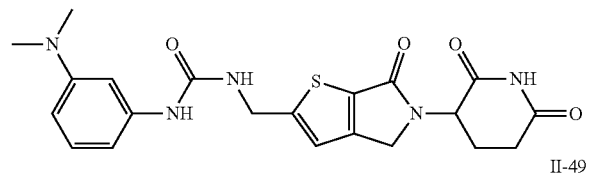

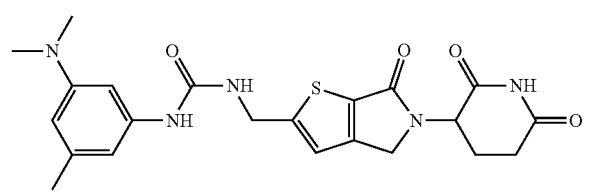

Compound II-50: 1-(3-(dimethylamino)-5-(trifluoromethyl)phenyl)-3-((5-(2,6-dioxopiperidin-3-yl)-6-oxo-5,6-dihydro-4H-thieno[2,3-c]pyrrol-2-yl)methyl)urea. MS (ESI) m/z: 510.1 [M+H]+.

Compound II-51: 1-(3-((dimethylamino)methyl)-4-methylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 470.2 [M+H]+.

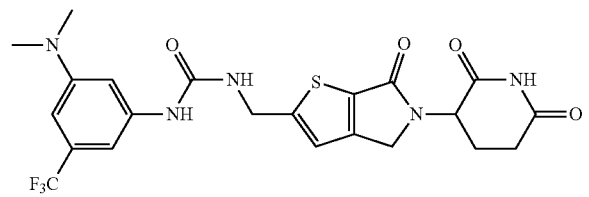

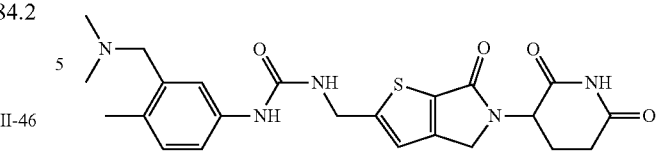

Compound II-52: 1-(4-(diethylamino)-3-methylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 484.2 [M+H]+.

Compound II-53: 1-(3-((dimethylamino)methyl)phenyl)-3-((5-(2,6-dioxopiperidin-3-yl)-6-oxo-5,6-dihydro-4H-thieno[2,3-c]pyrrol-2-yl)methyl)urea. MS (ESI) m/z: 456.2 [M+H]+.

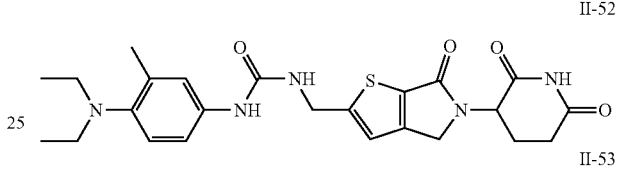

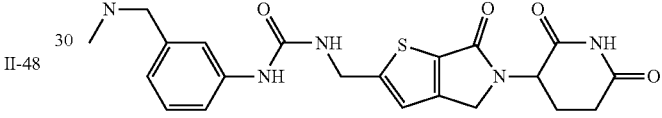

Compound II-54: 1-((5-(2,6-dioxopiperidin-3-yl)-6-oxo-5,6-dihydro-4H-thieno[2,3-c]pyrrol-2-yl)methyl)-3-(3-isopropyl-4-methylphenyl)urea. MS (ESI) m/z: 455.2 [M+H]+.

Compound II-55: 1-(3-(dimethylamino)-4-(trifluoromethyl)phenyl)-3-((5-(2,6-dioxopiperidin-3-yl)-6-oxo-5,6-dihydro-4H-thieno[2,3-c]pyrrol-2-yl)methyl)urea. MS (ESI) m/z: 510.1 [M+H]+.

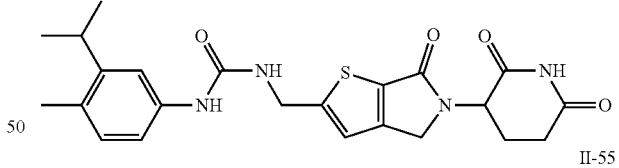

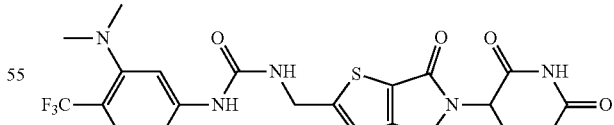

Compound II-56: 1-((5-(2,6-dioxopiperidin-3-yl)-6-oxo-5,6-dihydro-4H-thieno[2,3-c]pyrrol-2-yl)methyl)-3-(3-(isopropyl(methyl)amino)phenyl)urea. MS (ESI) m/z: 470.2 [M+H]+.

Compound II-57: 2-(3-chloro-4-methylphenyl)-N-((5-(2,6-dioxopiperidin-3-yl)-6-oxo-5,6-dihydro-4H-thieno[2,3-c]pyrrol-3-yl)methyl)acetamide. MS (ESI) m/z: 446.1 [M+H]+.

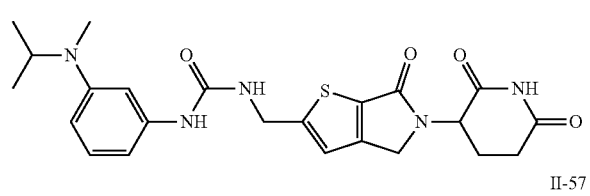

II-56

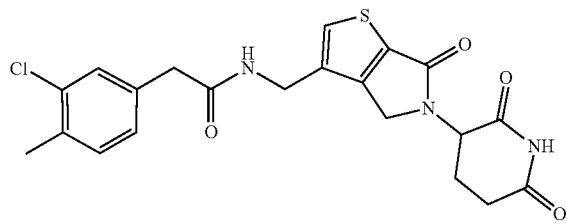

II-57

Compound II-58: 1-((5-(2,6-dioxopiperidin-3-yl)-6-oxo-5,6-dihydro-4H-thieno[2,3-c]pyrrol-2-yl)methyl)-3-(3-methoxy-4-methylphenyl)urea. MS (ESI) m/z: 443.1 [M+H]⁺.

Compound II-59: 1-(4-(dimethylamino)-3-methylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 456.1 [M+H]⁺.

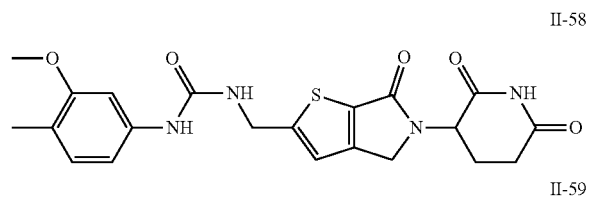

II-58

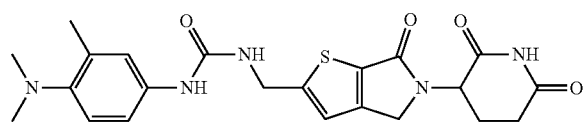

II-59

Compound II-60: 1-(3-(dimethylamino)-5-isopropylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 484.2 [M+H]⁺.

Compound II-61: 2-(4-(dimethylamino)phenyl)-N-((5-(2,6-dioxopiperidin-3-yl)-4-oxo-5,6-dihydro-4H-thieno[3,4-c]pyrrol-1-yl)methyl)acetamide. MS (ESI) m/z: 441.1 [M+H]⁺.

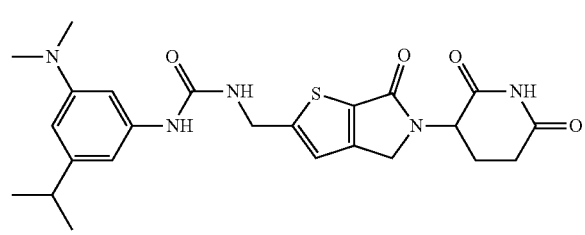

II-60

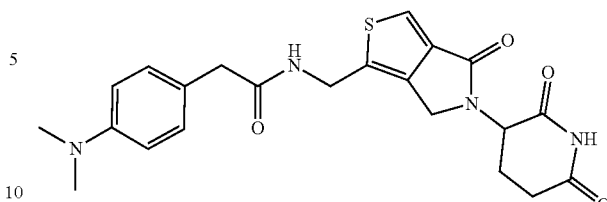

II-61

Compound II-62: 2-(4-(tert-butyl)phenyl)-N-((5-(2,6-dioxopiperidin-3-yl)-4-oxo-5,6-dihydro-4H-thieno[3,4-c]pyrrol-1-yl)methyl)acetamide. MS (ESI) m/z: 454.1 [M+H]⁺.

Compound II-63: N-((5-(2,6-dioxopiperidin-3-yl)-4-oxo-5,6-dihydro-4H-thieno[3,4-c]pyrrol-1-yl)methyl)-2-(3-isopropyl-4-methoxyphenyl)acetamide. MS (ESI) m/z: 470.1 [M+H]⁺.

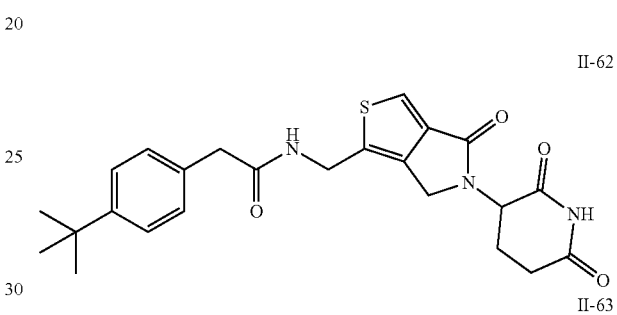

II-62

II-63

Compound II-64: 3-(1-(((5-((3-chloro-4-methylphenyl)amino)pentyl)amino)methyl)-4-oxo-4H-thieno[3,4-c]pyrrol-5(6H)-yl)piperidine-2,6-dione. MS (ESI) m/z: 489.1 [M+H]⁺.

Compound II-65: 3-(2-(((3-((3-chloro-4-methylphenyl)amino)propyl)amino)methyl)-6-oxo-4,6-dihydro-5H-thieno[2,3-c]pyrrol-5-yl)piperidine-2,6-dione. MS (ESI) m/z: 461.1 [M+H]⁺.

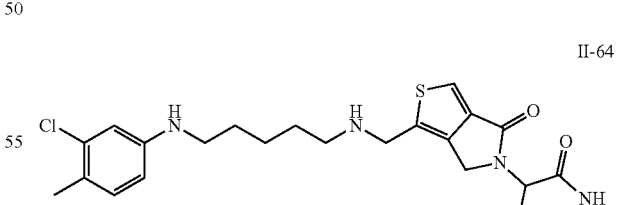

II-64

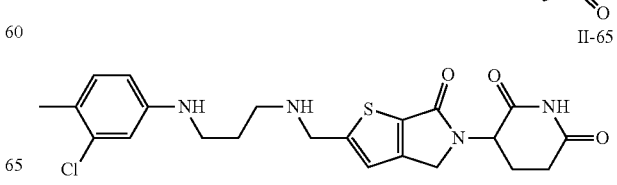

II-65

Compound II-66: 1-(3-chloro-4-methylphenethyl)-3-((5-(2,6-dioxopiperidin-3-yl)-6-oxo-5,6-dihydro-4H-thieno[2,3-c]pyrrol-2-yl)methyl)urea. MS (ESI) m/z: 475.1 [M+H]⁺.

Compound II-67: 2-(3-chloro-4-methylphenyl)-N-((5-(2,6-dioxopiperidin-3-yl)-4-oxo-5,6-dihydro-4H-thieno[3,4-c]pyrrol-1-yl)methyl)propanamide. MS (ESI) m/z: 460.1 [M+H]⁺.

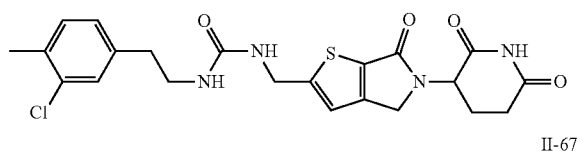

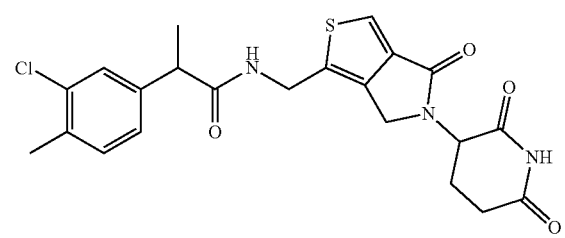

Compound II-68: 2-(3-(dimethylamino)-4-methylphenyl)-N-((5-(2,6-dioxopiperidin-3-yl)-4-oxo-5,6-dihydro-4H-thieno[3,4-c]pyrrol-1-yl)methyl)acetamide. MS (ESI) m/z: 455.1 [M+H]⁺.

Compound II-69: 1-(3-chloro-4-methylphenyl)-N-((5-(2,6-dioxopiperidin-3-yl)-4-oxo-5,6-dihydro-4H-thieno[3,4-c]pyrrol-1-yl)methyl)methanesulfonamide. MS (ESI) m/z: 482.0 [M+H]⁺.

Compound II-70: 1-((5-(2,6-dioxopiperidin-3-yl)-6-oxo-5,6-dihydro-4H-thieno[2,3-c]pyrrol-2-yl)methyl)-3-(3-isopropylphenyl)urea. MS (ESI) m/z: 441.1 [M+H]⁺.

Compound II-71: 1-(3-(diethylamino)phenyl)-3-((5-(2,6-dioxopiperidin-3-yl)-6-oxo-5,6-dihydro-4H-thieno[2,3-c]pyrrol-2-yl)methyl)urea. MS (ESI) m/z: 470.1 [M+H]⁺.

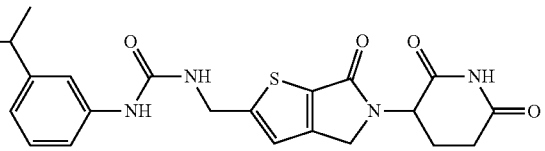

Compound II-72: 1-(3-chloro-4-methylphenyl)-3-((5-(2,5-dioxopyrrolidin-3-yl)-6-oxo-5,6-dihydro-4H-thieno[2,3-c]pyrrol-2-yl)methyl)urea. MS (ESI) m/z: 433.0 [M+H]⁺.

Compound II-73: 1-(3-chloro-4-methylphenyl)-3-((5-(3-methyl-2,6-dioxopiperidin-3-yl)-6-oxo-5,6-dihydro-4H-thieno[2,3-c]pyrrol-2-yl)methyl)urea. MS (ESI) m/z: 461.0 [M+H]⁺.

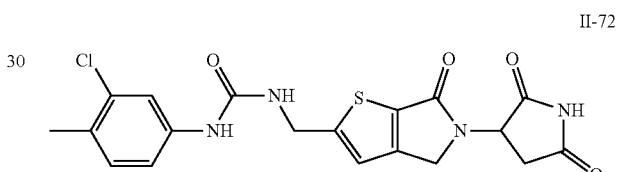

Compound II-74: N-((5-(2,6-dioxopiperidin-3-yl)-4-oxo-5,6-dihydro-4H-thieno[3,4-c]pyrrol-1-yl)methyl)-2-(4-isopropylphenyl)acetamide. MS (ESI) m/z: 440.2 [M+H]⁺.

Compound II-75: N-((5-(2,6-dioxopiperidin-3-yl)-4-oxo-5,6-dihydro-4H-thieno[3,4-c]pyrrol-1-yl)methyl)-2-(4-methylcyclohexyl)acetamide. MS (ESI) m/z: 418.1 [M+H]⁺.

II-75

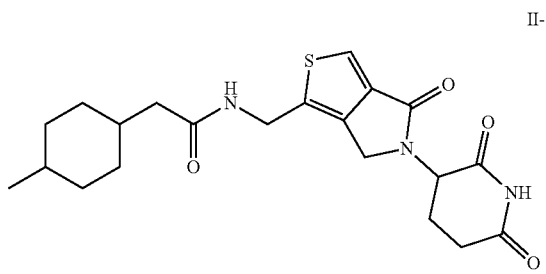

Compound II-76: N-((5-(2,6-dioxopiperidin-3-yl)-4-oxo-5,6-dihydro-4H-thieno[3,4-c]pyrrol-1-yl)methyl)-2-(3-(piperidin-1-yl)phenyl)acetamide. MS (ESI) m/z: 481.2 [M+H]⁺.

Compound II-77: 2-(3-(2-(dimethylamino)ethoxy)phenyl)-N-((5-(2,6-dioxopiperidin-3-yl)-4-oxo-4H-thieno[3,4-c]pyrrol-1-yl)methyl)acetamide. MS (ESI) m/z: 485.1 [M+H]⁺.

II-76

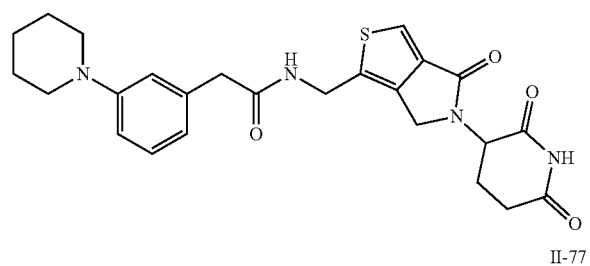

II-77

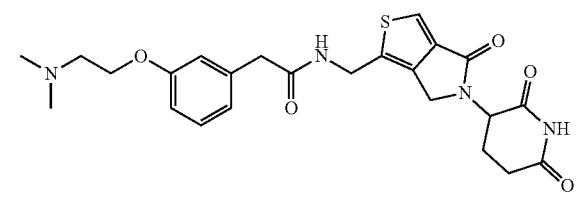

Compound II-78: N-((5-(2,6-dioxopiperidin-3-yl)-4-oxo-5,6-dihydro-4H-thieno[3,4-c]pyrrol-1-yl)methyl)-2-morpholinoacetamide. MS (ESI) m/z: 407.1 [M+H]⁺.

Compound II-79: 2-(3-chloro-4-methylphenyl)-N-((5-(2,6-dioxopiperidin-3-yl)-4-oxo-5,6-dihydro-4H-thieno[2,3-c]pyrrol-2-yl)methyl)acetamide. MS (ESI) m/z: 446.1 [M+H]⁺.

II-78

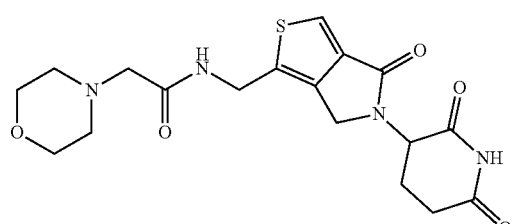

II-79

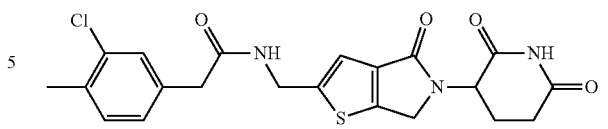

Compound II-80: 2-(4-(2-(dimethylamino)ethoxy)phenyl)-N-((5-(2,6-dioxopiperidin-3-yl)-4-oxo-5,6-dihydro-4H-thieno[3,4-c]pyrrol-1-yl)methyl)acetamide. MS (ESI) m/z: 485.2 [M+H]⁺.

Compound II-81: (3-(2-((3-(3-(dimethylamino)-4-methylphenyl)ureido)methyl)-6-oxo-4,6-dihydro-5H-thieno[2,3-c]pyrrol-5-yl)-2,6-dioxopiperidin-1-yl)methyl D-valinate. MS (ESI) m/z: 585.3 [M+H]⁺.

II-80

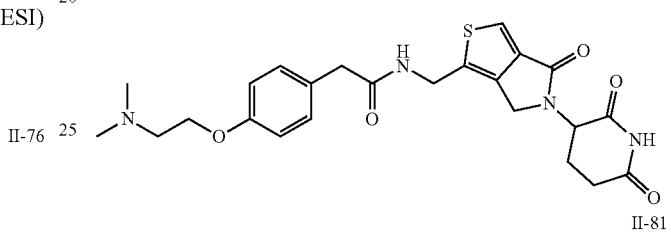

II-81

Compound II-82: (3-(2-((3-(3-chloro-4-methylphenyl)ureido)methyl)-6-oxo-4,6-dihydro-5H-thieno[2,3-c]pyrrol-5-yl)-2,6-dioxopiperidin-1-yl)methyl D-valinate. MS (ESI) m/z: 576.1 [M+H]⁺.

Compound II-83: N-((5-(2,6-dioxopiperidin-3-yl)-4-oxo-5,6-dihydro-4H-thieno[3,4-c]pyrrol-1-yl)methyl)-2-(4-morpholinophenyl)acetamide. MS (ESI) m/z: 483.1 [M+H]⁺.

II-82

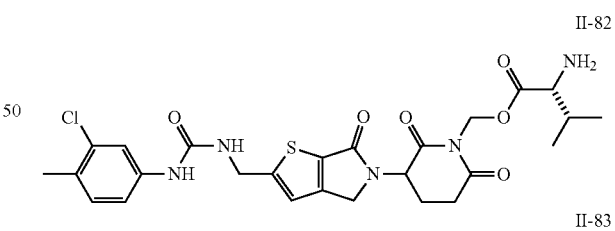

II-83

Compound II-84: 4-(4-(tert-butyl)phenyl)-N-((5-(2,6-dioxopiperidin-3-yl)-4-oxo-5,6-dihydro-4H-thieno[3,4-c]pyrrol-1-yl)methyl)butanamide. MS (ESI) m/z: 482.1 [M+H]⁺.

Compound II-85: 4-(4-(dimethylamino)phenyl)-N-((5-(2,6-dioxopiperidin-3-yl)-4-oxo-5,6-dihydro-4H-thieno[3,4-c]pyrrol-1-yl)methyl)butanamide. MS (ESI) m/z: 469.1 [M+H]+.

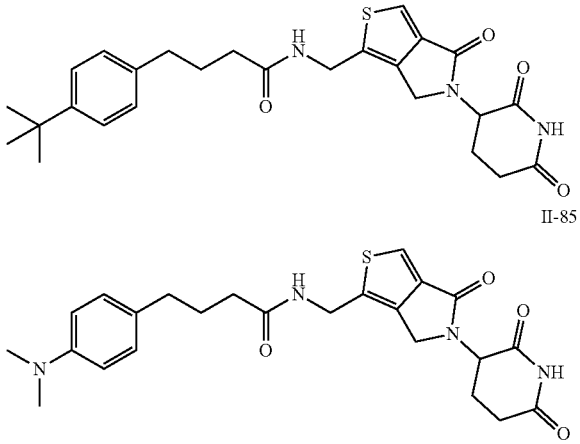

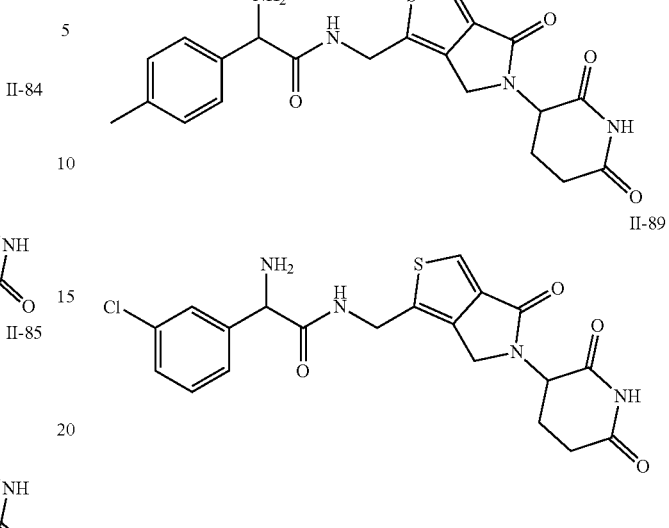

Compound II-86: 4-(4-(tert-butyl)phenyl)-N-((5-(2,6-dioxopiperidin-3-yl)-4-oxo-5,6-dihydro-4H-thieno[3,4-c]pyrrol-1-yl)methyl)-2-methylbutanamide. MS (ESI) m/z: 496.2 [M+H]+.

Compound II-87: 2-(3-chloro-4-methylphenyl)-N-((5-(2,6-dioxopiperidin-3-yl)-4-oxo-5,6-dihydro-4H-thieno[3,4-c]pyrrol-1-yl)methyl)butanamide. MS (ESI) m/z: 474.1 [M+H]+.

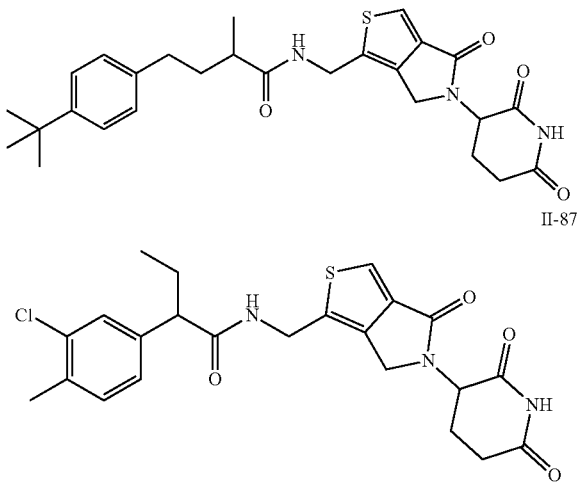

Compound II-88: 2-amino-N-((5-(2,6-dioxopiperidin-3-yl)-4-oxo-5,6-dihydro-4H-thieno[3,4-c]pyrrol-1-yl)methyl)-2-(p-tolyl)acetamide. MS (ESI) m/z: 427.0 [M+H]+.

Compound II-89: 2-amino-2-(3-chlorophenyl)-N-((5-(2,6-dioxopiperidin-3-yl)-4-oxo-5,6-dihydro-4H-thieno[3,4-c]pyrrol-1-yl)methyl)acetamide. MS (ESI) m/z: 447.0 [M+H]+.

Compound II-90: (S)-1-(3-chloro-4-methylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 447.0 [M+H]+.

Compound II-91: (R)-1-(3-chloro-4-methylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 447.0 [M+H]+.

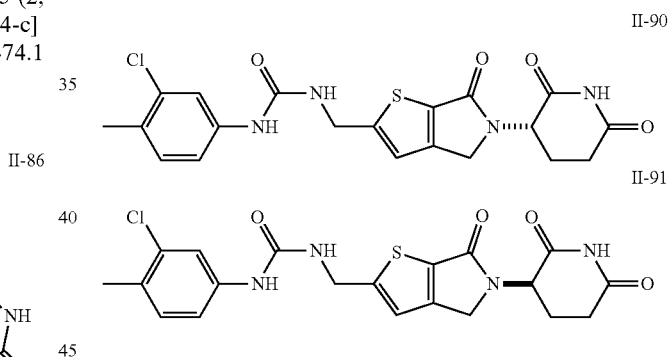

Compound II-92: 2-(4-(tert-butyl)phenyl)-N-((5-(2,6-dioxopiperidin-3-yl)-4-oxo-5,6-dihydro-4H-thieno[3,4-c]pyrrol-1-yl)methyl)propanamide. MS (ESI) m/z: 468.1 [M+H]+.

Compound II-93: N-((5-(2,6-dioxopiperidin-3-yl)-4-oxo-5,6-dihydro-4H-thieno[3,4-c]pyrrol-1-yl)methyl)-2-(4-(pyrrolidin-1-yl)phenyl)acetamide. MS (ESI) m/z: 467.1 [M+H]+.

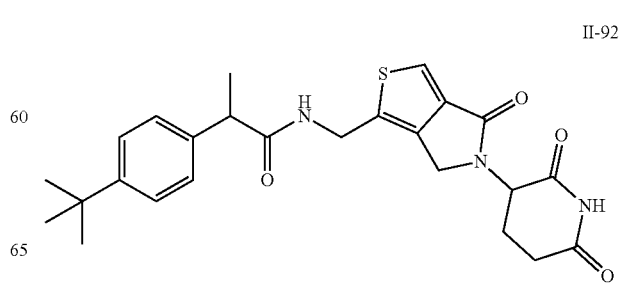

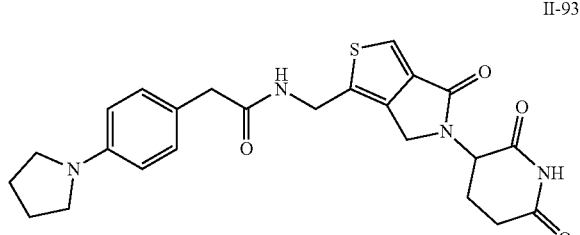
II-93

Compound II-94: 2-(4-(tert-butyl)phenyl)-N-((5-(2,6-dioxopiperidin-3-yl)-4-oxo-5,6-dihydro-4H-thieno[3,4-c]pyrrol-1-yl)methyl)-3-methylbutanamide. MS (ESI) m/z: 496.2 [M+H]⁺.

Compound II-95: 2-(3-chloro-4-methylphenyl)-N-((5-(2,6-dioxopiperidin-3-yl)-4-oxo-5,6-dihydro-4H-thieno[3,4-c]pyrrol-1-yl)methyl)-3-methylbutanamide. MS (ESI) m/z: 488.1 [M+H]⁺.

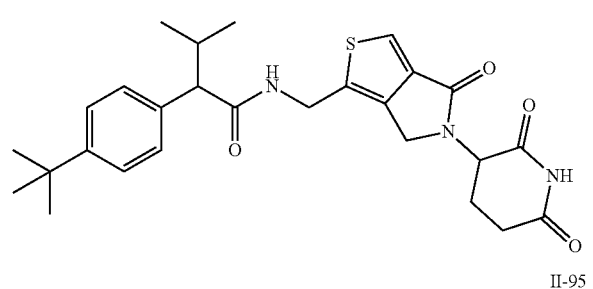
II-94

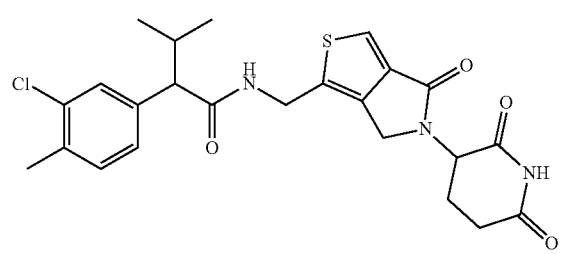
II-95

Compound II-96: 1-(3-(dimethylamino)-4-ethylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 470.1 [M+H]⁺.

Compound II-97: 1-(3-(diethylamino)-4-fluorophenyl)-3-((5-(2,6-dioxopiperidin-3-yl)-6-oxo-5,6-dihydro-4H-thieno[2,3-c]pyrrol-2-yl)methyl)urea. MS (ESI) m/z: 488.1 [M+H]⁺.

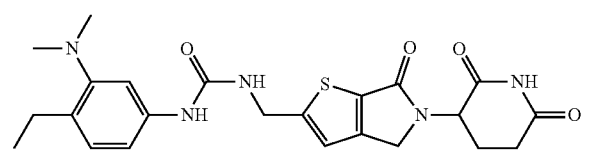
II-96

II-97

Compound II-98: 1-((5-(2,6-dioxopiperidin-3-yl)-6-oxo-5,6-dihydro-4H-thieno[2,3-c]pyrrol-2-yl)methyl)-3-(4-methyl-3-(pyrrolidin-1-yl)phenyl)urea. MS (ESI) m/z: 482.1 [M+H]⁺.

Compound II-99: 1-((5-(2,6-dioxopiperidin-3-yl)-6-oxo-5,6-dihydro-4H-thieno[2,3-c]pyrrol-2-yl)methyl)-3-(3-(pyrrolidin-1-yl)phenyl)urea. MS (ESI) m/z: 468.1 [M+H]⁺.

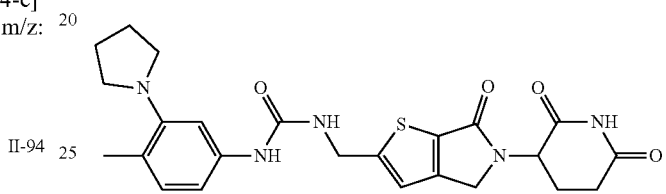
II-98

II-99

Compound II-100: 1-((5-(2,6-dioxopiperidin-3-yl)-6-oxo-5,6-dihydro-4H-thieno[2,3-c]pyrrol-2-yl)methyl)-3-(3-(ethyl(methyl)amino)-4-methylphenyl)urea. MS (ESI) m/z: 470.1 [M+H]⁺.

Compound II-101: 4-(3-chloro-4-methylphenyl)-N-((5-(2,6-dioxopiperidin-3-yl)-4-oxo-5,6-dihydro-4H-thieno[3,4-c]pyrrol-1-yl)methyl)-2-methylbutanamide. MS (ESI) m/z: 489.1 [M+H]⁺.

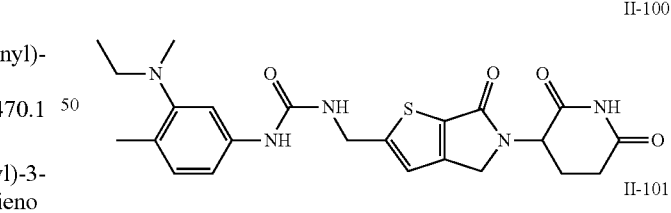
II-100

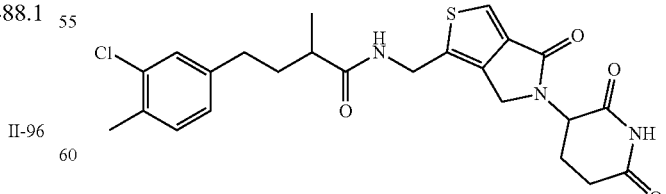
II-101

Compound II-102: (2S)-2-(3-chloro-4-methylphenyl)-N-((5-(2,6-dioxopiperidin-3-yl)-4-oxo-5,6-dihydro-4H-thieno[3,4-c]pyrrol-1-yl)methyl)propanamide. MS (ESI) m/z: 460.0 [M+H]⁺.

Compound II-103: (2R)-2-(3-chloro-4-methylphenyl)-N-((5-(2,6-dioxopiperidin-3-yl)-4-oxo-5,6-dihydro-4H-thieno[3,4-c]pyrrol-1-yl)methyl)propanamide. MS (ESI) m/z: 460.0 [M+H]+.

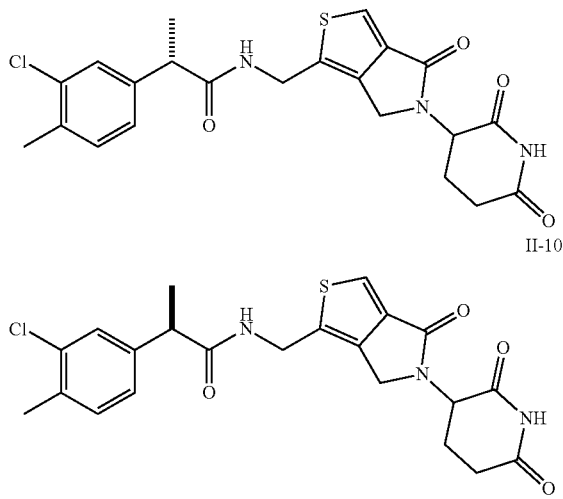

Compound II-104: (S)-4-(3-chloro-4-methylphenyl)-N-((5-(2,6-dioxopiperidin-3-yl)-4-oxo-5,6-dihydro-4H-thieno[3,4-c]pyrrol-1-yl)methyl)-2,2-dimethylbutanamide. MS (ESI) m/z: 502.1 and 504.1 [M+H]+.

Compound II-105: di-tert-butyl ((3-(2-((3-(3-(dimethylamino)-4-methylphenyl)ureido)-methyl)-6-oxo-4,6-dihydro-5H-thieno[2,3-c]pyrrol-5-yl)-2,6-dioxopiperidin-1-yl)methyl) phosphate. MS (ESI) m/z: 678.2 [M+H]+.

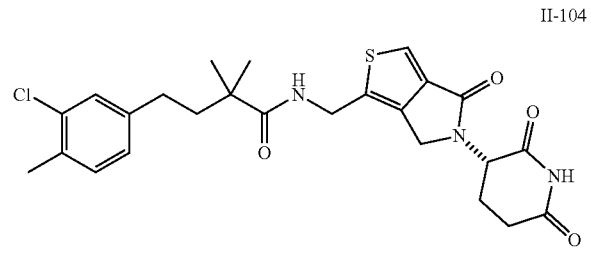

Compound II-106: N-((5-(2,6-dioxopiperidin-3-yl)-4-oxo-5,6-dihydro-4H-thieno[3,4-c]pyrrol-1-yl)methyl)-2-(4-isopropylphenyl)-3-methylbutanamide. MS (ESI) m/z: 482.2 [M+H]+.

Compound II-107: N-((5-(2,6-dioxopiperidin-3-yl)-6-oxo-5,6-dihydro-4H-thieno[2,3-c]pyrrol-2-yl)methyl)-2-(perfluorophenyl)acetamide. MS (ESI) m/z: 488.0 [M+H]+.

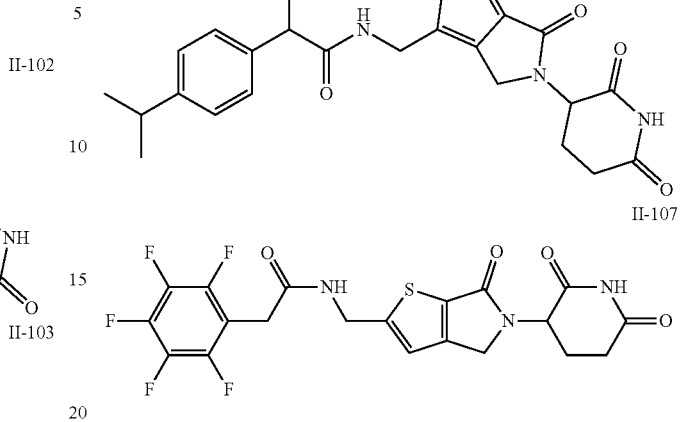

Compound II-108: 2-(dimethylamino)-N-((5-(2,6-dioxopiperidin-3-yl)-4-oxo-5,6-dihydro-4H-thieno[3,4-c]pyrrol-1-yl)methyl)-2-(2-fluorophenyl)acetamide. MS (ESI) m/z: 459.1 [M+H]+.

Compound II-109: N-((5-(2,6-dioxopiperidin-3-yl)-4-oxo-5,6-dihydro-4H-thieno[3,4-c]pyrrol-1-yl)methyl)-4-phenylbutanamide. MS (ESI) m/z: 426.1 [M+H]+.

Compound II-110: 1-((5-(2,6-dioxopiperidin-3-yl)-6-oxo-5,6-dihydro-4H-thieno[2,3-c]pyrrol-2-yl)methyl)-3-phenylthiourea. MS (ESI) m/z: 415.0 [M+H]+.

Compound II-11: 1-((5-(2,6-dioxopiperidin-3-yl)-4-oxo-5,6-dihydro-4H-thieno[3,4-c]pyrrol-1-yl)methyl)-3-(4-(trifluoromethoxy)phenyl)thiourea. MS (ESI) m/z: 498.9 [M+H]+.

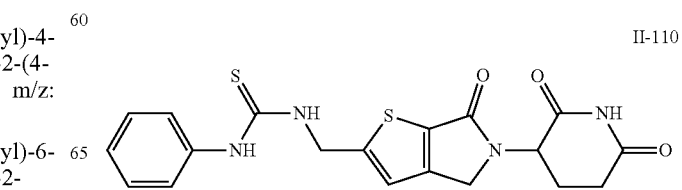

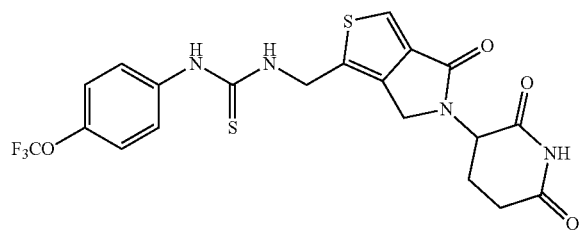

II-111

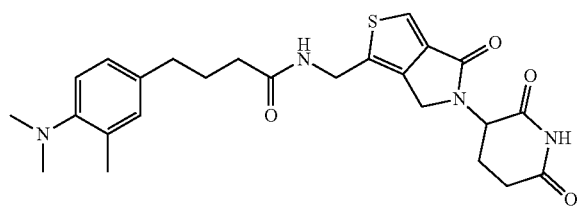

II-115

Compound II-112: 2-amino-N-((5-(2,6-dioxopiperidin-3-yl)-4-oxo-5,6-dihydro-4H-thieno[3,4-c]pyrrol-1-yl)methyl)-2-(4-propoxyphenyl)acetamide. MS (ESI) m/z: 470.9 [M+H]$^+$.

Compound II-113: 2-amino-N-((5-(2,6-dioxopiperidin-3-yl)-4-oxo-5,6-dihydro-4H-thieno[3,4-c]pyrrol-1-yl)methyl)-2-(4-hydroxyphenyl)acetamide. MS (ESI) m/z: 428.9 [M+H]$^+$.

Compound II-116: N-((5-(2,6-dioxopiperidin-3-yl)-6-oxo-5,6-dihydro-4H-thieno[2,3-c]pyrrol-2-yl)methyl)-2-(3-fluoro-2-methoxyphenyl)acetamide. MS (ESI) m/z: 446.1 [M+H]$^+$.

Compound II-117: 4-bromo-2,5-dichloro-N-((5-(2,6-dioxopiperidin-3-yl)-4-oxo-5,6-dihydro-4H-thieno[3,4-c]pyrrol-1-yl)methyl)thiophene-3-sulfonamide. MS (ESI) m/z: 573.8 [M+H]$^+$.

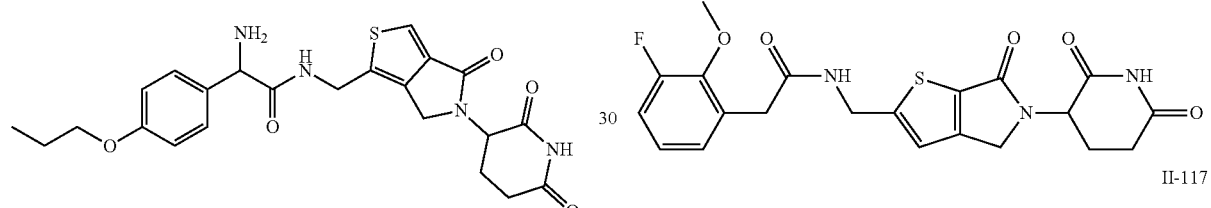

II-112

II-116

II-113

II-117

Compound II-114: 1-(3-(dimethylamino)-4-methylphenyl)-3-((5-(2,6-dioxopiperidin-3-yl)-4,6-dioxo-5,6-dihydro-4H-thieno[2,3-c]pyrrol-2-yl)methyl)urea. MS (ESI) m/z: 470.1 [M+H]$^+$.

Compound II-115: 4-(4-(dimethylamino)-3-methylphenyl)-N-((5-(2,6-dioxopiperidin-3-yl)-4-oxo-5,6-dihydro-4H-thieno[3,4-c]pyrrol-1-yl)methyl)butanamide. MS (ESI) m/z: 483.1 [M+H]$^+$.

Compound II-118: methyl 5-chloro-3-(N-((5-(2,6-dioxopiperidin-3-yl)-4-oxo-5,6-dihydro-4H-thieno[3,4-c]pyrrol-1-yl)methyl)sulfamoyl)thiophene-2-carboxylate. MS (ESI) m/z: 517.9 [M+H]$^+$.

Compound II-119: N-((5-(2,6-dioxopiperidin-3-yl)-4-oxo-5,6-dihydro-4H-thieno[3,4-c]pyrrol-1-yl)methyl)-4-methyl-1,2,3-thiadiazole-5-carboxamide. MS (ESI) m/z: 406.0 [M+H]$^+$.

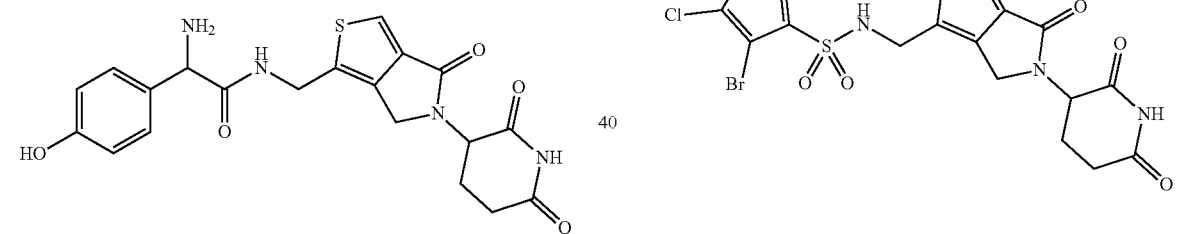

II-114

II-118

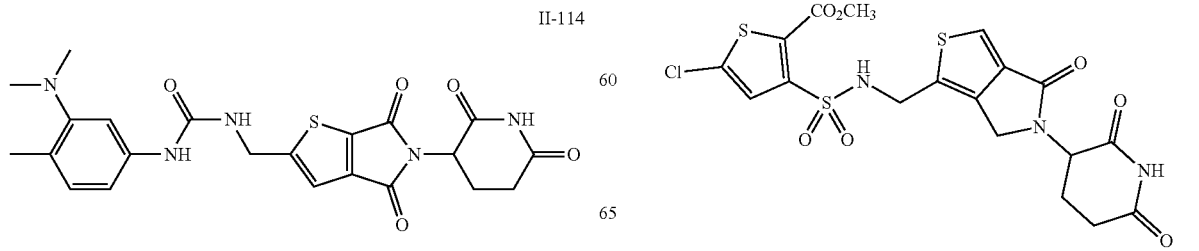

II-119

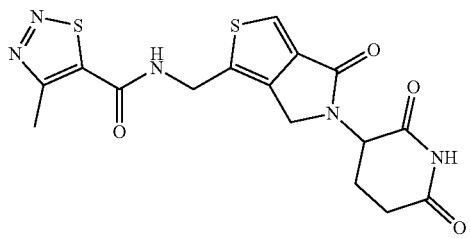

Compound II-120: N-(5-(N-((5-(2,6-dioxopiperidin-3-yl)-4-oxo-5,6-dihydro-4H-thieno[3,4-c]pyrrol-1-yl)methyl)sulfamoyl)-4-methylthiazol-2-yl)acetamide. MS (ESI) m/z: 498.2 [M+H]$^+$.

Compound II-121: N-((5-(2,6-dioxopiperidin-3-yl)-4-oxo-5,6-dihydro-4H-thieno[3,4-c]pyrrol-1-yl)methyl)-2,3,4,5,6-pentafluorobenzenesulfonamide. MS (ESI) m/z: 509.9 [M+H]$^+$.

II-120

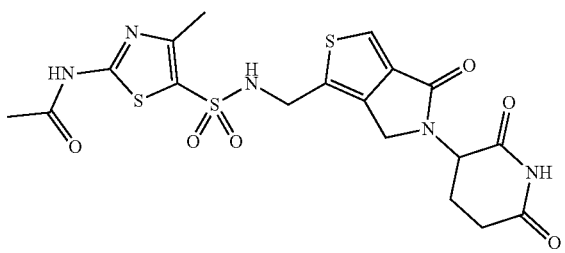

II-121

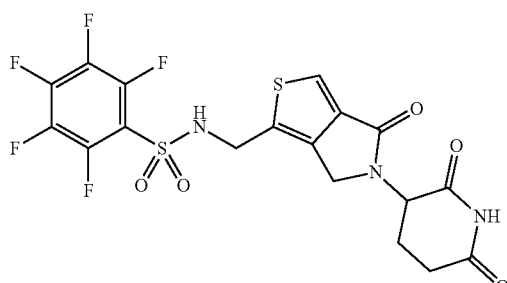

Compound II-122: N-((5-(2,6-dioxopiperidin-3-yl)-4-oxo-5,6-dihydro-4H-thieno[3,4-c]pyrrol-1-yl)methyl)-1-methyl-1H-imidazole-4-sulfonamide. MS (ESI) m/z: 424.0 [M+H]$^+$.

Compound II-123: 1-((5-(2,6-dioxopiperidin-3-yl)-4-oxo-5,6-dihydro-4H-thieno[3,4-c]pyrrol-1-yl)methyl)-3-(2,3,5,6-tetrachlorophenyl)thiourea. MS (ESI) m/z: 552.9 and 554.9 [M+H]$^+$.

II-122

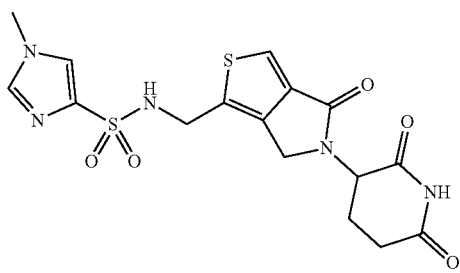

II-123

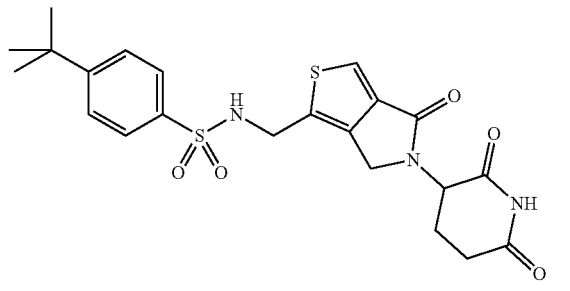

Compound II-124: 4-(tert-butyl)-N-((5-(2,6-dioxopiperidin-3-yl)-4-oxo-5,6-dihydro-4H-thieno[3,4-c]pyrrol-1-yl)methyl)benzenesulfonamide. MS (ESI) m/z: 476.1 [M+H]$^+$.

Compound II-125: methyl 3-(3-((5-(2,6-dioxopiperidin-3-yl)-4-oxo-5,6-dihydro-4H-thieno[3,4-c]pyrrol-1-yl)methyl)ureido)thiophene-2-carboxylate. MS (ESI) m/z: 463.0 [M+H]$^+$.

II-124

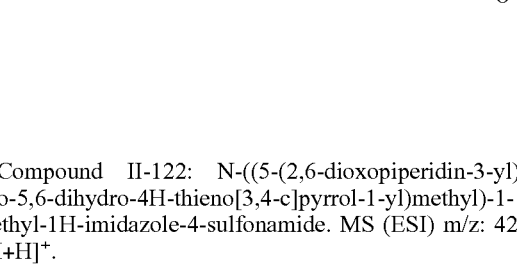

II-125

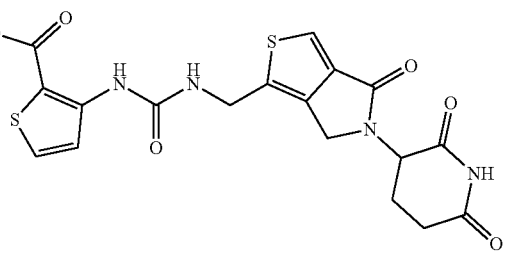

Compound II-126: N-((5-(2,6-dioxopiperidin-3-yl)-4-oxo-5,6-dihydro-4H-thieno[3,4-c]pyrrol-1-yl)methyl)thiazole-2-carboxamide. MS (ESI) m/z: 391.0 [M+H]$^+$.

Compound II-127: 1-(4-(tert-butyl)phenyl)-N-((5-(2,6-dioxopiperidin-3-yl)-4-oxo-5,6-dihydro-4H-thieno[3,4-c]pyrrol-1-yl)methyl)cyclopropane-1-carboxamide. MS (ESI) m/z: 480.1 [M+H]$^+$.

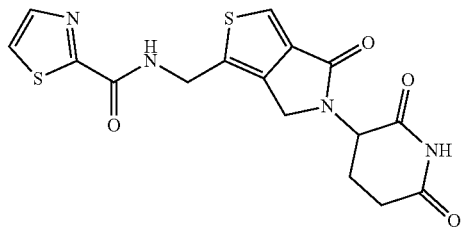

II-126

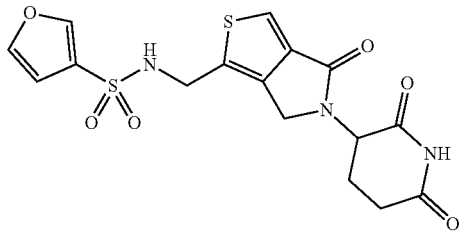

II-130

II-127

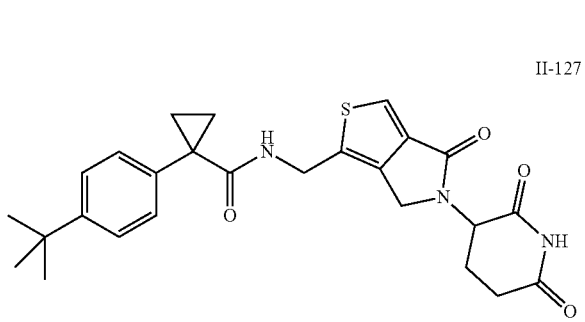

II-131

Compound II-128: 1-(4-(tert-butyl)phenyl)-N-((5-(2,6-dioxopiperidin-3-yl)-4-oxo-5,6-dihydro-4H-thieno[3,4-c]pyrrol-1-yl)methyl)methanesulfonamide. MS (ESI) m/z: 490.1 [M+H]+.

Compound II-129: 2-(4-(tert-butyl)phenyl)-N-((5-(2,6-dioxopiperidin-3-yl)-4-oxo-5,6-dihydro-4H-thieno[3,4-c]pyrrol-1-yl)methyl)-2,2-difluoroacetamide. MS (ESI) m/z: 490.1 [M+H]+.

Compound II-132: 2-(4-(tert-butyl)phenyl)-N-((5-(2,6-dioxopiperidin-3-yl)-4-oxo-5,6-dihydro-4H-thieno[3,4-c]pyrrol-1-yl)methyl)-2-hydroxyacetamide. MS (ESI) m/z: 470.1 [M+H]+.

Compound II-133: 2-(4-(tert-butyl)phenyl)-N-((5-(2,6-dioxopiperidin-3-yl)-4-oxo-5,6-dihydro-4H-thieno[3,4-c]pyrrol-1-yl)methyl)-3,3,3-trifluoro-2-hydroxypropanamide. MS (ESI) m/z: 538.1 [M+H]+.

II-128

II-132

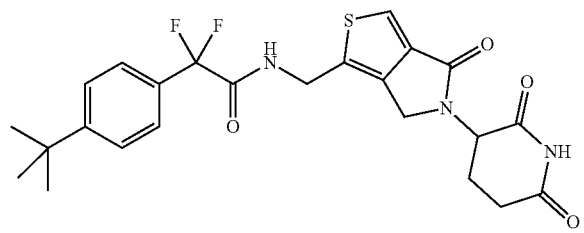

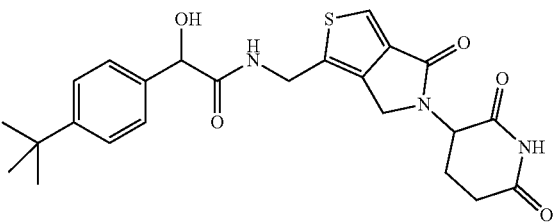

II-129

II-133

Compound II-130: N-((5-(2,6-dioxopiperidin-3-yl)-4-oxo-5,6-dihydro-4H-thieno[3,4-c]pyrrol-1-yl)methyl)furan-3-sulfonamide. MS (ESI) m/z: 410.0 [M+H]+.

Compound II-131: 4-(tert-butyl)-N-(2-(5-(2,6-dioxopiperidin-3-yl)-4-oxo-5,6-dihydro-4H-thieno[3,4-c]pyrrol-1-yl)ethyl)benzenesulfonamide. MS (ESI) m/z: 490.1 [M+H]+.

Compound II-134: 3-bromo-N-((5-(2,6-dioxopiperidin-3-yl)-6-oxo-5,6-dihydro-4H-thieno[2,3-c]pyrrol-2-yl)methyl)furan-2-carboxamide. MS (ESI) m/z: 452.0 [M+H]+.

Compound II-135: 4-bromo-N-((5-(2,6-dioxopiperidin-3-yl)-6-oxo-5,6-dihydro-4H-thieno[2,3-c]pyrrol-2-yl)methyl)-2-(trifluoromethoxy)benzenesulfonamide. MS (ESI) m/z: 583.9 [M+H]+.

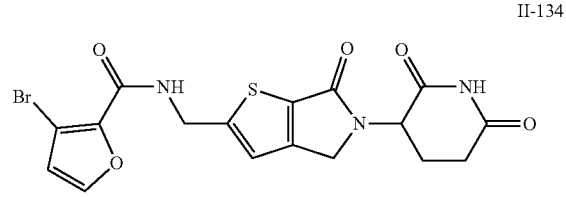

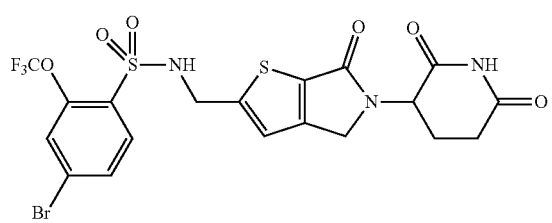

Compound II-136: 2-chloro-N-((5-(2,6-dioxopiperidin-3-yl)-6-oxo-5,6-dihydro-4H-thieno[2,3-c]pyrrol-2-yl)methyl)thiazole-5-carboxamide. MS (ESI) m/z: 424.9 and 426.9 [M+H]+.

Compound II-137: methyl 2-(3-((5-(2,6-dioxopiperidin-3-yl)-6-oxo-5,6-dihydro-4H-thieno[2,3-c]pyrrol-2-yl)methyl)ureido)thiophene-3-carboxylate. MS (ESI) m/z: 463.0 [M+H]+.

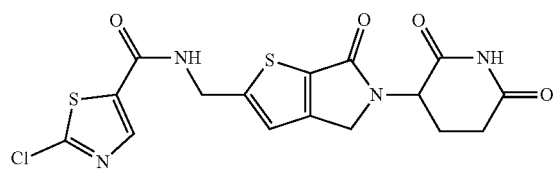

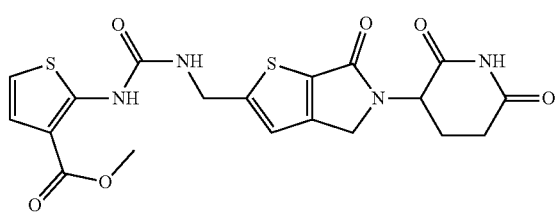

Compound II-138: 1-((5-(2,6-dioxopiperidin-3-yl)-6-oxo-5,6-dihydro-4H-thieno[2,3-c]pyrrol-2-yl)methyl)-3-(6-morpholinopyridin-3-yl)urea. MS (ESI) m/z: 485.1 [M+H]+.

Compound II-139: 1-(1,3-dimethyl-1H-pyrazol-5-yl)-3-((5-(2,6-dioxopiperidin-3-yl)-6-oxo-5,6-dihydro-4H-thieno[2,3-c]pyrrol-2-yl)methyl)urea. MS (ESI) m/z: 417.0 [M+H]+.

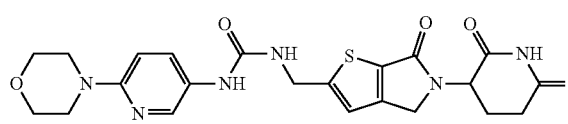

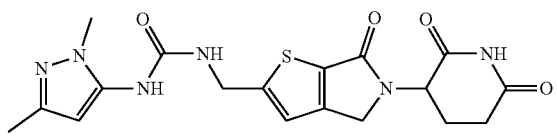

Compound II-140: N-((5-(2,6-dioxopiperidin-3-yl)-6-oxo-5,6-dihydro-4H-thieno[2,3-c]pyrrol-2-yl)methyl)-3,5-dimethylisoxazole-4-carboxamide. MS (ESI) m/z: 403.2 [M+H]+.

Compound II-141: N-(5-(N-((5-(2,6-dioxopiperidin-3-yl)-6-oxo-5,6-dihydro-4H-thieno[2,3-c]pyrrol-2-yl)methyl)sulfamoyl)-4-methylthiazol-2-yl)acetamide. MS (ESI) m/z: 498.0 [M+H]+.

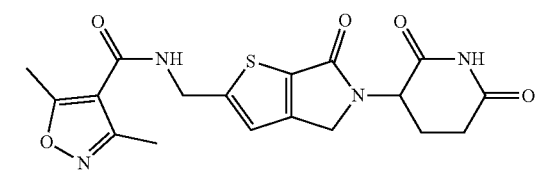

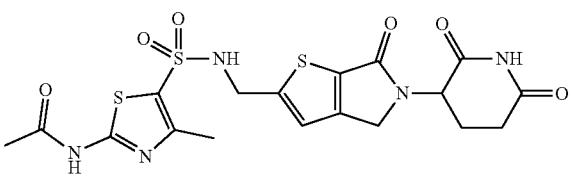

Compound II-142: N-((5-(2,6-dioxopiperidin-3-yl)-6-oxo-5,6-dihydro-4H-thieno[2,3-c]pyrrol-2-yl)methyl)-2,5-dimethylfuran-3-sulfonamide. MS (ESI) m/z: 438.0 [M+H]+.

Compound II-143: 5-(N-((5-(2,6-dioxopiperidin-3-yl)-6-oxo-5,6-dihydro-4H-thieno[2,3-c]pyrrol-2-yl)methyl)sulfamoyl)-2-methoxy-N,N-dimethylbenzamide. MS (ESI) m/z: 521.1 [M+H]+.

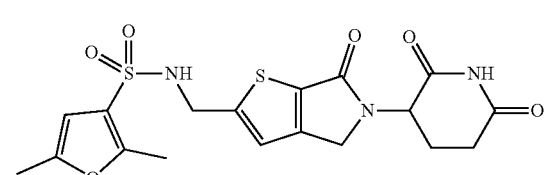

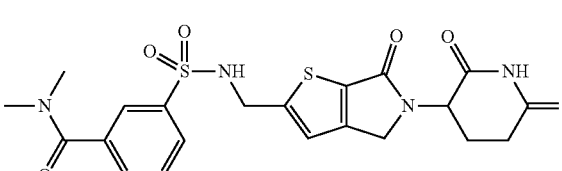

Compound II-144: N-((5-(2,6-dioxopiperidin-3-yl)-6-oxo-5,6-dihydro-4H-thieno[2,3-c]pyrrol-2-yl)methyl)-2-(propylthio)nicotinamide. MS (ESI) m/z: 459.0 [M+H]+.

Compound II-145: 1-((5-(2,6-dioxopiperidin-3-yl)-4-oxo-5,6-dihydro-4H-thieno[3,4-c]pyrrol-1-yl)methyl)-3-(3-phenoxypropyl)urea. MS (ESI) m/z: 457.2 [M+H]⁺.

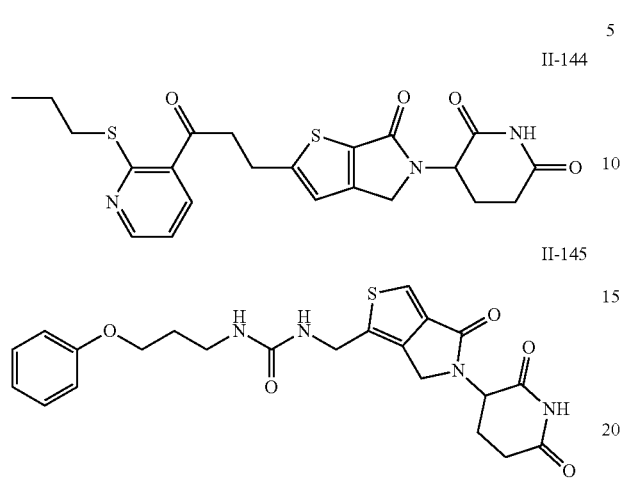

Compound II-146: N-((5-(2,6-dioxopiperidin-3-yl)-4-oxo-5,6-dihydro-4H-thieno[3,4-c]pyrrol-1-yl)methyl)-4-(4-morpholinophenyl)butanamide. MS (ESI) m/z: 511.1 [M+H]⁺.

Compound II-147: 2-(4-(tert-butyl)phenyl)-N-((5-(2,6-dioxopiperidin-3-yl)-4-oxo-5,6-dihydro-4H-thieno[3,4-c]pyrrol-1-yl)methyl)-3,3,3-trifluoropropanamide. MS (ESI) m/z: 522.3 [M+H]⁺; ¹HNMR (400 MHz, DMSO-d6) δ 10.98 (s, 1H), 8.95 (s, 1H), 7.87 (s, 1H), 7.42 (m, 4H), 5.00 (dd, 1H), 4.46 (m, 3H), 4.18 (m, 2H), 2.29 (m, 1H), 2.89 (m, 1H), 2.56 (s, 1H), 2.33 (m, 1H), 1.91 (m, 1H), 1.27 (s, 9H).

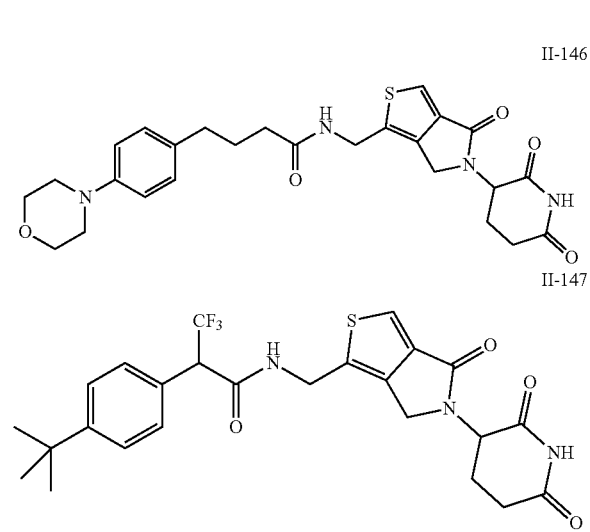

Compound II-148: 1-(4-(tert-butyl)phenyl)-3-((5-(2,6-dioxopiperidin-3-yl)-4-oxo-5,6-dihydro-4H-thieno[3,4-c]pyrrol-1-yl)methyl)urea. MS (ESI) m/z: 455.1 [M+H]⁺; HNMR (400 MHz, DMSO-d₆) δ 10.97 (s, 1H), 8.55 (s, 1H), 7.86 (s, 1H), 7.31-7.22 (m, 4H), 6.72 (t, J=5.2 Hz, 1H), 5.00 (dd, J=4.8, 13.2 Hz, 1H), 4.43-4.20 (m, 4H), 2.92-2.83 (m, 1H), 2.60-2.56 (m, 1H), 2.34-2.24 (m, 1H), 1.99-1.96 (m, 1H), 1.24 (s, 9H).

Compound II-150: 1-(2,3-dimethylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 427.1 [M+H]⁺.

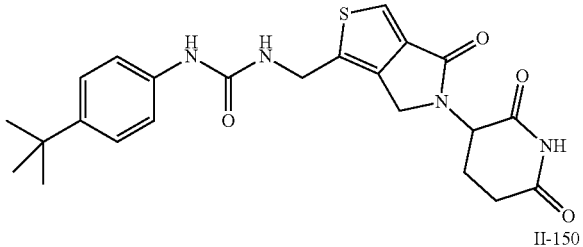

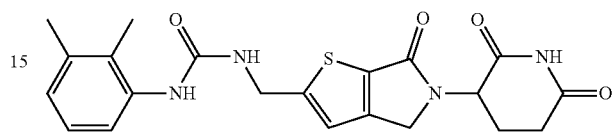

Compound II-151: 1-(2,4-dimethylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 427.1 [M+H]⁺.

Compound II-152: 1-(2,5-dimethylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 427.1 [M+H]⁺.

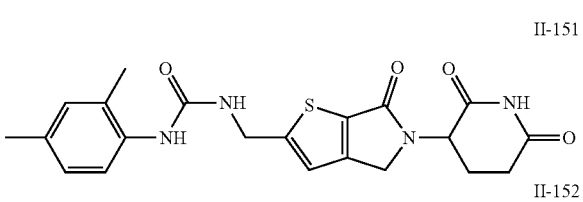

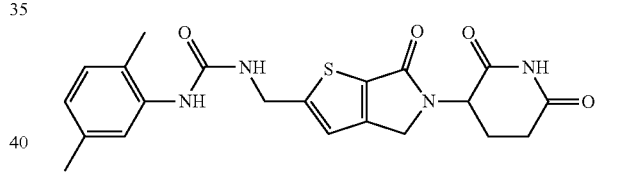

Compound II-153: 1-([1,1'-biphenyl]-4-yl)-3-((5-(2,6-dioxopiperidin-3-yl)-6-oxo-5,6-dihydro-4H-thieno[2,3-c]pyrrol-2-yl)methyl)urea. MS (ESI) m/z: 475.1 [M+H]⁺.

Compound II-154: 1-((5-(2,6-dioxopiperidin-3-yl)-6-oxo-5,6-dihydro-4H-thieno[2,3-c]pyrrol-2-yl)methyl)-3-(4-methoxyphenyl)urea. MS (ESI) m/z: 429.1 [M+H]⁺.

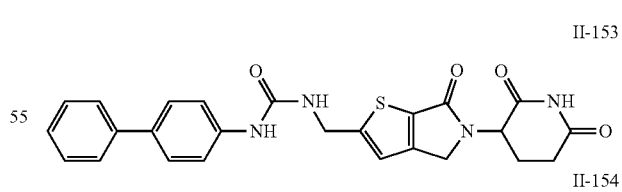

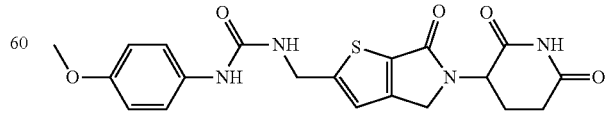

Compound II-155: 1-(4-cyanophenyl)-3-((5-(2,6-dioxopiperidin-3-yl)-6-oxo-5,6-dihydro-4H-thieno[2,3-c]pyrrol-2-yl)methyl)urea. MS (ESI) m/z: 424.0 [M+H]⁺.

Compound II-156: 1-(2,6-dimethylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 427.0 [M+H]⁺.

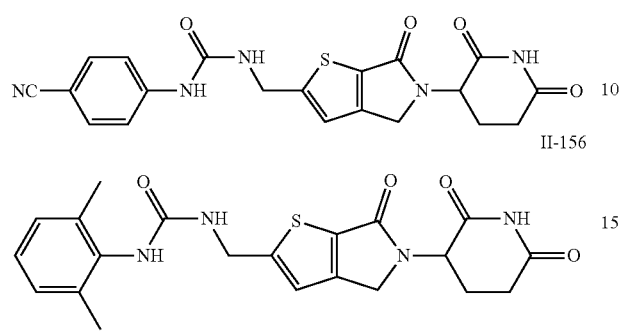

Compound II-157: 1-((5-(2,6-dioxopiperidin-3-yl)-6-oxo-5,6-dihydro-4H-thieno[2,3-c]pyrrol-2-yl)methyl)-3-phenethylthiourea. MS (ESI) m/z: 443.0 [M+H]⁺.

Compound II-158: 1-(2-trifluoromethylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 467.0 [M+H]⁺.

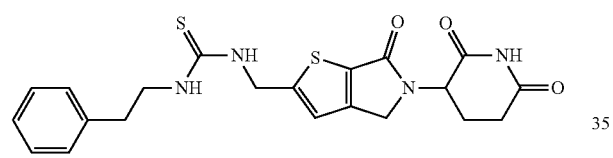

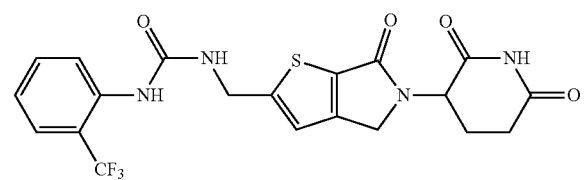

Compound II-159: 1-(3-cyanophenyl)-3-((5-(2,6-dioxopiperidin-3-yl)-6-oxo-5,6-dihydro-4H-thieno[2,3-c]pyrrol-2-yl)methyl)urea. MS (ESI) m/z: 424.1 [M+H]⁺.

Compound II-160: 1-(4-chloro-2-trifluoromethylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 501.0 [M+H]⁺; ¹HNMR (400 MHz, DMSO-d₆) δ 10.94 (s, 1H), 8.10 (s, 1H), 7.96 (d, J=8.8 Hz, 1H), 7.77 (t, J=5.6 Hz, 1H), 7.66-7.68 (m, 2H), 7.14 (s, 1H), 4.98 (dd, J=4.8, 13.2 Hz, 1H), 4.56 (d, J=5.6 Hz, 2H), 4.20-4.37 (m, 2H), 2.84-2.89 (m, 1H), 2.55-2.60 (m, 1H), 2.32-2.36 (m, 1H), 1.97-2.00 (m, 1H).

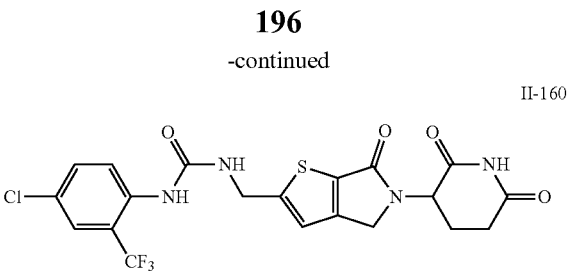

Compound II-161: 1-(2,4,6-trimethylphenyl)-3-((5-(2,6-dioxopiperidin-3-yl)-6-oxo-5,6-dihydro-4H-thieno[2,3-c]pyrrol-2-yl)methyl)urea. MS (ESI) m/z: 441.1 [M+H]⁺; ¹HNMR (400 MHz, DMSO-d₆) δ 10.94 (s, 1H), 7.56 (s, 1H), 7.06 (s, 1H), 6.85 (s, 2H), 6.70 (brs, 1H), 4.98 (dd, J=4.8, 13.2 Hz, 1H), 4.47 (d, J=5.6 Hz, 2H), 4.17-4.35 (m, 2H), 2.84-2.93 (m, 1H), 2.55-2.59 (m, 1H), 2.36-2.38 (m, 1H), 2.32 (s, 1H), 2.28 (s, 6H), 1.96-2.00 (m, 1H).

Compound II-162: 1-(3,5-dimethoxyphenyl)-3-((5-(2,6-dioxopiperidin-3-yl)-6-oxo-5,6-dihydro-4H-thieno[2,3-c]pyrrol-2-yl)methyl)urea. MS (ESI) m/z: 459.1 [M+H]⁺.

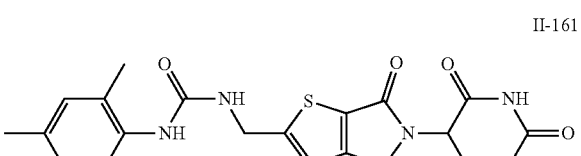

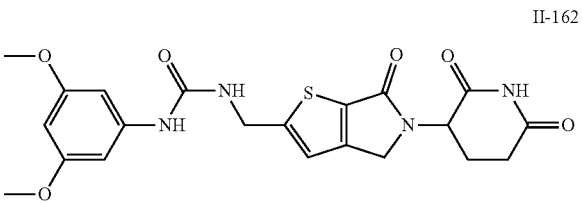

Compound II-163: 1-((5-(2,6-dioxopiperidin-3-yl)-6-oxo-5,6-dihydro-4H-thieno[2,3-c]pyrrol-2-yl)methyl)-3-(naphthalen-1-yl)urea. MS (ESI) m/z: 449.0 [M+H]⁺.

Compound II-164: N-((2-(2,6-dioxopiperidin-3-yl)-1-oxoisoindolin-5-yl)methyl)-2,2-difluoro-2-(4-(1-(trifluoromethyl)cyclopropyl)phenyl)acetamide. MS (ESI) m/z: 536.1 [M+H]⁺; ¹HNMR (400 MHz, DMSO-d₆) δ 10.9 (s, 1H), 9.68 (t, 1H), 7.35-7.68 (m, 7H), 5.09 (dd, 1H), 4.25-4.46 (m, 4H), 2.92 (m, 1H), 2.64 (m, 1H), 2.40 (m, 1H), 2.03 (m, 1H).

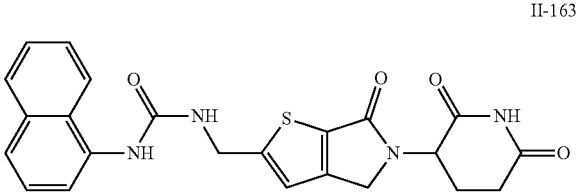

-continued

II-164

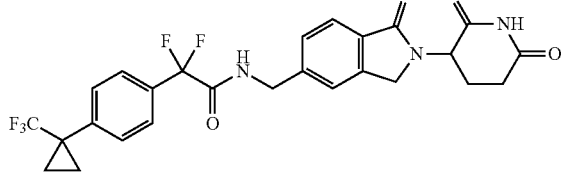

Example B1

Protein Degradation Assays

MV-4-11 cells were grown in RPMI 1640 media supplemented with 10% fetal bovine serum, streptomycin, and penicillin. The cells were cultured at approximately $10^6$ cells per mL and incubated in DMSO or a compound for 6-8 h. Whole cell extracts were prepared using a radioimmunoprecipitation assay (RIPA) buffer. Briefly, $3\times10^6$ cells were washed once in PBS, and the cell pellets were resuspended in the RIPA buffer and incubated for 15 min on ice. Cells debris was removed by centrifugation and the cleared whole cell lysates were transferred to new tubes for further analysis.

For Western blot analysis, whole cell protein extracts were separated on 4-12% SDS-polyacrylamide gels, transferred to nitrocellulose, and probed with primary antibodies. Membranes were subsequently washed and probed with IRDYE® secondary antibodies. The signal was detected using an ODYSSEY® Imaging System.

The following antibodies were used in the assays described herein: anti-eRF3/GSPT1: Abcam, ab126090 (Cambridge, Mass.); anti-Ikaros: Abcam, ab191394 (Cambridge, Mass.); anti-CK1α: Abcam, ab108296 (Cambridge, Mass.); β-actin ($8H_{10}D10$) mouse monoclonal antibody: Cell Signaling Technology, #3700 (Danvers, Mass.); IRDYE® 680RD goat anti-rabbit antibody: LI-COR, 926-68071 (Lincoln, Nebr.); and IRDYE® 800CW goat anti-mouse antibody: LI-COR, 926-32210 (Lincoln, Nebr.).

The protein degradation results are summarized in Table 1, wherein A represents a value no less than 80%, B represents a value less than 80% but no less than 50%, C represents a value less than 50% but no less than 25%, and D represents a value less than 25% protein degradation at a compound concentration of 0.1 μM.

TABLE 1

| Protein Degradation | | | |
|---|---|---|---|
| Compound | IKAROS | CK1α | GSPT1 |
| I-1 | A | B | B |
| I-2 | A | B | A |
| I-3 | A | A | B |
| I-4 | A | | C |
| I-5 | A | C | A |
| II-1 | | | B |

Example B2

Cytokine Modulation Assays

Frozen primary blood mononuclear cells (PBMCs) or frozen CD14+ mobilized peripheral blood monocytes were quick thawed, washed once with RPMI-1640 (10% FBS/1% Pen-Strep), and plated in 96 well plates at 200,000 cells per well. The cells were pretreated with DMSO only or with a compound for 1 h and then induced with 100 ng/mL lipopolysaccharide (LPS) for 18-24 h. The supernatant was analyzed for IL-1β, IL-6, and TNFα using Meso Scale assays. The negative control wells were treated with DMSO. The results are summarized in Table 2, wherein A represents a value no less than 80%, B represents a value less than 80% but no less than 50%, C represents a value less than 50% but no less than 25%, and D represents a value less than 25% inhibition at the specified compound concentration.

TABLE 2

| Cytokine Inhibition | | | | | |
|---|---|---|---|---|---|
| | IL-1β | | IL-6 | TNF-α | |
| Compound | 0.1 μM | 1 μM | 0.1 μM | 0.1 μM | 1 μM |
| I-1 | A | | B | A | |
| I-2 | | | | | |
| I-3 | A | A | C | A | A |
| I-4 | A | A | | A | A |
| I-5 | | | | | |
| II-1 | | C | | | C |

For the IL-2 analysis, 96 well plates were precoated with 1 μg/mL anti-human CD3 antibody (OKT3, eBioscience Inc., San Diego, Calif.). After washed with PBS, the compound was added (50 μL/well), followed by addition of PBMCs diluted at 3-4 million cells/mL (150 μL/well). The plates were incubated for 24 h and the supernatants were collected for IL-2 analysis. IL-2 activity was measured as fold difference from the DMSO control. At a concentration of 0.01 μM, compounds I-1 and I-3 stimulated IL-2 production with 3.7 and 3.9 fold change, respectively, over the DMSO control.

Example B3

Cell Viability Assays

MOLM-13 cells were cultured in RPMI 1640 media supplemented with 10% fetal bovine serum, streptomycin, and penicillin. The cells were plated in white walled 96-well plates at 2,500 cells/well. The cells were incubated in DMSO (control) or an indicated compound for 3 days at 37° C. and 5% $CO_2$. Following the incubation period, 100 μL of CELLTITER-GLO® (CTG) reagent was added to each well. Following a 10 minutes incubation with shaking, luminescence was measured using an ENVISION® Multimode plate reader. Antiproliferative activity of compounds in the MOLM-13 cell viability assay is summarized in Table 3, wherein A represents a value no less than 80%, B represents a value less than 80% but no less than 50%, C represents a value less than 50% but no less than 25%, and D represents a value less than 25% inhibition at a concentration of 1 μM.

TABLE 3

| Antiproliferative Activity | |
|---|---|
| Compound | Activity |
| I-1 | A |
| I-2 | A |
| I-3 | A |
| I-4 | A |

TABLE 3-continued

Antiproliferative Activity

| Compound | Activity |
|---|---|
| I-5 | A |
| I-6 | C |
| I-7 | D |
| I-8 | D |
| I-9 | D |
| I-10 | A |
| I-11 | D |
| I-12 | D |
| I-13 | D |
| I-14 | C |
| I-15 | C |
| I-16 | D |
| I-17 | D |
| I-18 | D |
| I-19 | A |
| I-20 | D |
| I-21 | C |
| I-22 | D |
| I-23 | D |
| I-24 | C |
| I-25 | D |
| I-26 | D |
| I-27 | A |
| I-28 | A |
| I-29 | A |
| I-30 | A |
| I-31 | D |
| I-32 | A |
| I-33 | A |
| I-34 | D |
| I-35 | D |
| I-36 | C |
| I-37 | A |
| I-38 | D |
| I-39 | A |
| I-40 | D |
| I-41 | A |
| I-42 | B |
| I-43 | D |
| I-44 | A |
| I-45 | B |
| I-46 | C |
| I-47 | D |
| I-48 | D |
| I-49 | B |
| I-50 | D |
| I-51 | D |
| I-52 | C |
| I-53 | A |
| I-54 | A |
| I-55 | A |
| I-56 | D |
| I-57 | D |
| I-58 | B |
| I-59 | C |
| I-60 | B |
| I-61 | D |
| I-62 | A |
| I-64 | A |
| I-65 | D |
| I-66 | D |
| I-67 | C |
| I-68 | D |
| I-72 | D |
| I-73 | D |
| I-74 | D |
| I-75 | C |
| I-76 | D |
| I-77 | D |
| I-78 | C |
| I-79 | D |
| I-80 | D |
| I-81 | C |
| I-82 | C |
| I-83 | A |
| I-84 | C |
| I-85 | B |
| I-86 | B |
| I-87 | C |
| I-88 | D |
| I-89 | A |
| I-90 | D |
| I-91 | A |
| I-92 | B |
| I-93 | A |
| I-94 | D |
| I-95 | A |
| I-96 | D |
| I-103 | D |
| I-104 | A |
| I-105 | D |
| I-106 | D |
| II-1 | A |
| II-20 | D |
| II-21 | B |
| II-22 | B |
| II-23 | D |
| II-24 | D |
| II-25 | D |
| II-26 | D |
| II-27 | D |
| II-28 | D |
| II-29 | D |
| II-30 | D |
| II-31 | A |
| II-32 | A |
| II-33 | D |
| II-34 | A |
| II-35 | C |
| II-36 | B |
| II-37 | A |
| II-38 | D |
| II-39 | A |
| II-40 | D |
| II-41 | C |
| II-42 | D |
| II-43 | C |
| II-44 | D |
| II-45 | A |
| II-46 | C |
| II-47 | A |
| II-48 | A |
| II-49 | A |
| II-50 | A |
| II-51 | D |
| II-52 | D |
| II-53 | D |
| II-54 | A |
| II-55 | A |
| II-56 | A |
| II-57 | B |
| II-58 | A |
| II-59 | D |
| II-60 | A |
| II-61 | D |
| II-62 | C |
| II-63 | A |
| II-64 | D |
| II-65 | D |
| II-66 | D |
| II-67 | D |
| II-68 | C |
| II-69 | B |
| II-70 | A |
| II-71 | A |
| II-72 | C |
| II-73 | D |
| II-74 | D |
| II-75 | D |
| II-76 | A |
| II-77 | D |
| II-78 | D |

TABLE 3-continued

Antiproliferative Activity

| Compound | Activity |
| --- | --- |
| II-79 | D |
| II-80 | D |
| II-81 | A |
| II-82 | A |
| II-83 | D |
| II-84 | D |
| II-85 | D |
| II-86 | D |
| II-87 | D |
| II-88 | D |
| II-89 | D |
| II-90 | A |
| II-91 | A |
| II-92 | D |
| II-93 | D |
| II-94 | D |
| II-95 | C |
| II-96 | A |
| II-97 | A |
| II-98 | A |
| II-99 | A |
| II-100 | A |
| II-101 | D |
| II-102 | D |
| II-103 | D |
| II-104 | D |
| II-105 | D |
| II-106 | D |
| II-108 | D |
| II-112 | D |
| II-113 | D |
| II-114 | C |
| II-115 | D |
| II-116 | D |
| II-123 | D |
| II-124 | D |
| II-127 | C |
| II-128 | A |
| II-129 | D |
| II-131 | D |
| II-132 | C |
| II-133 | D |
| II-145 | B |
| II-146 | D |
| II-147 | D |
| II-148 | A |
| II-149 | A |
| II-164 | A |
| II-165 | D |

THLE-2 cells were cultured using BEGM™ BULLET-KIT™ supplemented with 10% fetal bovine serum, streptomycin, and penicillin. The cells were plated in white walled 96-well plates at 5,000 cells/well. After the cells were incubated in DMSO (control) or a compound for 3 days at 37° C. and 5% $CO_2$, 100 μL of CELLTITER-GLO® (CTG) was added to each well. Following a 10 minutes incubation with shaking, luminescence was measured using an ENVISION® Multimode plate reader. In this example, compound II-1 was compared to reference compound A:

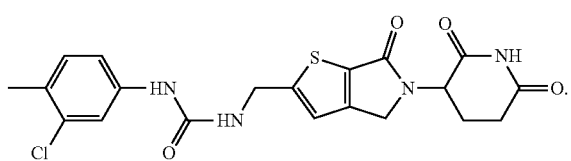 [SMILES: Cc1ccc(NC(=O)NCc2cc3c(s2)C(=O)N(C2CCC(=O)NC2=O)C3)cc1Cl]

THLE-2 $IC_{50}$ for compound II-1 and reference compound A are 8.9 and 0.80 μM, respectively.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula (III):

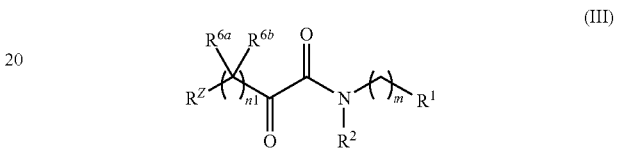

(III)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof; wherein:

$R^1$ is selected from the group consisting of

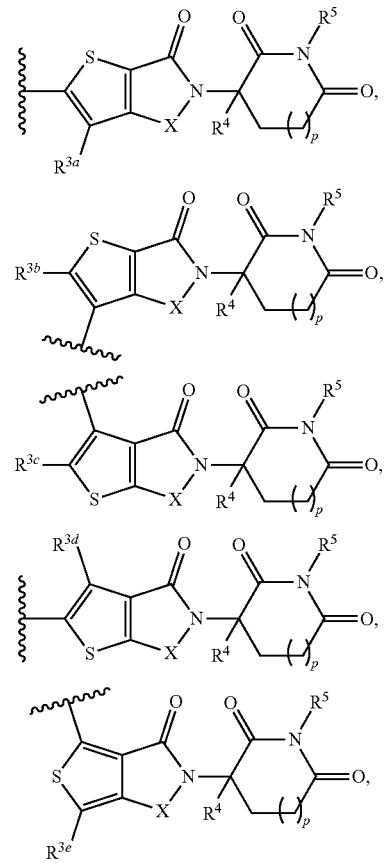

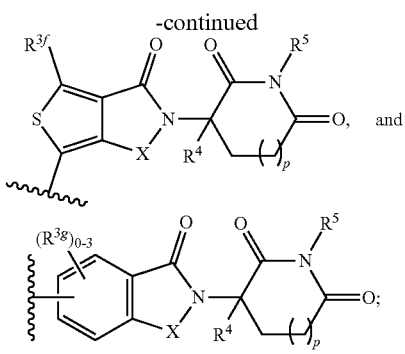

each X is independently $CH_2$ or $C(=O)$;

$R^Z$ is $-NR^{7a}R^{8a}$ or ring A; and ring A is $C_6$-$C_{10}$ aryl, 5 to 10 membered heteroaryl, $C_3$-$C_8$ carbocyclyl, or 3 to 10 membered heterocyclyl, each optionally substituted with one or more $R^A$;

$R^2$ is H, deuterium, optionally substituted $C_1$-$C_6$ alkyl, optionally substituted $C_3$-$C_8$ carbocyclyl, optionally substituted $C_6$-$C_{10}$ aryl, optionally substituted 3 to 10 membered heterocyclyl, or optionally substituted 5 to 10 membered heteroaryl;

$R^{3a}$, $R^{3b}$, $R^{3c}$, $R^{3d}$, $R^{3e}$, and $R^{3f}$ are each independently H, deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $-(CH_2)_t-NR^{7a}R^{8a}$, $-O(CH_2)_t-NR^{7a}R^{8a}$, $-C(O)NR^{7b}R^{8b}$, $-S(O)_2NR^{7c}R^{8c}$, $-OR^9$, $-SR^{10a}$, $-C(O)OR^{10b}$, $-C(O)R^{11a}$, $-NR^{7d}C(O)R^{11b}$, $-S(O)_2R^{11c}$, $-NR^{7e}S(O)_2R^{11d}$, $(C_1$-$C_6$ alkoxy)$C_1$-$C_6$ alkyl, $-O(C_1$-$C_6$ alkoxy)$C_1$-$C_6$ alkyl, optionally substituted $C_3$-$C_8$ carbocyclyl, optionally substituted $C_6$-$C_{10}$ aryl, optionally substituted 3 to 10 membered heterocyclyl, or optionally substituted 5 to 10 membered heteroaryl;

each $R^{3g}$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $-(CH_2)_t-NR^{7a}R^{8a}$, $-O(CH_2)_t-NR^{7a}R^{8a}$, $-C(O)NR^{7b}R^{8b}$, $-S(O)_2NR^{7c}R^{8c}$, $-OR^9$, $-SR^{10a}$, $-C(O)OR^{10b}$, $-C(O)R^{11a}$, $-NR^{7d}C(O)R^{11b}$, $-S(O)_2R^{11c}$, $-NR^{7e}S(O)_2R^{11d}$, $(C_1$-$C_6$ alkoxy)$C_1$-$C_6$ alkyl, $-O(C_1$-$C_6$ alkoxy)$C_1$-$C_6$ alkyl, optionally substituted $C_3$-$C_8$ carbocyclyl, optionally substituted $C_6$-$C_{10}$ aryl, optionally substituted 3 to 10 membered heterocyclyl, or optionally substituted 5 to 10 membered heteroaryl;

each $R^4$ is independently H, deuterium, halogen, or optionally substituted $C_1$-$C_6$ alkyl;

each $R^5$ is independently H, deuterium, $C_1$-$C_6$ alkyl,

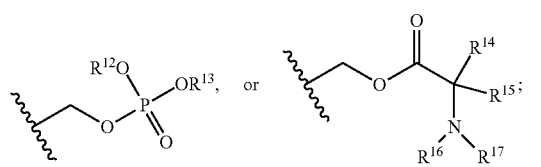

each $R^{6a}$, $R^{6b}$, $R^{14}$, and $R^{15}$ is independently H, substituted or unsubstituted amino, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl; or $R^{6a}$ and $R^{6b}$ together with the carbon atom to which they are attached form a $C_3$-$C_8$ carbocyclyl; wherein each $C_3$-$C_8$ carbocyclyl is optionally substituted with one or more $R^B$;

each $R^{7a}$, $R^{7b}$, $R^{7c}$, $R^{7d}$, $R^{7e}$, $R^{8a}$, $R^{8b}$, $R^{8c}$, $R^{16}$, and $R^{17}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl; or $R^{7a}$ and $R^{8a}$ together with the nitrogen atom to which they are attached form optionally substituted 3 to 7 membered heterocyclyl; or $R^{7b}$ and $R^{8b}$ together with the nitrogen atom to which they are attached form optionally substituted 3 to 7 membered heterocyclyl; or $R^{7c}$ and $R^{8c}$ together with the nitrogen atom to which they are attached form optionally substituted 3 to 7 membered heterocyclyl; or $R^{16}$ and $R^{17}$ together with the nitrogen atom to which they are attached form optionally substituted 3 to 7 membered heterocyclyl; wherein each of $C_6$-$C_{10}$ aryl, $C_7$-$C_{14}$ aralkyl, $C_3$-$C_8$ carbocyclyl, and 3 to 7 membered heterocyclyl is optionally substituted with one or more $R^B$;

each $R^9$ is independently optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{10a}$, $R^{11b}$, $R^{12}$, and $R^{13}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each $R^{11a}$, $R^{11b}$, $R^{11c}$, and $R^{11d}$ is independently optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each $R^A$ is independently halogen, cyano, nitro, hydroxyl, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $-(CH_2)_t-NR^{7a}R^{8a}$, $-O(CH_2)_t-NR^{7a}R^{8a}$, $-C(O)NR^{7b}R^{8b}$, $-S(O)_2NR^{7c}R^{8c}$, $-OR^9$, $-SR^{10a}$, $-C(O)OR^{10b}$, $-C(O)R^{11a}$, $-NR^{7d}C(O)R^{11b}$, $-S(O)_2R^{11c}$, $-NR^{7e}S(O)_2R^{11d}$, $(C_1$-$C_6$ alkoxy)$C_1$-$C_6$ alkyl, $-O(C_1$-$C_6$ alkoxy)$C_1$-$C_6$ alkyl, phenyl, 5 to 10 membered heteroaryl, $C_3$-$C_8$ carbocyclyl, or 3 to 10 membered heterocyclyl, wherein each of phenyl, 5 to 10 membered heteroaryl, $C_3$-$C_8$ carbocyclyl, and 3 to 10 membered heterocyclyl is optionally substituted with one or more $R^B$;

each $R^B$ is independently $C_1$-$C_6$ alkyl, $C_1$-$C_6$ alkoxy, $C_1$-$C_6$ haloalkyl, $C_1$-$C_6$ haloalkoxy, $(C_1$-$C_6$ alkoxy)$C_1$-$C_6$ alkyl, $-O(C_1$-$C_6$ alkoxy)$C_1$-$C_6$ alkyl, halogen, or cyano; or two geminal $R^B$ form oxo;

m is an integer of 0, 1, 2, 3, 4, or 5;

n1 is an integer of 0, 1, 2, or 3;

each p is independently an integer of 0, 1, or 2; and each t is independently an integer of 0, 1, 2, 3, 4, 5, 6, 7, or 8.

2. The compound of claim 1, being a compound of Formula (IIIa):

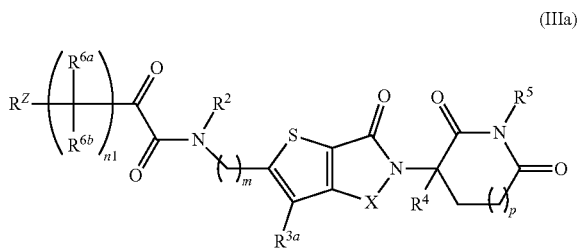

(IIIa)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate, thereof.

3. The compound of claim 1, being a compound of Formula (IIIb):

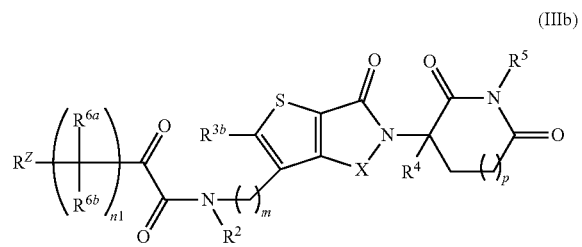

(IIIb)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

4. The compound of claim 1, being a compound of Formula (IIIc):

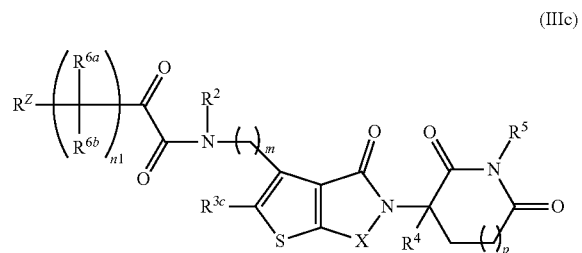

(IIIc)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

5. The compound of claim 1, being a compound of Formula (IIId):

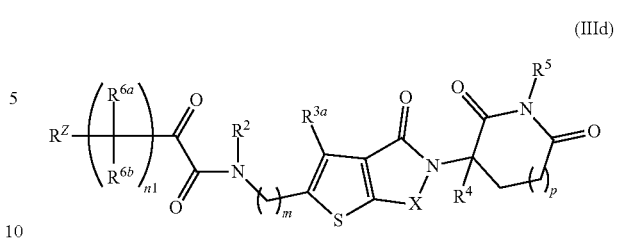

(IIId)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate, thereof.

6. The compound of claim 1, being a compound of Formula (IIIe):

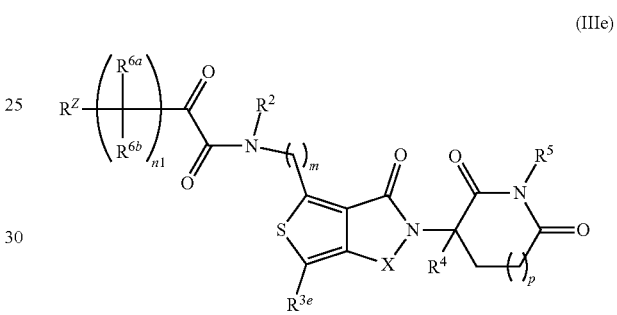

(IIIe)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate, thereof.

7. The compound of claim 1, being a compound of Formula (IIIf):

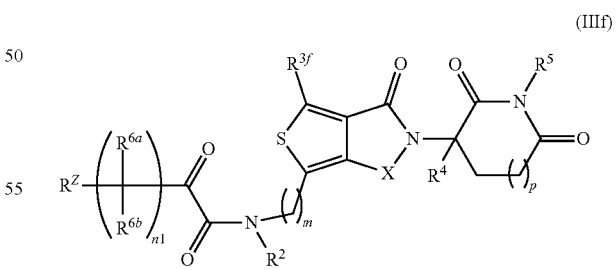

(IIIf)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate, thereof.

8. The compound of claim 1, being a compound of Formula (IIIg):

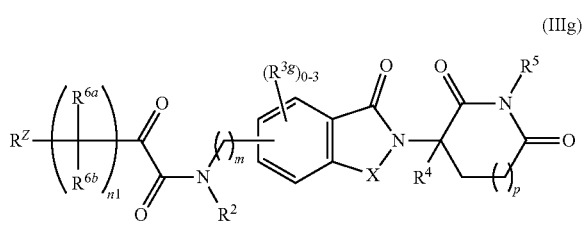

(IIIg)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate, thereof.

9. The compound of claim 1, being a compound of Formula (IIIh):

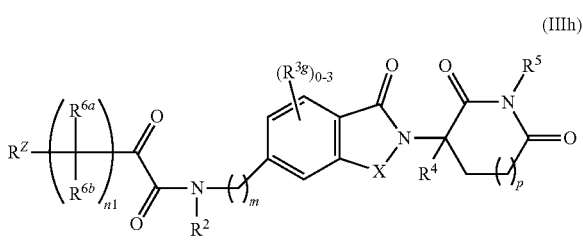

(IIIh)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate, thereof.

10. The compound of claim 1, being a compound of Formula (IIIi):

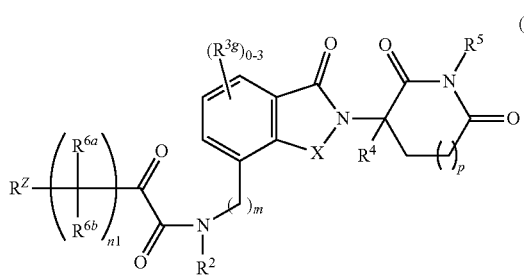

(IIIi)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate, thereof.

11. The compound of claim 1, wherein $R^Z$ is ring A.
12. The compound of claim 1, wherein X is $CH_2$.
13. The compound of claim 1, wherein X is C(=O).
14. The compound of claim 1, wherein p is 1.
15. The compound of claim 1, wherein $R^{3g}$ is halo, $C_1$-$C_6$ alkyl, or $C_1$-$C_6$ haloalkyl.
16. The compound of claim 15, wherein $R^{3g}$ is fluoro or methyl.
17. The compound of claim 1, wherein $R^4$ is H.
18. The compound of claim 1, wherein $R^5$ is H.
19. The compound of claim 1, wherein $R^2$ is H.

20. The compound of claim 11, wherein ring A is $C_6$-$C_{10}$ aryl, 5 to 10 membered heteroaryl, $C_3$-$C_8$ carbocyclyl, or 3 to 10 membered heterocyclyl, each of which is optionally substituted with one, two, or three substituents $R^A$.

21. The compound of claim 11, wherein ring A is $C_6$-$C_{10}$ aryl, optionally substituted with one, two, or three substituents $R^A$.

22. The compound of claim 11, wherein ring A is phenyl, optionally substituted with one, two, or three substituents $R^A$.

23. The compound of claim 11, wherein ring A is selected from the group consisting of pyridyl, thienyl, furyl, pyrimidinyl, pyrazolyl, imidazolyl, thiazolyl, isothiazolyl, oxazolyl, isoxazolyl, and thiadiazolyl, each optionally substituted with one, two, or three $R^A$.

24. The compound of claim 11, wherein ring A is phenyl, 4-cyanophenyl, 2-fluorophenyl, 3-fluorophenyl, 4-fluorophenyl, 3-chlorophenyl, 4-chlorophenyl, 4-bromophenyl, 4-methylphenyl, 4-(1-trifluoromethylethyl)-phenyl, 4-trifluoro-methylphenyl, 4-dimethylaminomethylphenyl, 4-morpholin-4-ylmethylphenyl, 4-isopropyl-phenyl, 4-sec-butylphenyl, 3-tert-butylphenyl, 4-tert-butylphenyl, 4-(hydroxyl-tert-butyl)phenyl, 4-cyclopropylphenyl, 4-(1-methyl-cyclopropyl)phenyl, 4-(1-trifluoromethylcyclopropyl)phenyl, 4-phenylphenyl, 4-(1-methylpiperidin-4-yl)phenyl, 4-hydroxylphenyl, 3-methoxyphenyl, 4-methoxyphenyl, 4-dimethylaminophenyl, 4-acetamidophenyl, 3,4-difluorophenyl, 3,4-dichloro-phenyl, 3-chloro-4-methylphenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 3-dimethylamino-4-methylphenyl, 2-naphthyl, thien-2-yl, 5-isopropylthien-2-yl, 4-pyridyl, 4-tert-butylcyclohexyl, piperdin-4-yl, or 4-tert-butylpiperidin-1-yl.

25. The compound of claim 11, wherein ring A is phenyl, 4-cyanophenyl, 2-fluorophenyl, 3-fluorophenyl, 3-chlorophenyl, 4-trifluoromethyl-phenyl, 3-tert-butylphenyl, 4-tert-butylphenyl, 4-(1-trifluoromethylcyclopropyl)-phenyl, 3-methoxyphenyl, 4-methoxyphenyl, 3,4-difluorophenyl, 3,4-dichlorophenyl, 3-chloro-4-methyl-phenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 2-naphthyl, 5-isopropylthien-2-yl, 4-pyridyl, 4-tert-butylcyclohexyl, or 4-tert-butylpiperidin-1-yl.

26. The compound of claim 11, wherein:
X is $CH_2$ or C(=O);
ring A is phenyl, 4-cyanophenyl, 2-fluorophenyl, 3-fluorophenyl, 4-fluorophenyl, 3-chlorophenyl, 4-chlorophenyl, 4-bromophenyl, 4-methylphenyl, 4-(1-trifluoromethyl-ethyl)-phenyl, 4-trifluoromethylphenyl, 4-dimethylaminomethylphenyl, 4-morpholin-4-ylmethylphenyl, 4-isopropylphenyl, 4-sec-butylphenyl, 3-tert-butylphenyl, 4-tert-butyl-phenyl, 4-(hydroxyl-tert-butyl)phenyl, 4-cyclopropylphenyl, 4-(1-methyl-cyclopropyl)-phenyl, 4-(1-trifluoromethylcyclopropyl)phenyl, 4-phenylphenyl, 4-(1-methylpiperidin-4-yl)phenyl, 4-hydroxylphenyl, 3-methoxyphenyl, 4-methoxyphenyl, 4-dimethylamino-phenyl, 4-acetamidophenyl, 3,4-difluorophenyl, 3,4-dichlorophenyl, 3-chloro-4-methyl-phenyl, 3-methyl-4-tert-butylphenyl, 3,5-dimethylphenyl, 2,4,6-trimethylphenyl, 2,4,6-trimethoxyphenyl, 2,6-dimethyl-4-tert-butylphenyl, 3-dimethylamino-4-methylphenyl, 2-naphthyl, thien-2-yl, 5-isopropylthien-2-yl, 4-pyridyl, 4-tert-butylcyclohexyl, piperdin-4-yl, or 4-tert-butylpiperidin-1-yl;
$R^2$ is H or methyl;
$R^4$ is H;

R[5] is H or D-valyloxymethyl;
R[3g] is fluoro or methyl;
p is an integer of 1 or 2; and
m is an integer of 0, 1, or 2.

27. A compound of:
2-(4-(tert-butyl)phenyl)-N-((5-(2,6-dioxopiperidin-3-yl)-4-oxo-5,6-dihydro-4H-thieno[3,4-c]pyrrol-1-yl)methyl)-2-oxoacetamide I-1;
N-((5-(2,6-dioxopiperidin-3-yl)-4-oxo-5,6-dihydro-4H-thieno[3,4-c]pyrrol-1-yl)-methyl)-2-oxo-2-(4-(1-(trifluoromethyl)cyclopropyl)phenyl)acetamide I-3;
N-((5-(2,6-dioxopiperidin-3-yl)-4-oxo-5,6-dihydro-4H-thieno[3,4-c]pyrrol-1-yl)-methyl)-2-(5-isopropylthiophen-2-yl)-2-oxoacetamide I-4;
2-(3-chloro-4-methylphenyl)-N-((5-(2,6-dioxopiperidin-3-yl)-4-oxo-5,6-dihydro-4H-thieno[3,4-c]pyrrol-1-yl)methyl)-2-oxoacetamide I-6;
2-(4-dimethylaminophenyl)-N-((5-(2,6-dioxopiperidin-3-yl)-4-oxo-5,6-dihydro-4H-thieno[3,4-c]pyrrol-1-yl)methyl)-2-oxoacetamide I-7;
2-phenyl-N-((5-(2,6-dioxopiperidin-3-yl)-4-oxo-5,6-dihydro-4H-thieno[3,4-c]pyrrol-1-yl)methyl)-2-oxoacetamide I-8;
N-((5-(2,6-dioxopiperidin-3-yl)-4-oxo-5,6-dihydro-4H-thieno[3,4-c]pyrrol-1-yl)-methyl)-2-(thiophen-2-yl)-2-oxoacetamide I-9;
2-(4-methoxyphenyl)-N-((5-(2,6-dioxopiperidin-3-yl)-4-oxo-5,6-dihydro-4H-thieno[3,4-c]pyrrol-1-yl)methyl)-2-oxoacetamide I-11;
2-(4-cyclopropylphenyl)-N-((5-(2,6-dioxopiperidin-3-yl)-4-oxo-5,6-dihydro-4H-thieno[3,4-c]pyrrol-1-yl)methyl)-2-oxoacetamide I-12;
2-(4-(tert-butyl)phenyl)-N-((5-(2,6-dioxopiperidin-3-yl)-4,6-dioxo-5,6-dihydro-4H-thieno[3,4-c]pyrrol-1-yl)methyl)-2-oxoacetamide I-13;
2-(4-isopropylphenyl)-N-((5-(2,6-dioxopiperidin-3-yl)-4-oxo-5,6-dihydro-4H-thieno[3,4-c]pyrrol-1-yl)methyl)-2-oxoacetamide I-14;
2-(4-(sec-butyl)phenyl)-N-((5-(2,6-dioxopiperidin-3-yl)-4-oxo-5,6-dihydro-4H-thieno[3,4-c]pyrrol-1-yl)methyl)-2-oxoacetamide I-15;
2-(4-hydroxyphenyl)-N-((5-(2,6-dioxopiperidin-3-yl)-4-oxo-5,6-dihydro-4H-thieno[3,4-c]pyrrol-1-yl)methyl)-2-oxoacetamide I-16;
2-(4-methylphenyl)-N-((5-(2,6-dioxopiperidin-3-yl)-4-oxo-5,6-dihydro-4H-thieno[3,4-c]pyrrol-1-yl)methyl)-2-oxoacetamide I-17;
2-(4-chlorophenyl)-N-((5-(2,6-dioxopiperidin-3-yl)-4-oxo-5,6-dihydro-4H-thieno[3,4-c]pyrrol-1-yl)methyl)-2-oxoacetamide I-18;
2-(3-tert-butylphenyl)-N-((5-(2,6-dioxopiperidin-3-yl)-4-oxo-5,6-dihydro-4H-thieno[3,4-c]pyrrol-1-yl)methyl)-2-oxoacetamide I-19;
2-(4-acetamidophenyl)-N-((5-(2,6-dioxopiperidin-3-yl)-4-oxo-5,6-dihydro-4H-thieno[3,4-c]pyrrol-1-yl)methyl)-2-oxoacetamide I-20;
2-([1,1'-biphenyl]-4-yl)-N-((5-(2,6-dioxopiperidin-3-yl)-4-oxo-5,6-dihydro-4H-thieno[3,4-c]pyrrol-1-yl)methyl)-2-oxoacetamide I-21;
2-(4-fluorophenyl)-N-((5-(2,6-dioxopiperidin-3-yl)-4-oxo-5,6-dihydro-4H-thieno[3,4-c]pyrrol-1-yl)methyl)-2-oxoacetamide I-22;
2-(4-trifluoromethylphenyl)-N-((5-(2,6-dioxopiperidin-3-yl)-4-oxo-5,6-dihydro-4H-thieno[3,4-c]pyrrol-1-yl)methyl)-2-oxoacetamide I-23;
2-(3,4-dichlorophenyl)-N-((5-(2,6-dioxopiperidin-3-yl)-4-oxo-5,6-dihydro-4H-thieno[3,4-c]pyrrol-1-yl)methyl)-2-oxoacetamide I-24;
2-(4-((dimethylamino)methyl)phenyl)-N-((5-(2,6-dioxopiperidin-3-yl)-4-oxo-5,6-dihydro-4H-thieno[3,4-c]pyrrol-1-yl)methyl)-2-oxoacetamide I-25;
2-(4-(morpholinomethyl)phenyl)-N-((5-(2,6-dioxopiperidin-3-yl)-4-oxo-5,6-dihydro-4H-thieno[3,4-c]pyrrol-1-yl)methyl)-2-oxoacetamide I-26;
2-(3-methyl-4-(tert-butyl)phenyl)-N-((5-(2,6-dioxopiperidin-3-yl)-4-oxo-5,6-dihydro-4H-thieno[3,4-c]pyrrol-1-yl)methyl)-2-oxoacetamide I-27;
N-((5-(2,6-dioxopiperidin-3-yl)-4-oxo-5,6-dihydro-4H-thieno[3,4-c]pyrrol-1-yl)-methyl)-2-(4-(1-methylpiperidin-4-yl)phenyl)-2-oxoacetamide I-31;
N-((5-(2,6-dioxopiperidin-3-yl)-4-oxo-5,6-dihydro-4H-thieno[3,4-c]pyrrol-1-yl)-methyl)-2-oxo-2-(4-(1,1,1-trifluoropropan-2-yl)phenyl)acetamide I-36;
2-(4-(tert-butyl)phenyl)-N-((5-(2,6-dioxopiperidin-3-yl)-4-oxo-5,6-dihydro-4H-thieno[3,4-c]pyrrol-1-yl)methyl)-2-oxoacetamide I-40;
2-(4-(tert-butyl)phenyl)-N-(2-(5-(2,6-dioxopiperidin-3-yl)-4-oxo-5,6-dihydro-4H-thieno[3,4-c]pyrrol-1-yl)ethyl)-2-oxoacetamide I-41;
N-((5-(2,6-dioxopiperidin-3-yl)-4-oxo-5,6-dihydro-4H-thieno[3,4-c]pyrrol-1-yl)-methyl)-2-(4-(1-methylcyclopropyl)phenyl)-2-oxoacetamide I-42;
N-((5-(2,6-dioxopiperidin-3-yl)-4-oxo-5,6-dihydro-4H-thieno[3,4-c]pyrrol-1-yl)-methyl)-2-(4-(1-hydroxy-2-methylpropan-2-yl)phenyl)-2-oxoacetamide I-43;
2-(3-(dimethylamino)-4-methylphenyl)-N-((5-(2,6-dioxopiperidin-3-yl)-4-oxo-5,6-dihydro-4H-thieno[3,4-c]pyrrol-1-yl)methyl)-2-oxoacetamide I-44;
N[1]-((5-(2,6-dioxopiperidin-3-yl)-4-oxo-5,6-dihydro-4H-thieno[3,4-c]pyrrol-1-yl)-methyl)-N[2],N[2]-dimethyloxalamide I-70;
2-(4-(tert-butyl)phenyl)-N-((2-(2,6-dioxopiperidin-3-yl)-1-oxoisoindolin-5-yl)methyl)-2-oxoacetamide I-2;
N-((2-(2,6-dioxopiperidin-3-yl)-1-oxoisoindolin-5-yl)methyl)-2-oxo-2-(4-(1-(trifluoro-methyl)cyclopropyl)phenyl)acetamide I-5;
(S)-2-(4-(tert-butyl)phenyl)-N-((2-(2,7-dioxoazepan-3-yl)-1-oxoisoindolin-5-yl)-methyl)-2-oxoacetamide I-10;
2-(4-(tert-butyl)phenyl)-N-((2-(2,6-dioxopiperidin-3-yl)-1,3-dioxoisoindolin-5-yl)-methyl)-2-oxoacetamide I-32;
2-(3-(tert-butyl)phenyl)-N-((2-(2,6-dioxopiperidin-3-yl)-1-oxoisoindolin-5-yl)methyl)-2-oxoacetamide I-33;
2-(4-(tert-butyl)phenyl)-N-((2-(2,6-dioxopiperidin-3-yl)-1-oxoisoindolin-5-yl)methyl)-N-methyl-2-oxoacetamide I-34;
N-((2-(2,6-dioxopiperidin-3-yl)-1-oxoisoindolin-5-yl)methyl)-2-(5-isopropylthiophen-2-yl)-2-oxoacetamide I-37;
N-(2-(2-(2,6-dioxopiperidin-3-yl)-1-oxoiso-indolin-5-yl)ethyl)-2-oxo-2-(4-(1-(trifluoro-methyl)cyclopropyl)phenyl)-acetamide I-52;
2-(3-chloro-4-methylphenyl)-N-((2-(2,6-dioxopiperidin-3-yl)-1-oxoisoindolin-5-yl)-methyl)-2-oxoacetamide I-53;
2-(3-methyl-4-(tert-butyl)phenyl)-N-((2-(2,6-dioxopiperidin-3-yl)-1-oxoisoindolin-5-yl)methyl)-2-oxoacetamide I-55;
N-((2-(2,6-dioxopiperidin-3-yl)-4-methyl-1-oxoisoindolin-5-yl)methyl)-2-oxo-2-(4-(1-(trifluoromethyl)cyclopropyl)phenyl)acetamide I-60;

2-(4-(tert-butyl)piperidin-1-yl)-N-((2-(2,6-dioxopiperidin-3-yl)-1-oxoisoindolin-5-yl)-methyl)-2-oxoacetamide I-62;

N-((2-(2,6-dioxopiperidin-3-yl)-1-oxoisoindolin-5-yl)methyl)-2-oxo-3-(4-(1-(trifluoro-methyl)cyclopropyl)phenyl)propanamide I-63;

2-(4-(tert-butyl)cyclohexyl)-N-((2-(2,6-dioxopiperidin-3-yl)-1-oxoisoindolin-5-yl)-methyl)-2-oxoacetamide I-68;

N-((2-(2,6-dioxopiperidin-3-yl)-1-oxoisoindolin-5-yl)methyl)-2-oxo-2-phenylacetamide I-83;

N-((2-(2,6-dioxopiperidin-3-yl)-1-oxoisoindolin-5-yl)methyl)-2-oxo-2-(2,4,6-trimethoxyphenyl)acetamide I-84;

N-((2-(2,6-dioxopiperidin-3-yl)-1-oxoisoindolin-5-yl)methyl)-2-oxo-2-(2,4,6-trimethyl-phenyl)acetamide I-85;

N-((2-(2,6-dioxopiperidin-3-yl)-1-oxoisoindolin-5-yl)methyl)-2-oxo-2-(2-fluoro-phenyl)acetamide I-86;

N-((2-(2,6-dioxopiperidin-3-yl)-1-oxoisoindolin-5-yl)methyl)-2-oxo-2-(4-trifluoro-methylphenyl)acetamide I-87;

N-((2-(2,6-dioxopiperidin-3-yl)-1-oxoisoindolin-5-yl)methyl)-2-(4-methoxyphenyl)-2-oxoacetamide I-89;

2-(4-cyanophenyl)-N-((2-(2,6-dioxopiperidin-3-yl)-1-oxoisoindolin-5-yl)methyl)-2-oxoacetamide I-90;

2-(3-chlorophenyl)-N-((2-(2,6-dioxopiperidin-3-yl)-1-oxoisoindolin-5-yl)methyl)-2-oxoacetamide I-91;

2-(3,4-difluorophenyl)-N-((2-(2,6-dioxopiperidin-3-yl)-1-oxoisoindolin-5-yl)methyl)-2-oxoacetamide I-93;

N-((2-(2,6-dioxopiperidin-3-yl)-1-oxoisoindolin-5-yl)methyl)-2-(3-methoxyphenyl)-2-oxoacetamide I-95;

N-((2-(2,6-dioxopiperidin-3-yl)-1-oxoisoindolin-5-yl)methyl)-2-(naphthalen-2-yl)-2-oxoacetamide I-97;

2-(3,5-dimethylphenyl)-N-((2-(2,6-dioxopiperidin-3-yl)-1-oxoisoindolin-5-yl)methyl)-2-oxoacetamide I-99;

N-((2-(2,6-dioxopiperidin-3-yl)-1-oxoisoindolin-5-yl)methyl)-2-(3-fluorophenyl)-2-oxoacetamide I-100;

2-(3,4-dichlorophenyl)-N-((2-(2,6-dioxopiperidin-3-yl)-1-oxoisoindolin-5-yl)methyl)-2-oxoacetamide I-102;

N-((2-(2,6-dioxopiperidin-3-yl)-1-oxoisoindolin-5-yl)methyl)-2-oxo-2-(pyridin-4-yl)-acetamide I-103;

2-(4-(tert-butyl)-2,6-dimethylphenyl)-N-((2-(2,6-dioxopiperidin-3-yl)-1-oxoisoindolin-5-yl)methyl)-2-oxoacetamide I-104;

2-(4-(tert-butyl)phenyl)-N-((2-(2,6-dioxopiperidin-3-yl)-1-oxoisoindolin-4-yl)methyl)-2-oxoacetamide I-28;

2-(4-(tert-butyl)phenyl)-N-((2-(2,6-dioxopiperidin-3-yl)-6-fluoro-1-oxoisoindolin-4-yl)methyl)-2-oxoacetamide I-29;

N-((2-(2,6-dioxopiperidin-3-yl)-1-oxoisoindolin-4-yl)methyl)-2-oxo-2-(4-(1-(trifluoro-methyl)cyclopropyl)phenyl)acetamide I-30;

2-(3-(tert-butyl)phenyl)-N-((2-(2,6-dioxopiperidin-3-yl)-1-oxoisoindolin-4-yl)methyl)-2-oxoacetamide I-46;

2-(4-(tert-butyl)phenyl)-N-((2-(2,6-dioxopiperidin-3-yl)-1-oxoisoindolin-4-yl)methyl)-N-methyl-2-oxoacetamide I-47;

2-(4-(tert-butyl)phenyl)-N-((2-(2,6-dioxopiperidin-3-yl)-1,3-dioxoisoindolin-4-yl)methyl)-2-oxoacetamide I-48;

(2R)-(3-(4-((2-(4-(tert-butyl)phenyl)-2-oxoacetamido)methyl)-1-oxoisoindolin-2-yl)-2,6-dioxopiperidin-1-yl)methyl 2-amino-3-methylbutanoate I-49;

2-(4-(tert-butyl)phenyl)-N-((2-(2,6-dioxopiperidin-3-yl)-5-fluoro-1-oxoisoindolin-4-yl)methyl)-2-oxoacetamide I-50;

2-(4-(tert-butyl)phenyl)-N-((2-(2,6-dioxopiperidin-3-yl)-5,6-difluoro-1-oxoisoindolin-4-yl)methyl)-2-oxoacetamide I-51;

2-(3-methyl-4-(tert-butyl)phenyl)-N-((2-(2,6-dioxopiperidin-3-yl)-1-oxoisoindolin-4-yl)methyl)-2-oxoacetamide I-54;

2-(4-(tert-butyl)phenyl)-N-(2-(2,6-dioxopiperidin-3-yl)-1-oxoisoindolin-4-yl)-2-oxoacetamide I-56;

N-(2-(2,6-dioxopiperidin-3-yl)-1-oxoisoindolin-4-yl)-2-oxo-2-(4-(1-(trifluoromethyl)-cyclopropyl)phenyl)acetamide I-57;

N-((2-(2,6-dioxopiperidin-3-yl)-1,3-dioxoisoindolin-4-yl)methyl)-2-oxo-2-(4-(1-(trifluoromethyl)cyclopropyl)phenyl)acetamide I-58;

N-((2-(2,6-dioxopiperidin-3-yl)-1-oxoisoindolin-4-yl)methyl)-2-(5-isopropylthiophen-2-yl)-2-oxoacetamide I-59;

2-(4-(tert-butyl)piperidin-1-yl)-N-((2-(2,6-dioxopiperidin-3-yl)-1-oxoisoindolin-4-yl)-methyl)-2-oxoacetamide I-61;

(2,6-dioxo-3-(1-oxo-4-((2-oxo-2-(4-(1-(trifluoromethyl)cyclopropyl)-phenyl)-acetamido)methyl)isoindolin-2-yl)piperidin-1-yl)methyl D-valinate I-64;

N-(2-(2-(2,6-dioxopiperidin-3-yl)-1-oxoisoindolin-4-yl)ethyl)-2-oxo-2-(4-(1-(trifluoro-methyl)cyclopropyl)phenyl)acetamide I-65;

N-((2-(2,6-dioxopiperidin-3-yl)-1-oxoisoindolin-4-yl)methyl)-2-oxo-2-(4-(piperidin-4-yl)phenyl)acetamide I-66;

2-(4-(tert-butyl)cyclohexyl)-N-((2-(2,6-dioxopiperidin-3-yl)-1-oxoisoindolin-4-yl)-methyl)-2-oxoacetamide I-67;

N-((2-(2,6-dioxopiperidin-3-yl)-1-oxoisoindolin-4-yl)methyl)-2-oxo-2-(p-tolyl)-acetamide I-72;

2-(3,4-difluorophenyl)-N-((2-(2,6-dioxopiperidin-3-yl)-1-oxoisoindolin-4-yl)methyl)-2-oxoacetamide I-73;

N-((2-(2,6-dioxopiperidin-3-yl)-1-oxoisoindolin-4-yl)methyl)-2-oxo-2-phenylacetamide I-74;

N-((2-(2,6-dioxopiperidin-3-yl)-1-oxoisoindolin-4-yl)methyl)-2-oxo-2-(4-(trifluoro-methyl)phenyl)acetamide I-75;

2-(4-cyanophenyl)-N-((2-(2,6-dioxopiperidin-3-yl)-1-oxoisoindolin-4-yl)methyl)-2-oxoacetamide I-76;

2-(4-chlorophenyl)-N-((2-(2,6-dioxopiperidin-3-yl)-1-oxoisoindolin-4-yl)methyl)-2-oxoacetamide I-77;

2-(4-methoxyphenyl)-N-((2-(2,6-dioxopiperidin-3-yl)-1-oxoisoindolin-4-yl)methyl)-2-oxoacetamide I-78;

2-(2,4,6-trimethoxyphenyl)-N-((2-(2,6-dioxopiperidin-3-yl)-1-oxoisoindolin-4-yl)-methyl)-2-oxoacetamide I-79;

2-(2,4,6-trimethylphenyl)-N-((2-(2,6-dioxopiperidin-3-yl)-1-oxoisoindolin-4-yl)-methyl)-2-oxoacetamide I-80;

2-(4-fluorophenyl)-N-((2-(2,6-dioxopiperidin-3-yl)-1-oxoisoindolin-4-yl)methyl)-2-oxoacetamide I-81;

2-(2-fluorophenyl)-N-((2-(2,6-dioxopiperidin-3-yl)-1-oxoisoindolin-4-yl)methyl)-2-oxoacetamide I-82;

2-(3-chlorophenyl)-N-((2-(2,6-dioxopiperidin-3-yl)-1-oxoisoindolin-4-yl)methyl)-2-oxoacetamide I-88;

2-(3-fluorophenyl)-N-((2-(2,6-dioxopiperidin-3-yl)-1-oxoisoindolin-4-yl)methyl)-2-oxoacetamide I-92;

2-(3-methoxyphenyl)-N-((2-(2,6-dioxopiperidin-3-yl)-1-oxoisoindolin-4-yl)methyl)-2-oxoacetamide I-94;

N-((2-(2,6-dioxopiperidin-3-yl)-1-oxoisoindolin-4-yl)methyl)-2-(naphthalen-2-yl)-2-oxoacetamide I-96;

2-(3,5-dimethylphenyl)-N-((2-(2,6-dioxopiperidin-3-yl)-1-oxoisoindolin-4-yl)methyl)-2-oxoacetamide I-98;

2-(3,4-dichlorophenyl)-N-((2-(2,6-dioxopiperidin-3-yl)-
1-oxoisoindolin-4-yl)methyl)-2-oxoacetamide I-101;
2-(4-(tert-butyl)-2,6-dimethylphenyl)-N-((2-(2,6-di-
oxopiperidin-3-yl)-1-oxoisoindolin-4-yl)methyl)-2-
oxoacetamide I-105;
2-(4-bromophenyl)-N-((2-(2,6-dioxopiperidin-3-yl)-1-
oxoisoindolin-4-yl)methyl)-2-oxoacetamide I-106;
2-(4-(tert-butyl)phenyl)-N-((5-(2,6-dioxopiperidin-3-yl)-
6-oxo-5,6-dihydro-4H-thieno[2,3-c]pyrrol-2-yl)
methyl)-2-oxoacetamide I-35;
2-(4-(tert-butyl)phenyl)-N-((2-(2,6-dioxopiperidin-3-yl)-
3-oxoisoindolin-4-yl)methyl)-2-oxoacetamide I-38;
2-(4-(tert-butyl)phenyl)-N-((5-(2,6-dioxopiperidin-3-yl)-
6-oxo-5,6-dihydro-4H-thieno[2,3-c]pyrrol-3-yl)
methyl)-2-oxoacetamide I-39;
2-(4-(tert-butyl)phenyl)-N-((5-(2,6-dioxopiperidin-3-yl)-
6-oxo-5,6-dihydro-4H-thieno[2,3-c]pyrrol-2-yl)
methyl)-2-oxoacetamide I-45;
N-((5-(2,6-dioxopiperidin-3-yl)-6-oxo-5,6-dihydro-4H-
thieno[2,3-c]pyrrol-2-yl)-methyl)-2-oxo-4-phenylbu-
tanamide I-69; or
$N^1$-((5-(2,6-dioxopiperidin-3-yl)-6-oxo-5,6-dihydro-4H-
thieno[2,3-c]pyrrol-2-yl)-methyl)-$N^2$,$N^2$-dimethyloxa-
lamide I-71;
or an enantiomer, a mixture of enantiomers, a diastereomer,
a mixture of two or more diastereomers, a tautomer, a
mixture of two or more tautomers, or an isotopic variant
thereof; or a pharmaceutically acceptable salt, solvate, or
hydrate thereof.

28. A pharmaceutical composition comprising a compound of claim 1 or a pharmaceutically acceptable salt thereof, and a pharmaceutically acceptable excipient.

29. The compound of claim 1, wherein $R^1$ is

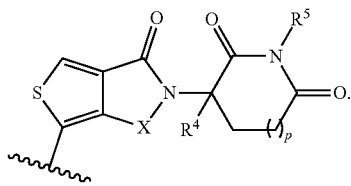

30. The compound of claim 1, wherein $R^1$ is

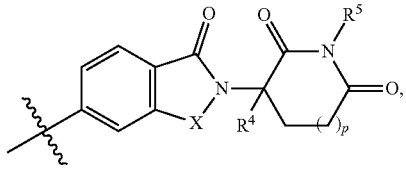

optionally substituted with one $R^{3g}$.

31. The compound of claim 1, wherein $R^1$ is

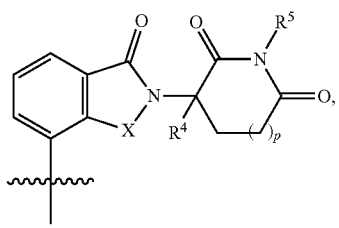

optionally substituted with one $R^{3g}$.

32. The compound of claim 1, wherein the compound is 2-(4-(tert-butyl)phenyl)-N-((5-(2,6-dioxopiperidin-3-yl)-4-oxo-5,6-dihydro-4H-thieno[3,4-c]pyrrol-1-yl)methyl)-2-oxoacetamide I-1, or a pharmaceutically acceptable salt thereof.

33. The compound of claim 1, wherein the compound is 2-(4-(tert-butyl)-phenyl)-N-((2-(2,6-dioxopiperidin-3-yl)-1-oxoisoindolin-5-yl)methyl)-2-oxoacetamide I-2, or a pharmaceutically acceptable salt thereof.

34. The compound of claim 1, wherein the compound is N-((5-(2,6-dioxopiperidin-3-yl)-4-oxo-5,6-dihydro-4H-thieno[3,4-c]pyrrol-1-yl)methyl)-2-oxo-2-(4-(1-(trifluoromethyl)cyclopropyl)phenyl)acetamide I-3, or a pharmaceutically acceptable salt thereof.

35. The compound of claim 1, wherein the compound is N-((5-(2,6-dioxopiperidin-3-yl)-4-oxo-5,6-dihydro-4H-thieno[3,4-c]pyrrol-1-yl)methyl)-2-(5-isopropyl-thiophen-2-yl)-2-oxoacetamide I-4, or a pharmaceutically acceptable salt thereof.

36. The compound of claim 1, wherein the compound is N-((2-(2,6-dioxopiperidin-3-yl)-1-oxoisoindolin-5-yl)methyl)-2-oxo-2-(4-(1-(trifluoromethyl)cyclopropyl)-phenyl)acetamide I-5, or a pharmaceutically acceptable salt thereof.

37. The compound of claim 1, wherein the compound is 2-(3-chloro-4-methylphenyl)-N-((5-(2,6-dioxopiperidin-3-yl)-4-oxo-5,6-dihydro-4H-thieno[3,4-c]pyrrol-1-yl)methyl)-2-oxoacetamide I-6, or a pharmaceutically acceptable salt thereof.

38. The compound of claim 1, wherein the compound is 2-(4-dimethyl-aminophenyl)-N-((5-(2,6-dioxopiperidin-3-yl)-4-oxo-5,6-dihydro-4H-thieno[3,4-c]pyrrol-1-yl) methyl)-2-oxoacetamide I-7, or a pharmaceutically acceptable salt thereof.

39. The compound of claim 1, wherein the compound is 2-phenyl-N-((5-(2,6-dioxopiperidin-3-yl)-4-oxo-5,6-dihydro-4H-thieno[3,4-c]pyrrol-1-yl)methyl)-2-oxo-acetamide I-8, or a pharmaceutically acceptable salt thereof.

40. The compound of claim 1, wherein the compound is N-((5-(2,6-dioxopiperidin-3-yl)-4-oxo-5,6-dihydro-4H-thieno[3,4-c]pyrrol-1-yl)methyl)-2-(thiophen-2-yl)-2-oxoacetamide I-9, or a pharmaceutically acceptable salt thereof.

41. The compound of claim 1, wherein the compound is (S)-2-(4-(tert-butyl)phenyl)-N-((2-(2,7-dioxoazepan-3-yl)-1-oxoisoindolin-5-yl)methyl)-2-oxoacetamide I-10, or a pharmaceutically acceptable salt thereof.

42. The compound of claim 1, wherein the compound is 2-(4-methoxy-phenyl)-N-((5-(2,6-dioxopiperidin-3-yl)-4-oxo-5,6-dihydro-4H-thieno[3,4-c]pyrrol-1-yl)methyl)-2-oxoacetamide I-11, or a pharmaceutically acceptable salt thereof.

43. The compound of claim 1, wherein the compound is 2-(4-cyclopropyl-phenyl)-N-((5-(2,6-dioxopiperidin-3-yl)-4-oxo-5,6-dihydro-4H-thieno[3,4-c]pyrrol-1-yl)methyl)-2-oxoacetamide I-12, or a pharmaceutically acceptable salt thereof.

44. The compound of claim 1, wherein the compound is 2-(4-(tert-butyl)-phenyl)-N-((5-(2,6-dioxopiperidin-3-yl)-4,6-dioxo-5,6-dihydro-4H-thieno[3,4-c]pyrrol-1-yl)methyl)-2-oxoacetamide I-13, or a pharmaceutically acceptable salt thereof.

45. The compound of claim 1, wherein the compound is 2-(4-isopropyl-phenyl)-N-((5-(2,6-dioxopiperidin-3-yl)-4- oxo-5,6-dihydro-4H-thieno[3,4-c]pyrrol-1-yl)methyl)-2-oxoacetamide I-14, or a pharmaceutically acceptable salt thereof.

46. The compound of claim 1, wherein the compound is 2-(4-(sec-butyl)-phenyl)-N-((5-(2,6-dioxopiperidin-3-yl)-4-oxo-5,6-dihydro-4H-thieno[3,4-c]pyrrol-1-yl)methyl)-2-oxoacetamide I-15, or a pharmaceutically acceptable salt thereof.

47. The compound of claim 1, wherein the compound is 2-(4-hydroxy-phenyl)-N-((5-(2,6-dioxopiperidin-3-yl)-4-oxo-5,6-dihydro-4H-thieno[3,4-c]pyrrol-1-yl)methyl)-2-oxoacetamide I-16, or a pharmaceutically acceptable salt thereof.

48. The compound of claim 1, wherein the compound is 2-(4-methyl-phenyl)-N-((5-(2,6-dioxopiperidin-3-yl)-4-oxo-5,6-dihydro-4H-thieno[3,4-c]pyrrol-1-yl)methyl)-2-oxoacetamide I-17, or a pharmaceutically acceptable salt thereof.

49. The compound of claim 1, wherein the compound is 2-(4-chloro-phenyl)-N-((5-(2,6-dioxopiperidin-3-yl)-4-oxo-5,6-dihydro-4H-thieno[3,4-c]pyrrol-1-yl)methyl)-2-oxoacetamide I-18, or a pharmaceutically acceptable salt thereof.

50. The compound of claim 1, wherein the compound is 2-(3-tert-butyl-phenyl)-N-((5-(2,6-dioxopiperidin-3-yl)-4-oxo-5,6-dihydro-4H-thieno[3,4-c]pyrrol-1-yl)methyl)-2-oxoacetamide I-19, or a pharmaceutically acceptable salt thereof.

51. The compound of claim 1, wherein the compound is 2-(4-acetamido-phenyl)-N-((5-(2,6-dioxopiperidin-3-yl)-4-oxo-5,6-dihydro-4H-thieno[3,4-c]pyrrol-1-yl)methyl)-2-oxoacetamide I-20, or a pharmaceutically acceptable salt thereof.

* * * * *